(12) United States Patent
Denis et al.

(10) Patent No.: US 8,722,746 B2
(45) Date of Patent: May 13, 2014

(54) HYDROXYPHENYL DERIVATIVES AND BIOLOGICAL APPLICATIONS THEREOF

(75) Inventors: Alexis Denis, Paris (FR); Vincent Gerusz, Paris (FR); Yannick Bonvin, Paris (FR)

(73) Assignee: Fab Pharma S.A.S., Paris (FR)

( * ) Notice: Subject to any disclaimer, the term of this patent is extended or adjusted under 35 U.S.C. 154(b) by 583 days.

(21) Appl. No.: 12/226,281

(22) PCT Filed: Apr. 16, 2007

(86) PCT No.: PCT/IB2007/002127
§ 371 (c)(1),
(2), (4) Date: Oct. 14, 2008

(87) PCT Pub. No.: WO2007/135562
PCT Pub. Date: Nov. 29, 2007

(65) Prior Publication Data
US 2010/0041658 A1    Feb. 18, 2010

(30) Foreign Application Priority Data

Apr. 14, 2006 (EP) .................................... 06290611

(51) Int. Cl.
*A61K 31/075* (2006.01)
*A61K 31/015* (2006.01)
*C07C 43/23* (2006.01)

(52) U.S. Cl.
USPC ............................ 514/721; 514/765; 568/635

(58) Field of Classification Search
USPC .................... 514/721, 765; 568/635
See application file for complete search history.

(56) References Cited

U.S. PATENT DOCUMENTS

| | | | |
|---|---|---|---|
| 3,391,195 | A | 7/1968 | Blake et al. |
| 3,634,484 | A | 1/1972 | Walter et al. |
| 5,578,295 | A | 11/1996 | Francis et al. |
| 2012/0232155 | A1 | 9/2012 | Gerusz |

FOREIGN PATENT DOCUMENTS

| | | |
|---|---|---|
| FR | 2 839 448 | 11/2003 |
| GB | 1 390 616 | 4/1975 |
| WO | 99/31036 | 6/1999 |
| WO | WO 00/35848 | 6/2000 |
| WO | WO 01/74753 | 10/2001 |
| WO | 03/088913 | 10/2003 |
| WO | 2004/043400 | 5/2004 |
| WO | WO 2006/018723 | 2/2006 |
| WO | WO 2006/071471 | 7/2006 |
| WO | WO 2006/137840 | 12/2006 |
| WO | WO 2007/027878 | 3/2007 |
| WO | WO2011/026529 | 3/2011 |

OTHER PUBLICATIONS

Kim YK and Ryu SY, "Cytotoxic components from stem bark of *Magnolia obovata*," Planta Medica, Apr. 1999, 65(3), 291-292.*
Heath RJ, Yu YT, Shapiro MA, Olson E, Rock CO. Broad spectrum antimicrobial biocides target the FabI component of fatty acid synthesis. Journal of Biological Chemistry. Nov. 1998;273(46):30316-20.*
King, F.D. (Ed.), "Bioisosteres, conformational restriction and pro-drugs—case history: an example of a conformational restriction approach," Medical Chemistry: Principles and Practice, 1994, Chapter 14, 206-209.*
Ito N, Tamano S, Shirai T. A medium-term rat liver bioassay for rapid in vivo detection of carcinogenic potential of chemicals. Cancer Sci. Jan. 2003;94(1):3-8.*
International Search Report for PCT/IB2007/002127, mailed Nov. 12, 2007.
Written Opinion of the International Searching Authority for PCT/IB2007/002127, mailed Nov. 12, 2007.
Leitner etal, "Kinetics and Mechanisms of the Photolytic and OH° Radical Induced Oxidation of Fluorinated Aromatic Compounds in Aqueous Solutions", Chemosphere, vol. 32, No. 5, pp. 893-906, 1996.

* cited by examiner

*Primary Examiner* — Paul Zarek
(74) *Attorney, Agent, or Firm* — Nixon & Vanderhye P.C.

(57) ABSTRACT

The invention relates to hydroxyphenyl derivatives of formula (I); and uses thereof as anti-bacterial and/or anti-parasitic agents.

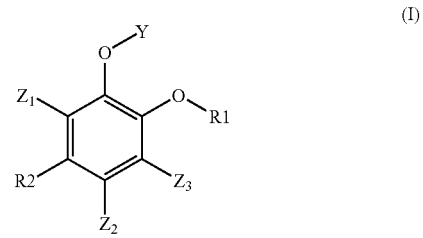

17 Claims, 2 Drawing Sheets

Figure 1 Treatment by molecules of example 21 at 50 mg/kg mean results of 4 experiments :
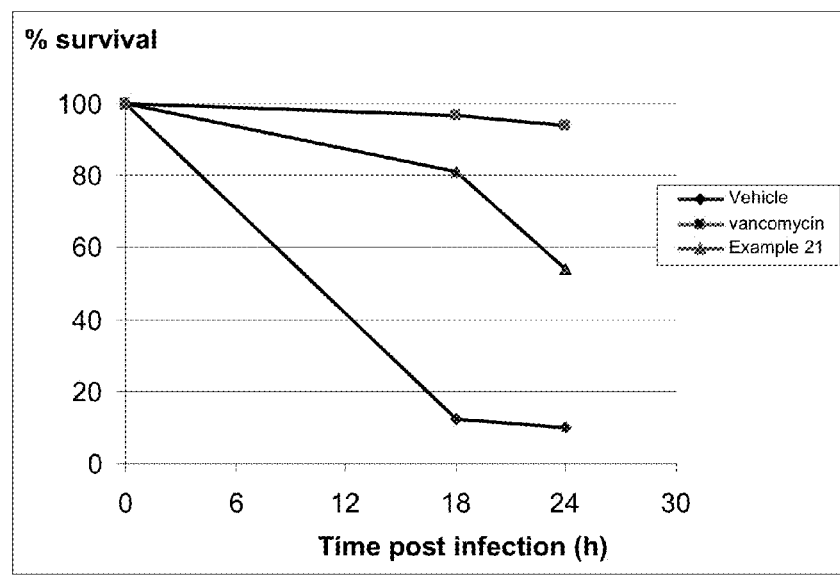

Figure 2 Treatment by molecules of example 48 at 100 mg/kg mean results of 4 experiments:
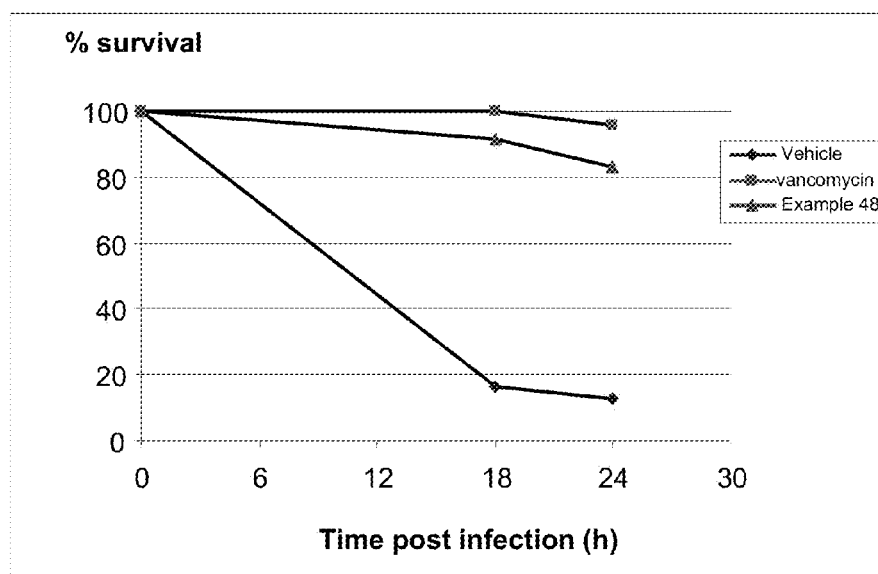

HYDROXYPHENYL DERIVATIVES AND BIOLOGICAL APPLICATIONS THEREOF

This application is the U.S. national phase of International Application No. PCT/IB2007/002127, filed 16 Apr. 2007, which designated the U.S. and claims priority to EP 06290611.0, filed 14 Apr. 2006, the entire contents of each of which are hereby incorporated by reference.

The invention relates to hydroxyphenyl derivatives and a process for making the same. It also relates to the biological applications thereof, particularly as anti-bacterial and/or anti-parasites agents.

The invention more particularly relates to Triclosan derivatives. Triclosan (TCL) 5-chloro-2-(2,4-dichloro-phenoxy)-phenol (A) is a broad-spectrum biocide that has been in use for over 30 years, mainly as a component of antimicrobial wash products in health-care settings, of formula (A)

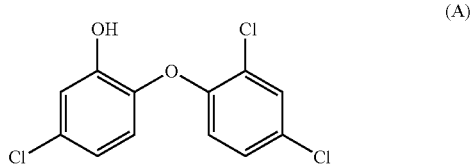 [SMILES: Oc1cc(Cl)ccc1Oc1ccc(Cl)cc1Cl]

More recently, Triclosan has found extensive use in consumer products such as toothpaste, mouthwashes, deodorants, hand soaps, and lotions. It is also incorporated in children's toys, cutting boards, and the plastic film used to wrap meat products. Until recently, it was thought that Triclosan, being a small hydrophobic molecule, was absorbed via diffusion into the bacterial cell wall and that unspecific disruption of the cell wall was the mechanism by which Triclosan exhibited its antibacterial activity. However, the first evidence that Triclosan inhibits fatty acid biosynthesis came when a strain of $E.\ coli$ resistant to Triclosan was isolated, and the resistance was mapped to the fabI gene which codes for the $E.\ coli$ trans enoyl-acyl carrier protein reductase (ENR). Fatty acid biosynthesis in bacteria is essential to the production of a number of lipid-containing components including the cell membrane. The bacterial fatty acid synthase system (FASII) utilizes discrete monofunctional enzymes that operate in conjunction with acyl carrier protein (ACP)-associated substrates. Mammalian fatty acid synthase (FASI) differs from FASII in that lipid biosynthesis is mediated by a single multifunctional enzyme-ACP complex. The differences in prokaryote and eukaryote fatty acid biosynthesis offer an attractive opportunity for selective FASII inhibition. FabI is an enoyl-ACP reductase that catalyzes the ultimate and rate-limiting step of the chain elongation process of FASII. The reaction involves the conjugate reduction of an enoyl-ACP to the corresponding acyl-ACP using the cofactor NAD(P)H as a hydride source.

Subsequently, extensive biochemical and structural studies have been performed to substantiate Triclosan as a specific $E.\ coli$ FabI inhibitor. Two ENR isoforms, FabK and FabL, have been discovered in the gram-positive bacteria, *Streptococcus pneumoniae* and *Bacillus subtilis*, respectively. FabK is resistant to Triclosan, whereas FabL is reversibly inhibited by Triclosan. Triclosan also directly inhibits the FabI from *Staphylococcus aureus, Haemophilus influenzae*, the ENR from *Mycobacterium tuberculosis*, InhA, and the ENR from *Plasmodium falciparum*, the malarial parasite.

Since the discovery of FabI as the bacterial target of Triclosan, several specific inhibitors not structurally related to TCL have been reported, few of them displaying antibacterial activities.

Some analogues of Triclosan itself have been described in separate chemo-enzymatic studies of the Triclosan mode of action against FabI. Especially, the antibacterial activity of several 2-hydroxydiphenyl ethers hexachlorophene and 2-hydroxydiphenylmethanes as well as 5-alkylated, -fluorinated or -formylated derivatives have been determined. On the other hand, before the discovery of the potent inhibition of FabI by TCL, some modifications of the dichlorophenol part of TCL were also reported. For instance broad spectrum, but non specific antibacterial and antifungal derivatives were reported by introducing a pyridine instead of a phenyl ring.

In contrast to TCL, which displays a broad spectrum biocidal effect with no distinction between microorganisms, new TCL derivatives that would target only the microorganisms which carry the FabI enzyme such as $S.\ aureus$ or $E.\ coli$ would be selective antibacterial or antiparasitic agents of interest with no antibacterial effect or selective pressure against other bacterial species.

The inventors have found that specific substitutions of hydroxyphenyl derivatives having triclosan basic structure lead to derivatives that surprisingly display a selective and narrow spectrum of activity against relevant pathogens, particularly bacteria or parasites.

An object of the invention is then to provide new substituted hydroxyphenyl derivatives which selectively inhibit the growth of bacteria carrying Fab enzymes such as FabI, FabL, FabK, InhA.

Another object of the invention is to provide a process for the synthesis of said derivatives.

Still another object is to take advantage of the biological properties of said molecules to provide means, i.e. pharmaceutical compositions and methods, particularly useful for treating microbial infections.

The hydroxyphenyl derivatives of the invention have formula (A)

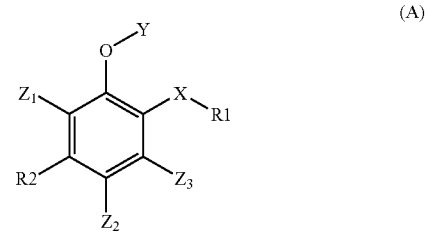

wherein
R1 is aryl, heterocycle, aliphatic heterocycle, cycloalkyl, all having one or several cycles, alkyl, all substituted or not by one or several R identical or different, selected in the group comprising, H, alkyl, alkenyl, alkynyl, aryl, heterocycle, aliphatic heterocycle, fluoro-alkyl, halogen, COOH, $CO_2R_a$, $COR_a$, $CONR_aR_b$, $OCOR_a$, CN, $OR_a$, aryloxy $NR_aR_b$, $CR_a$=$NOR_b$, $NR_a$-aryl, $NR_aCOR_b$, $NR_aCOOR_b$, $OCONR_aR_b$, $NR_aCONR_bR_c$, $SR_a$, $SO_2R_a$, $SO_2NR_aR_b$, $NR_aSO_2R_b$, $NR_aC(S)NR_bR_c$,
R2 is aryl, aryloxy, heterocycle, aliphatic heterocycle, cycloalkyl, all having one or several cycles, H, alkyl, alkenyl, alkynyl, halogen, fluoro-alkyl, fluoro-alkenyl, $OCF_3$, $OCHF_2$, $NR_aR_b$, $CO_2R_a$, $COR_a$, $OR_a$, $CONR_aR_b$, $CR_a$=$NOR_b$, $SR_a$, all being substituted or not by one or several R, identical or different, being such as above defined, $R_a$, $R_b$ and $R_c$, identical or different, being H or as above defined with respect to R, two adjacent R, or two adjacent $R_a$ and/or $R_b$, and /or $R_c$ optionally forming together a cycle X=O or S Y represents C(O)R, CO(O)R, C(S)R, C(S)OR, C(O)$NR_a$, $R_b$, phosphate, P(O)(OR)$_2$, CH$_2$OR, or any labile group which may act as a prodrug to regenerate the free phenol, Z1, Z2, Z3, identical or different, are halogen or H, and the pharmaceutically acceptable salts, the organic and mineral salts, as well as the racemic derivatives and each unique non racemic derivatives, in case the derivatives of formula (A) have one or more chiral centers, both the cis (Z) and trans (E) isomers in case the derivatives of formula (A) have unsaturated carbon=carbon double bonds, both forms of tautomers in cases the derivatives of formula (A) may exist in tautomeric forms, provided that with respect to formula (A), when R2 is H, C1 to C26 alkyl substituted or not by OH, NH2, SH, halo or CO$_2$H or OR, SR, NHR, COOR, COR, CONHR, SO$_2$NHR, R being H, C1 to C26 substituted or not by OH, NH$_2$, SH, halo or CO$_2$H; Y=H; X=O; Z1, Z2 Z3 are H; and R1 is a group of formula,

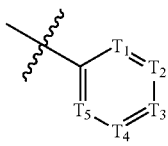

if T1 and T5 are independently N or C—R, R being H, methyl, ethyl, halo, then
either
T2 or T4 are different from CH or N,
or
T3 is different from N or C—R, wherein R represent H, methyl, ethyl, halo, nitro, hydroxy, amino, amido or a methyl or an ethyl group substituted with halo, nitro, hydroxy, amino, amido;
if T2 and T4 are independently CH or N, then
either
T1 or T5 are different from N or C—R, R being H, Me, ethyl, halo,
or
T3 is different from N or C—R, wherein R represent H, methyl, ethyl, halo, nitro, hydroxy, amino, amido or a methyl or an ethyl group substituted with halo, nitro, hydroxy, amino, amido;
if T3 represent N or C—R, wherein R represent H, methyl, ethyl, halo, nitro, hydroxy, amino, amido or a methyl or an ethyl group substituted with halo, nitro, hydroxy, amino, amido; then.
either
T1 or T5 are different from N or C—R, R being H, Me, ethyl, halo,
or
T2 or T4 are different from CH or N.

When R1 is an heterocycle and more specifically a pyridine, the invention also includes the N-oxide form.

"Alkyl" as applied herein means an optionally substituted alkyl group and preferably methyl, ethyl, n-propyl, isopropyl, n-butyl, isobutyl and t-butyl, pentyl, n-pentyl, isopentyl, neopentyl,hexyl and octyl.

"Alkoxy" and "thioalkyl" mean any O or S atom substituted by a substituted or not alkyl group.

"Aryloxy", "thioaryl", "NH-aryl" mean any O, S, N substituted by a substituted or not aryl, or heterocyclic group.

"Aryl" (or "Ar") means phenyl or naphtyl optionally substituted by R.

"Alkenyl" and "alkynyl" mean optionally substituted C=C or C≡C groups.

"Halogen" or "halo" means F, Cl, Br, and I.

"Aliphatic heterocycle" or "heterocycle" indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are for example selected in the group comprising benzofuryl, benzimidazolyl, benzopyranyl, benzothienyl, furyl, imidazolyl, indolinyl, morpholinyl, piperidinyl, piperazinyl, pyrrolyl, pyrrolidinyl, tetrahydropyridinyl, pyridinyl, thiazolyl, thienyl, quinolinyl, isoquinolinyl, and tetra- and perhydro-quinolinyl and isoquinolinyl, pyrazinyl, pyrazidinyl, triazinyl, purine, indolyl, indazolyl, pyrimidinyl, pyridonyl, oxazolyl, tetrahydropyranyl, tetrahydrofuranyl.

The invention more particularly relates to hydroxyphenyl derivatives having formula (I)

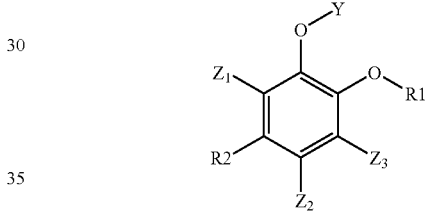

wherein
R1 is phenyl or a 6 membered monocyclic nitrogenous heteroaryl of formula

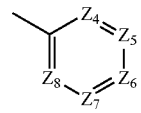

Z4, Z5, Z6, Z7 and Z8 independently are C or N with a maximum of three N, R1 being possibly substituted by 1 to 3 R identical or different, R being selected from the group comprising H, $C_1$-$C_8$ alkyl, $C_2$-$C_8$ alkenyl, $C_2$-$C_8$ alkynyl, 5 or 6 membered monocyclic heteroaryl or aliphatic heterocycle containing 1 to 3 heteroatoms selected from N, O and S, COOR$_a$, COR$_a$, CONR$_a$R$_b$, OCOR$_a$, CN, OR$_a$, NR$_a$R$_b$, CR$_a$=NOR$_b$, NR$_a$COR$_b$, NR$_a$COOR$_b$, OCONR$_a$R$_b$, NR$_a$CONR$_b$R$_c$, SR$_a$, SO$_2$R$_a$, SO$_2$NR$_a$R$_b$, NR$_a$SO$_2$R$_b$ and NR$_a$C(S)NR$_b$R$_c$, all being possibly substituted by R', or R is $C_1$-$C_4$ fluoro-alkyl, or R is fluor when R1 is phenyl, or R is halogeno when R1 is nitrogenous heteroaryl, R2 is phenyl, $C_1$-$C_8$ alkyl, $C_2$-$C_8$ alkenyl, $C_2$-$C_8$ alkynyl, $C_1$-$C_4$ fluoro-alkyl, $C_2$-$C_4$ fluoro-alkenyl, OR$_a$, SR$_a$, all being possibly substituted by 1 to 3 identical or different R', R$_a$, R$_b$ and R$_c$, identical or different, are selected from the group consisting of H, $C_1$-$C_8$ alkyl, $C_2$-$C_8$ alkenyl, $C_2$-$C_8$ alkynyl, phenyl, heteroaryl and aliphatic heterocycle as defined above for R2, the heteroaryl and the heterocycle being possibly formed with the carbon and nitrogen atoms to which $R_a$, $R_b$ and $R_c$ are linked, R' is selected from the group comprising heteroaryl and aliphatic heterocycle as defined above for R2, $C_1$-$C_8$alkyl, $CH_2CO_2R''$, $CO_2R''$, COR'', CONR''R''', OCOR'', OR'', NR''R''', NR''COR''', NR''COOR''', OCONR''R''', NR''CONR''R''', NR''SO$_2$R''', SO$_2$R'', NR''SO$_2$R''', halogen and CN, R'' and R''', identical or different, are H, $C_1$-$C_8$ alkyl or form together a 4 to 6 membered heterocycle with 1 to 3 heteroatoms selected from N, O and S, Y represents H or a labile chemical group able to regenerate in vivo the free phenol selected from the group consisting of $C(O)R_a$, $C(O)OR_a$, $C(O)NR_a,R_b$, $P(O)(OH)_2$, and $COCHR_aNR_bR_c$, Z1 and Z3, identical or different, are halogen or H, Z2 is fluor or H, provided that either Z2 is fluor and all the other definitions are as defined above, or Z6 is a carbon atom substituted by R as defined above, R being different from H, alkyl, halogen, $NH_2$, OH, $CONH_2$ or fluoro alkyl and all the other definitions are as defined above, or Z4 or Z5, or Z7 or Z8 are carbon atoms substituted by $NR_aR_b$ or $OR_a$ being different from H and all the other definitions are as defined above, or Z5, or Z7, is a carbon atom substituted by R, R being different from H and all the other definitions are as defined above, or R2 is a $C_1$-$C_8$ alkyl-heteroaryl radical or a $C_1$-$C_8$ alkyl-$OR_a$ and all the other definitions are as defined above, and the pharmaceutically acceptable organic and mineral salts, as well as the racemic derivatives and each unique non racemic derivatives, in case the derivatives of formula (I) have one or more chiral centers, both the cis (Z) and trans (E) isomers in cases the derivatives of formula (I) have unsaturated carbon=carbon double bonds, and any N-oxide form of the derivatives.

In formula I:

"$C_1$-$C_8$ alkyl" as applied herein means linear, branched or cyclic hydrocarbon groups having 1 to 8 carbon atoms preferably methyl, ethyl, n-propyl, isopropyl, n-butyl, isobutyl and t-butyl, pentyl, n-pentyl, isopentyl, neopentyl, hexyl, octyl, cyclopropyl cyclobutyl, cyclopentyl, cyclohexyl;

"$C_2$-$C_8$ alkenyl and "$C_2$-$C_8$ alkynyl" as applied herein means linear, branched or cyclic hydrocarbon groups of 2 to 8 carbon atoms, having at least one double bond or one triple bond and preferably, ethenyl, propenyl, butenyl, cyclohexenyl, ethynyl, propargyl, butynyl;

"$C_1$-$C_4$ fluoro alkyl and $C_2$-$C_4$ alkenyl" means a $C_1$-$C_4$ alkyl or $C_2$-$C_4$ alkenyl group substituted by 1 to 7 fluorine atoms.

"Halogen" means F, Cl, Br, and I;

"Heteroaryl" and "Aliphatic Heterocycle" as applied herein means a 5-10 membered aromatic or non-aromatic mono or bicyclic ring, containing at least one heteroatom selected from N, O and S. Illustrative heterocycles are for example selected in the group comprising benzofuryl, benzimidazolyl, benzopyranyl, benzothienyl, furyl, imidazolyl, indolinyl, azetidinyl, morpholinyl, piperidinyl, piperazinyl, oxazolidinyl, pyrrolyl, pyrrolidinyl, pyrazolyl, tetrahydropyridinyl, pyridinyl, thiazolyl, thienyl, quinolinyl, isoquinolinyl, and tetra- and perhydro-quinolinyl and isoquinolinyl, pyrazinyl, pyrazidinyl, triazinyl, triazolyl, tetrazolyl, indolyl, indazolyl, pyrimidinyl, pyridonyl, oxazolyl, isoxazolyl, isothienyl, quinazolinyl, oxadiazolyl, thiadiazolyl, phtalimidyl.

"$C_1$-$C_8$ alkyl-heteroaryl" means a $C_1$-$C_8$ alkyl such as above defined substituted with one heteroaryl group such as above defined.

"$C_1$-$C_8$ alkyl-$OR_a$" means a $C_1$-$C_8$ alkyl such as above defined substituted with one $OR_a$ group such as above defined, $OR_a$ being different from OH.

According to a first family, the invention particularly relates to derivatives of formula (I) wherein R1 is a 6-membered monocyclic heteroaryl group such as above defined. Preferably, the nitrogeneous heteroaryl with one or 3 nitrogen atoms is selected in the group comprising a pyridine, a pyrimidine, a pyridazine, a pyrazine or a triazine.

In particularly preferred derivatives of said first family, R1 is a substituted heteroaryl group such as above defined.

Advantageously, the nitrogeneous heteroaryl group is substituted by one or several substituents selected in the group comprising F, $COR_a$, $OR_a$, $NR_aR_b$, alkynyl, $SO_2R_a$, $NR_aSO_2R_b$, $SO_2NR_aR_b$, $NR_aCOOR_b$ and $CR_a=NOR_b$.

According to a second family, the invention particularly relates to derivatives of formula (I) wherein R1 is a phenyl group.

Particularly preferred derivatives of said second family are substituted by one or several substituents selected in the group comprising F, $COR_a$, $OR_a$, $NR_aR_b$, alkynyl, $SO_2R_a$, $NR_aSO_2R_b$, $SO_2NR_aR_b$, $NR_aCOOR_b$ and $CR_a=NOR_b$.

In a preferred embodiment, in the above defined derivatives of said first and/or second family, Z2 is fluor. The fluorine atom being advantageously positioned in para of the OH group of compound of formula I when Y=H to prevent the in vitro or in vivo oxidation of the phenolic compound into the corresponding quinone.

According to another embodiment, Z6 is a carbon atom substituted by R as defined above, R being different from H, alkyl, halogen, $NH_2$, OH, $CONH_2$, or fluoro alkyl and all the other definitions are as defined with respect to formula (I).

According to still another preferred embodiment, Z4 or Z5, or Z7 or Z8, are carbon atoms substituted by $NR_aR_b$ or $OR_a$, $OR_a$ being different from OH and all the other definitions are as defined with respect to formula (I).

In a further embodiment, Z5 or Z7 is a carbon atom substituted by R, R being different from H and all the other definitions are as defined with respect to formula (I).

According to an other embodiment family, the invention particularly relates to derivatives of formula (I) wherein, R2 is a $C_1$-$C_8$alkyl-heteroaryl or a $C_1$-$C_8$alkyl-$OR_a$, $OR_a$ being different from OH.

In a more preferred embodiment, Y represents H.

Also included in this invention are compounds in which Y is different from H, Y being a labile chemical group able to regenerate in vivo the free phenol compounds of formula I with Y being H such $C(O)R_a$, $C(O)OR_a$, $C(O)NR_a$, $C(O)NR_a$, $R_b$, $P(O)(OH)_2$, $COCHR_aNR_bR_c$ It will be understood that the above defined embodiment can be used in combination with any one of the other defined embodiments.

The invention also relates to a process for making the above defined derivatives.

In a first embodiment of the invention, said process comprises the steps of a) reacting with AR1, a phenol derivative of formula (II)

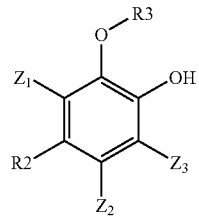

(II)

wherein R1, R2 and Z1, Z2, Z3 are as above defined, R3 represents an alkyl group, and A is a reactive group such as an halogen or a nitro capable of reacting with the OH group of (II) under basic conditions known to the one skilled in the art to give a derivative of formula (III)

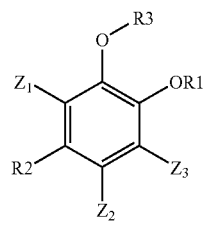

(III)

b) reacting the protected phenol derivative of formula (III) with any suitable Lewis acid for example $BBr_3$ or $BCl_3$, under conditions to give the desired derivatives of formula (I).

To obtain derivatives wherein R2 represents a functional group, the desired function is introduced prior removal of R3.

Alternatively, the derivatives of formula (I) are advantageously obtained from the protected phenols of formula (II) by introducing a R4 group different from R3=alkyl which can be smoothly remove in a non restrictive manner by hydrogenation, acidic conditions or treatment with fluoride derivatives to generate compound of formula (I) according to a process comprising:

a) reacting the protected phenol derivative of formula (II) with TosCl under conditions to give a derivative of formula (IV)

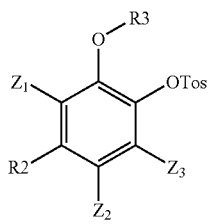

(IV)

b) reacting the derivative of formula (IV) with any suitable Lewis acid such as $BBr_3$, $BCl_3$ under appropriate conditions to give a derivative of formula (V)

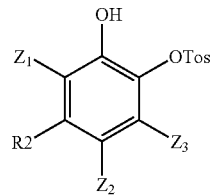

(V)

c) treating the derivative of formula (V) under basic or acidic conditions, to introduce R4, R4 being a protecting group different from a linear alkyl, such as benzyl, BOM, SEM, MOM, MEM, TBDMS, THP or analogs, resulting in a derivative of formula (VI),

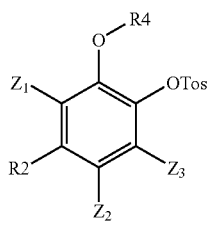

(VI)

d) reacting said derivative of formula (VI) under appropriate conditions, to obtain the removal of Tosyl group, resulting in of a derivative of formula (VII)

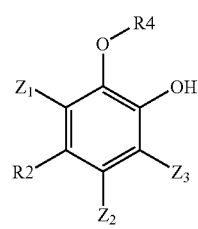

(VII)

e) reacting the derivative of formula (VII) thus obtained with AR1 such as above defined to obtain a compound of formula (III')

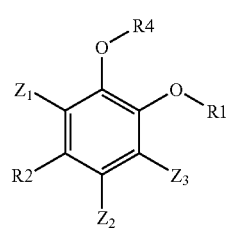

(III')

and f) deprotecting the phenol group to obtain the desired derivative of formula (I) with Y representing H, wherein R2 is functionalized if desired as above mentioned, optionally from derivative of formula (VI).

According to a second embodiment, compounds of formula (I) with Z2=F can be obtained according to the following synthetic scheme 1 by a process comprising:

a) reacting the bromophenol of formula (VIII) first with AR1 such as above defined and a base to generate a derivative of formula (IX); then reacting derivatives of formula (IX) with a suitable palladium catalyst with its ligands, choosen from the group, as non restrictive examples of Pd(PPh$_3$)$_4$ or Pd(dppf)Cl$_2$.DCM, a suitable base such as potassium carbonate or cesium carbonate and R2B, R2 being as above defined and B being a boronic ester residue to obtain the derivatives of formula (X):

Scheme 1:

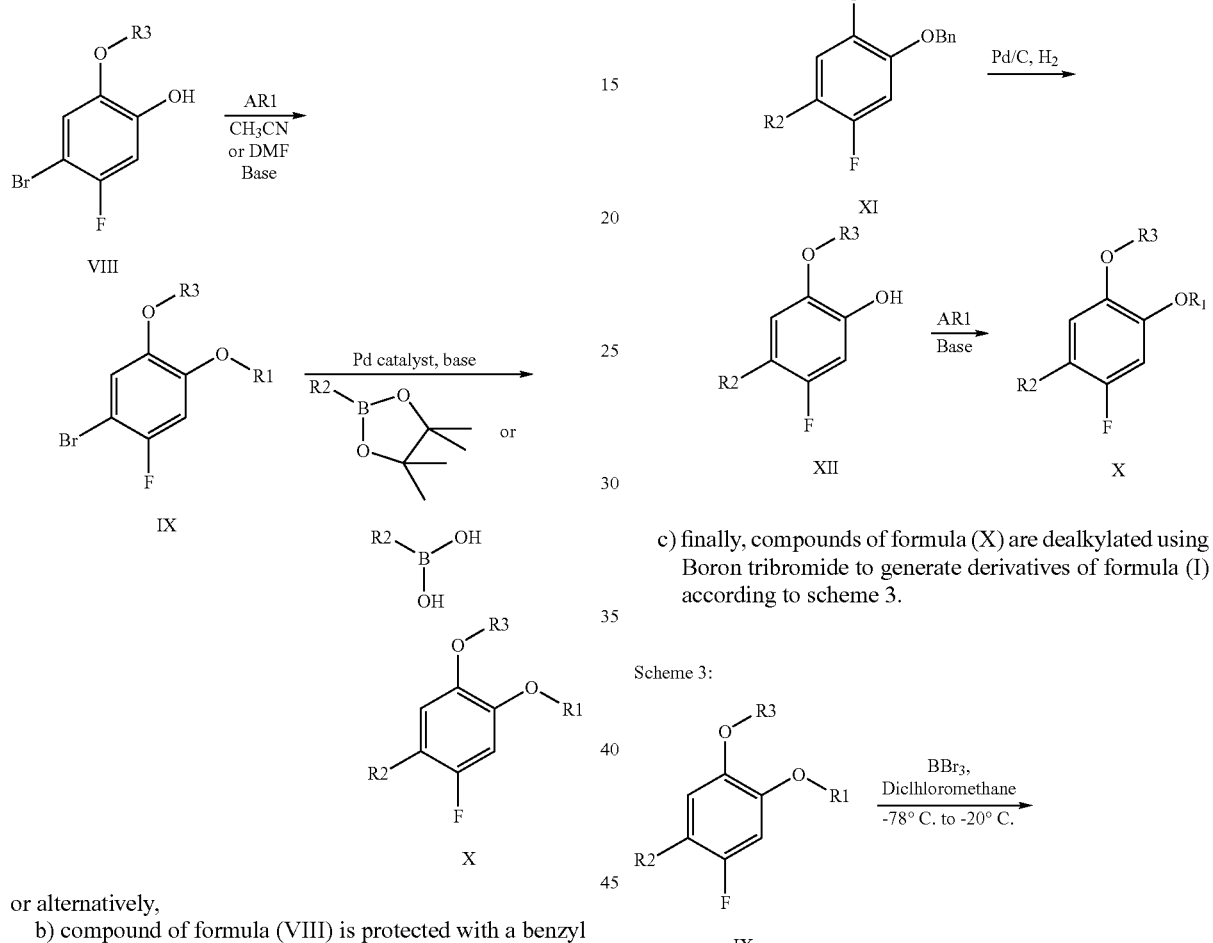

or alternatively, b) compound of formula (VIII) is protected with a benzyl group prior to be reacted with a palladium catalyst in the presence of a base and a boronic reactant of formula R2B, such as defined above, to generate the benzylated derivative (XI), debenzylation with palladium on charcoal and hydrogen generates the free phenol (XII) which is then reacted with AR1 according to step the process described above to generates derivatives of formula (X)

Scheme 2:

c) finally, compounds of formula (X) are dealkylated using Boron tribromide to generate derivatives of formula (I) according to scheme 3.

Scheme 3:

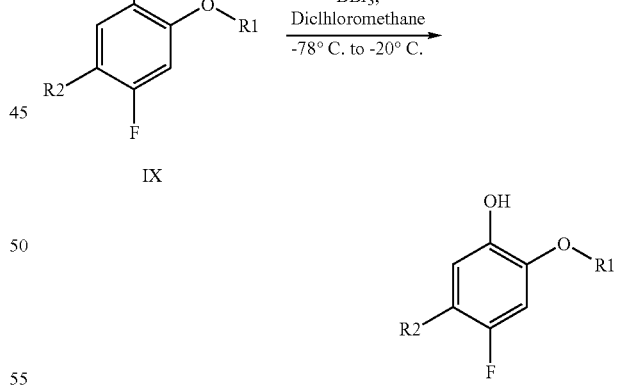

According to a third embodiment, the invention also comprises a process wherein a compound of formula (XIII), corresponding to compounds of formula (III), (VI), (VII), (X) or (I) in which R2 is vinyl and R5 is R3 or R4 as above defined or H, is reduced by hydrogenation with palladium on charcoal (according to scheme 4) to give the R2=ethyl compound derivative (XIV), corresponding to compounds of formula (III), (VI), (VII), (X) or (I) which can be further deprotected according to the above process when R5=R3 or R4.

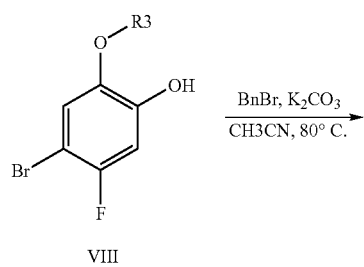

Scheme 4:

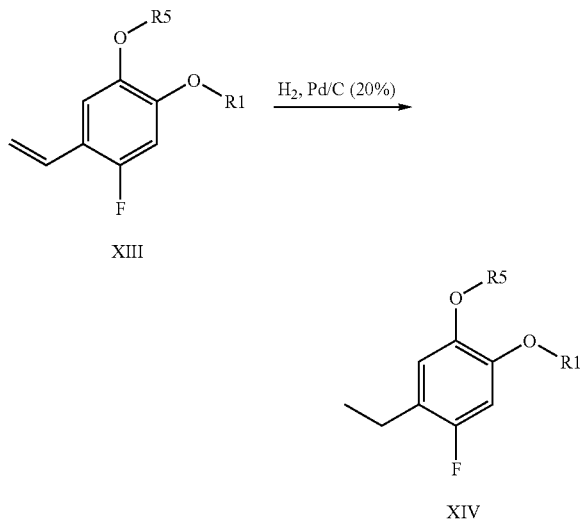

According to a fourth embodiment, the process of the invention for making a compound of formula (I) consists of converting, derivatives of formula I in which Y=H advantageously by methods known by one skilled of the art into a compound in which Y is $C(O)R_a$, $CO(O)R_a$, $C(O)NR_a,R_b$, $P(O)(OH)_2$, and $COCHR_aNR_bR_c$.

As illustrated by the examples given hereinafter, the above disclosed phenol derivatives of the invention have valuable biological properties.

They are particularly useful as antibacterial agents having a selective spectrum of activity in vitro against standard bacterial strains which are used to screen for activity against pathogenic bacteria. Notably, the derivatives of the present invention show a high activity against bacteria carrying Fab enzymes such as FabI, FabL, FabK, InhA. Particularly against *Staphyloccus aureus* including multiresistant strains, *Escherichia coli, Helicobacter pylori* and also bacteria such as *Mycobacterium tuberculosis* carrying homologous Fab enzymes such as InhA or other organisms such as *Plasmodium falciparum*. Said derivatives are then particularly suitable as active principle of drugs.

The invention thus also relates to compositions comprising a phenol derivative of formula (I) such as above defined for use as drug.

It also relates to pharmaceutical compositions comprising a phenol derivative of formula (I) such as above defined in combination with a pharmaceutically acceptable carrier.

Said pharmaceutical compositions are formulated to be administered under oral, injectable, parental routes, with doses appropriate for the patient to be treated.

The compositions of the invention may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

A suitable daily dose of the compounds of the invention will be that amount of the compound that is the lowest dose effective to produce a therapeutic effect. Generally, topical, intravenous and subcutaneous doses of the compositions of this invention for a patient, when used for the indicated effects, will range from about 0.0001 to about 100 mg per kilogram of body weight per day, given in one or several doses administered separately at appropriate intervals throughout the day, optionally, in unit dosage forms.

Said compositions are particularly useful to treat human or animal infections by microbial pathogens such as *E. coli, H. pylori* or *S. aureus* or *M. tuberculosis* and parasites such as *Plasmodium falciparum*.

Said compositions are also useful in multitherapy, in combination with other drugs, for example with antibiotics.

The invention also relates to a method of treatment of microbial infections which comprises administering to a patient in need thereof an efficient amount of a pharmaceutical composition such as above defined.

Other characteristics and advantages of the invention are given in the examples hereafter wherein it is referred to FIGS. 1 and 2, which represent, the protection of mice against the lethal effect of bacterial multiplication.

Synthesis of example compounds:

Proton nuclear magnetic resonance ($^1$H NMR) spectra were recorded at either 300 or 400 MHz, and chemical shifts are reported in parts per million (δ) downfield from the internal standard tetramethylsilane (TMS). Abbreviations for NMR data are as follows: s=singlet, d=doublet, t=triplet, q=quadruplet, qt=quintuplet, se=sextuplet, m=multiplet, dd=doublet of doublets, dt=doublet of triplets, br=broad. J indicates the NMR coupling constant measured in Hertz. $CDCl_3$ is deuteriochloroform, DMSO-$d^6$ is hexadeuteriodimethylsulfoxide, and $CD_3OD$ is tetradeuteriomethanol. Mass spectra were obtained using either electrospray (ESI) or atmospheric pressure photoionization (APPI) techniques. Analtech Silica Gel GF and E. Merck Silica Gel 60 F-254 thin layer plates were used for thin layer chromatography. Flash chromatography was carried out on Flashsmartpack cartridge, irregular silica 40-60 μm or spherical silica 20-40 μm TLC refers to thin layer chromatography, MS refers to mass spectra, HPLC refers to high pressure liquid chromatography, NMR refers to nuclear magnetic resonance, APT refers to attached proton test, HSQC refers to heteronuclear single quantum correlation, NOESY refers to nuclear Overhauser enhancement spectroscopy.

Certain reagents and radical groups are abbreviated herein are abbreviated herein. t-Bu refers to the tertiary butyl radical, Boc refers to the t-butyloxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Nph refers to 1- or 2-naphthyl and cHex refers to cyclohexyl. DCC refers to dicyclohexylcarbodiimide, DMAP refers to 4-dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, $PPh_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, TEA refers to triethylamine, TFA refers to trifluoroacetic acid, PCC refers to pyridinium chlorochromate, TBAF refers to tetrabutyl ammonium fluoride, Tos refers to Tosyl and TosCl refers to tosyl Chloride, BOM refers to p-methoxybenzyl, MOM refers to methoxy-methyl, MEM refers to methoxy-ethoxymethyl, SEM refers to trimethyl-silyl-ethoxymethyl, THP refers to tetrahydropyranyl, TSI refers to triethylsilyl, TBDMS refers to tButyl-dimethyl-silyl, DCM refers to dichloromethane, CAN refers to acetonitrile, Pet ether refers to petroleum ether.

EXAMPLE 1

2-[(3-amino-6-chloropyridin-2-yl)oxy]-5-propylphenol a) 2-chloro-6-(2-methoxy-4-propylphenoxy)pyridin-3-amine (A) and 6-chloro-2-(2-methoxy-4-propylphenoxy)pyridin-3-amine (B)

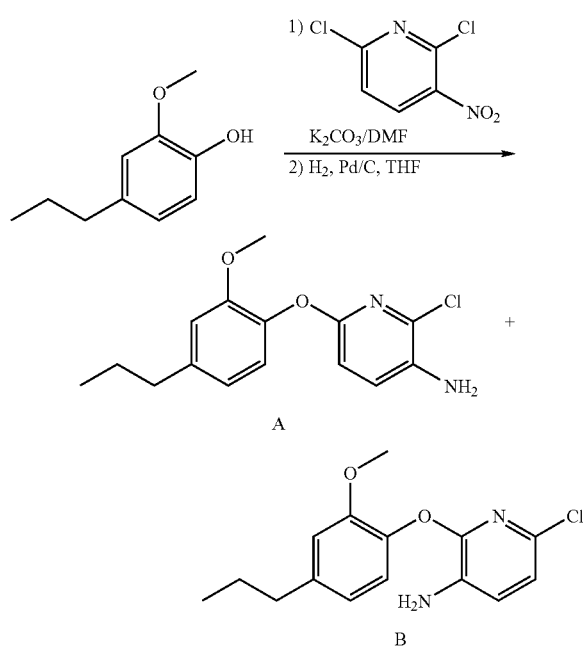

To a suspension of K$_2$CO$_3$ (2.4 mmol; 331 mg) in anhydrous DMF (1 mL) under argon, was added 2-methoxy-4-propylphenol (1 mmol; 0.16ml) followed by 2.6-Dichloro-3-nitropyridine (1 mmol; 176 mg). The reaction mixture was stirred at 40° C. over 48H.

After quenching with NaOH (0.1N; 3 mL), the mixture was extracted with ethyl acetate (3*3 mL). Combined organic phases were dried over Na$_2$SO$_4$, concentrated in vacuo, to give a yellow solid (480 mg; 1.49 mmol; 74%), used without further purification. 240 mg of that solid (0.75 mmol) were dissolved in THF (3 mL) under argon. Palladium on activated carbon (50 mg) was added then the reaction was flushed twice with hydrogen, then left to stir overnight. The reaction mixture was then filtered on celite, and then rinsed with ethyl acetate (3*5 mL), to give a mixture of regioisomers. After purification by preparative TLC (dichloromethane), the regioisomers were isolated as light yellow oils. (A: 40 mg, 0.14 mmol, B: 30 mg, 0.1 mmol, global yield: 32%)

A: $^1$H NMR (CDCl$_3$) δ (ppm): 7.08 (d, 1H, J=8.3 Hz); 6.97 (d, 1H, J=7.9 Hz); 6.76 (m, 2H); 6.59 (d, 1H, J=8.5 Hz); 2.59 (t, 2H, J=7.6 Hz,); 1.65 (se, 2H, J=7.4 Hz); 0.98 (t, 3H, J=7.2 Hz).

B: $^1$H NMR (CDCl$_3$) δ (ppm): 7.6 (d, 1H, J=7.9 Hz); 6.98 (d, 1H, J=7.9 Hz); 6.79 (m, 3H); 2.59 (t, 2H, J=7.6 Hz,); 1.67 (se, 2H, J=7.4 Hz); 0.97 (t, 3H, J=7.2 Hz).

b) 2-[(3-amino-6-chloropyridin-2-yl)oxy]-5-propylphenol

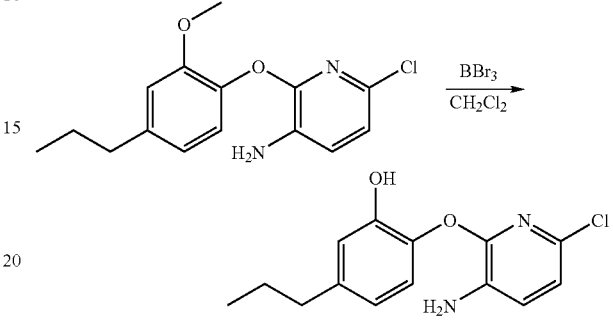

To a solution of 6-chloro-2-(2-methoxy-4-propyl phenoxy) pyridin-3-amine (0.1 mmol; 30 mg) under argon, in dichloromethane (2 mL), cooled to −78° C., was added BBr$_3$ (0.5 mmol; 0.5 mL) dropwise. The reaction mixture was allowed to stir for 5 hr, with gradual warming to −20° C. At −20° C., the reaction was hydrolysed with saturated NH$_4$Cl (4 mL), extracted with dichoromethane (3*10 mL). Combined organic phases dried over Na$_2$SO$_4$, concentrated in vacuo, to give the desired product as a light brown solid without further purification (27 mg 0.1 mmol; 97%).

$^1$H NMR (CDCl$_3$) δ (ppm): 7.06 (d, 1H, J=8.0 Hz); 6.99 (d, 1H, J=8.2 Hz); 6.89(m, 2H); 6.69 (d, 1H, J=8.1 Hz); 2.52 (t, 2H, J=7.7 Hz,); 1.64 (se, 2H, J=7.5 Hz); 0.93 (t, 3H, J=7.4 Hz).

EXAMPLE 2

2-[(5-amino-6-chloropyridin-2-yl)oxy]-5-propylphenol

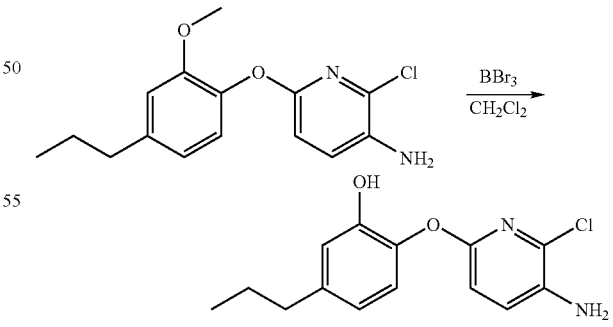

According to the procedure of example 1(b) except substituting 6-chloro-2-(2-methoxy-4-propylphenoxy)pyridin-3-amine for 2-chloro-6-(2-methoxy-4-propylphenoxy)pyridin-3-amine (0.14 mmol; 40 mg) the title compound (30 mg; 0.11 mmol; 77%). was prepared without any purification as a light brown solid.

¹H NMR (CDCl₃) δ (ppm): 7.13 (d, 1H, J=8.4 Hz), 6.94 (d, 1H, J=8.2 Hz); 6.88(s, 1H); 6.74 (d, 1H, J=8.4 Hz); 6.66 (d, 1H, J=8.2 Hz); 2.52 (t, 2H, J=7.6 Hz,), 1.63 (se, 2H, J=7.5 Hz); 0.95 (t, 3H, J=7.3 Hz).

EXAMPLE 3

5-ethyl-2-[(6-fluoropyridin-2-yl)oxy]phenol a) 2-(4-ethyl-2-methoxyphenoxy)-6-fluoropyridine

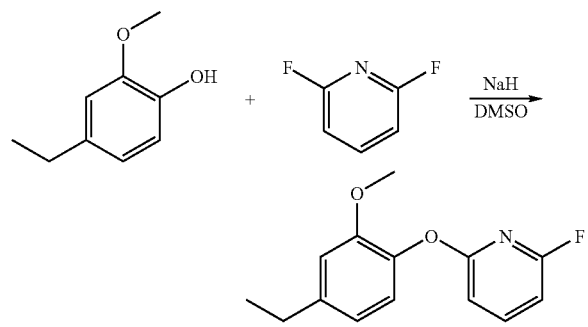

To a suspension of NaH (1.2 mmol; 50 mg) in anhydrous DMSO (1 mL) under argon, was added 4-ethyl-2-methoxyphenol (1 mmol; 152.2 mg) followed by 2,6-difluoropyridine (1 mmol; 0.1 ml). The reaction mixture was stirred at 120° C. overnight. After quenching with NaOH (0.1N; 3 mL), the mixture was extracted with dichloromethane (3*5 mL). Combined organic phases were dried over Na₂SO₄, concentrated in vacuo, to give the title compound as a light yellow oil (250 mg; 1 mmol; 100%), used without further purification.
MS(ES): m/e 248 (M+H)⁺.

b) 5-ethyl-2-[(6-fluoropyridin-2-yl)oxy]phenol

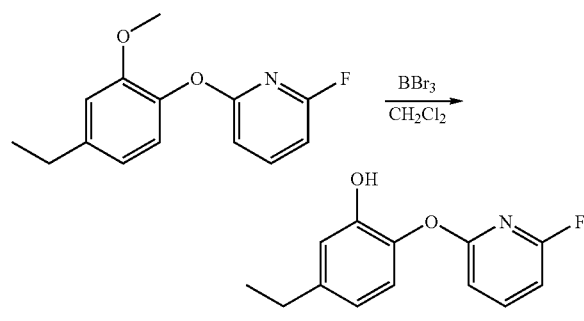

According to the procedure of example 1(b) except substituting 6-chloro-2-(2-methoxy-4-propylphenoxy)pyridin-3-amine for 2-(4-ethyl-2-methoxyphenoxy)-6-fluoropyridine (250 mg, 1 mmol) the title compound (80 mg, 34%) was prepared as a white solid after purification by flash chromatography on silica gel (gradient dichloromethane/methanol).
MS(ES): m/e 234 (M+H)⁺
¹H NMR (CDCl₃) δ (ppm): 7.77 (q, 1H, J1=7.9 Hz, J2=8.0 Hz); 7.01 (d, 1H, J=8.2 Hz,); 6.92 (d, 1H, J=1.9 Hz); 6.75 (td, 2H, J1=8.2 Hz, J2=2.0 Hz); 6.64 (dd, 1H, J1=7.9 Hz, J2=2.4 Hz); 2.62 (q, 2H, J1=7.6 Hz, J2=7.6 Hz); 1.23 (t, 3H, J=7.6 Hz).

Alternatively compound of example 3 can be synthesized starting from 2-Benzyloxy-4-ethyl-phenol instead of 4-ethyl-2-methoxyphenol according to the following procedure:

c) 4-ethyl-2-hydroxyphenyl-4-methylbenzenesulfonate

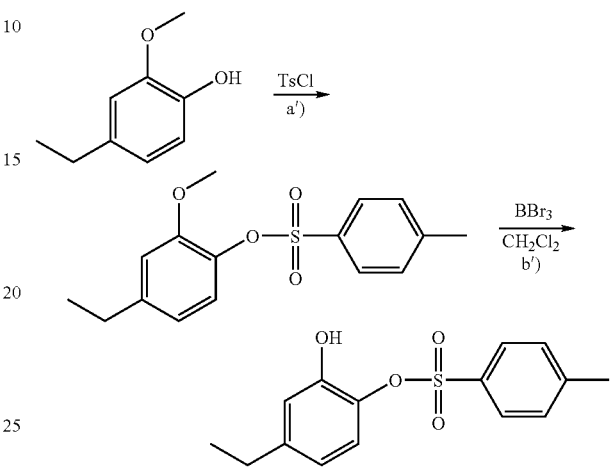

a') To a solution of 2-methoxy-4-ethylphenol (26.3 mmol; 4.0 g), NaI (5.25 mmol; 788 mg), and K₂CO₃ (28.9 mmol; 3.98 g), under argon, in acetonitrile (20 mL) was added tosyl chloride (27.6 mmol; 5.24 g). The reaction mixture was stirred at 70° C. for 30 hr, then quenched with NaOH (0.1N; 50 mL), and extracted with ethyl acetate (3*20 mL). Combined organic phases were washed with saturated NaHCO₃ sat. (50 mL) then water (50 mL), dried over MgSO₄ and concentrated in vacuo. The crude was recrystallized in cyclohexane (10 mL) to yield a brown oil (5.53 g; 18.1 mmol; 68%) engaged without further purification in step b'.

b') To a solution of 5 g of Toluene-4-sulfonic acid 4-ethyl-2-methoxy-phenyl ester (16.3 mmol), under argon, in dichloromethane (15 mL), cooled to −78° C., was added BBr₃ (35 mmol; 35 mL) dropwise. The reaction mixture was allowed to stir for 6 hr, with gradual warming to −20° C. At −78° C., the reaction was hydrolysed with saturated NH₄Cl (30 mL), extracted with dichoromethane (2*10 mL). Combined organic phases were washed with 100 mL of satured NaHCO₃, dried over Na₂SO₄, concentrated in vacuo, the title compound (1.97 g; 41%) was obtained as a colourless oil, after purification on silica gel (dichloromethane/cyclohexane: gradient).
¹H NMR (CDCl₃) δ (ppm): 7.76 (d, 2H, J=8.1 Hz); 7.34 (d, 2H, J=7.9 Hz); 6.84 (s, 1H); 6.65 (d, 1 H, J=8.4 Hz); 6.58 (d, 1H, J=6.8 Hz); 5.86 (sl, 1H); 2.56 (q, 2H, J=7.6 Hz); 2.46 (s, 3H); 1.18 (t, 3H, J=7.6 Hz).

d) 2-(benzyloxy)-4-ethylphenyl-4-methylbenzenesulfonate

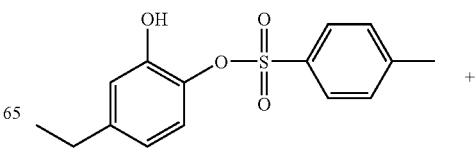

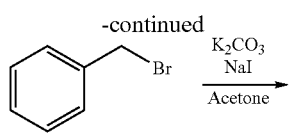

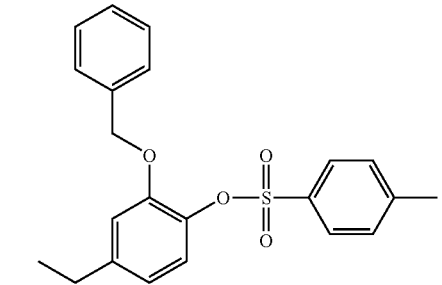

To a solution of 4-ethyl-2-hydroxyphenyl-4-methylbenzenesulfonate (5 mmol; 1.46 g) under argon, in acetone (10 mL), were added K$_2$CO$_3$ (6 mmol; 0.83 g), NaI (1 mmol; 0.15 g), and benzylbromide (5.5 mmol; 0.65 mL). The reaction was stirred at 40° C. for 5 hr. The reaction mixture was concentrated then hydrolysed with NH$_4$Cl sat. (10 mL) and extracted with ethyl acetate (3*5 mL). Combined organic phases were washed with saturated NaHCO$_3$ (10 mL), dried over Na$_2$SO$_4$, concentrated. The residue was purified on silica gel (dichloromethane/cyclohexane: gradient) to yield the title compound as a clear oil (1.68 g; 4.39 mmol; 87%).

$^1$H NMR (CDCl$_3$) δ (ppm): 7.69 (d, 2H, J=8.3 Hz); 7.34 (m, 5H); 7.11 (m, 3H); 6.74 (m, 2H); 4.87 (s, 2H); 2.59 (q, 2H, J=7.6 Hz); 2.37 (s, 3H); 1.19 (t, 3H, J=7.6 Hz).

e) 2-Benzyloxy-4-ethyl-phenol

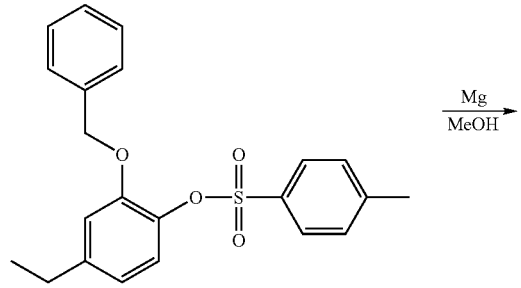

To a solution of 2-(benzyloxy)-4-ethylphenyl-4-methylbenzenesulfonate methylbenzenesulfonate (0.26 mmol; 100 mg) under argon, in methanol (2 mL), was added magnesium (2.61 mmol; 0.63 g). The reaction was stirred at room temperature overnight. The reaction mixture was hydrolysed with HCl 1N (3 mL) and extracted with ethyl acetate (3*5 mL). Combined organic phases were washed with saturated NaHCO$_3$ (10 mL), dried over Na$_2$SO$_4$, concentrated. The residue was purified with preparative TLC (dichloromethane/cyclohexane: 9/1) to yield the title compound as a yellow oil (48 mg; 0.21 mmol; 80%).

MS (ES) m/e 229 (M+H)$^+$ $^1$H NMR (CDCl$_3$) δ (ppm): 7.43 (m, 5H); 6.90 (d, 1H, J=8.0 Hz); 6.82 (s, 1H); 6.75 (d, 1H, J=8.0 Hz); 5.55 (s, 1H); 5.12 (s, 2H); 2.61 (q, 2H, J=7.6 Hz); 1.25 (t, 3H, J=7.6 Hz).

f) 2-[2-(benzyloxy)-4-ethylphenoxy]-6-fluoropyridine

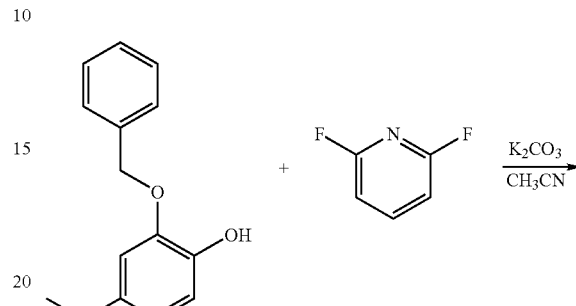

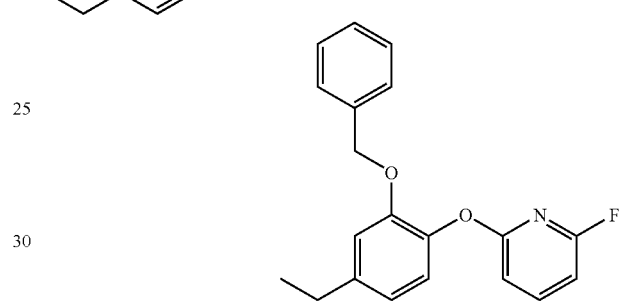

To a suspension of K$_2$CO$_3$ (0.25 mmol; 35 mg) in anhydrous acetonitrile (2 mL) under argon, was added 2-Benzyloxy-4-ethyl-phenol (48 mg; 0.21 mmol) followed by 2,6-difluoropyridine (100 μL; 1.10 mmol). The reaction mixture was stirred at 80° C. overnight.

Concentrated under argon, washed with NH$_4$Cl (0.1N; 3 mL), the mixture was extracted with ethyl acetate (3*3 mL). Combined organic phases were washed with NaHCO$_3$ dried over MgSO$_4$, concentrated in vacuo, to give the title product as a light oil (28.5 mg; 42%), after purification by preparative TLC (cyclohexane/ethyl acetate: 9/1).

$^1$H NMR (CDCl$_3$) δ (ppm): 7.70 (q, 1H, J=8.0 Hz); 7.27 (m, 3H); 7.17 (d, 2H, J=5.8 Hz); 7.11 (d, 1H, J=8.0 Hz); 6.90 (s, 1H); 6.86 (d, 1H, J=8.1 Hz); 6.73 (d, 1H, J=7.5 Hz); 6.56 (dd, 1H, J$_1$=7.8 Hz, J$_2$=2.4 Hz); 5.06 (s, 2H); 2.66 (q, 2H, J=7.6 Hz); 1.27 (t, 3H, J=7.6 Hz).

g) 5-ethyl-2-[(6-fluoropyridin-2-yl)oxy]phenol

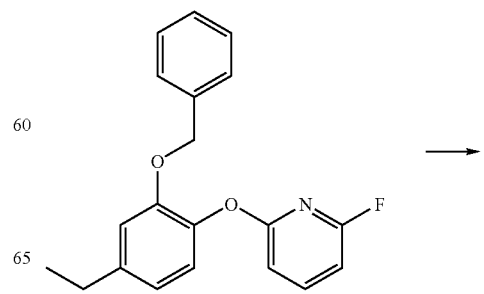

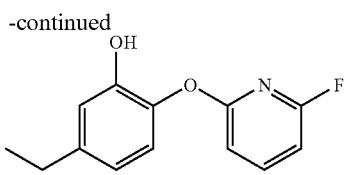

2-[2-(benzyloxy)-4-ethylphenoxy]-6-fluoropyridine (28 mg; 0.09 mmol) was dissolved in ethanol (4 mL), under argon. Palladium on charcoal (4 mg; 0.02 mmol) was added and the reaction was flushed twice with hydrogen, then left to stir overnight at room temperature. The reaction mixture was filtered on celite, then rinsed with methanol (3*3 mL). Concentration yielded a white solid (25 mg; 98%) of title compound.

MS (ES) m/e 234 (M+H)$^+$.

EXAMPLE 4

2-[(6-fluoropyridin-2-yl)oxy]-5-{2-[(6-fluoropyridin-2-yl)oxy]ethyl}phenol a) 2-fluoro-6-(4-{2-[(6-fluoropyridin-2-yl)oxy]ethyl}-2-methoxyphenoxy)pyridine

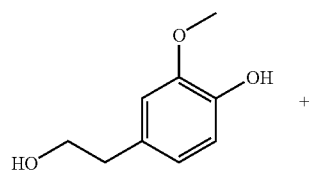

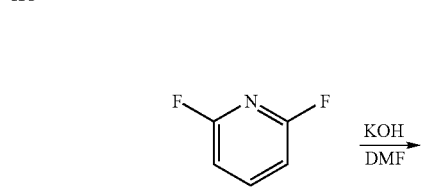

To a suspension of KOH (2 mmol; 112 mg) in anhydrous DMF (1 mL) under argon, was added 4-(2-hydroxyethyl)-2-methoxyphenol (1 mmol; 168 mg) followed by 2,6-Difluoropyridine (1 mmol; 0.1 ml). The reaction mixture was stirred at 110° C. for 20 h.

After quenching with NaOH (0.1N; 3 mL), the mixture was extracted with ethyl acetate (3*5 mL). Combined organic phases were dried over Na$_2$SO$_4$, concentrated in vacuo, to give a clear oil (50 mg; 0.14 mmol; 28%), after purification by flash chromatography on silica gel (gradient cylohexane/dichloromethane).

MS(ES): m/e 359 (M+H)$^+$ b) 2-[(6-fluoropyridin-2-yl)oxy]-5-{2-[(6-fluoropyridin-2-yl)oxy]ethyl}phenol

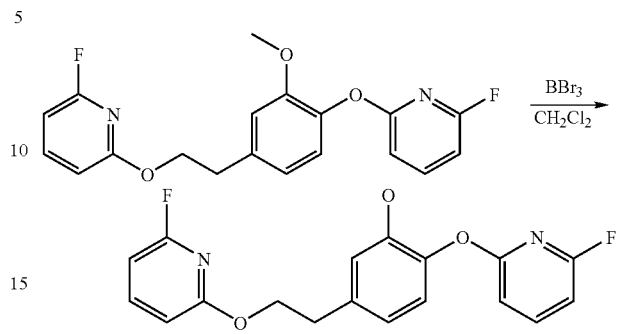

According to the procedure of example 1(b) except substituting 6-chloro-2-(2-methoxy-4-propylphenoxy)pyridin-3-amine for 2-fluoro-6-(4-{2-[(6-fluoropyridin-2-yl)oxy]ethyl}-2-methoxyphenoxy)pyridine (50 mg, 0.14 mmol) the title compound (20 mg, 30%) was prepared as a white solid after purification by preparative TLC (dichloromethane/methanol—9/1).

MS(ES): m/e 234 (M+H)$^+$.

$^1$H NMR (CDCl$_3$) δ (ppm): 7.76 (q, 1H, J1=7.9 Hz, J2=8.0 Hz); 7.62 (q, 1H, J1=8.3 Hz, J2=7.99); 7.02 (m, 2H); 6.83 (dd, 1H, J1=8.2 Hz, J2=2.0 Hz); 6.76 (d, 1H, J1=7.8 Hz,); 6.65 (dd, 1H, J1=7.7 Hz, J2=1.8 Hz); 6.59 (dd, 1H, J1=8.0 Hz, J2=1.1 Hz); 6.45 (dd, 1H, J1=7.7 Hz, J2=2.1 Hz); 6.09 (s, 1H); 4.47 (t, 2H, J=6.9 Hz); 3.03 (t, 2H, J=6.9 Hz).

EXAMPLE 5

2-[(6-fluoropyridin-2-yl)oxy]-5-propylphenol a) 2-fluoro-6-(2-methoxy-4-propylphenoxy)pyridine

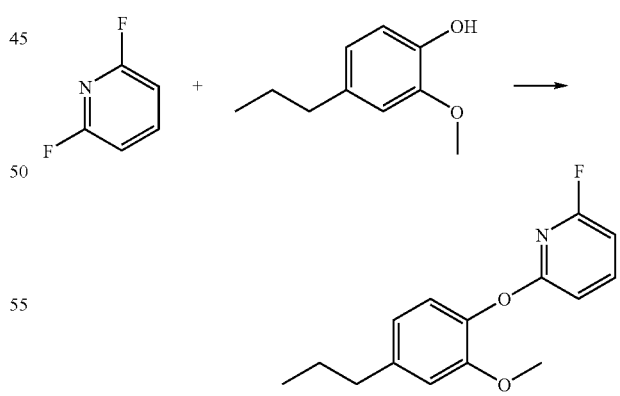

According to the procedure of example 4(a) except substituting 4-(2-hydroxyethyl)-2-methoxyphenol for 2-methoxy-4-propylphenol (2.1 mmol; 0.34 mL) the title compound (449 mg; 86%) was prepared as a white solid, after purification by silica gel chromatography (gradient cyclohexane/dichloromethane).

MS (ES) m/e 262 (M+H)$^+$ b) 2-[(6-fluoropyridin-2-yl)oxy]-5-propylphenol

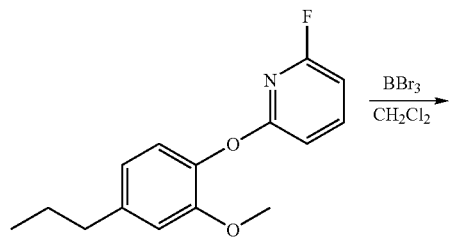

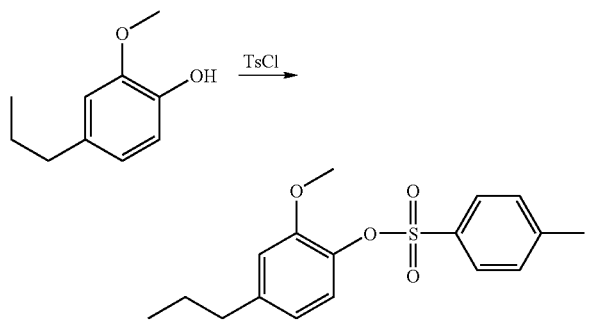

To a solution of 2-fluoro-6-(2-methoxy-4-propylphenoxy)pyridine (1.7 mmol; 449 mg) under argon, in dichloromethane (1.5 mL), cooled to −78° C., was added BBr₃ (17 mmol; 1M in CH₂Cl₂; 17 mL). The reaction mixture was allowed to stir overnight, with gradual heating to room temperature. At −20° C., the reaction was hydrolysed with saturated NH₄Cl (3 mL), extracted with ethyl acetate (3*10 mL). Combined organic phases were dried over MgSO₄, concentrated in vacuo. The residue was chromatographed on silica gel (gradient cyclohexane/dichloromethane) to give the desired product as a white solid (160 mg; 0.65 mmol; 38%).

MS (ES) m/e 248 (M+H)⁺

NMR¹H (CDCl₃) δ (ppm): 7.78 (q, 1H, J=8 Hz); 7.02 (d, 1H, J=8.4 Hz); 6.92 (d, 1H, J=2 Hz); 6.76 (ta, 2H, J=9.2 Hz); 6.65 (dd, 1H, J₁=8 Hz, J₂=2.4 Hz); 2.58 (t, 2H, J=7.6 Hz); 1.67 (s, 2H, J=7.6 Hz); 0.98 (t, 3H, J=7.2 Hz).

Aletrnatively compound of example 5 can be synthesized starting from the 2-(benzyloxy)-4-propylphenol instead of -methoxy-4-propylphenol using the same protocol as example 3 step f) and g).

Synthesis of 2-(benzyloxy)-4-propylphenol a) 2-methoxy-4-propylphenyl 4-methylbenzenesulfonate To a solution of 2-methoxy-4-propylphenol (10.0 mmol; 1.6 mL), NaI (1.0 mmol; 150 mg), and K₂CO₃ (11.0 mmol; 1.52 g), under argon, in acetonitrile (20 mL) was added tosyl chloride (10.5 mmol; 2.0 g). The reaction mixture was stirred at 70° C. for 36 hr, then quenched with NaOH (0.1N; 3 mL), and extracted with ethyl acetate (2*10 mL). Combined organic phases were washed with saturated NaHCO₃ sat. (5 mL), dried over MgSO₄, concentrated in vacuo. The crude was chromatographed on silica gel (gradient cyclohexane/dichloromethane) to yield the desired compound as a clear oil (2.13 g; 6.6 mmol; 66%).

MS (ES) m/e 321 (M+H)⁺

NMR¹H (CDCl₃) δ (ppm): 7.77 (d, 2H, J=8.2 Hz); 7.31 (d, 2H, J=8.0 Hz); 7.03 (d, 1H, J=8.2 Hz); 6.70 (m, 2H); 3.57 (s, 3H); 2.54 (t, 2H, J=7.7 Hz); 2.46 (s, 3H); 1.63 (se, 2H, J=7.6 Hz); 0.95 (t, 3H, J=7.3 Hz).

b) 2-hydroxy-4-propylphenyl 4-methylbenzenesulfonate

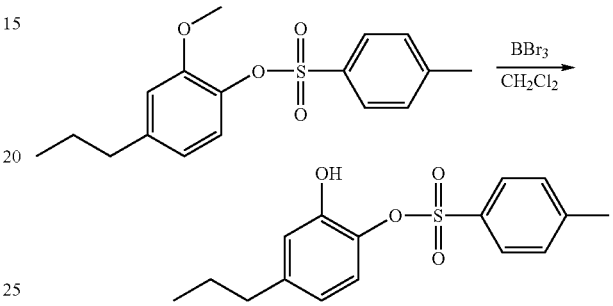

According to the procedure of example 1(b) except substituting 6-chloro-2-(2-methoxy-4-propylphenoxy)pyridin-3-amine for 2-methoxy-4-propylphenyl 4-methylbenzenesulfonate (64 mg, 0.2 mmol), the title compound (40 mg; 65%) was prepared as a clear oil, after purification by silica gel chromatography (gradient cyclohexane/dichloromethane).

MS (ES) m/e 305 (M−H)⁻

NMR¹H (CDCl₃) δ (ppm): 7.80 (d, 2H, J=8.3 Hz); 7.37 (d, 2H, J=8.1 Hz); 6.85 (s, 1H); 6.71 (d, 1H, J=8.3 Hz); 6.60 (d, 1H, J=8.3 Hz); 6.11 (s, 1H); 2.53 (t, 2H, J=7.6 Hz); 2.50 (s, 3H); 1.63 (se, 2H, J=7.5 Hz); 0.95 (t, 3H, J=7.3 Hz).

c) 2-(benzyloxy)-4-propylphenyl 4-methylbenzenesulfonate

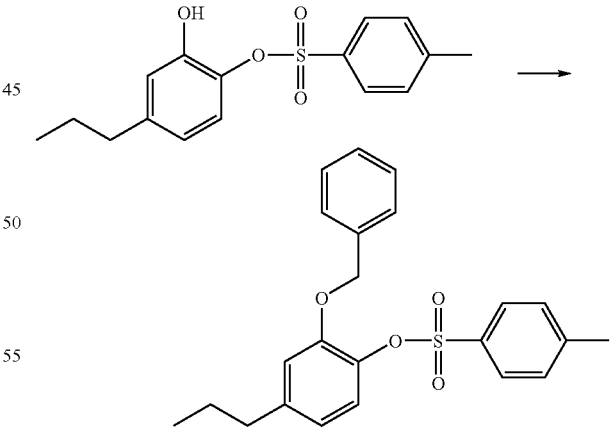

To a solution of 2-hydroxy-4-propylphenyl 4-methylbenzenesulfonate (0.11 mmol; 33 mg) under argon, in acetone (0.2 mL), were added K₂CO₃ (0.13 mmol; 18 mg), NaI (0.02 mmol; 3 mg), and benzylbromide (0.12 mmol; 0.015 mL). The reaction was stirred at 40° C. for 5 hr. The reaction mixture was then hydrolysed with NH₄Cl sat. (3 mL) and extracted with ethyl acetate (3*5 mL). Combined organic phases were washed with saturated NaHCO₃ (3 mL), dried over MgSO₄, concentrated. The residue was purified by preparative TLC (dichlorométhane) to yield the title compound as a clear oil (28 mg; 0.07 mmol; 64%).

MS (ES) m/e 397 (M+H)+

NMR¹H (CDCl₃) δ (ppm): 7.71 (d, 2H, J=8.1 Hz); 7.34 (m, 5H); 7.12 (d, 3H, J=8.3 Hz); 6.74 (s, 2H); 4.88 (s, 2H); 2.54 (t, 2H, J=7.6 Hz); 2.39 (s, 3H); 1.61 (se, 2H, J=7.4 Hz); 0.92 (t, 3H, J=7.3 Hz).

d) 2-(benzyloxy)-4-propylphenol

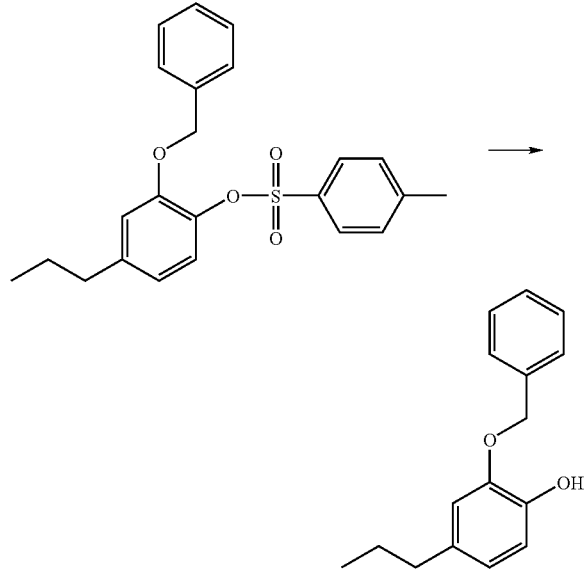

To a solution of 2-(benzyloxy)-4-propylphenyl 4-methylbenzenesulfonate (0.07 mmol; 28 mg) under argon, in a mixture of ethanol (0.2 mL) and water (0.1 mL), was added KOH (0.09 mmol; 5 mg). The reaction was refluxed for 1 hr, then hydrolysed with NH₄Cl sat. (3 mL), and extracted with ethyl acetate (3*5 mL). Combined organic phases were washed with saturated NaHCO₃ (3 mL), dried over MgSO₄, concentrated. The residue was purified by preparative TLC (cyclohexane/dichlorométhane) to yield the title compound as a clear oil (16 mg; 0.06 mmol; 86%).

MS (ES) m/e 243 (M+H)+

NMR¹H (CDCl₃) δ (ppm): 7.41 (m, 5H); 6.87 (d, 1H, J=8.0 Hz); 6.79 (s, 1H); 6.71 (d, 1H, J=8.0 Hz); 5.51 (s, 1H); 5.11 (s, 2H); 2.53 (t, 2H, J=7.6 Hz); 1.61 (se, 2H, J=7.5 Hz); 0.94 (t, 3H, J=7.3 Hz).

EXAMPLE 6

2-[(6-chloropyridin-2-yl)oxy]-5-propylphenol a) 2-chloro-6-(2-methoxy-4-propylphenoxy)pyridine

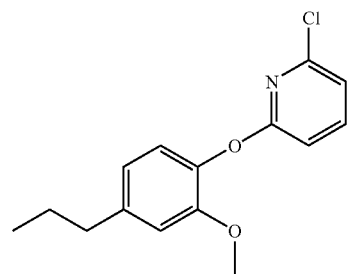 [SMILES: CCCc1ccc(Oc2cccc(Cl)n2)c(OC)c1]

According to the procedure of example 5(a) except substituting 2,6-difluoropyridine for 2,6-dichlororopyridine (296 mg, 2 mmol), the title compound (450 mg; 81%) was prepared as a clear oil, after purification by silica gel chromatography (gradient cyclohexane/ethyl acetate).

MS (ES) m/e 278 (M+H)+ b) 2-[(6-chloropyridin-2-yl)oxy]-5-propylphenol

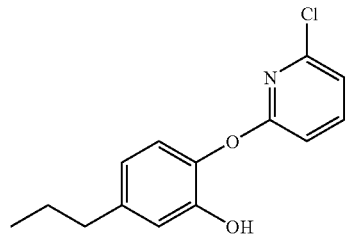 [SMILES: CCCc1ccc(Oc2cccc(Cl)n2)c(O)c1]

According to the procedure of example 5(b), except substituting 2-fluoro-6-(2-methoxy-4-propylphenoxy)pyridine for 2-chloro-6-(2-methoxy-4-propylphenoxy)pyridine (450 mg, 1.62 mmol), the title compound (148 mg; 35%) was prepared as white solid after purification by silica gel chromatography (gradient cyclohexane/ethyl acetate).

MS (ES) m/e 264 (M+H)+

NMR¹H (CD₃OD) δ (ppm): 7.70 (t, 1H, J=8.0 Hz); 7.06 (d, 1H, J=7.7 Hz); 6.93 (d, 1H, J=8.1 Hz); 6.78 (s, 1H); 6.69 (m, 2H); 2.53 (t, 2H, J=7.8 Hz); 1.65 (se, 2H, J=7.6 Hz); 0.95 (t, 3H, J=7.4 Hz).

EXAMPLE 7

2-[(6-aminopyridin-2-yl)oxy]-5-propylphenol a) 6-(2-methoxy-4-propylphenoxy)pyridin-2-amine

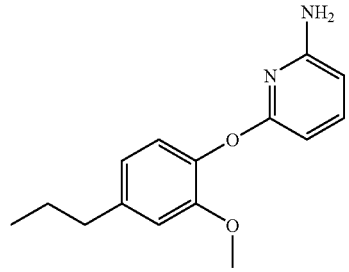

According to the procedure of example 5(a) except substituting 2,6-difluoropyridine for 2-amino-6-bromopyridine (173 mg, 1 mmol) the title compound (125 mg; 48%) was prepared as a clear oil, after purification by silica gel chromatography (gradient cyclohexane/dichloromethane).

MS (ES) m/e 259 (M+H)+ b) 2-[(6-aminopyridin-2-yl)oxy]-5-propylphenol

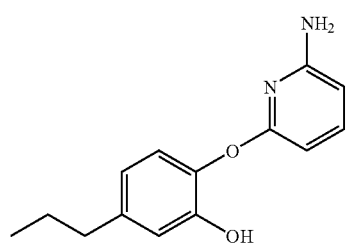 [SMILES: CCCc1ccc(Oc2cccc(N)n2)c(O)c1]

According to the procedure of example 5(b) except substituting 2-fluoro-6-(2-methoxy-4-propylphenoxy)pyridine for 6-(2-methoxy-4-propylphenoxy)pyridin-2-amine (125 mg, 0.48 mmol), the title compound (5 mg; 4%) was prepared as a clear oil, after preparative TLC (cyclohexane/dichloromethane).

MS (ES) m/e 245 (M+H)$^+$

NMR$^1$H (CDCl$_3$) δ (ppm): 7.45 (t, 1H, J=7.9 Hz); 7.02 (d, 1H, J=8.1 Hz); 6.90 (s, 1H); 6.70 (d, 1H, J=8.0 Hz); 6.27 (d, 1H, J=7.8 Hz); 6.22 (d, 1H, J=7.9 Hz); 4.45 (br, 2H); 2.55 (t, 2H, J=7.6 Hz); 1.66 (se, 2H, J=7.6 Hz); 0.97 (t, 3H, J=7.3 Hz).

EXAMPLE 8

4-[(6-fluoropyridin-2-yl)oxy]-3-hydroxy benzaldehyde a) 4-[(6-fluoropyridin-2-yl)oxy]-3-methoxybenzaldehyde

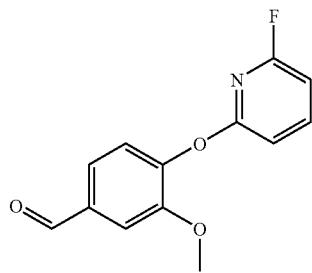 [SMILES: COc1cc(C=O)ccc1Oc1cccc(F)n1]

According to the procedure of example 4(a), except substituting 4-(2-hydroxyethyl)-2-methoxyphenol for 4-hydroxy-3-methoxybenzaldehyde (304 mg, 2 mmol) the title compound (220 mg; 44%) was prepared as a white solid, after purification by silica gel chromatography (gradient cyclohexane/ethyl acetate).

MS (ES) m/e 248 (M+H)$^+$ b) 4-[(6-fluoropyridin-2-yl)oxy]-3-hydroxybenzaldehyde

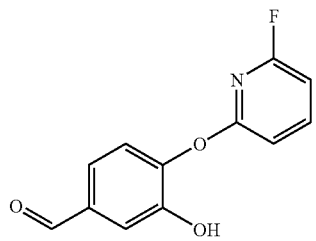 [SMILES: O=Cc1ccc(Oc2cccc(F)n2)c(O)c1]

According to the procedure of example 5(b) except substituting 2-fluoro-6-(2-methoxy-4-propylphenoxy)pyridine for 4-[(6-fluoropyridin-2-yl)oxy]-3-methoxybenzaldehyde (220 mg, 0.89 mmol), the title compound (10 mg; 7%) was prepared as a white solid, after purification by preparative TLC (cyclohexane/ethyl acetate).

MS (ES) m/e 234 (M+H)$^+$

NMR$^1$H (CD$_3$OD) δ (ppm): 9.95 (s, 1H); 7.88 (q, 1H, J$_1$=8.0 Hz); 7.59 (d, 1H, J=2.0 Hz); 7.49 (dd, 1H, J$_1$=8.4 Hz, J$_2$=2.0 Hz); 7.29 (da, 2H, J=8.0 Hz); 6.93 (d, 1H, J=7.6 Hz); 6.75 (dd, 1H, J$_1$=8.0 Hz, J$_2$=2.0 Hz).

EXAMPLE 9

2-[(6-fluoropyridin-2-yl)oxy]-5-methylphenol a) 2-fluoro-6-(2-methoxy-4-methylphenoxy)pyridine

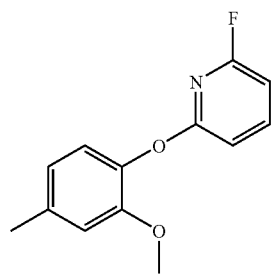 [SMILES: COc1cc(C)ccc1Oc1cccc(F)n1]

According to the procedure of example 4(a), except substituting 4-(2-hydroxyethyl)-2-methoxyphenol for 2-methoxy-4-methylphenol (0.25 mL, 2 mmol) the title compound (457 mg; 97%) was prepared as a white solid, after purification by silica gel chromatography (gradient cyclohexane/dichloromethane).

MS (ES) m/e 234 (M+H)$^+$ b) 2-[(6-fluoropyridin-2-yl)oxy]-5-methylphenol

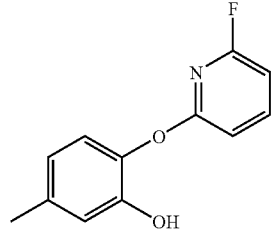 [SMILES: Cc1ccc(Oc2cccc(F)n2)c(O)c1]

According to the procedure of example 5(b) except substituting 2-fluoro-6-(2-methoxy-4-propylphenoxy)pyridine for 2-fluoro-6-(2-methoxy-4-methylphenoxy)pyridine (457 mg, 1.93 mmol), the title compound (71 mg; 16%) was prepared as a white solid, after washing with diethyl ether.

MS (ES) m/e 220 (M+H)$^+$

NMR$^1$H (CD$_3$OD) δ (ppm): 7.81 (q, 1H, J$_1$=8.0 Hz); 6.79 (m, 2H); 6.63 (m, 3H); 2.28 (s, 3H).

EXAMPLE 10

4-[(6-fluoropyridin-2-yl)oxy]-4'-methylbiphenyl-3-ol a) 2-(4-chloro-2-methoxyphenoxy)-6-fluoropyridine

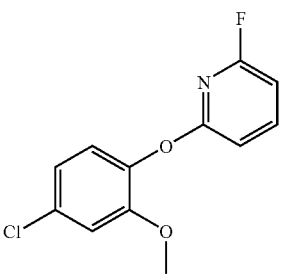

According to the procedure of example 4(a) except substituting 4-(2-hydroxyethyl)-2-methoxyphenol for 2-methoxy-4-chlorophenol (0.24 mL, 2 mmol) the title compound (423 mg; 84%) was prepared as a white solid, after purification by silica gel chromatography (gradient cyclohexane/dichloromethane).

MS (ES) m/e 254 (M+H)+ b) 2-fluoro-6-[(3-methoxy-4'-methylbiphenyl-4-yl)oxy]pyridine

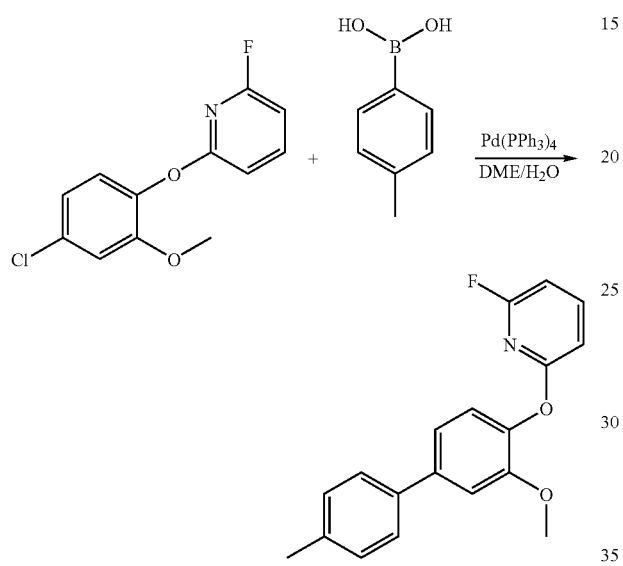

To a solution of 2-(4-chloro-2-methoxyphenoxy)-6-fluoropyridine (0.53 mmol; 135 mg) and 4-methylphenylboronic acid (0.94 mmol; 127 mg) in a degased DME/water mixture (1.5/0.5 mL), under argon were added $K_2CO_3$ (2.0 mmol; 276 mg), then tetrakis(triphenylphosphine)palladium (0.07 mmol; 47 mg). The reaction was stirred at 105° C. for 48 hr. After concentration, the residue was purified by flash chromatography (gradient cyclohexane/dichloromethane) to yield the desired product along with remaining starting material (160 mg; 0.53 mmol; 100% max).

MS (ES) m/e 310 (M+H)+ c) 4-[(6-fluoropyridin-2-yl)oxy]-4'-methylbiphenyl-3-ol

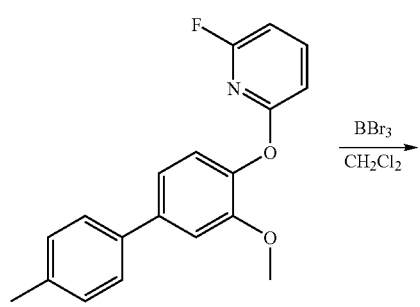

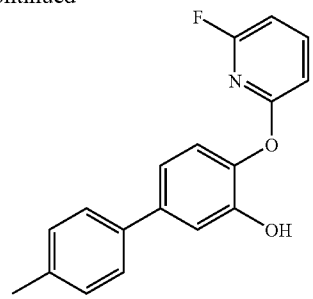

According to the procedure of example 5(b) except substituting 2-fluoro-6-(2-methoxy-4-propylphenoxy)pyridine for 2-fluoro-6-[(3-methoxy-4'-methyl-1,1'-biphenyl-4-yl)oxy]pyridine (160 mg, 0.53 mmol), the title compound (37 mg; 24%) was prepared as a white solid, after purification by preparative TLC (dichloromethane).

MS (ES) m/e 296 (M+H)+

NMR[1]H (CDCl$_3$) δ (ppm): 7.81 (q, 1H, J=8.0 Hz); 7.50 (d, 2H, J=8.1 Hz); 7.32 (d, 1H, J=1.6 Hz); 7.27 (d, 2H, J=8.0 Hz); 7.17 (m, 2H); 6.84 (d, 1H, J=8.0 Hz); 6.68 (dd, 1H, $J_1$=7.9 Hz, $J_2$=2.2 Hz); 6.33 (sb, 1H); 2.42 (s, 3H).

EXAMPLE 11

2-{[5-(4-bromobut-1-yn-1-yl)pyridin-2-yl]oxy}-5-propylphenol a) 4-[6-(2-methoxy-4-propylphenoxy)pyridin-3-yl]but-3-yn-1-ol

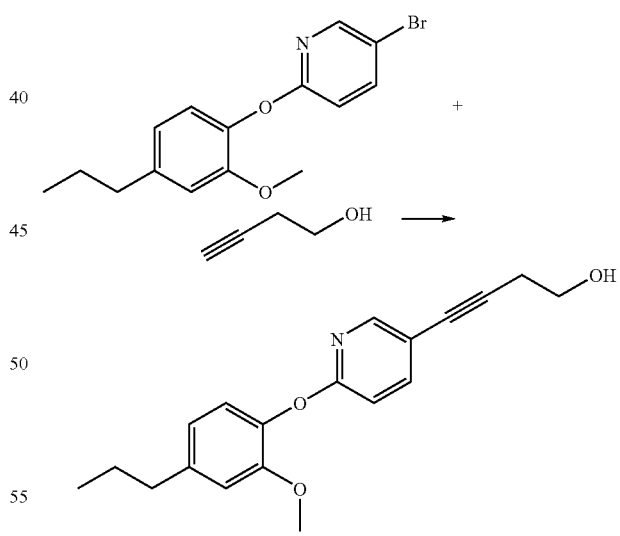

To a solution of 5-bromo-2-(2-methoxy-4-propylphenoxy)pyridine (0.19 mmol; 60 mg) under argon, in degased DME (1 mL) were added 3-butyn-1-ol (0.47 mmol; 33 mg), Pd/C (0.02 mmol; 42 mg), CuI (0.04 mmol; 7.6 mg), $K_2CO_3$ (0.47 mmol; 64 mg), and triphenylphosphine (0.08 mmol; 21 mg). The reaction mixture was stirred at 80° C. overnight, then filtered on celite, washed with ether (3 mL) then ethyl acetate (3 mL). Combined organic phases were washed with saturated NH$_4$Cl (3 mL), dried over MgSO$_4$, concentrated. The residue was purified by preparative TLC (dichloromethane/ethyl acetate) to yield the desired compound as a clear oil (25 mg; 0.08 mmol; 42%).

MS (ES) m/e 312 (M+H)+

NMR$^1$H (CDCl$_3$) δ (ppm): 8.21 (d, 1H, J=1.8 Hz); 7.67 (dd, 1H, J$_1$=8.6 Hz, J$_2$=2.3 Hz); 7.04 (d, 1H, J=7.9 Hz); 6.82 (m, 3H); 3.81 (t, 2H, J=6.3 Hz); 3.75 (s, 3H); 2.68 (t, 2H, J=6.3 Hz); 2.60 (t, 2H, J=7.8 Hz); 2.07 (sb, 1H); 1.69 (se, 2H, J=7.6 Hz); 0.98 (t, 3H, J=7.4 Hz).

b) 2-{[5-(4-bromobut-1-yn-1-yl)pyridin-2-yl]oxy}-5-propylphenol

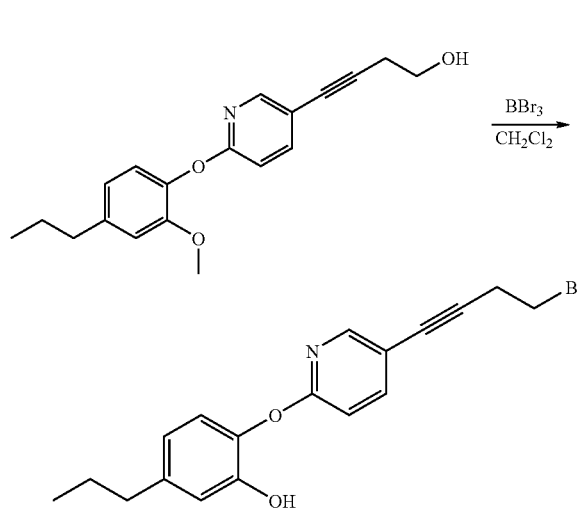

According to the procedure of example 5(b) except substituting 2-fluoro-6-(2-methoxy-4-propylphenoxy)pyridine for 4-[6-(2-methoxy-4-propylphenoxy)pyridin-3-yl]but-3-yn-1-ol (25 mg, 0.08 mmol), the title compound (6 mg; 21%) was prepared as a clear oil, after purification by preparative TLC (dichloromethane).

MS (ES) m/e 361 (M+H)+

NMR$^1$H (CDCl$_3$) δ (ppm): 8.24 (s, 1H); 7.75 (d, 1H, J=8.5 Hz); 7.01 (d, 1H, J=8.2 Hz); 6.93 (m, 2H); 6.74 (d, 1H, J=8.1 Hz); 3.54 (t, 2H, J=7.2 Hz); 2.99 (t, 2H, J=7.2 Hz); 2.56 (t, 2H, J=7.8 Hz); 1.66 (se, 2H, J=7.6 Hz); 0.96 (t, 3H, J=7.4 Hz)

EXAMPLE 12

2-{[5-(4-hydroxybut-1-yn-1-yl)pyridin-2-yl]oxy}-5-propylphenol

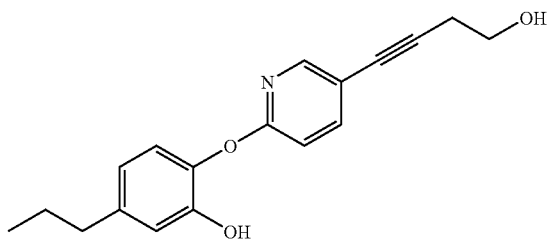 [SMILES: CCCc1ccc(Oc2ccc(C#CCCO)cn2)c(O)c1]

The title compound (1 mg; 4%) was isolated from the example 11 (b) as a white solid, after purification by preparative TLC (dichloromethane).

MS (ES) m/e 298 (M+H)+

NMR$^1$H (CDCl$_3$) δ (ppm): 8.25 (s, 1H); 7.75 (d, 1H, J=8.4 Hz); 7.02 (d, 1H, J=8.5 Hz); 6.93 (m, 2H); 6.74 (d, 1H, J=8.0 Hz); 3.84 (t, 2H, J=6.2 Hz); 2.71 (t, 2H, J=6.2 Hz); 2.56 (t, 2H, J=7.9 Hz); 1.66 (se, 2H, J=7.6 Hz); 0.96 (t, 3H, J=7.4 Hz).

EXAMPLE 13

2-[(6-fluoropyridin-2-yl)oxy]-5-isobutylphenol a) 2-(4-bromo-2-methoxyphenoxy)-6-fluoropyridine

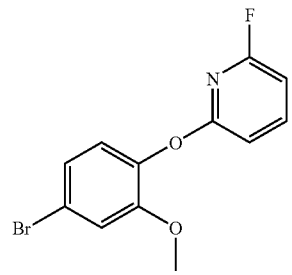 [SMILES: COc1cc(Br)ccc1Oc1cccc(F)n1]

According to the procedure of example 4(a) except substituting 4-(2-hydroxyethyl)-2-methoxyphenol for 2-methoxy-4-bromophenol (406 mg, 2 mmol) the title compound compound (540 mg; 90%) was prepared as a clear oil, after purification by silica gel chromatography (gradient cyclohexane/dichloromethane).

MS (ES) m/e 299 (M+H)+

NMR$^1$H (CDCl$_3$) δ (ppm): 7.79 (q, 1H, J=8.0 Hz); 7.16 (m, 2H); 7.06 (d, 1H, J=9.0 Hz); 6.80 (d, 1H, J=8.0 Hz); 6.62 (d, 1H, J=7.8 Hz); 3.81 (s, 3H).

b) 2-fluoro-6-(4-isobutyl-2-methoxyphenoxy)pyridine

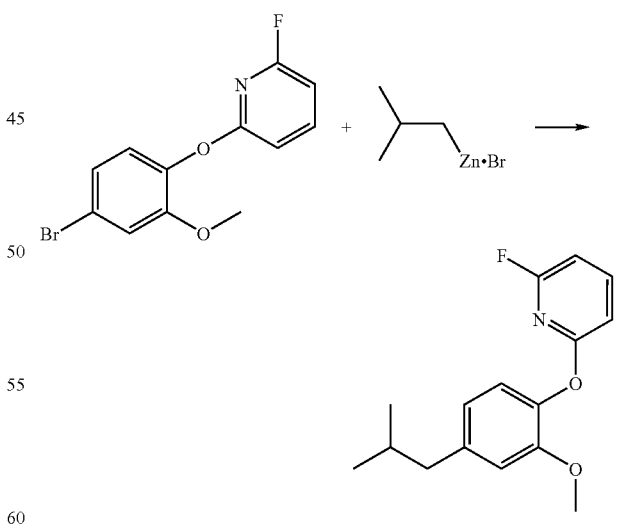

To a suspension of Pd(PPh$_3$)$_4$ (0.025 mmol; 17 mg) under argon, in anhydrous, degased dioxane (2 mL), sheltered from light, were added 2-(4-bromo-2-methoxyphenoxy)-6-fluoropyridine (0.51 mmol; 151 mg), then isobutyl zinc bromide (1.0 mmol; 2.0 mL). The reaction was heated to 105° C. for 24 hr. The mixture was then hydrolysed with water (3 mL), extracted with ethyl acetate (3*3 mL). Combined organic phases were dried over MgSO$_4$, concentrated under reduced pressure. The crude was then purified by preparative chromatography (cyclohexane/dichloromethane) to yield the desired product as a clear oil (28 mg; 0.10 mmol; 20%).

MS (ES) m/e 276 (M+H)$^+$

NMR$^1$H (CDCl$_3$) δ (ppm): 7.71 (q, 1H, J=8.0 Hz); 7.04 (d, 1H, J=7.9 Hz); 6.78 (m, 2H); 6.68 (d, 1H, J=7.3 Hz); 6.56 (d, 1H, J=7.8 Hz); 3.77 (s, 3H); 2.50 (d, 2H, J=7.2 Hz); 1.90 (se, 1H, J=6.7 Hz); 0.96 (d, 6H, J=6.6 Hz).

c) 2-[(6-fluoropyridin-2-yl)oxy]-5-isobutylphenol

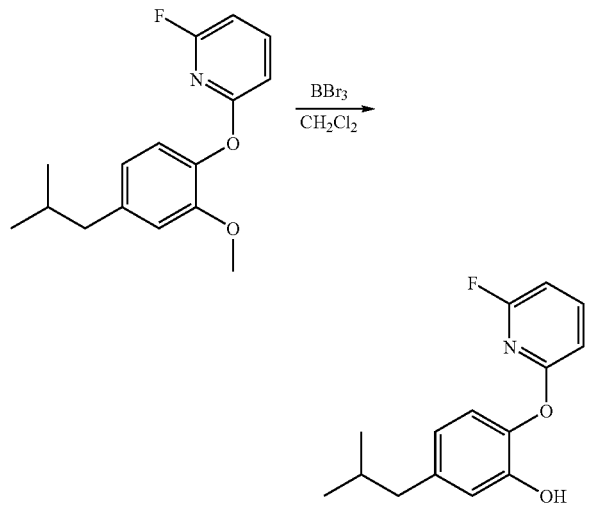

According to the procedure of example 5(b) except substituting 2-fluoro-6-(2-methoxy-4-propylphenoxy)pyridine for 2-fluoro-6-(4-isobutyl-2-methoxyphenoxy)pyridine (25 mg, 0.1 mmol), the title compound (18 mg; 69%) was prepared as a clear oil, without purification.

MS (ES) m/e 262 (M+H)$^+$

NMR$^1$H (CDCl$_3$) δ (ppm): 7.78 (q, 1H, J=8.0 Hz); 7.02 (d, 1H, J=8.2 Hz); 6.89 (s, 1H); 6.77 (d, 1H, J=8.0 Hz); 6.72 (d, 1H, J=8.2 Hz); 6.66 (d, 1H, J=7.9 Hz); 2.46 (d, 2H, J=7.2 Hz); 1.88 (se, 1H, J=6.7 Hz); 0.94 (d, 6H, J=6.6 Hz).

EXAMPLE 14

2-[(6-fluoropyridin-2-yl)oxy]-5-(hydroxymethyl) phenol a) {4-[(6-fluoropyridin-2-yl)oxy]-3-methoxyphenyl}methanol

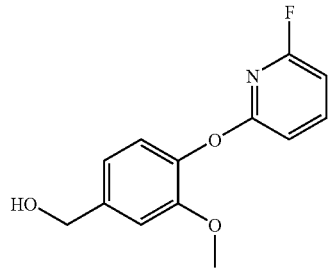 [SMILES: COc1cc(CO)ccc1Oc1cccc(F)n1]

According to the procedure of example 4(a) except substituting 4-(2-hydroxyethyl)-2-methoxyphenol for 4-(hydroxymethyl)-2-methoxyphenol (308 mg; 2 mmol) the title compound (200 mg; 40%) was prepared as a clear oil, after purification by silica gel chromatography (gradient cyclohexane/ethyl acetate).

MS (ES) m/e 250 (M+H)$^+$ b) 2-[(6-fluoropyridin-2-yl)oxy]-5-(hydroxymethyl) phenol

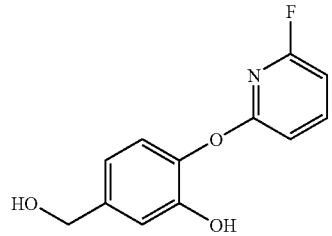 [SMILES: OCc1ccc(Oc2cccc(F)n2)c(O)c1]

According to the procedure of example 5(b) except substituting 2-fluoro-6-(2-methoxy-4-propylphenoxy)pyridine for {4-[(6-fluoropyridin-2-yl)oxy]-3-methoxyphenyl}methanol (104 mg, 0.42 mmol), the title compound (98 mg; 98%) was prepared as a white solid, after washing with diethyl ether.

MS (ES) m/e 236 (M+H)$^+$

NMR$^1$H (CDCl$_3$) δ (ppm): 7.81 (q, 1H, J=8.0 Hz); 7.11 (s, 1H); 7.08 (d, 1H, J=8.3 Hz); 6.95 (d, 1H, J=8.3 Hz); 6.83 (d, 1H, J=7.9 Hz); 6.68 (d, 1H, J=7.9 Hz); 4.46 (s, 2H).

EXAMPLE 15

4-[(6-fluoropyridin-2-yl)oxy]-3-hydroxybenzyl acetate

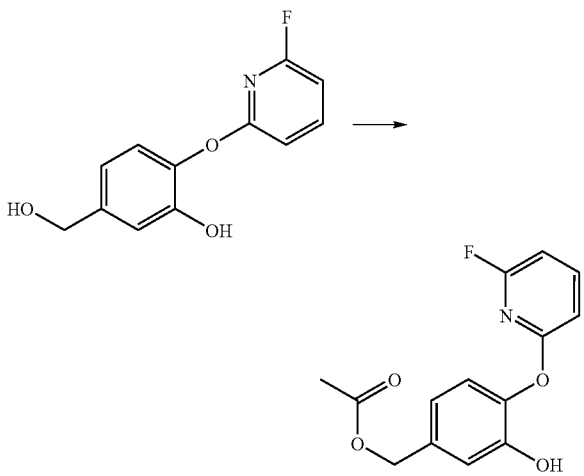

To a solution of 2-[(6-fluoropyridin-2-yl)oxy]-5-(hydroxymethyl)phenol (0.42 mmol; 104 mg) under argon, in anhydrous DMF (0.8 mL), were added K$_2$CO$_3$ (0.5 mmol; 68 mg), DMAP (0.08 mmol; 12 mg), and acetic anhydride (0.41 mmol; 0.04 mL). The reaction was stirred at room temperature overnight. After dilution with ethyl acetate (4 mL), the organic phase was washed with saturated NaHCO$_3$ (3*3 mL), dried (MgSO$_4$), concentrated in vacuo, purified by preparative TLC (dichlorométhane) to yield the title compound as a clear oil (3 mg; 0.01 mmol; 3%).

MS (ES) m/e 278 (M+H)$^+$

NMR$^1$H (CDCl$_3$) δ (ppm): 7.82 (q, 1H, J=8.0 Hz); 7.56 (m, 3H); 6.82 (d, 1H, J=6.9 Hz); 6.68 (dd, 1H, J$_1$=7.8 Hz, J$_2$=2.6 Hz); 5.16 (s, 2H); 2.17 (s, 3H).

EXAMPLE 16

2-(4-methoxyphenoxy)-5-propylphenol a)
2-methoxy-1-(4-methoxyphenoxy)-4-propylbenzene

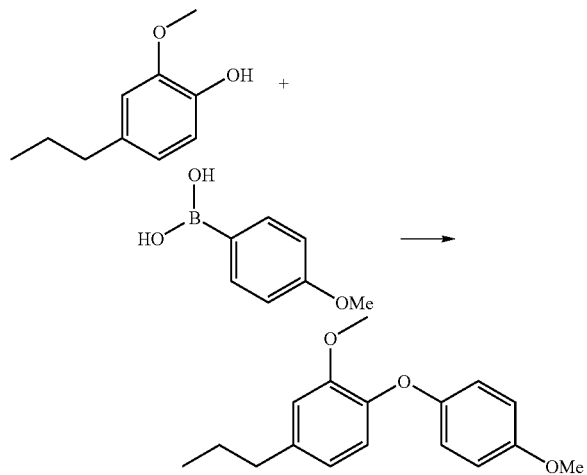

A mixture containing 2-methoxy-4-propylphenol (0.625 mmol; 100 µl), copper(II) acetate (0.625 mmol; 114 mg), 4-methoxyphenylboronic acid (1.25 mmol; 190 mg), triethylamine (3.12 mmol; 0.43 ml), some crushed molecular sieves 4 Å in dichloromethane (3 ml) was stirred at rt under air for 24 h. The residue is filtered with chloroform on Celite. The organic phase is washed with saturated NH$_4$Cl, saturated NaHCO$_3$ and brine. After drying (MgSO$_4$), concentration and purification by preparative TLC on silica gel (ethyl acetate/cyclohexane—20/80), the title compound is collected as a colorless oil (70 mg; 0.26 mmol; 41%).

MS (ES) 273 [M+1]$^+$ and 295 [M+Na]$^+$

NMR$^1$H (CDCl$_3$) δ (ppm): 6.94 (d, 2H, J=9.1 Hz); 6.85 (d, 2H, J=9.1 Hz); 6.82 (s, 1H); 6.80 (d, 1H, J=8.1 Hz); 6.70 (d, 1H, J=8.2 Hz); 3.87 (s, 3H); 3.80 (s, 3H); 2.58 (t, 2H, J=7.7 Hz); 1.67 (se, 2H, J=7.6 Hz); 0.98 (t, 3H, J=7.3 Hz).

b) 2-(4-methoxyphenoxy)-5-propylphenol

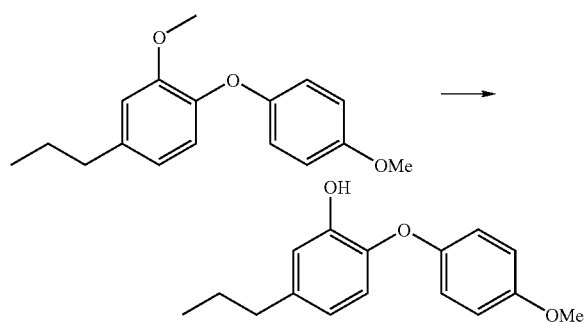

According to the procedure of example 5(b) except substituting 2-fluoro-6-(2-methoxy-4-propylphenoxy)pyridine for 2-methoxy-1-(4-methoxyphenoxy)-4-propylbenzene (0.18 mmol; 50 mg) and adding 4 equivalents (0.735 mmol; 735 µl) of boron tribromide, the title compound was prepared in 32% yield (0.06 mmol; 15 mg) after purification by preparative TLC on silica gel (ethyl acetate/cyclohexane—20/80).

MS (ES) 257 [M–1]$^-$

NMR$^1$H (CDCl$_3$) δ (ppm): 6.99 (d, 2H, J=9.0 Hz); 6.89 (d, 2H, J=9.0 Hz); 6.87 (s, 1H); 6.72 (d, 1H, J=8.2 Hz); 6.63 (d, 1H, J=8.1 Hz); 5.57 (s br, 1H); 3.82 (s, 3H); 2.54 (t, 2H, J=7.8 Hz); 1.64 (se, 2H, J=7.5 Hz); 0.96 (t, 3H, J=7.3 Hz). NOE observed between δ 3.82 and 6.89 ppm.

EXAMPLE 17

N-[3-(2-hydroxy-4-propylphenoxy)phenyl]acetamide a) N-[3-(2-methoxy-4-propylphenoxy)phenyl]acetamide

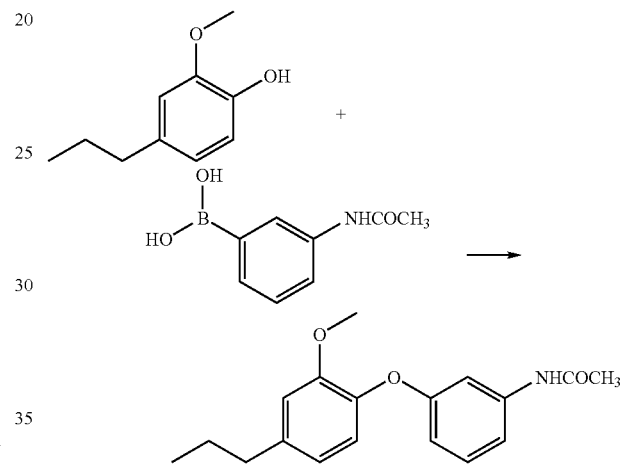

According to the procedure of example 16(a) except substituting 4-methoxyphenylboronic acid for 3-acetamidophenylboronic acid (1.25 mmol; 224 mg) the title compound was prepared in 10% yield (0.06 mmol; 18 mg) after purification by preparative TLC on silica gel (ethyl acetate/cyclohexane—70/30).

NMR$^1$H (CDCl$_3$) δ (ppm): 7.28-7.16 (m, 3H); 7.05 (s, 1H); 6.92 (d, 1H, J=8.0 Hz); 6.83 (s, 1H); 6.76 (d, 1H, J=7.9 Hz); 6.68 (d, 1H, J=7.4 Hz); 3.82 (s, 3H); 2.60 (t, 2H, J=7.4 Hz); 2.15 (s, 3H); 1.68 (t, 3H, J=7.4 Hz).

b)
N-[3-(2-hydroxy-4-propylphenoxy)phenyl]acetamide

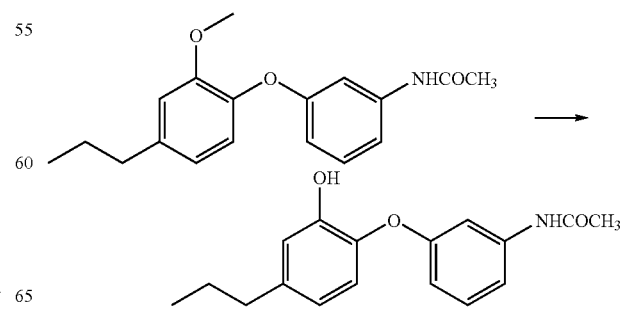

According to the procedure of example 5(b) except substituting 2-fluoro-6-(2-methoxy-4-propylphenoxy)pyridine for N-[3-(2-methoxy-4-propylphenoxy)phenyl]acetamide (0.06 mmol; 17 mg), the title compound was prepared in 56% yield (0.03 mmol; 9 mg) after purification by preparative TLC on silica gel (ethyl acetate/cyclohexane—70/30).

MS (ES) 286 [M+1]$^+$ and 308 [M+Na]$^+$

NMR$^1$H (DMSO) δ (ppm): 9.90 (s, 1H); 9.37 (s, 1H); 7.28-7.19 (m, 3H); 6.86 (d, 1H, J=8.1 Hz); 6.79 (s, 1H); 6.64 (d, 1H, J=8.1 Hz); 6.52 (d, 1H, J=7.9 Hz); 2.00 (s, 3H); 1.59 (se, 2H, J=7.5 Hz); 0.92 (t, 3H, J=7.3 Hz).

EXAMPLE 18

2-{[6-(butylamino)pyridin-2-yl]oxy}-5-ethylphenol a) N-butyl-6-(4-ethyl-2-methoxyphenoxy)pyridin-2-amine

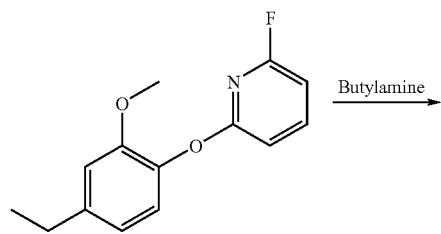

To 2-(4-ethyl-2-methoxyphenoxy)-6-fluoropyridine (94 mg; 0.32 mmol), under argon, was added butylamine (0.5 mL). The reaction was heated to 80° C. for 18 hours. The mixture was concentrated in vacuo. After quenching with saturated NaHCO$_3$ (10 mL), extractions with dichloromethane (3*5 mL), the organic phase was dried over NaSO$_4$, and concentrated in vacuo to give the title compound as a light brown oil used without further purification (87 mg; 0.29 mmol; 89%).

MS (ES) m/e 301 (M+H)$^+$ b) 2-{[6-(butylamino)pyridin-2-yl]oxy}-5-ethylphenol

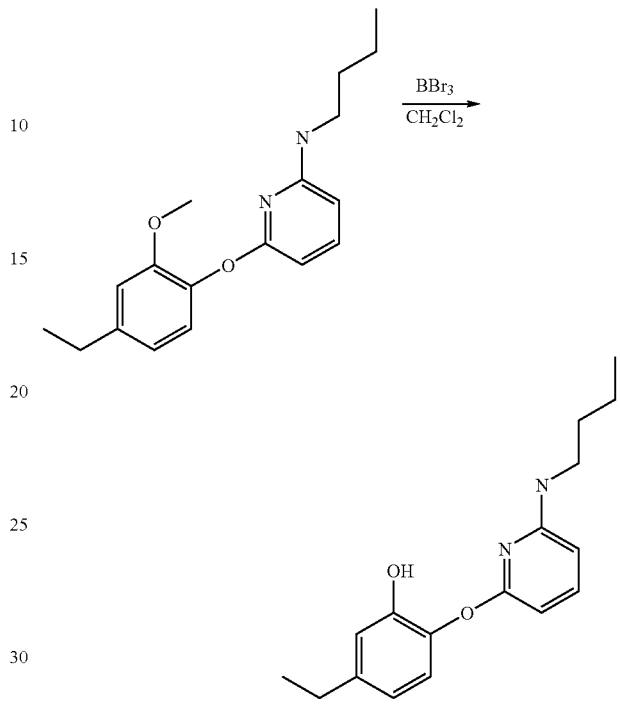

According to the procedure of example 1(b) except substituting 6-chloro-2-(2-methoxy-4-propylphenoxy)pyridin-3-amine for N-butyl-6-(4-ethyl-2-methoxyphenoxy)pyridin-2-amine (87 mg; 0.29 mmol), the title compound(36 mg; 43%) was obtained as a light brown oil, after purification by preparative TLC (cyclohexane/ethyl acetate: 8/2)

MS (ES) m/e 287 (M+H)$^+$ $^1$H NMR (CDCl$_3$) δ (ppm): 7.41 (t, 1H, J=7.9 Hz); 7.01 (d, 1H, J=8.1 Hz); 6.91 (s, 1H); 6.69 (d, 1H, J=8.0 Hz); 6.17 (d, 1H, J=7.8 Hz); 6.06 (d, 1H, J=8.1 Hz); 4.56 (sl, 1H); 3.18 (t, 2H, J=7.0 Hz); 2.61 (q, 2H, J=7.5 Hz); 1.55 (qt, 2H, J=7.5 Hz); 1.39 (se, 2H, J=7.4 Hz); 1.23 (t, 3H, J=7.6 Hz); 0.93 (t, 3H, J=7.3 Hz).

EXAMPLE 19

2-[(6-ethoxypyridin-2-yl)oxy]-5-ethylphenol a) 2-ethoxy-6-(4-ethyl-2-methoxyphenoxy)pyridine

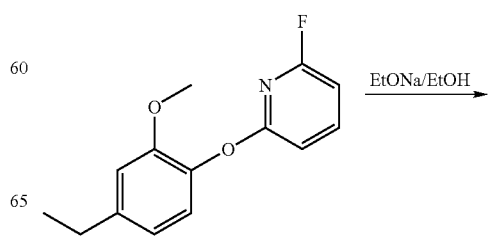

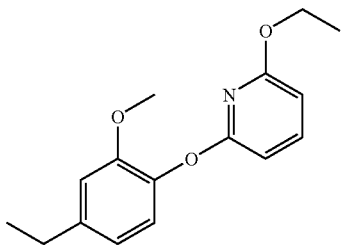

To a solution of sodium (55 mg; 2.39 mmol), under argon, in ethanol (2 mL), was added 2-(4-ethyl-2-methoxyphenoxy)-6-fluoropyridine (82 mg; 0.33 mmol). The reaction was heated to 80° C. for 16 hours then to 90° C. for 26 hours. The mixture was concentrated in vacuo. After quenching with saturated NaHCO$_3$ (10 mL), extractions with ethyl acetate (3*5 mL), the organic phase was dried over NaSO$_4$, and concentrated in vacuo to give the desired product as a light brown oil used without further purification (82 mg; 0.30 mmol; 90%).

MS (ES) m/e 274 (M+H)$^+$ b) 2-[(6-ethoxypyridin-2-yl)oxy]-5-ethylphenol

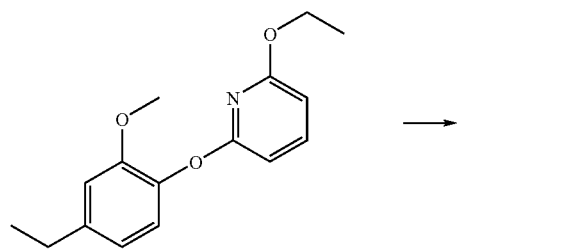

According to the procedure of example 1(b) except substituting 6-chloro-2-(2-methoxy-4-propylphenoxy)pyridin-3-amine for 2-ethoxy-6-(4-ethyl-2-methoxyphenoxy)pyridine (82 mg; 0.30 mmol), the title compound (31 mg; 37%) was prepared as a light brown oil, after purification by preparative TLC (cyclohexane/ethyl acetate: 8/2).

MS (ES) m/e 260 (M+H)$^+$ $^1$H NMR (CDCl$_3$) δ (ppm): 7.56 (t, 1H, J=7.6 Hz); 7.01 (d, 1H, J=8.2 Hz); 6.91 (d, 1H, J=1.8 Hz); 6.70 (dd, 1H, J$_1$=1.9 Hz, J$_2$=8.2 Hz); 6.46 (d, 1H, J=5.1 Hz); 6.43 (d, 1H, J=4.8 Hz); 4.22 (q, 2H, J=7.0 Hz); 2.61 (q, 2H, J=7.6 Hz); 1.33 (t, 3H, J=7.1 Hz); 1.23 (t, 3H, J=7.0 Hz).

EXAMPLE 20

2-[4-amino-2-(trifluoromethyl)phenoxy]-5-ethyl phenol a) 4-ethyl-2-methoxy-1-[4-nitro-2(trifluoromethyl)phenoxy]benzene

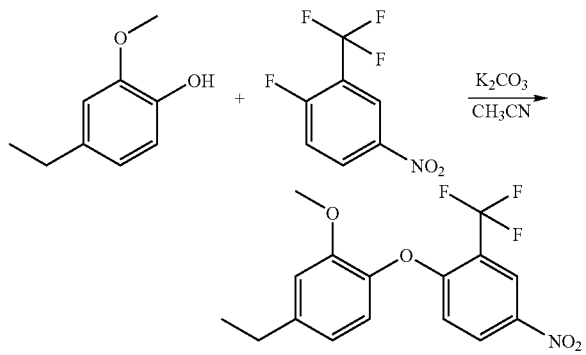

To a suspension of K$_2$CO$_3$ (2 mmol; 276 mg) in anhydrous acetonitrile (1 mL) under argon, was added 2-methoxy-4-ethylphenol (0.285 mL; 2 mmol) followed by 1-fluoro-4-nitro-2-(trifluoromethyl)benzene (418 mg; 2 mmol). The reaction mixture was stirred at 80° C. overnight. Concentrated under argon, washed with NaOH (0.1N; 3 mL), the mixture was extracted with ethyl acetate (2*3 mL). Combined organic phases were dried over MgSO$_4$, concentrated in vacuo, to give the title product as a light brown oil (651 mg; 95%), used without further purification.

MS (ES) m/e 342 (M+H)$^+$.

b) 4-(4-ethyl-2-methoxyphenoxy)-3-(trifluoromethyl)aniline

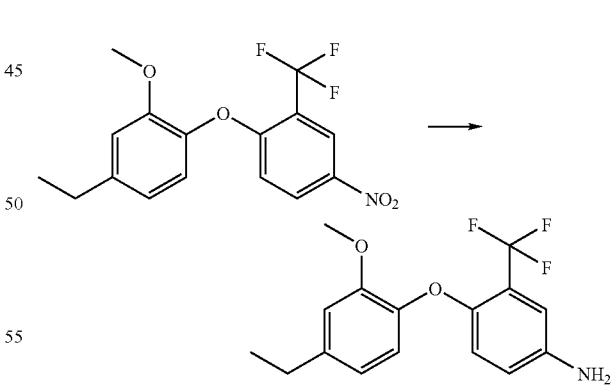

4-ethyl-2-methoxy-1-[4-nitro-2-(trifluoromethyl)phenoxy]benzene (1.90 mmol; 651 mg) was dissolved in anhydrous THF (8 mL) under argon. Palladium on charcoal (0.095 mmol; 20 mg) was added and the reaction was flushed twice with hydrogen, then left to stir overnight. The reaction mixture was filtered on celite, rinsed with methanol (3*10 mL). Concentration yielded a light brown oil (579 mg; 98%) used without further purification.

MS (ES) m/e 312 (M+H)$^+$.

c) 2-[4-amino-2-(trifluoromethyl)phenoxy]-5-ethylphenol

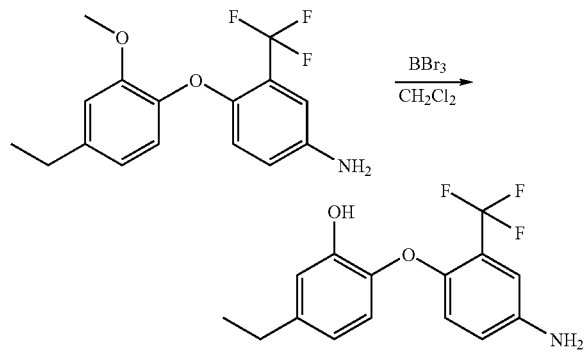

According to the procedure of example 1(b) except substituting 6-chloro-2-(2-methoxy-4-propylphenoxy)pyridin-3-amine for 4-(4-ethyl-2-methoxyphenoxy)-3-(trifluoromethyl)aniline (54 mg; 0.170 mmol), the title compound (24 mg; 47%) was prepared as a light brown solid, after purification by preparative TLC (dichloromethane/methanol: 98/2).

MS (ES) m/e 298 (M+H)$^+$ $^1$H NMR (CDCl$_3$) δ (ppm): 6.95 (d, 1H, J=2.1 Hz); 6.88 (s, 1H); 6.81 (d, 1H, J=8.7 Hz); 6.75 (dd, 1H, J$_1$=2.2 Hz, J$_2$=8.4 Hz); 6.70 (d, 1H, J=8.2 Hz); 6.64 (d, 1H, 8.0 Hz); 2.59 (q, 2H, J=7.6 Hz); 1.22 (t, 3H, 7.6 Hz).

EXAMPLE 21

2-[(2-aminopyridin-3-yl)oxy]-5-ethylphenol a1) 3-(4-ethyl-2-methoxyphenoxy)-2-nitropyridine

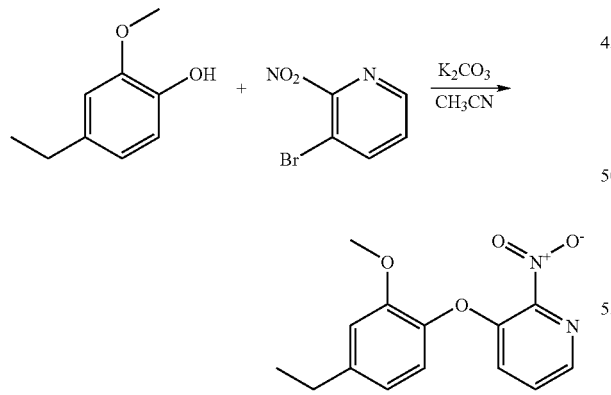

According to the procedure of example 20(a), except substituting 4-ethyl-2-methoxy-1-[4-nitro-2-(trifluoromethyl)phenoxy]benzene for 3-bromo-2-nitropyridine (2 mmol; 406 mg), the title compound (73 mg; 13%) was prepared after chromatography on silica gel (gradient cyclohexane/ethyl acetate).

MS (ES) m/e 275 (M+H)$^+$

Alternatively 3-(4-ethyl-2-methoxyphenoxy)-2-nitropyridine can be synthezized using the following procedure:

a2) 3-Fluoro-2-nitropyridine

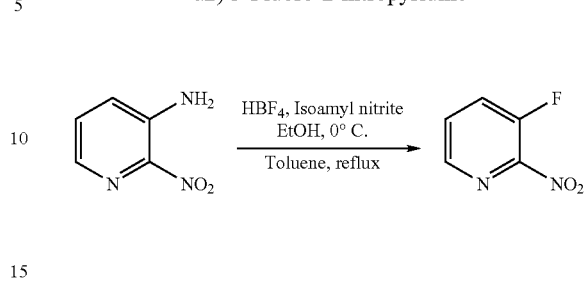

To a stirred solution of 3-Amino 2-nitro pyridine (2.5 g, 17.97 mmol) in dry ethanol (20 ml) was added 10 ml of tetrafluoroboric acid (48% in water). The reaction mixture was cooled to 0° C. and isoamyl nitrite (2.6 g, 22.4 mmol) was added dropwise at 0° C. and stirred at 0° C. for 1 hour. The reaction mixture was filtered, and the solid obtained was washed with diethyl ether. The filtered solid was added to preheated (150 mL) toluene with stirring and reaction mixture was refluxed for 24 hours. The solvent was evaporated and the residue taken in ethyl acetate (200 ml) and washed with water followed by brine, dried over anhydrous sodium sulfate and concentrated under reduced pressure to get the crude 3-fluoro-2-nitropyridine. This was purified by column over silica gel using 10% ethyl acetate in pet ether as eluant to get 1 g (39%) of the title compound as a yellow solid.

$^1$H NMR (CDCl$_3$), δ (ppm): 8.45 (d, J=4.24 Hz, 1H), 7.78-7.83 (m, 1H), 7.70-7.74 (m, 1H)

a3) 3-(4-ethyl-2-methoxyphenoxy)-2-nitropyridine

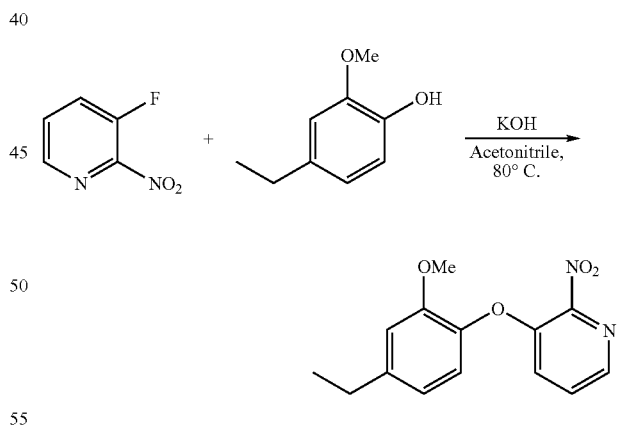

To a stirred solution of 3-Fluoro 2-nitro pyridine (1.6 g, 0.01126 mol) in dry Acetonitrile (20 ml) was added 4-Ethyl-2-methoxy phenol (1.71 g, 11.3 mmol) in dry acetonitrile (10 ml) followed by potassium hydroxide (0.696 g, 12.4 mmol). The reaction mixture was heated to 80° C. and maintained for 2 hours. The solvent was evaporated and taken in ethyl acetate (200 ml). The organic layer was washed with water followed by brine, dried over anhydrous sodium sulfate and concentrated under reduced pressure to give 2.6 g of crude product purified by column chromatography (5% Ethyl acetate in Petroleum ether) to yield: 1.75 g (56%) of title compound.

b) 3-(4-ethyl-2-methoxyphenoxy)pyridin-2-amine

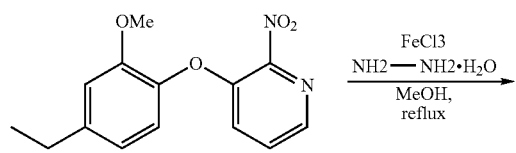

To a stirred solution of 3-(4-ethyl-2-methoxyphenoxy)-2-nitropyridine (1.3 g, 4.7 mmol) in methanol (30 ml) were added anhydrous Ferric chloride (66 mg) and activated charcoal (66 mg). The resulting mixture was heated to reflux and Hydrazine hydrate (80%) (2 mL, 39 mmol) was added dropwise. The reaction was allowed to stir under reflux condition for 5 hours, then filtered through celite. The filtrate was concentrated under reduced pressure, taken in ethyl acetate (150 ml). The organic phase was washed with water followed by brine, dried over anhydrous sodium sulfate and concentrated under reduced pressure to give 1.11 g of the title compound, 100% yield.

c) 2-[(2-aminopyridin-3-yl)oxy]-5-ethylphenol

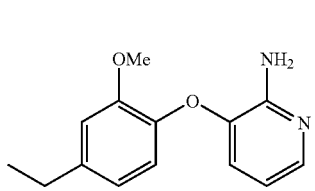

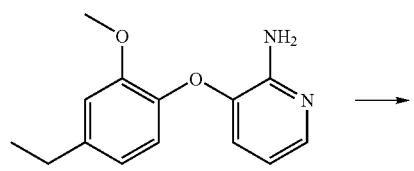

According to the procedure of example 1(b) except substituting 6-chloro-2-(2-methoxy-4-propylphenoxy)pyridin-3-amine for 3-(4-ethyl-2-methoxyphenoxy)pyridin-2-amine (63 mg; 0.26 mmol) the title compound (13 mg; 22%) was obtained as a light brown oil, after two purifications by preparative TLC (dichloromethane/methanol: 9/1).

MS (ES) m/e 231 (M+H)$^+$ $^1$H NMR (MeOD) δ (ppm): 7.61 (m, 1H); 6.84 (m, 3H); 6.70 (d, 1H, J=8.2 Hz); 6.55 (m, 1H); 2.60 (q, 2H, J=7.5 Hz); 1.23 (t, 3H, J=7.6 Hz)

EXAMPLE 22

N-[5-(2-hydroxy-4-propylphenoxy)pyridin-2-yl]methanesulfonamide a) 5-(2-methoxy-4-propylphenoxy)-2-nitropyridine

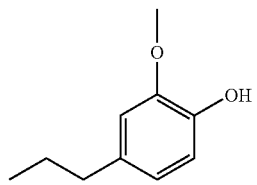

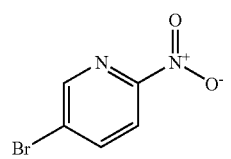

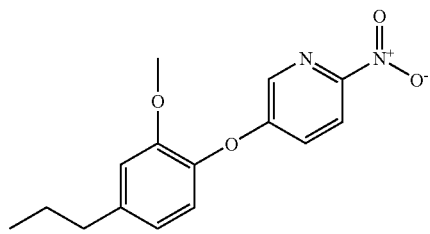

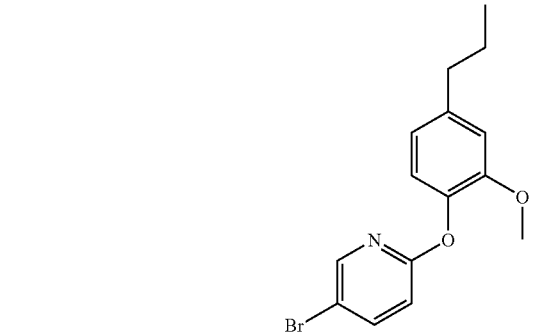

According to the procedure of example 20(a), except substituting 1-fluoro-4-nitro-2-(trifluoromethyl)benzene for 5-bromo-2-nitropyridine (406 mg, 2 mmol), the title compound (220 mg; 38%) was prepared as a white solid, after chromatography on silica gel (gradient cyclohexane/dichloromethane), along with 5-bromo-2-(2-methoxy-4-propylphenoxy)pyridine (238 mg; 37%).

MS (ES) m/e 289 (M+H)$^+$ b) 5-(2-methoxy-4-propylphenoxy)pyridin-2-amine

According to the procedure of example 20(b), except substituting 4-ethyl-2-methoxy-1-[4-nitro-2-(trifluoromethyl)phenoxy]benzene for 5-(2-methoxy-4-propylphenoxy)-2-nitropyridine (144 mg; 0.5 mmol), the title compound (130 mg; 100%) was prepared as a white solid, without purification.

MS (ES) m/e 259 (M+H)+ c) 2-[(6-aminopyridin-3-yl)oxy]-5-propylphenol

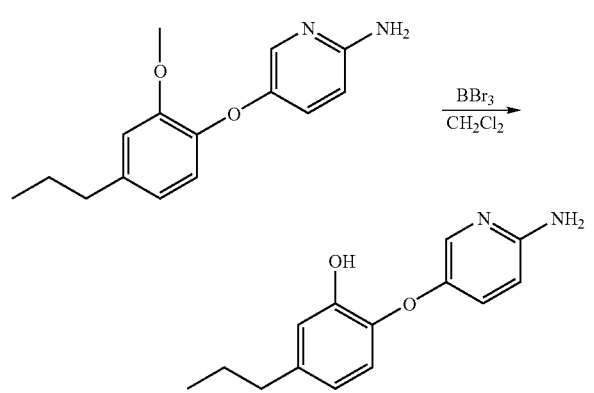

According to the procedure of example 1(b) except substituting 6-chloro-2-(2-methoxy-4-propylphenoxy)pyridin-3-amine for 2-[(6-aminopyridin-3-yl)oxy]-5-propylphenol (130 mg, 0.50 mmol), the title compound (112 mg, 92%) was prepared as a white solid after washing with diethyl ether.

MS (ES) m/e 245 (M+H)+

$^1$H NMR (CDCl$_3$) δ (ppm): 7.92 (s, 1H); 7.22 (d, 1H, J=8.8 Hz); 6.90 (s, 1H); 6.68 (q, 2H, J=9.3 Hz); 6.54 (d, 1H, J=8.8 Hz); 2.55 (t, 2H, J=7.7 Hz); 1.66 (se, 2H, J=7.4 Hz); 0.97 (t, 3H, J=7.3 Hz).

EXAMPLE 23

N-[5-(2-hydroxy-4-propylphenoxy)pyridin-2-yl]methane sulfonamide a) 2-({6-[(methylsulfonyl)amino]pyridin-3-yl}oxy)-5-propyl phenyl methanesulfonate

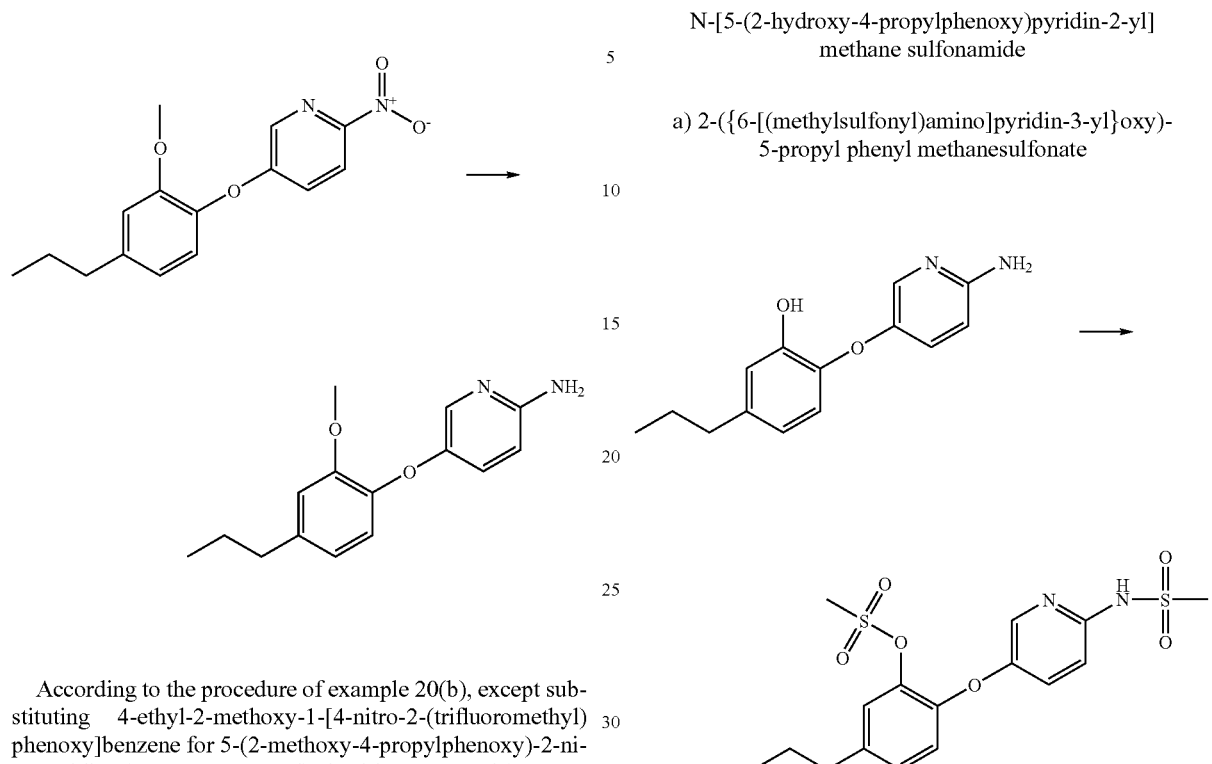

To a solution of 2-[(6-aminopyridin-3-yl)oxy]-5-propylphenol (0.12 mmol; 30 mg) under argon, in anhydrous dichlorométhane (0.5 mL), cooled to −40° C., were added pyridine (0.13 mmol; 0.01 mL) and MsCl (0.12 mmol; 0.01 mL). The reaction mixture was stirred overnight while progressively heating to room temperature. After quenching with NH$_4$Cl (1 mL), extraction with ethyl acetate (3*3 mL), combined organic phases were washed with water (3 mL), dried over MgSO$_4$, concentrated in vacuo. The crude was purified by preparative TLC (dichloromethane/ethyl acetate) to yield the title compound as a white solid (37 mg; 0.09 mmol; 77%).

MS (ES) m/e 401 (M+H)+

$^1$H NMR (acetone-d$_6$) δ (ppm): 8.16 (s, 1H); 7.52 (d, 1H, J=8.7 Hz); 7.33 (s, 1H); 7.22 (t, 2H, J=8.5 Hz); 7.04 (d, 1H, J=7.7 Hz); 3.35 (s, 3H); 3.28 (s, 3H); 2.63 (m, 2H); 1.67 (m, 2H); 0.95 (m, 3H).

b) N-[5-(2-hydroxy-4-propylphenoxy)pyridin-2-yl]methane sulfonamide

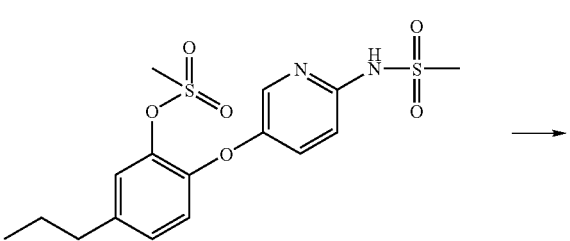

-continued

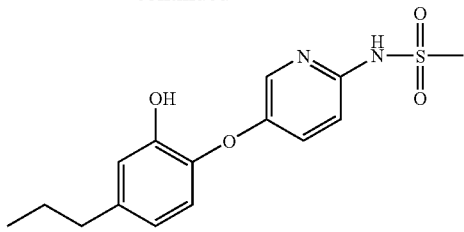

To a solution of 2-({6-[(methylsulfonyl)amino]pyridin-3-yl}oxy)-5-propylphenyl methanesulfonate (0.09 mmol; 30 mg), under argon, in water (0.5 mL), was added KOH (0.26 mmol; 15 mg). The reaction mixture was refluxed for 4 hr. After quenching with NH$_4$Cl (1 mL), extraction with ethyl acetate (3*3 mL), combined organic phases were washed with water (3 mL), dried over MgSO$_4$, concentrated in vacuo, to yield the title compound as a white solid (37 mg; 0.09 mmol; 77%).

MS (ES) m/e 323 (M+H)$^+$ $^1$H NMR (acetone-d$_6$) δ (ppm): 7.99 (d, 1H, J=13.2 Hz); 7.31 (d, 1H, J=9.1 Hz); 7.16 (d, 1H, J=9.0 Hz); 6.94 (d, 1H, J=7.8 Hz); 6.89 (s, 1H); 6.73 (d, 1H, J=7.3 Hz); 3.24 (s, 3H); 2.80 (s, 3H); 2.54 (t, 2H, J=6.8 Hz); 1.64 (se, 2H, J=6.4 Hz); 0.95 (t, 3, J=6.3 Hz).

EXAMPLE 24

2-[(6-ethoxypyridin-3-yl)oxy]-5-propylphenol a) 5-(2-hydroxy-4-propylphenoxy)pyridin-2-ol

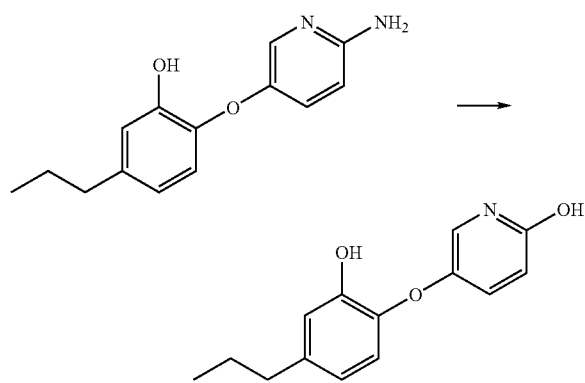

To a solution of 2-[(6-aminopyridin-3-yl)oxy]-5-propylphenol (0.20 mmol; 50 mg) under argon, in H$_2$SO$_4$ (35%; 0.2 mL), cooled to 0° C., was slowly added NaNO$_2$ (0.26 mmol; 18 mg) in water (0.2 mL). After 30 min, CuSO$_4$ (3 mmol; 477 mg) in water (1 mL), then Cu$_2$O (0.18 mmol; 26 mg) were added. After 30 min, the mixture was neutralised with NaHCO$_3$ sat. (1 mL), extracted with ethyl acetate (3*3 mL). Combined organic phases were washed with water (3 mL), dried over MgSO$_4$, concentrated in vacuo. An analytical sample was obtained by preparative TLC to yield the title compound as a white solid (5 mg; 0.02 mmol; ca 20%).

MS (ES) m/e 246 (M+H)$^+$ $^1$H RMN (CD$_3$OD) δ (ppm): 7.48 (dd, 1H, J$_1$=9.8 Hz, J$_2$=3.2 Hz); 7.01 (d, 1H, J=3.1 Hz); 6.80 (d, 1H, J=8.2 Hz); 6.76 (d, 1H, J=1.9 Hz); 6.63 (dd, 1H, J$_1$=8.1 Hz, J$_2$=2.0 Hz); 6.54 (d, 1H, J=9.8 Hz); 2.48 (t, 2H, J=7.8 Hz); 1.60 (se, 2H, J=7.5 Hz); 0.91 (t, 3H, J=7.4 Hz).

b) 5-(2-ethoxy-4-propylphenoxy)-1-ethylpyridin-2 (1H)-one

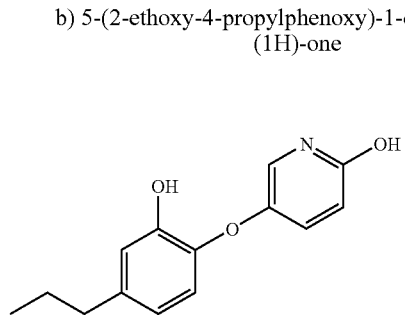

To a solution of 5-(2-hydroxy-4-propylphenoxy)pyridin-2-ol (0.08 mmol; 20 mg) under argon, in anhydrous DMF (0.5 mL) cooled to 0° C., were added LiOH (0.09 mmol; 2 mg), then EtBr (0.09 mmol; 0.007 mL). After allowing the mixture to warm overnight up to room temperature, the reaction was neutralised with NaHCO$_3$ (1 mL), extracted with ethyl acetate (3*3 mL). Combined organic phases were washed with water (3 mL), dried over MgSO$_4$, concentrated in vacuo to yield the title compound as a brown oil (14 mg; 0.05 mmol; 58%), used as such.

MS (ES) m/e 302 (M+H)$^+$ c) 2-[(6-ethoxypyridin-3-yl)oxy]-5-propylphenol

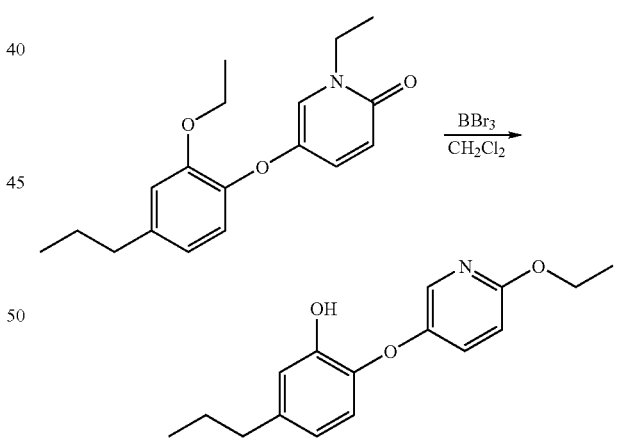

According to the procedure of example 1(b) except substituting 6-chloro-2-(2-methoxy-4-propylphenoxy)pyridin-3-amine for 5-(2-ethoxy-4-propylphenoxy)-1-ethylpyridin-2 (1H)-one(14 mg; 0.05 mmol), the title compound (7 mg; 51%) was prepared as a white solid, after purification by preparative TLC (dichloromethane/ethyl acetate).

MS (ES) m/e 274 (M+H)$^+$ $^1$H RMN (CDCl$_3$) δ (ppm): 7.23 (d, 1H, J=6.8 Hz); 7.10 (s, 1H); 6.86 (s, 1H); 6.69 (d, 1H, J=8.0 Hz); 6.63 (d, 1H, J=8.0 Hz); 6.58 (d, 1H, J=9.8 Hz); 3.95 (q, 2H, J=7.1 Hz); 2.51 (t, 2H, J=7.7 Hz); 1.62 (se, 2H, J=7.8 Hz); 1.34 (t, 3H, J=7.2 Hz); 0.92 (t, 3H, J=7.3 Hz).

EXAMPLE 25

2-[(4,6-difluoropyridin-2-yl)oxy]-5-propylphenol (25A) and 2-[(2,6-difluoropyridin-4-yl)oxy]-5-propylphenol (25B)

a) 2,4-difluoro-6-(2-methoxy-4-propylphenoxy)pyridine and 2,6-difluoro-4-(2-methoxy-4-propylphenoxy)pyridine

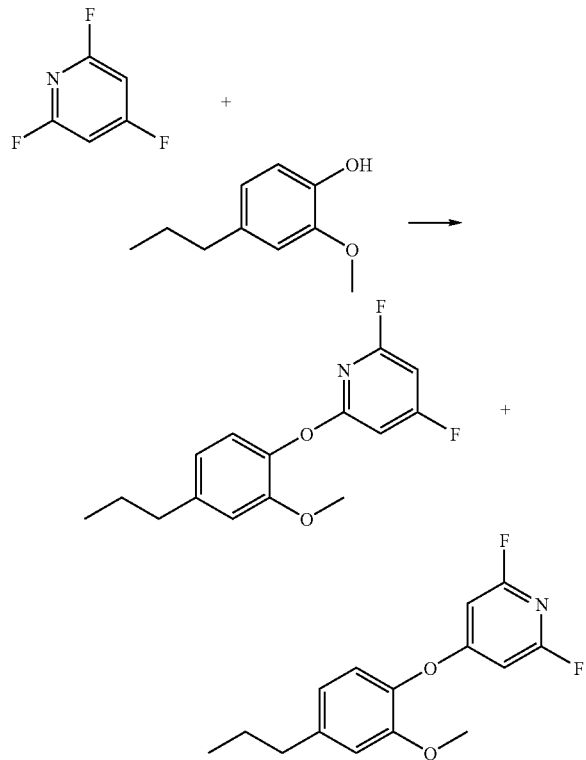

According to the procedure of example 5(a) except substituting 2,6-difluoropyridine for 2,4,6-trifluoropyridine (0.32 mL, 2 mmol), the title compounds (265 mg; 47%) were prepared together as a clear oil, after purification by silica gel chromatography (gradient cyclohexane/dichloromethane).

MS (ES) m/e 280 (M+H)$^+$ b) 2-[(4,6-difluoropyridin-2-yl)oxy]-5-propylphenol (25A) and 2-[(2,6-difluoropyridin-4-yl)oxy]-5-propylphenol (25B)

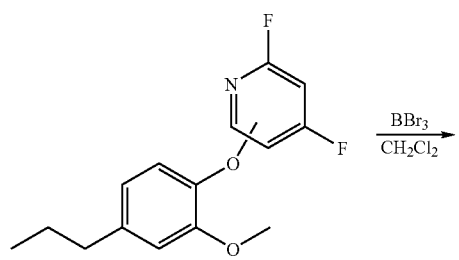

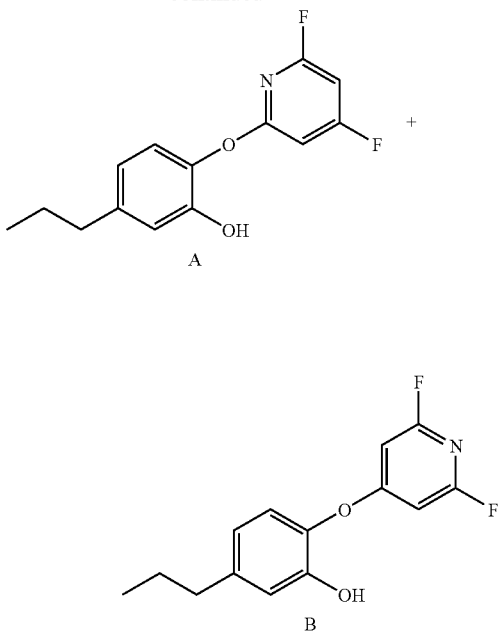

According to the procedure of example 5(b), except substituting 2-fluoro-6-(2-methoxy-4-propylphenoxy)pyridine for 2,4-difluoro-6-(2-methoxy-4-propylphenoxy)pyridine and 2,6-difluoro-4-(2-methoxy-4-propylphenoxy)pyridine (67 mg, 0.24 mmol), title compound A, as a white solid (11 mg; 17%), and title compound B as a clear oil (22 mg; 35%) were prepared after purification by preparative TLC (dichloromethane/ethyl acetate).

A: MS (ES) m/e 266 (M+H)$^+$

NMR$^1$H (CDCl$_3$) δ (ppm): 7.01 (d, 1H, J=8.2 Hz); 6.92 (s, 1H); 6.77 (d, 1H, J=8.3 Hz); 6.49 (d, 1H, J=8.7 Hz); 6.41 (d, 1H, J=7.7 Hz); 5.72 (br, 1H); 2.57 (t, 2H, J=7.8 Hz); 1.67 (se, 2H, J=7.3 Hz); 0.97 (t, 3H, J=7.3 Hz).

B: MS (ES) m/e 266 (M+H)$^+$

NMR$^1$H (CDCl$_3$) δ (ppm): 6.97 (d, 1H, J=8.2 Hz); 6.92 (s, 1H); 6.80 (d, 1H, J=8.3 Hz); 6.36 (s, 2H); 5.37 (br, 1H); 2.58 (t, 2H, J=7.8 Hz); 1.68 (se, 2H, J=7.6 Hz); 0.97 (t, 3H, J=7.4 Hz).

EXAMPLE 26

2-[(6-fluoropyridin-2-yl)oxy]-5-(2,2,2-trifluoro-1-hydroxyethyl)phenol a) 2,2,2-trifluoro-1-{4-[(6-fluoropyridin-2-yl)oxy]-3-methoxyphenyl}ethanol

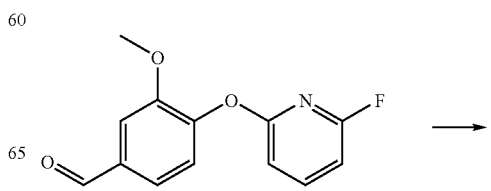

-continued

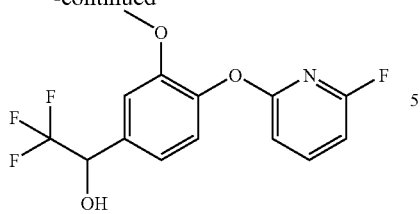

To a solution of 4-[(6-fluoropyridin-2-yl)oxy]-3-methoxy benzaldehyde (300 mg; 1.2 mmol) with trifluoro methyltrimethylsilane (228 µl; 1.46 mmol) in THF (3 ml) under argon at 0° C. was added a molar solution of TBAF in THF (10 µl; 0.012 mmol). The reaction mixture was allowed to stir at rt for 2 h and a molar aqueous solution of HCl was added dropwise (2.5 ml; 2.5 mmol). The reaction mixture was stirred for another 2 h. water and diethylether were added. The aqueous phase was further extracted (2×EtOAc). Combined organic phases were dried over MgSO$_4$, concentrated in vacuo to afford the title compound as a white solid (333 mg; 1.05 mmol; 88%).

$^1$H NMR (CDCl$_3$) δ (ppm): 7.79 (q, 1H, J=8.0 Hz); 7.24-7.20 (m, 2H); 7.17-7.09 (m, 1H); 6.81 (d, 1H, J=8.0 Hz); 6.64 (d, 1H, J=7.8 Hz); 5.10 (m, 1H); 3.85 (s, 3H).

b) 2-[(6-fluoropyridin-2-yl)oxy]-5-(2,2,2-trifluoro-1-hydroxy ethyl)phenol

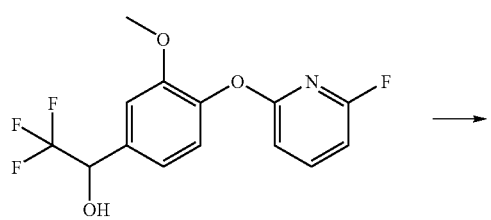

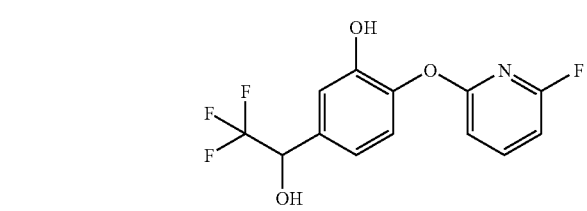

According to the procedure of example 5(b) except substituting 2-fluoro-6-(2-methoxy-4-propylphenoxy)pyridine by 2,2,2-trifluoro-1-{4-[(6-fluoropyridin-2-yl)oxy]-3 methoxyphenyl}ethanol (0.15 mmol; 50 mg) and adding 3.5 equivalents (0.47 mmol; 470 µl) of boron tribromide, the title compound was prepared in 84% yield (0.13 mmol; 38 mg) after purification by preparative TLC on silica gel (ethyl acetate/cyclohexane—40/60).

MS (ES) 304 [M+1]$^+$ $^1$H NMR (DMSO) δ (ppm): 9.79 (s, 1H); 7.97 (q, 1H, J=8.3 Hz); 7.12 (s, 1H); 7.11 (d, 1H, J=8.1 Hz); 6.96 (d, 1H, J=9.1 Hz); 6.85 (d, 1H, J=8.0 Hz); 6.81 (d, 2H, J=5.4 Hz); 5.11 (qt, 1H).

EXAMPLE 27

2-[(6-fluoropyridin-2-yl)oxy]-5-(2,2,2-trifluoroethyl) phenol a) 2,2,2-trifluoro-1-{4-[(6-fluoropyridin-2-yl)oxy]-3-methoxy phenyl}ethyl 4-methylbenzenesulfonate

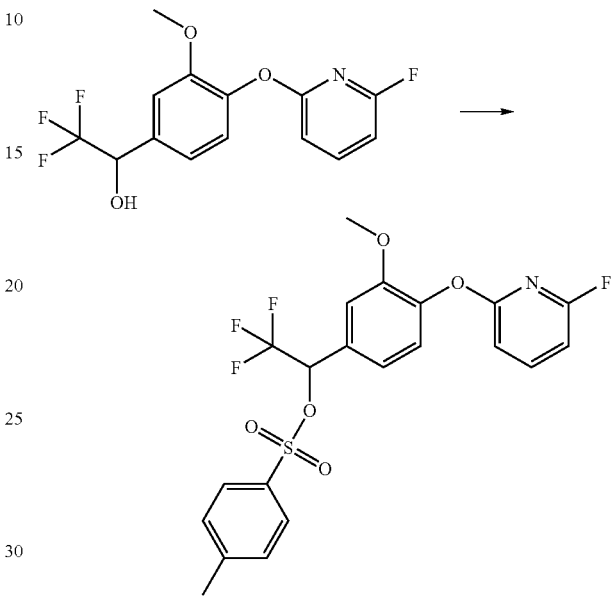

To a solution of 2,2,2-trifluoro-1-{4-[(6-fluoropyridin-2-yl)oxy]-3-methoxyphenyl}ethanol (0.52 mmol; 165 mg), tosyl chloride (0.57 mmol; 109 mg) and DMAP (0.01 mmol; 1.5 mg) under argon in dichloromethane (4 mL) at 0° C. was added TEA (1.04 mmol; 145 µl). The reaction mixture was stirred at rt for 3 h, then washed with brine (2×), dried over MgSO$_4$, concentrated and purified by preparative TLC on silica gel (ethyl acetate/cyclohexane—30/70) to yield the title compound (101 mg; 0.21 mmol; 41%).

$^1$H NMR (CDCl$_3$) δ (ppm): 7.78 (q, 1H, J=8.6 Hz); 7.65 (d, 2H, J=8.2 Hz); 7.29 (d, 2H, J=8.6 Hz); 7.06 (d, 1H, J=8.2 Hz); 6.92 (d, 1H, J=9.7 Hz); 6.86 (s, 1H); 6.77 (d, 1H, J=8.0 Hz); 6.63 (d, 1H, J=8.1 Hz); 5.69 (q, 1H, J=6.3 Hz); 3.67 (s, 3H); 2.40 (s, 3H).

b) 2-fluoro-6-[2-methoxy-4-(2,2,2-trifluoroethyl) phenoxy]pyridine

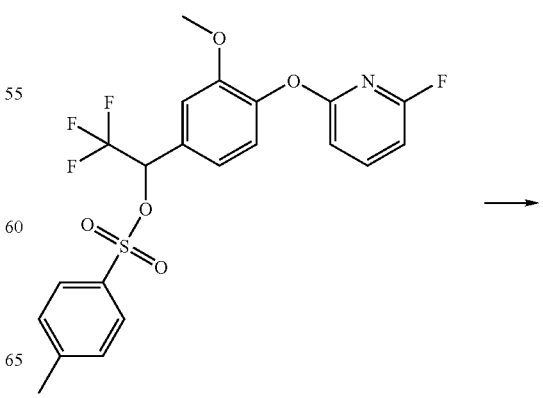

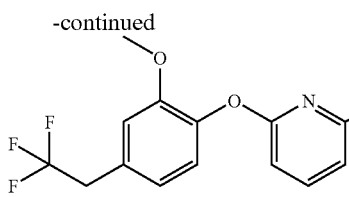

A solution of 2,2,2-trifluoro-1-{4-[(6-fluoropyridin-2-yl)oxy]-3-methoxyphenyl}ethyl 4-methylbenzenesulfonate (0.2 mmol; 96 mg) in ethanol (3 ml) containing a catalytic amount of Pd/C (10% wet; 0.014 mmol; 30 mg) was stirred for 16 h at rt under 2.5 atm of hydrogen. Purification by preparative TLC on silica gel (ethyl acetate/cyclohexane—30/70) afforded the title compound (48 mg; 0.16 mmol; 80%).

MS (ES) 302 [M+1]+

$^1$H NMR (CDCl$_3$) δ (ppm): 7.75 (q, 1H, J=7.9 Hz); 7.13 (d, 1H, J=8.5 Hz); 6.96-6.90 (m, 2H); 6.76 (d, 1H, J=7.3 Hz); 6.59 (d, 1H, J=7.9 Hz); 3.80 (s, 3H); 3.40 (q, 1H, J=10.9 Hz).

c) 2-[(6-fluoropyridin-2-yl)oxy]-5-(2,2,2-trifluoroethyl)phenol

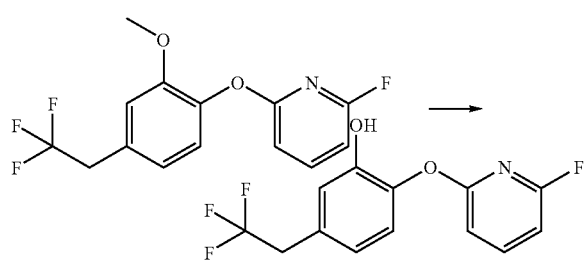

According to the procedure of example 5(b) except substituting 2-fluoro-6-(2-methoxy-4-propylphenoxy)pyridine by 2-fluoro-6-[2-methoxy-4-(2,2,2-trifluoroethyl)phenoxy]pyridine (0.14 mmol; 43 mg) and adding 3.5 equivalents (0.5 mmol; 500 µl) of boron tribromide, the title compound was prepared in 75% yield (0.11 mmol; 30 mg) after purification by preparative TLC on silica gel (ethyl acetate/cyclohexane—30/70).

MS (ES) 288 [M+1]+

$^1$H NMR (CDCl$_3$) δ (ppm): 7.84 (q, 1H, J=7.6 Hz); 7.12 (d, 1H, J=8.7 Hz); 7.05 (s, 1H); 6.89-6.82 (m, 2H); 6.71 (d, 1H, J=6.3 Hz); 6.02 (s br, 1H); 3.36 (q, 1H, J=10.3 Hz).

EXAMPLE 28

2-[(6-fluoropyridin-2-yl)oxy]-5-(trifluorovinyl)phenol a) 2-fluoro-6-[2-methoxy-4-(1,2,2,2 tetrafluoroethyl)phenoxy]pyridine

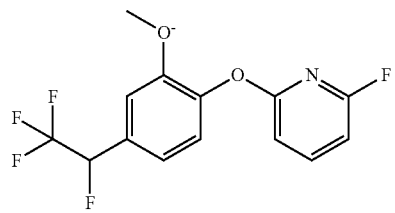

To a solution of 2,2,2-trifluoro-1-{4-[(6-fluoropyridin-2-yl)oxy]-3-methoxyphenyl}ethanol (0.22 mmol; 70 mg) under argon in dichloromethane (2 mL) at −78° C. was added dropwise DAST (0.22 mmol; 29 µl). The reaction mixture was let come back to rt for 2 h and quenched with brine (3 ml). The aqueous phase was collected, neutralized with sodium bicarbonate and extracted twice with chloroform. The organic phases were combined, dried over MgSO$_4$, concentrated and purified by preparative TLC on silica gel (ethyl acetate/cyclohexane—30/70) to yield the title compound (25 mg; 0.08 mmol; 37%).

$^1$H NMR (CDCl$_3$) δ (ppm): 7.78 (q, 1H, J=8.1 Hz); 7.22 (d, 1H, J=8.0 Hz); 7.10 (m, 2H); 6.80 (d, 1H, J=8.0 Hz); 6.62 (d, 1H, J=7.8 Hz); 5.62 (dq, 1H, J=37.8 and 6.2 Hz); 3.82 (s, 3H).

b) 2-fluoro-6-[2-methoxy-4-(trifluorovinyl)phenoxy] pyridine

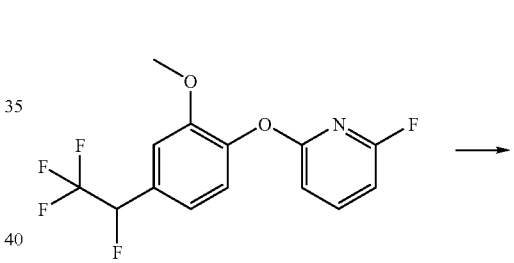

To a solution of 2-fluoro-6-[2-methoxy-4-(1,2,2,2-tetrafluoroethyl)phenoxy]pyridine (0.078 mmol; 25 mg) under argon in THF (1 mL) at 0° C. was added dropwise a one molar solution of LiHMDS in THF (0.094 mmol; 94 µl). The reaction mixture was let come back to rt for 16 h. Concentration and purification by preparative TLC on silica gel (ethyl acetate/cyclohexane—30/70) afforded the title compound (10 mg; 0.033 mmol; 43%).

¹H NMR (CDCl₃) δ (ppm): 7.73 (q, 1H, J=7.9 Hz); 7.21 (d, 1H, J=8.1 Hz); 7.12 (d, 1H, J=9.9 Hz); 7.11 (s, 1H); 6.80 (d, 1H, J=7.9 Hz); 6.61 (d, 1H, J=7.7 Hz); 3.81 (s, 3H).

c) 2-[(6-fluoropyridin-2-yl)oxy]-5-(trifluorovinyl)phenol

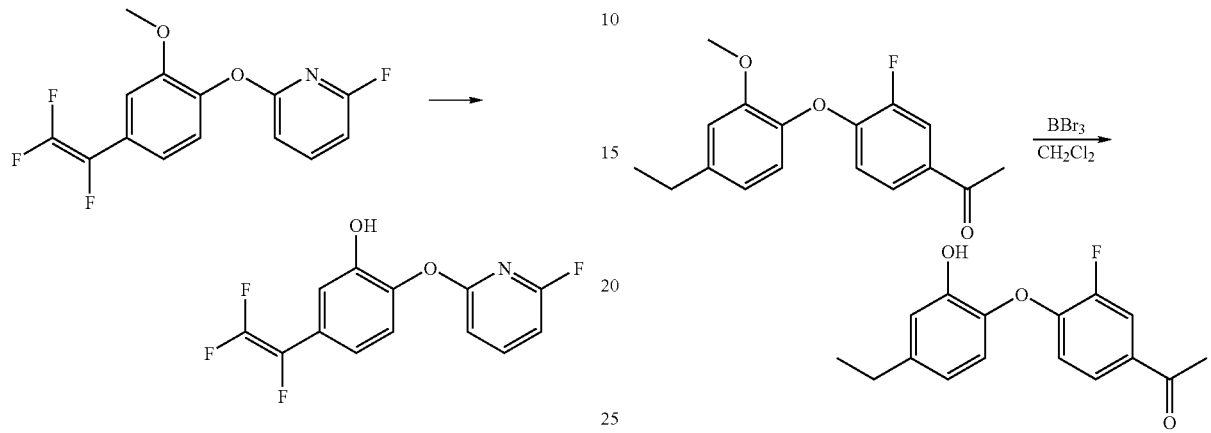

According to the procedure of example 5(b) except substituting 2-fluoro-6-(2-methoxy-4-propylphenoxy)pyridine by 2-fluoro-6-[2-methoxy-4-(trifluorovinyl)phenoxy]pyridine (0.033 mmol; 10 mg) and adding 3.5 equivalents (0.117 mmol; 117 μl) of boron tribromide, the title compound was prepared in 64% yield (0.021 mmol; 6 mg) after purification by preparative TLC on silica gel (ethyl acetate/cyclohexane—30/70).

¹H NMR (CDCl₃) δ (ppm): 7.76 (q, 1H, J=8.0 Hz); 7.13 (d, 1H, J=1.9 Hz); 7.11 (d, 1H, J=8.6 Hz); 6.98 (d, 1H, J=10.0 Hz); 6.80 (d, 1H, J=8.0 Hz); 6.63 (d, 1H, J=9.6 Hz); 6.00 (s br, 1H).

EXAMPLE 29

1-[4-(4-ethyl-2-hydroxyphenoxy)-3-fluorophenyl]ethanone a) 1-[4-(4-ethyl-2-methoxyphenoxy)-3-fluorophenyl]ethanone According to the procedure of example 4(a) except substituting 2,6-Difluoropyridine for 1-(3,4-difluorophenyl)ethanone (0.77 mmol; 0.97 ml), the title compound was isolated as a light brown oil (244 mg; quantitative) used without purification.

MS (ES) m/e 289 (M+H)⁺ b) 1-[4-(4-ethyl-2-hydroxyphenoxy)-3-fluorophenyl]ethanone

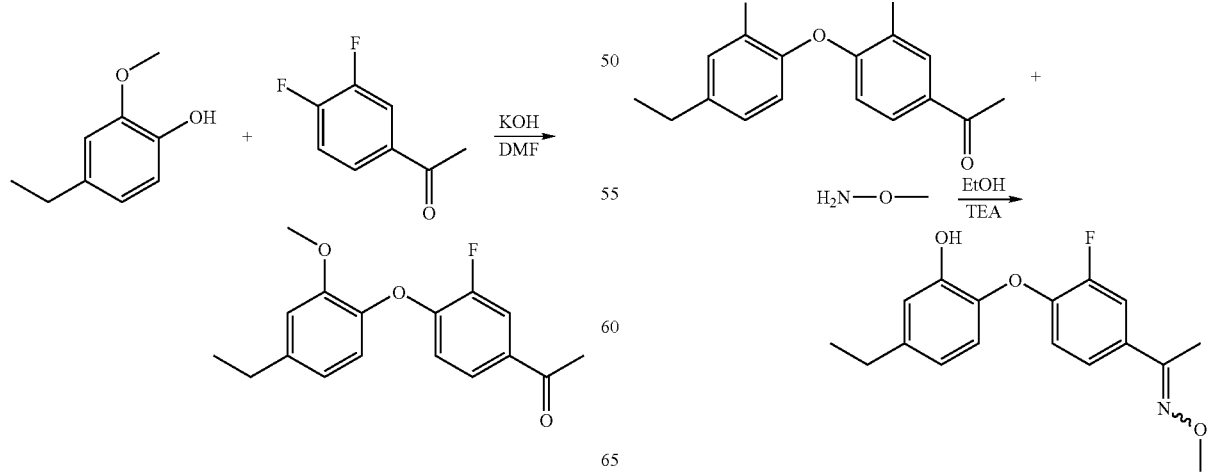

According to the procedure of example 1(b) except substituting 6-chloro-2-(2-methoxy-4-propylphenoxy)pyridin-3-amine for 1-[4-(4-ethyl-2-methoxyphenoxy)-3-fluorophenyl]ethanone (244 mg; 0.70 mmol), an analytical sample of the title compound (11 mg; 5%) was prepared as a light brown oil, after purification by preparative TLC (cyclohexane/ethyl acetate: 7/3).

MS (ES) m/e 275 (M+H)⁺

¹H NMR (CDCl₃) δ (ppm): 9.38 (dd, 1H, J₁=2.0 Hz, J₂=11.6 Hz); 7.65 (d, 1H, J=8.4 Hz); 6.95 (t, 2H, J=8.0 Hz); 6.85 (d, 1H, J=8.1 Hz); 6.72 (d, 1H, J=8.0 Hz); 5.59 (sl, 1H); 2.62 (q, 2H, J=7.6 Hz); 2.56 (s, 3H); 1.24 (t, 3H, J=7.5 Hz).

EXAMPLE 30

(1E)-1-[4-(4-ethyl-2-hydroxyphenoxy)-3-fluoro phenyl]ethanone-O-methyloxime

To a solution of 1-[4-(4-ethyl-2-hydroxyphenoxy)-3-fluorophenyl]ethanone (46 mg; 0.17 mmol), under argon, in ethanol (1 mL), was added O-methylhydroxylamine hydrochloride (14 mg; 0.17 mmol) and 0.05 mL of triethylamine. The reaction was stirred to room temperature overnight. The mixture was concentrated in vacuo to give the desired product as light brown oil after purification by preparative TLC (14.5 mg; 0.048 mmol; 28%).

$^1$H NMR (CDCl$_3$) δ (ppm): 7.53 (dd, 1H, J$_1$=1.9 Hz, J$_2$=12.0 Hz); 7.33 (d, 1H, J=8.5 Hz); 6.99 (t, 1H, J=8.5 Hz); 6.90 (d, 1 H, J=1.5 Hz); 6.75 (d, 1 H, J=8.3 Hz); 6.66 (dd, 1 H, J$_1$=1.4 Hz, J$_2$=8.2 Hz); 5.54 (s, 1H); 3.99 (s, 3H); 2.60 (q, 2H, J=7.6 Hz); 2.19 (s, 3H); 1.23 (t, 3H, J=7.6 Hz).

EXAMPLE 31

2-[(6-fluoropyridin-2-yl)oxy]-5-(1H-imidazol-1-ylmethyl)phenol a) 2-[4-(chloromethyl)-2-methoxyphenoxy]-6-fluoro pyridine

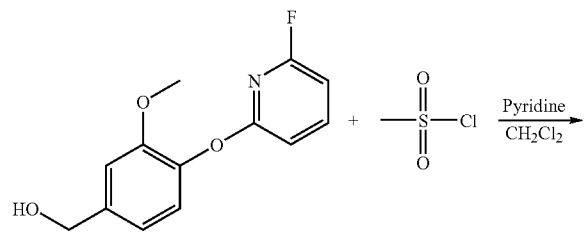

To a solution of {4-[(6-fluoropyridin-2-yl)oxy]-3-methoxyphenyl}methanol (367 mg; 1.47 mmol), under argon, in dichloromethane (6 mL), cooled to −40° C., was added pyridine (131 µL; 1.62 mmol) then methanesulfonyl chloride (115 µL; 1.47 mmol). The reaction mixture was allowed to stir for 6 hr, with gradual warming to room temperature. The mixture was cooled to −40° C., pyridine (50 µL; 0.62 mmol) and methanesulfonyl chloride (40 µL; 0.51 mmol) were added. The reaction was stirred overnight, with gradual warming to room temperature.

The reaction was hydrolysed with saturated NH$_4$Cl (10 mL), extracted with ethyl acetate (2*5 mL). Combined organic phases were dried over Na$_2$SO$_4$, concentrated in vacuo. The title compound (185 mg; 47%) was obtained as a light oil, after purification on silica gel (cyclohexane/ethyl acetate: 95/5).

$^1$H NMR (CDCl$_3$) δ (ppm): 7.75 (q, 1H, J=7.6 Hz); 7.10 (d, 1H, J=7.9 Hz); 7.04 (s, 1H); 7.00 (d, 1H, J=8.1 Hz); 6.74 (d, 1H, J=7.9 Hz); 6.57 (dd, 1 H, J$_1$=7.8 Hz, J$_2$=1.8 Hz); 4.60 (s, 2H); 3.79 (s, 3H).

b) 2-fluoro-6-[4-(1H-imidazol-1-ylmethyl)-2-methoxyphenoxy]pyridine

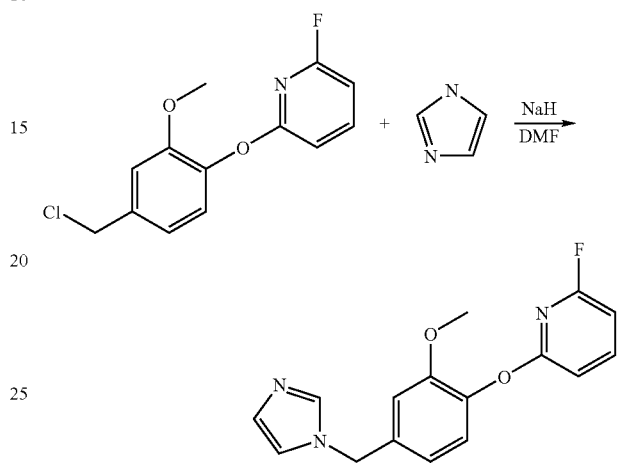

To a solution of imidazole (18 mg; 0.27 mmol) and NaH (12 mg; 0.30 mmol) in DMF (1 mL), under argon, was added a solution of 2-[4-(chloromethyl)-2-methoxyphenoxy]-6-fluoropyridine (65 mg; 0.24 mmol) in DMF (1 mL). The reaction mixture was allowed to stir overnight, to 40° C. After concentration, the reaction was hydrolysed with saturated NH$_4$Cl (1 mL), extracted with AcOEt (2*1 mL). Combined organic phases were dried over Na$_2$SO$_4$, concentrated in vacuo, the title compound (68 mg; 93%) was obtained.

c) 2-[(6-fluoropyridin-2-yl)oxy]-5-(1H-imidazol-1-ylmethyl)phenol

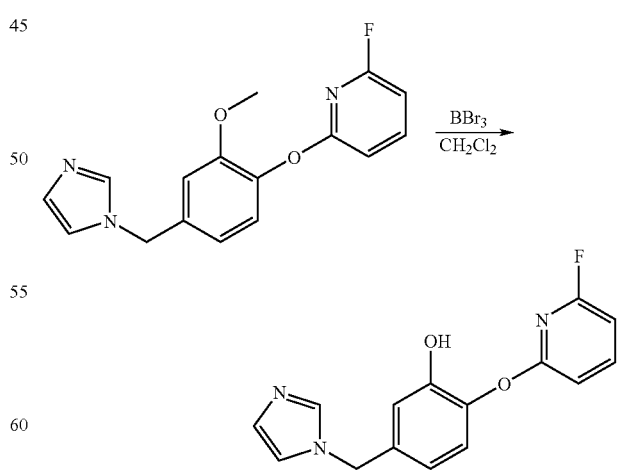

According to the procedure of example 1(b) except substituting 6-chloro-2-(2-methoxy-4-propylphenoxy)pyridin-3-amine for 2-fluoro-6-[4-(1H-imidazol-1-ylmethyl)-2-methoxy phenoxy]pyridine (68 mg; 0.23 mmol), the title compound (16 mg; 24%) was obtained as a white solid, after purification by preparative TLC (dichloromethane/methanol: 9/1).

MS (ES) m/e 286 (M+H)+

$^1$H NMR (MeOD) δ (ppm): 7.93 (m, 2H); 7.28 (sl, 1H); 7.12 (m, 2H); 6.84 (m, 3H); 6.72 (dd, 1H, $J_1$=7.8 Hz, $J_2$=2.0 Hz); 5.27 (s, 2H).

EXAMPLE 32

2-[(6-fluoropyridin-2-yl)oxy]-5-(1H-1,2,4-triazol-1-ylmethyl)phenol a) 2-fluoro-6-[2-methoxy-4-(1H-1,2,4-triazol-1-ylmethyl)phenoxy]pyridine

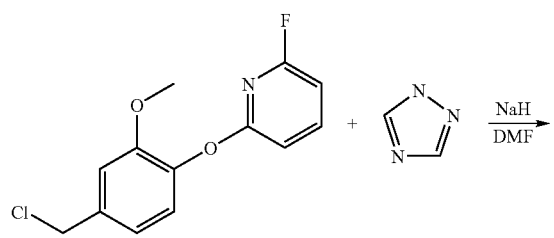

To a solution of triazole (18 mg; 0.267 mmol) and NaH (10 mg; 0.25 mmol) in DMF (1 mL), under argon, was added a solution of 2-[4-(chloromethyl)-2-methoxyphenoxy]-6-fluoropyridine (65 mg; 0.243 mmol) in DMF (1 mL). The reaction mixture was allowed to stir overnight at 40° C. After concentration, the reaction was hydrolysed with saturated NH$_4$Cl (1 mL), extracted with AcOEt (2*1 mL). Combined organic phases were dried over Na$_2$SO$_4$, concentrated in vacuo, the title compound (72 mg; quantitative) was obtained.

b) 2-[(6-fluoropyridin-2-yl)oxy]-5-(1H-1,2,4-triazol-1-yl methyl)phenol

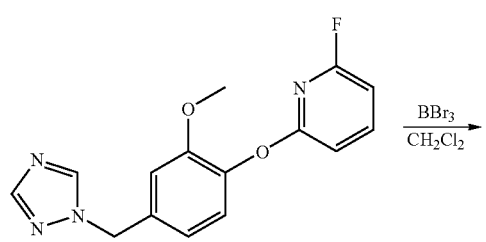

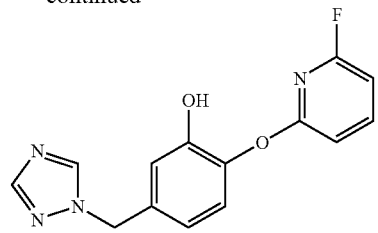

According to the procedure of example 1(b) except substituting 6-chloro-2-(2-methoxy-4-propylphenoxy)pyridin-3-amine by 2-fluoro-6-[2-methoxy-4-(1H-1,2,4-triazol-1-ylmethyl)phenoxy]pyridine (71 mg; 0.24 mmol), the title compound was prepared (37 mg; 54%) after purification by preparative TLC on silica gel (dichloromethane/methanol—9/1).

$^1$H NMR (MeOD) δ (ppm): 8.75 (s, 1H); 8.08 (s, 1H); 7.74 (q, 1H, J=7.7 Hz); 6.95 (d, 1H, J=8.2 Hz); 6.82 (d, 1H, J=1.8 Hz); 6.76 (dd, 1H, $J_1$=8.1 Hz, $J_2$=1.8 Hz); 6.64 (dd, 1H, $J_1$=8.0 Hz, $J_2$=1.0 Hz); 6.55 (dd, 1H, $J_1$=7.8 Hz, $J_2$=2.2 Hz); 5.32 (s, 2H).

EXAMPLE 33

5-ethyl-2-[(6-fluoropyridin-2-yl)oxy]phenyl acetate

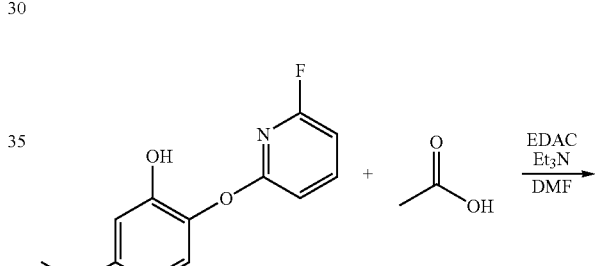

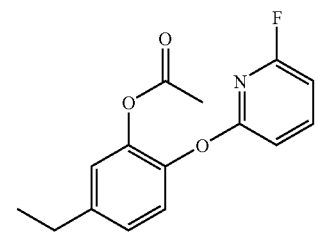

To a solution of 5-Ethyl-2-(6-fluoro-pyridin-2-yloxy)-phenol (20 mg; 0.09 mmol), under argon, in dimethylformamide (2 mL), cooled to 0° C., was added triethylamine (36 μL; 0.26 mmol) and acetic acid (10 μL; 0.18 mmol). The reaction mixture was allowed to stir overnight, with gradual warming to roomtemperature. The reaction was concentrated, diluted with saturated NaHCO$_3$ (5 mL) and extracted with ethyl acetate (3*3 mL). Combined organic phases were dried over Na$_2$SO$_4$, concentrated in vacuo, the title compound (8 mg; 34%) was obtained as clear oil, after purification on neutral alumina gel (cyclohexane/ethyl acetate: 9/1).

¹H RMN (CDCl₃) (ppm): 7.73 (q, 1H, J=8.0 Hz); 7.11 (m, 2H); 6.72 (d, 1H, J=8.0 Hz); 6.60 (dd, 1H, J₁=7.8 Hz, J₂=2.4 Hz); 2.67 (q, 2H, J=7.6 Hz); 2.11 (s, 3H); 1.26 (t, 3H, J=7.6 Hz).

EXAMPLE 34

2-(2-aminophenoxy)-5-ethylphenol a) 4-ethyl-2-methoxy-1-(2-nitrophenoxy)benzene

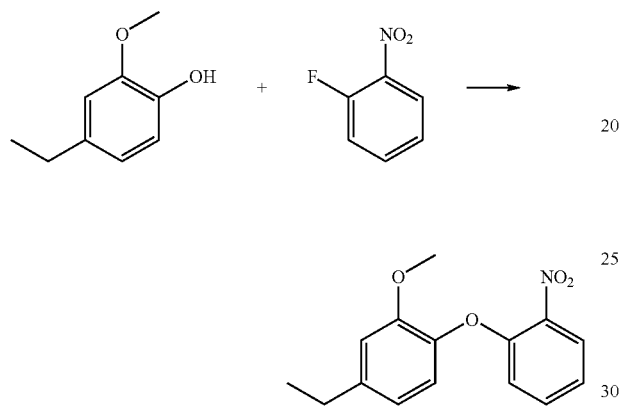

According to the procedure of example 21 (a3) except substituting 3-Fluoro 2-nitro pyridine by 2-fluoronitrobenzene (0.72 mmol; 102 mg), the title compound was prepared in quantitative yield (205 mg) and used without further purification.

MS (ES) m/e 274 (M+H)⁺ b) 2-(4-ethyl-2-methoxyphenoxy)aniline

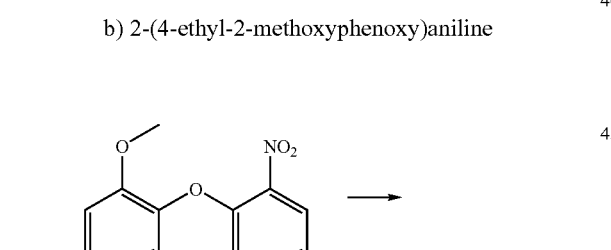

According to the procedure of example 20(b) except substituting 4-ethyl-2-methoxy-1-[4-nitro-2-(trifluoromethyl)phenoxy]benzene by 4-ethyl-2-methoxy-1-(2-nitrophenoxy)benzene (0.66 mmol; 180 mg) and THF by ethanol, the title compound was prepared in quantitative yield (181 mg) and used without further purification.

MS (ES) m/e 244 (M+H)⁺ c) 2-(2-aminophenoxy)-5-ethylphenol

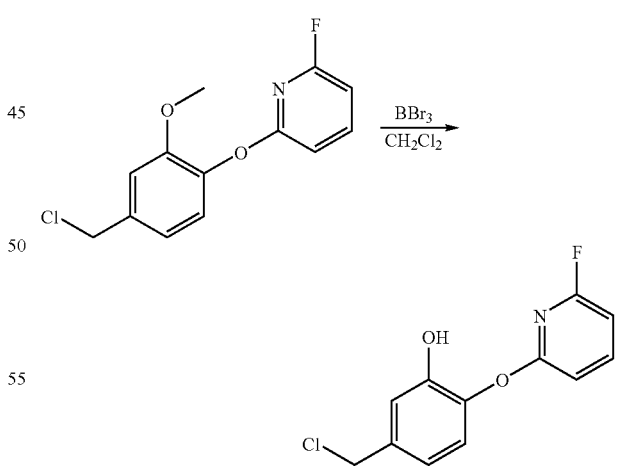

According to the procedure of example 1(b) except substituting 6-chloro-2-(2-methoxy-4-propylphenoxy)pyridin-3-amine by 2-(4-ethyl-2-methoxyphenoxy)aniline (50 mg; 0.21 mmol), the title compound was prepared in 42% yield (0.09 mmol; 20 mg) after purification by preparative TLC on silica gel (dichloromethane/methanol—40/60).

MS (ES) m/e 244 (M+H)⁺

¹H RMN (CDCl₃) δ (ppm): 6.93 (t, 1H, J=7.4 Hz); 6.89-6.85 (m, 2H); 6.82-6.79 (m, 2H); 6.76-6.72 (m, 1H) 6.64 (dd, 1H, J₁=8.1 Hz; J₂=1.8 Hz); 2.58 (q, 2H, J=7.6 Hz); 1.22 (t, 3H, J=7.6 Hz).

EXAMPLE 36

2-[(6-fluoropyridin-2-yl)oxy]-5-(methoxymethyl)phenol a) 5-(chloromethyl)-2-[(6-fluoropyridin-2-yl)oxy]phenol According to the procedure of example 1(b) except substituting 6-chloro-2-(2-methoxy-4-propylphenoxy)pyridin-3-amine by 2-[4-(chloromethyl)-2-methoxyphenoxy]-6-fluoro pyridine (205 mg; 0.77 mmol), the title compound (185 mg; 95%) was prepared as a light brown solid without further purification.

MS (ES) m/e 254 (M+H)⁺

$^1$H NMR (CDCl$_3$) δ (ppm): 7.81 (q, 1H, J=8.0 Hz); 7.11 (m, 2H); 6.95 (dd, 1H, J$_1$=8.2 Hz, J$_2$=1.9 Hz); 6.83 (d, 1H, J=8.0 Hz); 6.68 (dd, 1H, J$_1$=7.9 Hz, J$_2$=2.1 Hz); 4.55 (s, 2H).

b) 2-[(6-fluoropyridin-2-yl)oxy]-5-(methoxymethyl)phenol

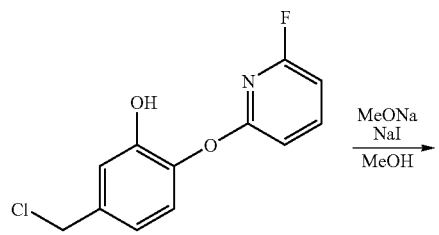

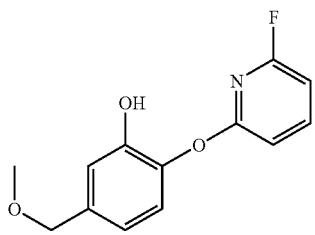

To a solution of 5-(chloromethyl)-2-[(6-fluoropyridin-2-yl)oxy]phenol (50 mg; 0.20 mmol), under argon, in methanol (1 mL) was added sodium methoxylate (3.94 mmol; 22 mg) and sodium iodide (0.07 mmol; 10 mg). The reaction mixture was allowed to stir at room temperature overnight. The reaction was hydrolysed with saturated NH$_4$Cl (5 mL), extracted with ethyl acetate (3*2 mL), and washed with 5 mL of satured NaHCO$_3$. Combined organic phases were dried over Na$_2$SO$_4$, concentrated in vacuo, the title compound (49 mg; 100%) was prepared as a light yellow oil without further purification.

MS (ES) m/e 250 (M+H)$^+$ $^1$H NMR (CDCl$_3$) δ (ppm): 7.77 (q, 1H, J=8.0 Hz); 7.07 (m, 2H); 6.89 (dd, 1H, J$_1$=8.1 Hz, J$_2$=1.3 Hz); 6.77 (d, 1H, J=7.8 Hz); 6.65 (dd, 1H, J$_1$=7.8 Hz, J$_2$=2.1 Hz); 4.42 (s, 2H); 3.40 (s, 3H).

EXAMPLE 37

5-ethyl-2-{2-fluoro-4-[(4-hydroxybutyl)amino]phenoxy}phenol a) 4-ethyl-1-(2-fluoro-4-nitrophenoxy)-2-methoxybenzene

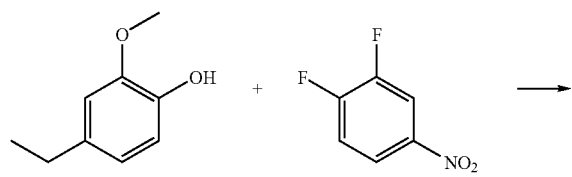

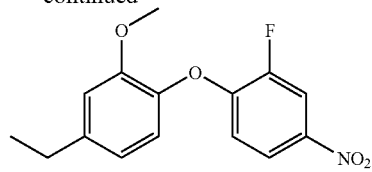

According to the procedure of example 20(a) except substituting 1-fluoro-4-nitro-2-(trifluoromethyl)benzene for 3,4-difluoronitrobenzene (318 mg; 2.0 mmol), the title compound (551 mg; 95%) was prepared as a yellow solid, used without further purification.

MS (ES) m/e 292 (M+H)$^+$.

b) 4-(4-ethyl-2-methoxyphenoxy)-3-fluoroaniline and 4-{[4-(4-ethyl-2-methoxyphenoxy)-3-fluorophenyl]amino}butan-1-ol

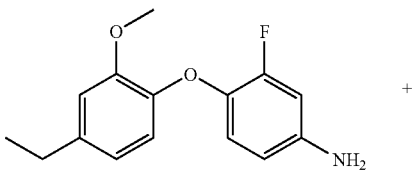

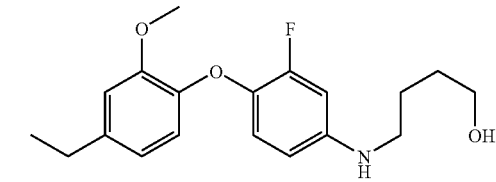

According to the procedure of example 20(b) except substituting 4-ethyl-2-methoxy-1-[4-nitro-2-(trifluoromethyl)phenoxy]benzene for 4-ethyl-1-(2-fluoro-4-nitrophenoxy)-2-methoxybenzene (551 mg; 1.89 mmol), two compounds were obtained after purification on silica gel (gradient: cyclohexane/ethyl acetate):

4-(4-ethyl-2-methoxyphenoxy)-3-fluoroaniline (202 mg; 40%)

MS (ES) m/e 262 (M+H)$^+$.

4-{[4-(4-ethyl-2-methoxyphenoxy)-3-fluorophenyl]amino}butan-1-ol (30 mg; 5%) MS (ES) m/e 334 (M+H)$^+$.

c) 5-ethyl-2-{2-fluoro-4-[(4-hydroxybutyl)amino]phenoxy}phenol

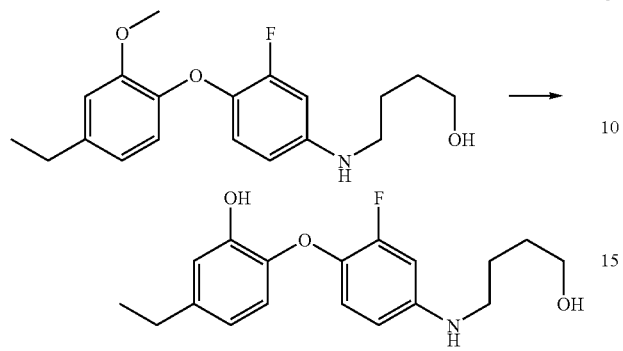

According to the procedure of example 1(b) except substituting 6-chloro-2-(2-methoxy-4-propylphenoxy)pyridin-3-amine for 4-{[4-(4-ethyl-2-methoxyphenoxy)-3-fluorophenyl]amino}butan-1-ol (30 mg; 0.009 mmol), the title compound (24 mg; 83%) was prepared as a light brown solid, after purification by preparative TLC (dichloromethane/methanol: 95/5).

MS (ES) m/e 320 (M+H)$^+$ $^1$H RMN (CDCl$_3$) δ (ppm): 6.90 (m, 2H); 6.60 (m, 2H); 6.42 (d, 1H, J=12.8 Hz); 6.33 (d, 1H, J=8.7 Hz); 3.71 (m, 2H); 3.12 (t, 2H, J=5.9 Hz); 2.56 (q, 2H, J=7.6 Hz); 1.70 (sl, 4H); 1.20 (t, 3H, J=7.6 Hz).

EXAMPLE 38

2-{3-[4-(4-Ethyl-2-hydroxy-phenoxy)-3-fluoro-phenoxy]-propyl}-isoindole-1,3-dione a) 4-(4-ethyl-2-methoxyphenoxy)-3-fluorophenol

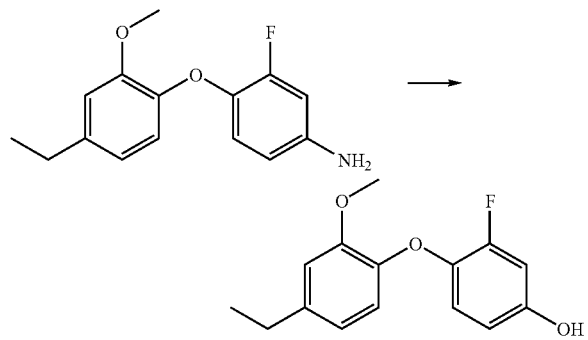

To a solution of 4-(4-ethyl-2-methoxyphenoxy)-3-fluoroaniline (215 mg; 0.82 mmol) in H$_2$SO$_4$ 35%, at 0° C., was added a solution of NaNO$_2$ (69 mg; 1 mmol) in water (1 mL). The mixture was stirred 30 min. at 0° C. A solution of copper (II) sulphate (1.85 g; 11.6 mmol) in 6 mL of water was added, followed by copper(I) oxide(99 mg; 0.69 mmol). The reaction was stirred 45 min. at room temperature, then hydrolysed with NaHCO$_3$ sat(6 mL) and NH$_4$OH. The mixture was extracted with ethyl acetate (3*5 mL). Combined organic phases were dried over Na$_2$SO$_4$, concentrated in vacuo. The title compound (85 mg; 0.032 mmol; 39%) was obtained as an oil, after purification by preparative TLC (cyclohexane/ethyl acetate: 7/3).

MS (ES) m/e 285 (M+Na)$^+$ b) 2-{3-[4-(4-Ethyl-2-methoxy-phenoxy)-3-fluoro-phenoxy]-propyl}-isoindole-1,3-dione

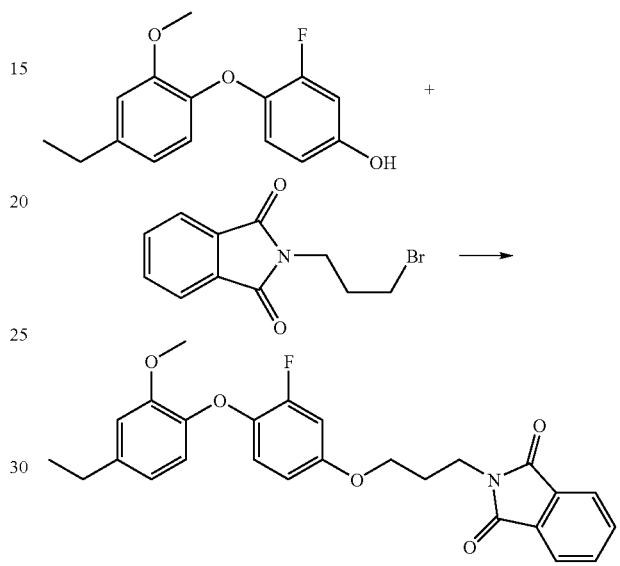

To a solution of 4-(4-ethyl-2-methoxyphenoxy)-3-fluorophenol (0.32 mmol; 85 mg) in dry acetone (3 mL), under argon, were added potassium hydroxide (0.39 mmol; 54 mg), NaI (0.065 mmol; 10 mg) and N-(3-bromopropyl)phtalimide (0.40 mmol; 107 mg). The reaction was stirred 3 days at 50° C. The mixture was concentrated in vacuo, hydrolysed with NH$_4$Cl sat.(5 mL) and extracted with ethyl acetate (3*3 mL). Combined organic phases were dried over Na$_2$SO$_4$, concentrated in vacuo. The title compound (75 mg; 0.17 mmol; 51%) was obtained as an oil, after purification by preparative TLC (cyclohexane/ethyl acetate: 7/3).

MS (ES) m/e 285 (M+Na)$^+$ $^1$H RMN (CDCl$_3$) δ (ppm): 7.83 (dd, 2H, J$_1$=5.2 Hz; J$_2$=3.0 Hz); 7.71 (dd, 2H, J$_1$=5.2 Hz; J$_2$=2.9 Hz); 6.86 (t, 1H, J=9.1 Hz); 6.80 (s, 1H); 6.67 (s, 2H); 6.61 (dd, 1H, J$_1$=12.1 Hz; J$_2$=2.5 Hz); 6.50 (d, 1H, J=8.9 Hz); 3.98 (t, 2H, J=5.9 Hz); 3.91-3.87 (m, 5H); 2.61 (q, 2H, J=7.6 Hz); 2.20-2.16 (m, 2H); 1.23 (t, 3H, J=7.6 Hz).

c) 2-{3-[4-(4-Ethyl-2-hydroxy-phenoxy)-3-fluoro-phenoxy]-propyl}-isoindole-1,3-dione

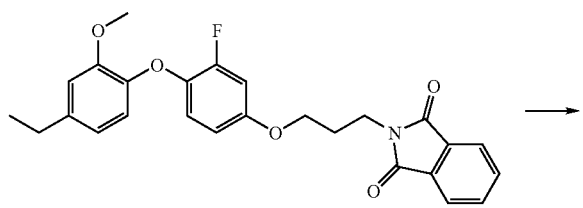

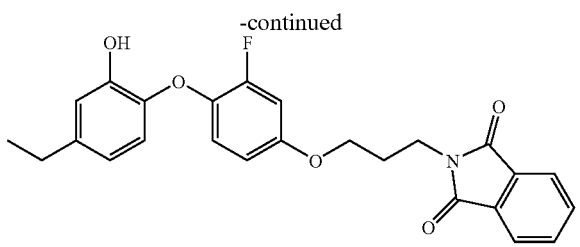

According to the procedure of example 1(b) except substituting 6-chloro-2-(2-methoxy-4-propylphenoxy)pyridin-3-amine by 2-{3-[4-(4-Ethyl-2-methoxy-phenoxy)-3-fluorophenoxy]-propyl}-isoindole-1,3-dione (64 mg; 0.14 mmol), the title compound was prepared in 83% yield (0.12 mmol; 52 mg) after purification by preparative TLC on silica gel (ethyl acetate/cyclohexane—30/70).

MS (ES) m/e 436 (M+H)$^+$ $^1$H RMN (CDCl$_3$) δ (ppm): 7.84 (dd, 2H, J$_1$=5.4 Hz; J$_2$=3.1 Hz); 7.71 (dd, 2H, J$_1$=5.4 Hz; J$_2$=3.0 Hz); 6.94 (t, 1H, J=9.0 Hz); 6.86 (s, 1H); 6.63-6.60 (m, 2H); 6.54-6.50 (m,1H); 3.98 (t, 2H, J=5.9 Hz); 3.90 (t, 2H, J=6.8 Hz); 2.56 (q, 2H, J=7.6 Hz); 2.17 (qt, 2H, J=6.2 Hz); 1.20 (t, 3H, J=7.6 Hz).

EXAMPLE 39

2-[4-(3-aminopropoxy)-2-fluorophenoxy]-5-ethyl phenol

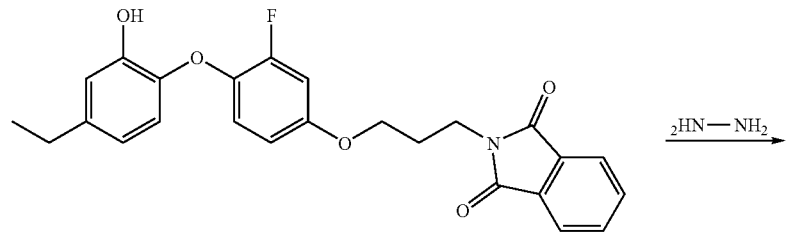

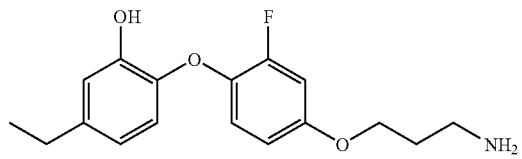

To a solution of 2-{3-[4-(4-Ethyl-2-hydroxy-phenoxy)-3-fluoro-phenoxy]-propyl}-isoindole-1,3-dione (0.096 mmol; 42 mg) in methanol (2 mL), under argon, was added hydrazine monohydrate (0.21 mmol; 10 µL). The reaction was heated to reflux for 1 h 30. After cooling to 0° C., the mixture was hydrolysed with HCl 1N and filtered. The filtrate was basified with NaOH 0.1 N (pH=11) and extracted with chloroform (3*5 ml). Combined organic phases were dried over Na$_2$SO$_4$, concentrated in vacuo. The title compound (13 mg; 0.04 mmol; 44%) was obtained as yellow oil, after purification by preparative TLC (dichloromethane/methanol/NH$_4$OH: 90/10/1).

MS (ES) m/e 306 (M+H)$^+$ $^1$H RMN (CDCl$_3$) δ (ppm): 6.92 (t, 1H, J=9.1 Hz); 6.85 (s, 1H); 6.68 (dd, 1H, J$_1$=12.1 Hz, J$_2$=2.6 Hz); 6.63-6.56 (m,3H); 3.90 (t, 2H, J=6.8 Hz); 3.86 (sl, 2H); 2.96(sl, 2H); 2.56 (q, 2H, J=7.6 Hz); 1.97 (qt, 2H, J=6.2 Hz); 1.19 (t, 3H, J=7.6 Hz).

EXAMPLE 40

[1-[4-(4-Ethyl-2-hydroxy-phenoxy)-3-fluoro-phenyl]-eth-(E)-ylideneaminooxy]-acetic acid ethyl ester

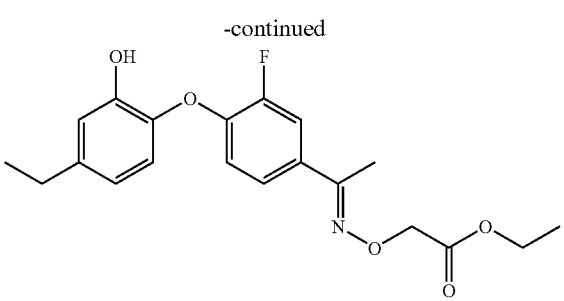

According to the procedure of example 30 except substituting O-methylhydroxylamine hydrochloride by (aminooxy)acetic acid hydrochloride (0.21 mmol; 23 mg), the title compound was isolated (43 mg; 65%) after purification by preparative (ethyl acetate/cyclohexane/acetic acid—40/60/1).

MS (ES) m/e 376 (M+H)$^+$ $^1$H RMN (CDCl$_3$) δ (ppm): 7.51 (dd, 1H, J$_1$=12.0 Hz, J$_2$=1.9 Hz); 7.32 (d, 1H, J=8.0 Hz); 6.96 (t, 1H, J=8.4 Hz); 6.89 (s, 1H); 6.75 (d, 1H, J=8.3 Hz); 6.66 (dd, 1H, J$_1$=8.2 Hz, J$_2$=1.6 Hz); 4.72 (s, 2H); 4.24 (q, 2H, J=7.1 Hz); 2.60 (q, 2H, J=7.6 Hz); 2.27 (s, 3H); 1.29 (t, 3H, J=7.1 Hz); 1.22 (t, 3H, J=7.6 Hz).

EXAMPLE 41

[({(1E)-1-[4-(4-ethyl-2-hydroxyphenoxy)-3-fluorophenyl]ethylidene}amino)oxy]acetic acid

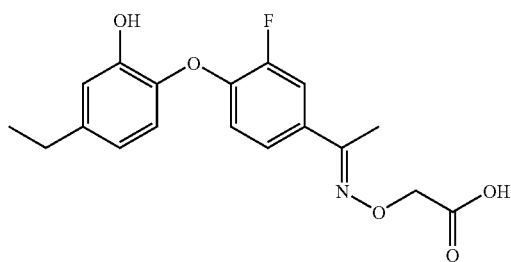 [SMILES: CCc1ccc(Oc2ccc(/C(C)=N/OCC(=O)O)cc2F)c(O)c1]

The title compound (11 mg; 18%) was isolated from the example 40 as a white solid, after purification by preparative TLC ethyl acetate/cyclohexane/acetic acid—40/60/1).

MS (ES) m/e 348 (M+H)$^+$ $^1$H RMN (MeOD) δ (ppm): 7.52 (d, 1H, J=12.5 Hz); 7.33 (d, 1H, J=8.3 Hz); 6.83-6.80 (m, 2H); 6.77 (t, 1H, J=8.0 Hz); 6.68 (dd, 1H, J$_1$=8.2 Hz, J$_2$=1.8 Hz); 4.86 (sl, 2H); 2.59 (q, 2H, J=7.6 Hz); 2.26 (s, 3H); 1.23 (t, 3H, J=7.6 Hz).

EXAMPLE 42

3-Morpholin-4-yl-propane-1-sulfonic acid [4-(4-ethyl-2-hydroxy-phenoxy)-3-fluoro-phenyl]-amide a) 3-chloro-N-[4-(4-ethyl-2-methoxyphenoxy)-3-fluorophenyl]propane-1-sulfonamide

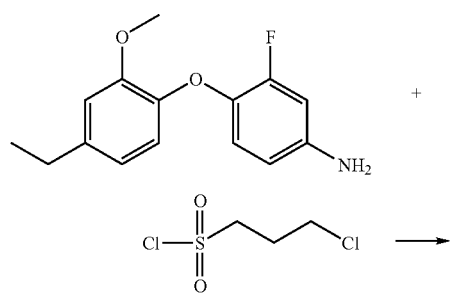

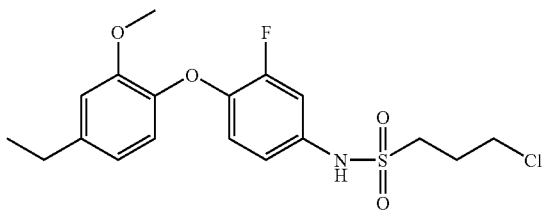

To a solution of 4-(4-ethyl-2-methoxyphenoxy)-3-fluoroaniline (0.38 mmol; 100 mg) in dry dichloromethane (1 mL), under argon, at 0° C. were added pyridine (0.46 mmol; 37 μL) and 3-chloropropanesulfonyle chloride (0.46 mmol; 56 μL). The reaction was stirred overnight at room temperature. The mixture was hydrolysed with NH$_4$Cl sat.(2 mL) and extracted with dichloromethane (3*1 mL). Combined organic phases were dried over Na$_2$SO$_4$, concentrated in vacuo. The title compound (200 mg; 0.38 mmol; quantitative) was obtained as a brown oil, used without further purification.

MS (ES) m/e 306 (M+H)$^+$ b) 3-Morpholin-4-yl-propane-1-sulfonicacid[4-(4-ethyl-2-methoxy-phenoxy)-3-fluoro-phenyl]-amide

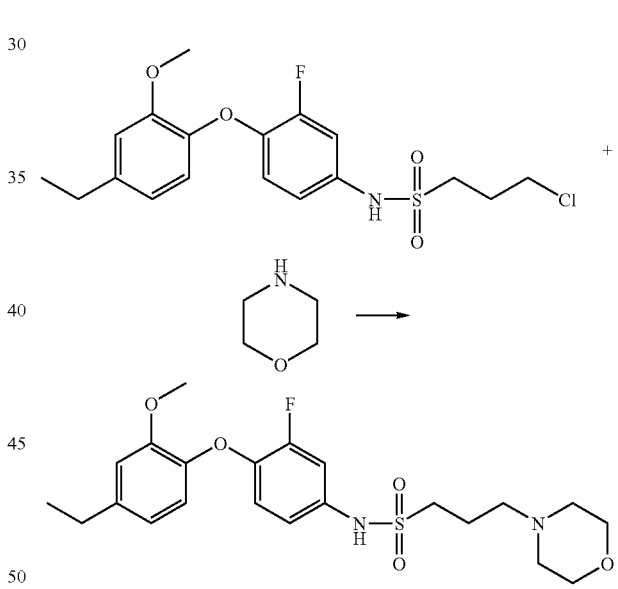

To a solution of 3-chloro-N-[4-(4-ethyl-2-methoxyphenoxy)-3-fluorophenyl]propane-1-sulfonamide (0.38 mmol; 153 mg) in dry acetonitrile (2 mL), under argon, was added morpholine (1.1 mmol; 100 μL). The reaction was heated at 50° C. overnight. After cooling to room temperature, the mixture was hydrolysed with 5 mL of water and extracted with dichloromethane (3*2 mL). Combined organic phases were dried over Na$_2$SO$_4$, concentrated in vacuo, the title compound (62 mg; 36%) was obtained after purification by preparative TLC on silica gel (ethyl acetate/cyclohexane—40/60).

MS (ES) m/e 453 (M+H)$^+$ $^1$H RMN (CDCl$_3$) δ (ppm): 7.11 (dd, 1H, J$_1$=12.0 Hz, J$_2$=2.1 Hz); 6.84-6.72 (m, 5H); 3.83 (s, 3H); 3.69 (m, 4H);

3.19 (t, 2H, J=7.1 Hz); 2.64 (q, 2H, J=7.6 Hz); 2.51-2.47 (m, 6H); 2.04 (qt, 2H, J=6.8 Hz); 1.25 (t, 3H, J=7.6 Hz).

c) 3-Morpholin-4-yl-propane-1-sulfonic acid [4-(4-ethyl-2-hydroxy-phenoxy)-3-fluoro-phenyl]-amide

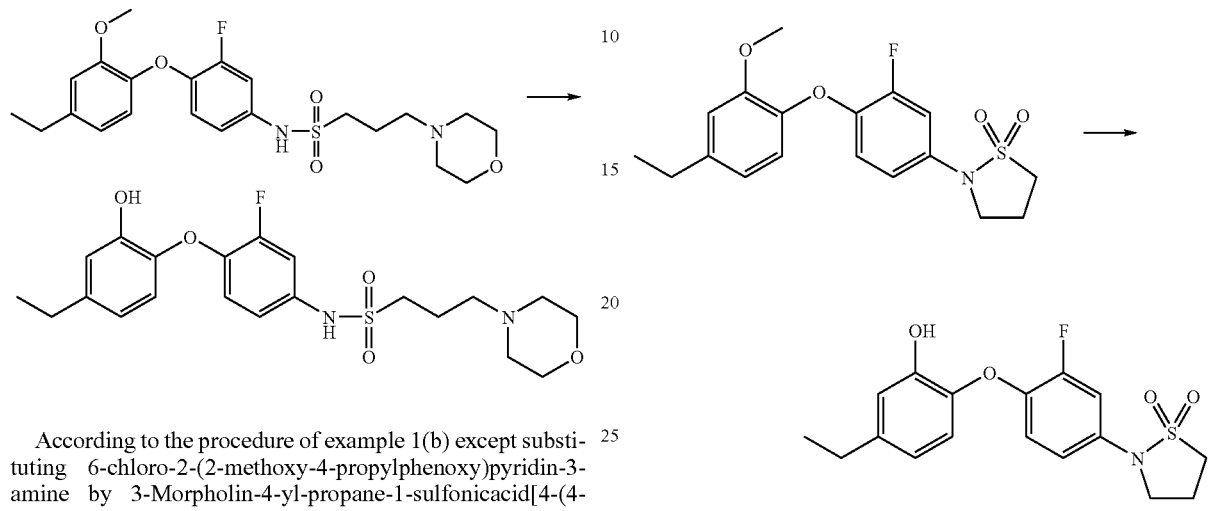

According to the procedure of example 1(b) except substituting 6-chloro-2-(2-methoxy-4-propylphenoxy)pyridin-3-amine by 3-Morpholin-4-yl-propane-1-sulfonicacid[4-(4-ethyl-2-methoxy-phenoxy)-3-fluoro-phenyl]-amide (0.11 mmol; 50 mg), the title compound was prepared in 60% yield (0.07 mmol; 29 mg) after purification by preparative TLC (dichloromethane/methanol—95/5).

MS (ES) m/e 439 (M+H)$^+$ $^1$H RMN (CDCl$_3$) δ (ppm): 7.16 (dd, 1H, J$_1$=11.7 Hz, J$_2$=2.3 Hz); 6.95-6.88 (m, 3H); 6.73 (d, 1H, J=8.2 Hz); 6.65 (dd, 1H, J$_1$=8.2 Hz, J$_2$=1.9 Hz); 3.71 (t, 4H, J=4.2 Hz); 3.18 (t, 2H, J=7.0 Hz); 2.61-2.53(m, 8H); 2.06 (qt, 2H, J=6.8 Hz); 1.21 (t, 3H, J=7.6 Hz).

EXAMPLE 43

2-[4-(1,1-Dioxo-isothiazolidin-2-yl)-2-fluoro-phenoxy]-5-ethyl-phenol a) 2-[4-(4-Ethyl-2-methoxy-phenoxy)-3-fluoro-phenyl]-isothiazolidine 1,1-dioxide

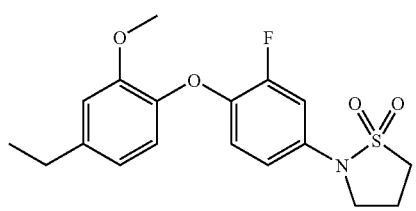 [SMILES: CCc1ccc(Oc2ccc(N3CCCS3(=O)=O)cc2F)c(OC)c1]

The title compound (44 mg; 31%) was isolated from the example 42(b) as a white solid, after purification by preparative TLC on silica gel (ethyl acetate/cyclohexane—40/60).

MS (ES) m/e 388 (M+Na)$^+$ $^1$H RMN (CDCl$_3$) δ (ppm): 7.11 (dd, 1H, J$_1$=12.0 Hz, J$_2$=2.5 Hz); 6.94 (d, 1H, J=8.9 Hz); 6.87-6.80 (m,3H); 6.72 (dd, 1H, J$_1$=8.1 Hz, J$_2$=1.3 Hz); 3.83 (s, 3H); 3.71 (t, 2H, J=6.6 Hz); 3.38 (t, 2H, J=7.4 Hz); 2.63 (q, 2H, J=7.6 Hz); 2.51 (qt, 2H, J=7.6 Hz); 1.24 (t, 3H, J=7.6 Hz).

b) 2-[4-(1,1-Dioxo-isothiazolidin-2-yl)-2-fluoro-phenoxy]-5-ethyl-phenol

According to the procedure of example 1(b) except substituting 6-chloro-2-(2-methoxy-4-propylphenoxy)pyridin-3-amine by 2-[4-(4-Ethyl-2-methoxy-phenoxy)-3-fluoro-phenyl]-isothiazolidine 1,1-dioxide (0.10 mmol; 38 mg), the title compound was prepared in 76% yield (0.08 mmol; 28 mg) after purification by preparative TLC on silica gel (dichloromethane/methanol—95/5).

MS (ES) m/e 374 (M+H)$^+$ $^1$H RMN (CDCl$_3$) δ (ppm): 7.11 (dd, 1H, J$_1$=12.0 Hz, J$_2$=2.5 Hz); 7.03-6.96 (m, 2H); 6.88 (sl, 1H); 6.70 (d, 1H, J=8.2 Hz); 6.63 (dd, 1H, J$_1$=8.2 Hz, J$_2$=1.8 Hz); 3.73 (t, 2H, J=6.6 Hz); 3.39 (t, 2H, J=7.4 Hz); 2.61-2.50 (m, 4H); 1.21 (t, 3H, J=7.6 Hz).

EXAMPLE 44 ethyl[4-(4-ethyl-2-hydroxyphenoxy)-3-fluorophenyl]carbamate a) ethyl[4-(4-ethyl-2-methoxyphenoxy)-3-fluorophenyl]carbamate

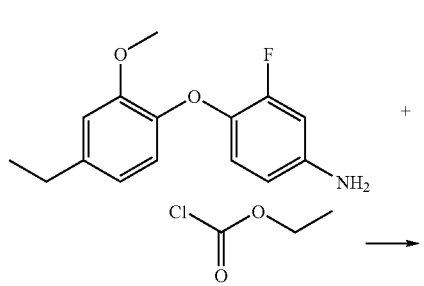

-continued

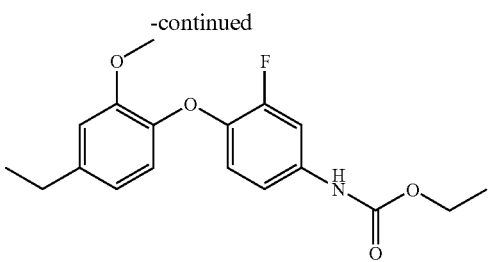

4-(4-ethyl-2-methoxyphenoxy)-3-fluoroaniline (0.19 mmol; 50 mg) in 1 mL THF/NaHCO₃ sat. (1/1), at 0° C. were added ethylchloroformate (0.38 mmol; 41 mg). The reaction was stirred overnight at room temperature. The mixture was hydrolysed with NH₄Cl sat.(4 mL) and extracted with dichloromethane (3*2 mL). Combined organic phases were dried over Na₂SO₄, concentrated in vacuo. The title compound (36 mg; 56%) was obtained as a brown oil, after purification by preparative TLC on silica gel (ethyl acetate/cyclohexane—70/30).

MS (ES) m/e 334 (M+H)⁺ b) ethyl[4-(4-ethyl-2-hydroxyphenoxy)-3-fluorophenyl]carbamate

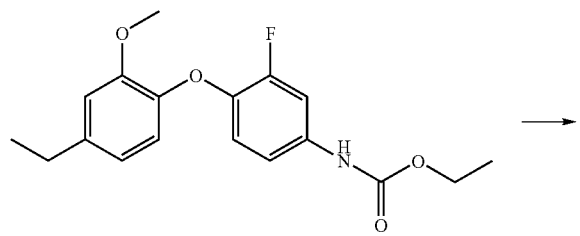

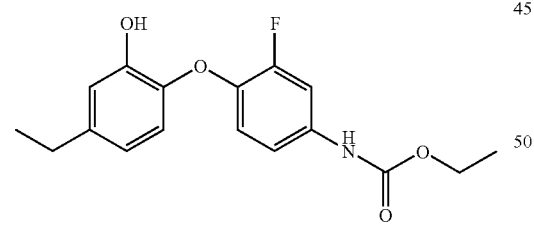

According to the procedure of example 1(b) except substituting 6-chloro-2-(2-methoxy-4-propylphenoxy)pyridin-3-amine by ethyl[4-(4-ethyl-2-methoxyphenoxy)-3-fluorophenyl]carbamate (0.11 mmol; 35 mg), the title compound was prepared in 69% yield (0.07 mmol; 23 mg) after purification by preparative TLC (ethyl acetate/cyclohexane—70/30).

MS (ES) m/e 320 (M+H)⁺

¹H RMN (CDCl₃) δ (ppm): 7.41 (d, 1H, J=12.0 Hz); 6.99-6.96 (m, 2H); 6.88 (sl, 1H); 6.67 (d, 1H, J=8.1 Hz); 6.62 (dd, 1H, J₁=8.2 Hz, J₂=1.8 Hz); 4.23 (q, 2H, J=7.1 Hz); 2.58 (q, 2H, J=7.6 Hz); 1.31 (t, 3H, J=7.1 Hz); 1.21 (t, 3H, J=7.6 Hz).

EXAMPLE 45

5-ethyl-2-[4-(ethylamino)-2-fluorophenoxy]phenol a) N-ethyl-4-(4-ethyl-2-methoxyphenoxy)-3-fluoroaniline

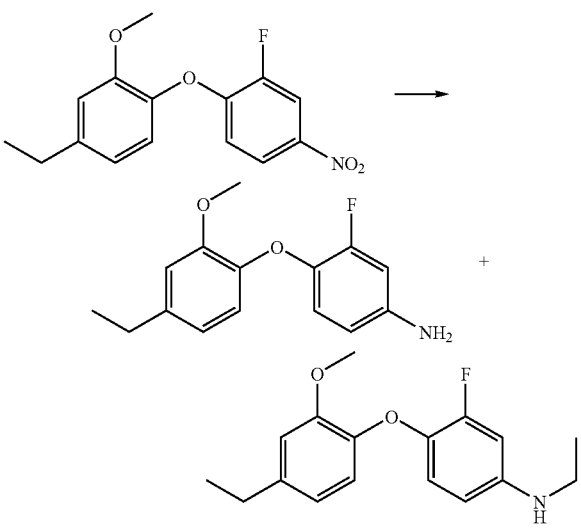

According to the procedure of example 20(b) except substituting 4-ethyl-2-methoxy-1-[4-nitro-2-(trifluoromethyl)phenoxy]benzene for 4-ethyl-1-(2-fluoro-4-nitrophenoxy)-2-methoxybenzene (1.16 g; 4.0 mmol) and tetrahydrofurane for ethanol (16 mL), two compounds were obtained after purification on silica gel (gradient cyclohexane/dichloromethane) 4-(4-ethyl-2-methoxyphenoxy)-3-fluoroaniline (466 mg; 45%)

MS (ES) m/e 262 (M+H)⁺

N-ethyl-4-(4-ethyl-2-methoxyphenox)-3-fluoroaniline (461 mg; 40%) MS (ES) m/e 290 (M+H)⁺ b) 5-ethyl-2-[4-(ethylamino)-2-fluorophenoxy]phenol

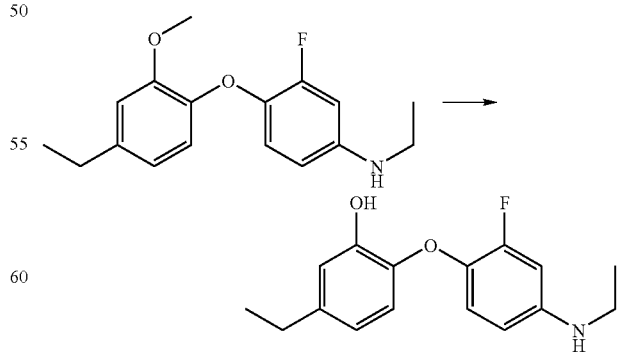

According to the procedure of example 1(b) except substituting 6-chloro-2-(2-methoxy-4-propylphenoxy)pyridin-3-amine for N-ethyl-4-(4-ethyl-2-methoxyphenoxy)-3-fluoroaniline (461 mg; 1.59 mmol), the title compound (270 mg; 62%) was prepared as a light brown solid, after purification by chromatography on silica gel (gradient dichloromethane/ethyl acetate).

MS (ES) m/e 276 (M+H)$^+$ $^1$H RMN (CDCl$_3$) δ (ppm): 6.93 (t, 1H, J=8.9 Hz); 6.87 (s, 1H); 6.62 (q, 2H, J=6.6 Hz); 6.46 (dd, 1H, J$_1$=12.7 Hz, J$_2$=2.5 Hz); 6.37 (d, 1H, J=8.7 Hz); 3.15 (q, 2H, J=7.2 Hz); 2.59 (q, 2H, J=7.6 Hz); 1.30 (t, 3H, J=7.1 Hz); 1.21 (t, 3H, J=7.6 Hz).

EXAMPLE 46

5-ethyl-2-[2-(methylamino)phenoxy]phenol a)
N-[2-(4-ethyl-2-methoxyphenoxy)phenyl]formamide

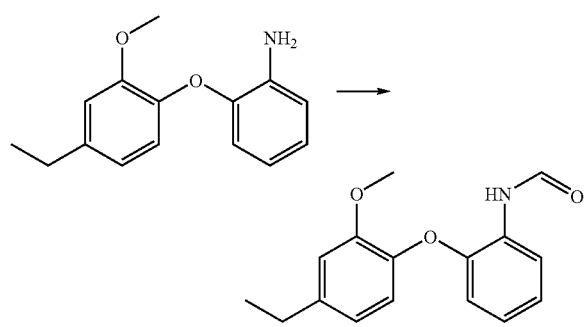

To acetic anhydride (0.53 mmol; 51 µL) under argon, at 0° C., was added formic acid (0.66 mmol; 25 µL). The reaction was stirred 2 hours at 60° C. After cooling to 0° C., the mixture was diluted with 1 mL of dry THF, followed by a solution of 2-(4-ethyl-2-methoxyphenoxy)aniline (0.21 mmol; 50 mg) in dry THF (1 mL). The reaction was stirred 2 hours at room temperature. The mixture was concentrated in vacuo to give the title compound (72 mg; quantitative) as a brown oil, used without further purification.

MS (ES) m/e 272 (M+H)$^+$.

b) 2-(4-ethyl-2-methoxyphenoxy)-N-methylaniline

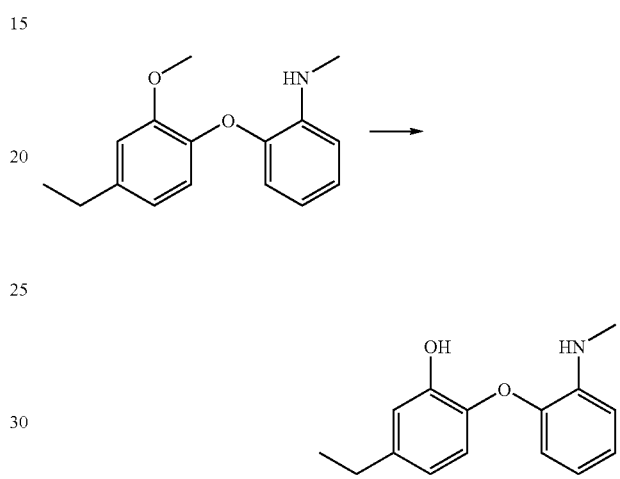

To a solution of N-[2-(4-ethyl-2-methoxyphenoxy)phenyl]formamide (0.21 mmol; 72 mg), under argon, in dry THF was added at 0° C., borane dimethylsulfide complex (0.51 mmol, 49 µL). The reaction was stirred at reflux for 3 h 30. After cooling to 0° C., the mixture was diluted with 1 mL of dry methanol and stirred 1 hour. HCl (4M in dioxane) was added at 0° C. until pH 2, then the mixture was refluxed 1 hour. After cooling to room temperature, the reaction was diluted with 5 mL of methanol and concentrated in vacuo. The crude was treated with 5 mL of NaOH (1N), until pH 12, and extracted with ethyl acetate (3*2mL). Combined organic phases were dried over Na$_2$SO$_4$ and concentrated in vacuo to yield the title compound (66 mg, quantitative) as a red oil used without further purification.

MS (ES) m/e 258 (M+H)$^+$.

c) 5-ethyl-2-[2-(methylamino)phenoxy]phenol

According to the procedure of example 1(b) except substituting 6-chloro-2-(2-methoxy-4-propylphenoxy)pyridin-3-amine by 2-(4-ethyl-2-methoxyphenoxy)-N-methylaniline (0.26 mmol; 66 mg), the title compound was prepared in 50% yield (0.13 mmol; 31 mg) after purification by preparative TLC (ethyl acetate/cyclohexane—70/30).

MS (ES) m/e 244 (M+H)$^+$ $^1$H RMN (CDCl$_3$) δ (ppm): 7.07 (t, 1H, J=6.6 Hz); 6.88 (s, 1H); 6.81-6.76 (m, 3H); 6.69-6.64 (m, 2H); 2.89 (s, 3H); 2.60 (q, 2H, J=7.6 Hz); 1.23 (t, 3H, J=7.6 Hz).

EXAMPLE 47

5-ethyl-2-[4-(methylsulfonyl)phenoxy]phenol a) 4-(4-ethyl-2-methoxyphenoxy)phenyl methyl sulfone

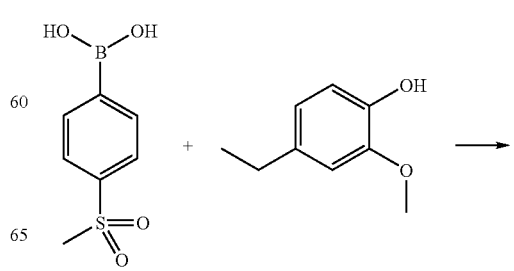

-continued

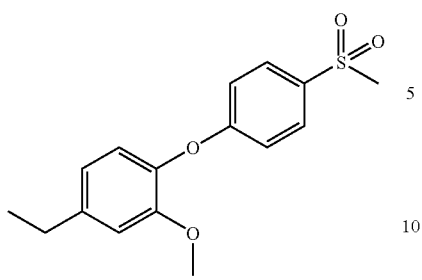

To a suspension of Cu(OAc)₂ (3.0 mmol; 543 mg), 4-(methanesulphonyl)benzeneboronic acid (4.0 mmol; 800 mg) and activated molecular sieves (800 mg) under air, in anhydrous dichloromethane (5 mL), were added 2-methoxy-4-ethylphenol (2.0 mmol; 0.28 mL), anhydrous triethylamine (10 mmol; 1.4 mL), and anhydrous pyridine (10 mmol; 0.8 mL). The reaction was stirred for 2 days at room temperature. The crude was filtered on silica gel, washed with ethyl acetate, concentrated. The residue was then purified by column chromatography (gradient cyclohexane/dichloromethane) to yield the title compound as clear oil (617 mg; 2.0 mmol; quantitative).

MS (ES) m/e 307 (M+H)⁺ b) 5-ethyl-2-[4-(methylsulfonyl)phenoxy]phenol

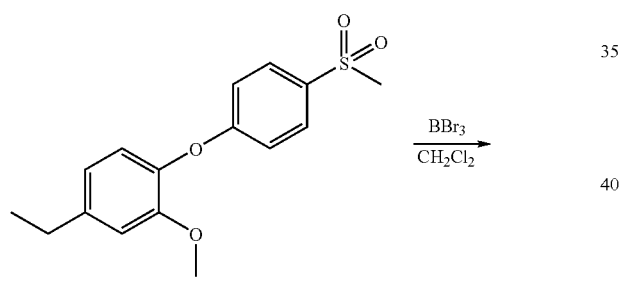

According to the procedure of example 1(b) except substituting 6-chloro-2-(2-methoxy-4-propylphenoxy)pyridin-3-amine for 4-(4-ethyl-2-methoxyphenoxy)phenyl methyl sulfone (130 mg; 0.42 mmol), the title compound (94 mg; 76%) was prepared as a white solid, after purification by preparative TLC (dichloromethane).

MS (ES) m/e 293 (M+H)⁺

¹H RMN (CDCl₃) δ (ppm): 7.91 (d, 2H, J=8.8 Hz); 7.13 (d, 2H, J=8.9 Hz); 6.95 (s, 1H) 6.92 (d, 1H, J=8.2 Hz); 6.78 (d, 1H, J=8.2 Hz); 3.07 (s, 3H); 2.66 (q, 2H, J=7.6 Hz); 1.26 (t, 3H, J=7.6 Hz).

EXAMPLE 48

5-Ethyl-2-[2-fluoro-4-(3-hydroxy-propylamino)-phenoxy]-phenol a) 2-(benzyloxy)-4-ethyl-1-(2-fluoro-4-nitrophenoxy)benzene

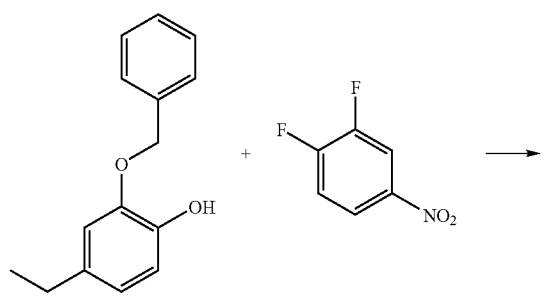

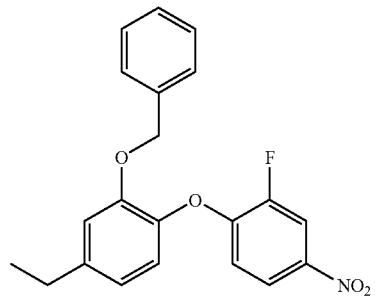

According to the procedure of example 20(a) except substituting 1-fluoro-4-nitro-2-(trifluoromethyl)benzene for 3,4-difluoronitrobenzene (30.5 g; 192 mmol), and 2-methoxy-4-ethylphenol for 2-(benzyloxy)-4-ethylphenol (33.6 g; 147 mmol) the title compound (58.1 g; 100%) was prepared as a brown oil, used without further purification.

b) 4-[2-(benzyloxy)-4-ethylphenoxy]-3-fluoroaniline

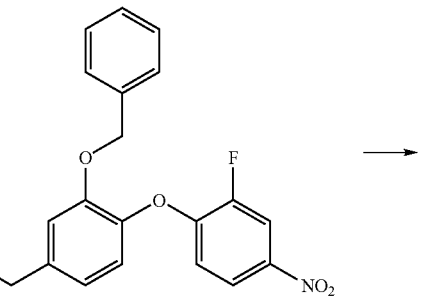

-continued

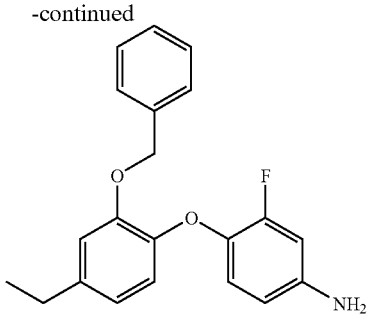

To a solution of 2-(benzyloxy)-4-ethyl-1-(2-fluoro-4-nitro phenoxy)benzene (25 g; 68 mmol) in ether (86 mL), under argon cooled to 0° C., was added a suspension of tin dichloride (153 g; 801 mmol) in HCl (50 mL; 2 mol). The mixture was allowed to warm up to room temperature overnight, then a 10% NaOH solution was added dropwise. The resulting mixture was extracted with ethyl acetate (5*400 mL). Combined organic phases were washed with water (400 mL) and brine, then dried over $Na_2SO_4$ and concentrated. The residue was purified on silica gel (ethyl acetate/cyclohexane 1:9) to yield the title compound as a light brown solid (15.8 g; 68.8%)

MS (ES) m/e 338 (M+H)$^+$ c) 3-[4-(2-Benzyloxy-4-ethyl-phenoxy)-3-fluoro-phenylamino]-propan-1-ol

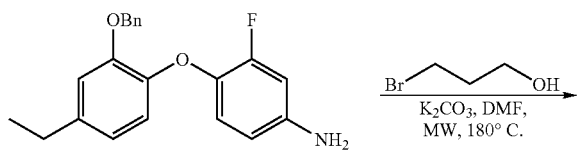

4-[2-(benzyloxy)-4-ethylphenoxy]-3-fluoroaniline (500 mg, 1.48 mmol), $K_2CO_3$ (1.23 g, 8.9 mmol) and 3-bromo-1-propanol (410 mg, 2.9 mmol) were taken in dry DMF (2 ml) in a microwave vial and was subjected to microwave at 180° C. for 2 h. The reaction mixture was filtered over celite and the residue washed thouroughly with ethyl acetate. The combined organic fractions including the filtrate were washed with water, brine, dried over $Na_2SO_4$ and concentrated. The crude obtained was combined with earlier crude products obtained from a 100 mg and 200 mg batches and purified together by column chromatography over silica gel using 40% ethylacetate in pet ether as eluant to get 400 mg (42.6%) of pure title compound.

d) 5-Ethyl-2-[2-fluoro-4-(3-hydroxy-propylamino)-phenoxy]-phenol

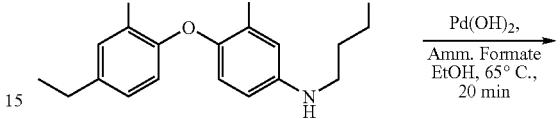

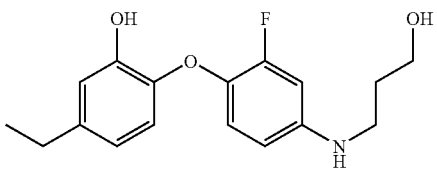

3-[4-(2-Benzyloxy-4-ethyl-phenoxy)-3-fluoro-phenylamino]-propan-1-ol (400 mg, 1.01 mmol) was taken in 15 ml of absolute ethanol, under nitrogen. To this was added Pd(OH)$_2$, (20%, 50 mg) followed by ammonium formate (200 mg, 3.1 mmol). The reaction mixture was heated at 65° C. and monitored by TLC. After complete consumption of starting material (20 minutes), the heating was stopped and mixture cooled to rt. The reaction mixture was filtered through celite and the residue was washed with methanol. The combined filtrate was concentrated to obtain 300 mg of crude compound showing 70% by HPLC. The crude was purified by preparative HPLC (Column: C18 Symmetry (300×19 mm), 7µ, Mobile phase A: 20 mM ammonium acetate, Mobile phase B: Acetonitrile) to get 140 mg (45.3%) of title compound.

EXAMPLE 49

5-ethyl-2-(4-{[(E)-pyrrolidin-2-ylidenemethyl]sulfonyl}phenoxy)phenol a) (2E)-2-({[4-(4-ethyl-2-methoxyphenoxy)phenyl]sulfonyl}methylene)pyrrolidine

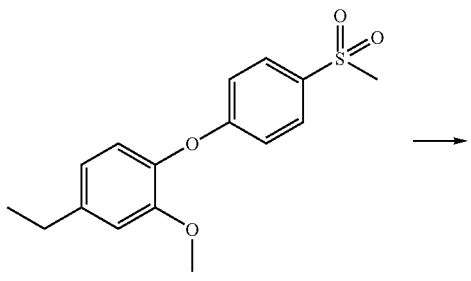

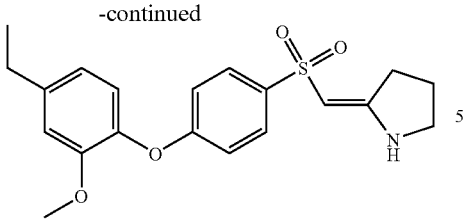

To a solution of 4-(4-ethyl-2-methoxyphenoxy)phenyl methyl sulfone (0.44 mmol; 136 mg), in anhydrous THF (1 mL), under argon, cooled to 0° C., was added sBuLi (1.2M in cyclohexane; 0.89 mmol; 0.74 mL). After stirring for 30 min, a solution of 1-BOC-2-Pyrrolidinone (0.44 mmol; 0.08 mL) in anhydrous THF (1 mL) was slowly added. The reaction was stirred at 0° C. for 30 min. then slowly warmed up to toom temperature overnight. The mixture was quenched with water and NH$_4$Cl sat. (3 mL), extracted with ethyl acetate (2*3 mL), to yield a light yellow oil (164 mg), used without further purification.

MS (ES) m/e 374 (M+H)$^+$ b) 5-ethyl-2-(4-{[(E)-pyrrolidin-2-ylidenemethyl]sulfonyl}phenoxy)phenol

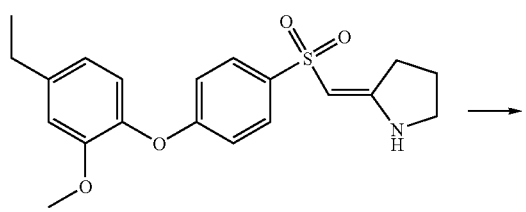

According to the procedure of example 1(b) except substituting 6-chloro-2-(2-methoxy-4-propylphenoxy)pyridin-3-amine for (2E)-2-({[4-(4-ethyl-2-methoxyphenoxy)phenyl]sulfonyl}methylene)pyrrolidine (164 mg; 0.44 mmol), the title compound (34 mg; 0.09 mmol; 22%) was prepared as a clear oil, after purification by preparative TLC (dichloromethane/ethyl acetate).

MS (ES) m/e 378 (M+H$_2$O+H)$^+$ $^1$H RMN (CDCl$_3$) δ (ppm): 7.78 (d, 2H, J=8.8 Hz); 6.99 (d, 2H, J=8.8 Hz); 6.90 (s, 1H); 6.87 (d, 1H, J=8.3 Hz); 6.73 (d, 1H, J=8.0 Hz); 4.66 (s, 1H); 3.75 (t, 2H, J=1.8 Hz); 2.79 (q, 2H, J=6.7 Hz); 2.63 (t, 2H, J=7.6 Hz); 1.95 (qu, 2H, J=7.1 Hz); 1.24 (t, 3H, J=7.6 Hz).

EXAMPLE 50

2-(2-amino-5-fluorophenoxy)-5-ethylphenol a) 4-ethyl-1-(3-fluoro-4-nitrophenoxy)-2-methoxybenzene and 4-ethyl-1-(5-fluoro-2-nitrophenoxy)-2-methoxybenzene

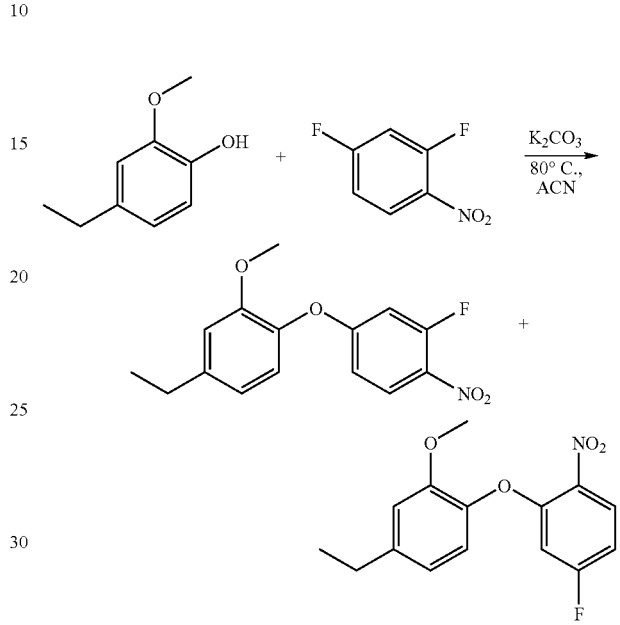

According to the procedure of example 20(a) except substituting 1-fluoro-4-nitro-2-(trifluoromethyl)benzene for 1,3-difluoro-4-nitrobenzene (110 µL; 1 mmol), the title products were obtained as a yellow solid (253 mg; 87%), after purification by preparative TLC (cyclohexane/ethyl acetate: 9/1).

MS (ES) m/e 292 (M+H)$^+$.

b) 4-(4-ethyl-2-methoxyphenoxy)-2-fluoroaniline and 2-(4-ethyl-2-methoxyphenoxy)-4-fluoroaniline

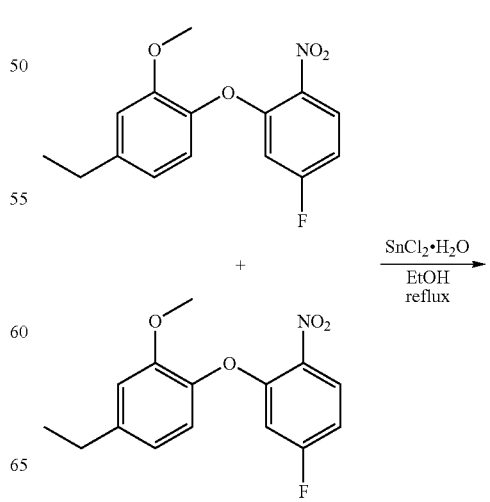

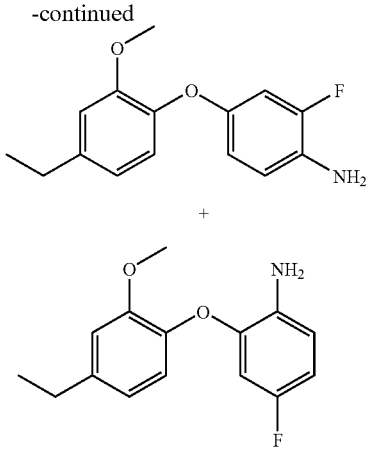

To a solution of 4-ethyl-1-(3-fluoro-4-nitrophenoxy)-2-methoxybenzene and 4-ethyl-1-(5-fluoro-2-nitrophenoxy)-2-methoxybenzene (100.5 mg, 0.69 mmol) in ethanol (5 mL) was added Tin(II)chloride dihydrate (794 mg, 3.45 mmol). The reaction mixture was heated to reflux for 1 h 30. The reaction mixture was washed with water, solid sodium hydrogenocarbonate and a NaOH solution (1 N). The mixture was extracted with ethyl acetate. Combined organic phases were dried over $Na_2SO_4$, concentrated in vacuo, to give the title products as a light brown oil (51 mg; 28%), after purification by preparative TLC (cyclohexane/ethyl acetate: 7/3).

MS (ES) m/e 262 (M+H)$^+$.

c) 2-(2-amino-5-fluorophenoxy)-5-ethylphenol

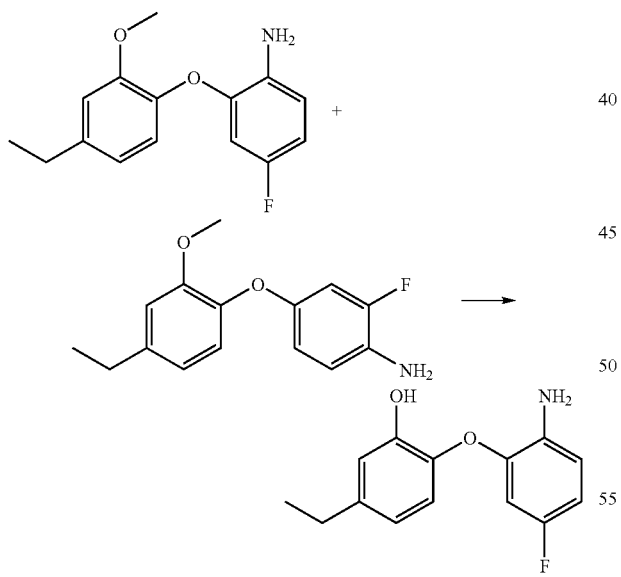

According to the procedure of example 5(b), except substituting 2-fluoro-6-(2-methoxy-4-propylphenoxy)pyridine for a mixture of 4-(4-ethyl-2-methoxyphenoxy)-2-fluoroaniline and 2-(4-ethyl-2-methoxyphenoxy)-4-fluoroaniline (50.9 mg, 0.19 mmol), the title compound (8.9 mg; 19%) was obtained after purification by preparative TLC (dichloromethane/ethyl acetate: 9/1).

MS (ES) m/e 248 (M+H)$^+$ $^1$H NMR (CDCl$_3$) δ (ppm): 6.90-6.87 (m, 2H); 6.80-6.67 (m, 3H); 6.59 (dd, 1H, J$_1$=2.8 Hz; J$_2$=9.6 Hz); 2.62 (q, 2H, J=7.6 Hz); 1.25 (t, 3H, J=7.6 Hz).

EXAMPLE 51

N-[4-(4-ethyl-2-hydroxyphenoxy)-3-fluorophenyl]-2,2,2-trifluoroethanesulfonamide a) N-[4-(4-ethyl-2-methoxyphenoxy)-3-fluorophenyl]-2,2,2-trifluoroethanesulfonamide

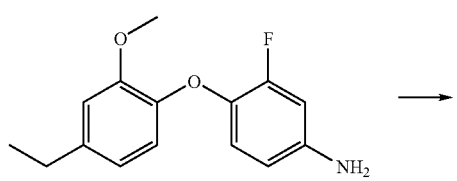

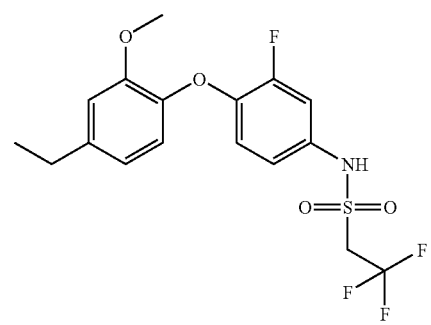

According to the procedure of example 42(a) except substituting 3-chloropropanesulfonyle chloride by Trifluoroethanesulfonyl chloride (0.4 6 mmol; 84 mg), the title compound was prepared (177 mg; quantitative yield) as a brown oil used without further purification.

MS (ES) m/e 408 (M+H)$^+$ b) N-[4-(4-ethyl-2-hydroxyphenoxy)-3-fluorophenyl]-2,2,2-trifluoroethanesulfonamide

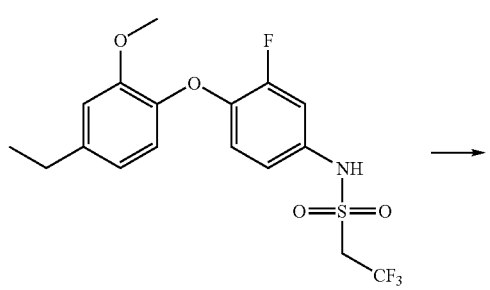

-continued

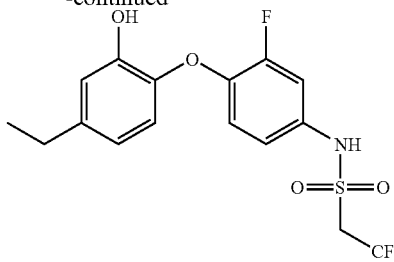

According to the procedure of example 1(b) except substituting 6-chloro-2-(2-methoxy-4-propylphenoxy)pyridin-3-amine by N-[4-(4-ethyl-2-methoxyphenoxy)-3-fluorophenyl]-2,2,2-trifluoroethanesulfonamide (0.38 mmol; 156 mg), the title compound was prepared in 53% yield (0.20 mmol; 80 mg) after purification by preparative TLC (cyclohexane/ethyl acetate—7/3).

MS (ES) m/e 394 (M+H)+

$^1$H RMN (CDCl$_3$) δ (ppm): 7.19 (dd, 1H, J$_1$=11.4 Hz, J$_2$=2.4 Hz); 7.11 (sl, 1H); 7.01-6.93 (m, 2H); 6.90 (d, 1H, J=1.9 Hz); 6.77 (d, 1H, J=8.2 Hz); 6.69 (dd, 1H, J$_1$=8.2 Hz, J$_2$=2.0 Hz); 3.83 (q, 2H, J=8.8 Hz); 2.60 (q, 2H, J=7.6 Hz); 1.24 (t, 3H, J=7.6 Hz).

EXAMPLE 52

N-[4-(4-ethyl-2-hydroxyphenoxy)-3-fluorophenyl]cyclopropane sulfonamide a) N-[4-(4-ethyl-2-methoxyphenoxy)-3-fluorophenyl]cyclopropane sulfonamide

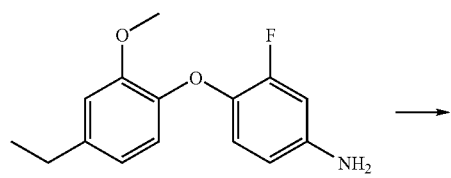

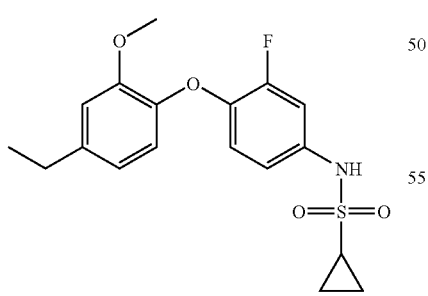

According to the procedure of example 42(a) except substituting 3-chloropropanesulfonyle chloride by cyclopropanesulfonyl chloride (0.46 mmol; 47 μL), the title compound was prepared (170 mg; quantitative yield) as a brown oil used without further purification.

MS (ES) m/e 366 (M+H)+ b) N-[4-(4-ethyl-2-hydroxyphenoxy)-3-fluorophenyl]cyclopropane sulfonamide

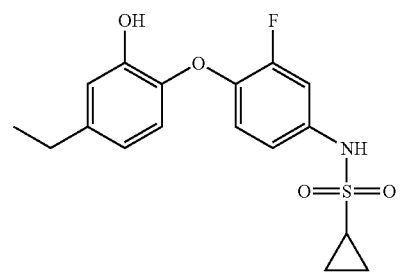

According to the procedure of example 1(b) except substituting 6-chloro-2-(2-methoxy-4-propylphenoxy)pyridin-3-amine by N-[4-(4-ethyl-2-methoxyphenoxy)-3-fluorophenyl]cyclopropane sulfonamide (0.38 mmol; 140 mg), the title compound was prepared in 94% yield (0.36 mmol; 126 mg) after purification by preparative TLC (cyclohexane/ethyl acetate—7/3).

MS (ES) m/e 352 (M+H)+

$^1$H RMN (CDCl$_3$) δ (ppm): 7.19 (d, 1H, J=11.8 Hz); 6.97 (m, 2H); 6.87 (m, 2H); 6.72 (d, 1H, J=8.3 Hz); 6.66 (dd, 1H, J$_1$=8.3 Hz, J$_2$=2.0 Hz); 2.59 (q, 2H, J=7.6 Hz); 2.51 (m, 1H); 1.24-1.17 (m, 5H); 1.03-0.98 (m; 2H)

EXAMPLE 53

5-ethyl-2-{4-[(3-hydroxybutyl)sulfonyl]phenoxy}phenol a) 4-{[4-(4-ethyl-2-methoxyphenoxy)phenyl]sulfonyl}butan-2-ol

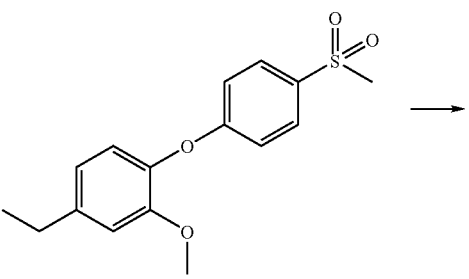

85

-continued

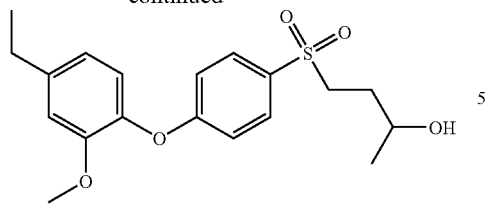

According to the procedure of example 49(a) except substituting 1-BOC-2-Pyrrolidinone for propylene oxide (0.2 mL; 2.8 mmol), the title compound (200 mg; 0.56 mmol; 100%) was prepared as a yellow oil, used without purification.

MS (ES) m/e 365 (M+H)$^+$ b) 5-ethyl-2-{4-[(3-hydroxybutyl)sulfonyl]phenoxy}phenol

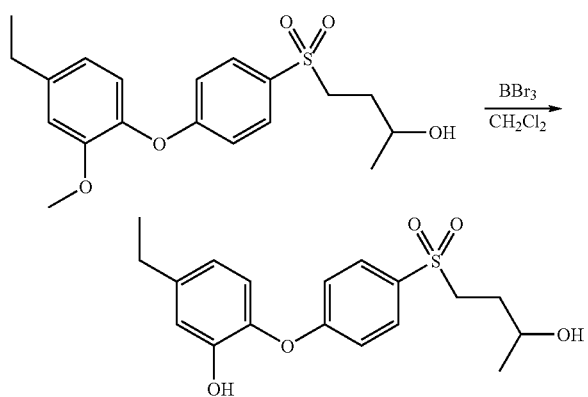

According to the procedure of example 1(b) except substituting 6-chloro-2-(2-methoxy-4-propylphenoxy)pyridin-3-amine for 4-{[4-(4-ethyl-2-methoxyphenoxy)phenyl]sulfonyl}butan-2-ol (200 mg; 0.56 mmol), the title compound (11 mg; 0.03 mmol; 6%) was prepared as a clear oil, after purification by preparative TLC (dichloromethane/ethyl acetate).

MS (ES) m/e 351 (M+H)$^+$ $^1$H RMN (CDCl$_3$) δ (ppm): 7.81 (d, 2H, J=8.9 Hz); 7.08 (d, 2H, J=8.9 Hz); 6.90 (d, 2H, J=9.9 Hz); 6.75 (d, 1H, J=8.2 Hz); 5.6 (sl, 1H); 3.90 (m, 1H); 3.21 (m, 2H); 2.63 (q, 2H, J=7.6 Hz); 1.91 (m, 1H); 1.74 (m, 1H); 1.26 (t, 3H, J=7.6 Hz); 1.20 (d, 3H, J=6.2 Hz).

EXAMPLE 54

2-(2-amino-5-methylphenoxy)-5-ethylphenol a) 4-ethyl-2-methoxy-1-(5-methyl-2-nitrophenoxy)benzene

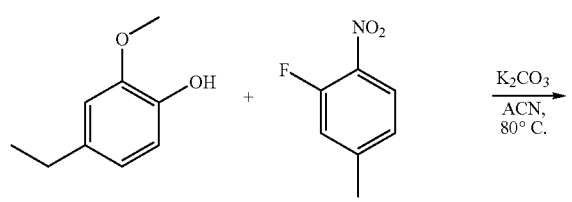

86

-continued

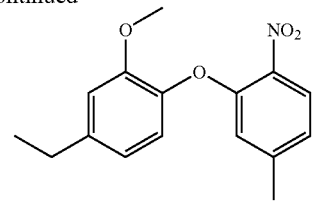

According to the procedure of example 20(a) except substituting 1-fluoro-4-nitro-2-(trifluoromethyl)benzene for 2-fluoro-4-nitrotoluene (157 mg; 1 mmol), the title compound (258 mg; 90%) was prepared as a yellow oil after purification by preparative TLC (cyclohexane/ethyl acetate: 7/3).

MS (ES) m/e 288 (M+H)$^+$.

b) 4-ethyl-2-methoxy-1-[(3-methyl-5-amino)phenoxy]benzene

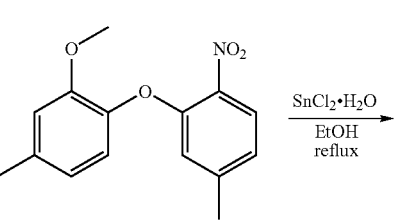

According to the procedure of example 50(b) except substituting 4-(4-ethyl-2-methoxyphenoxy)-2-fluoroaniline and 2-(4-ethyl-2-methoxyphenoxy)-4-fluoroaniline for 4-ethyl-2-methoxy-1-[(5-methyl-2-nitro)phenoxy]benzene (257 mg, 0.90 mmol), the title compound was prepared as a brown oil (167 mg; 72%), after purification by preparative TLC (cyclohexane/ethyl acetate: 7/3).

MS (ES) m/e 258 (M+H)$^+$.

c) 2-(2-amino-5-methylphenoxy)-5-ethylphenol

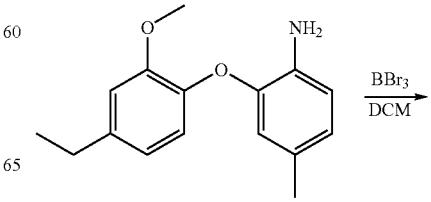

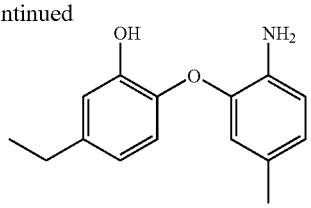

According to the procedure of example 1(b) except substituting 6-chloro-2-(2-methoxy-4-propylphenoxy)pyridin-3-amine for 2-(4-ethyl-2-methoxyphenoxy)-4-methylaniline (66.4 mg, 0.26 mmol), the title compound was prepared as a brown solid (4.9 mg; 8%), after purification by preparative TLC (cyclohexane/ethyl acetate: 7/3).

MS (ES) m/e 244 (M+H)$^+$ $^1$H NMR (CDCl$_3$) δ (ppm): 6.89 (d, 1H, J=2 Hz); 6.83 (d, 1H, J=8 Hz); 6.79 (d, 1H, J=8 Hz); 6.75 (d, 1H, J=8 Hz); 6.68 (s, 1H); 6.66 (d, 1H, J=2 Hz); 2.61 (q, 2H, J=7.6 Hz); 2.21 (s, 3H); 1.24 (t, 3H, 1.24 Hz).

EXAMPLE 55

2-(2-Fluoropyridin-3yloxy)-5-propylphenol a) 3-(2-Methoxy-4-propylphenoxy)-2-nitropyridine

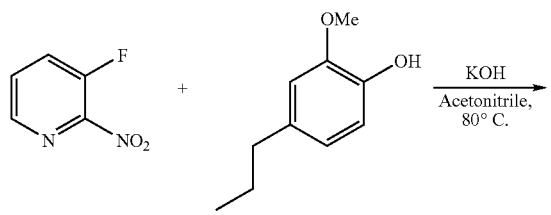

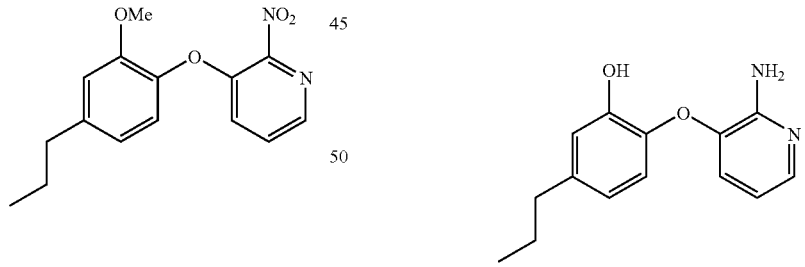

According to the procedure of example 21(a3) except substituting 4-ethyl-2-methoxyphenol by 2-methoxy-4-propylphenol (1.93 g, 11.61 mmol), the title compound was prepared in 86% yield (2.6 g) after purification on silica gel (eluant ethyl acetate/pet ether 15:85) as a pale yellow liquid.

$^1$H NMR (CDCl$_3$), δ (ppm): 8.16 (d, J=4.4 Hz, 1H), 7.42 (dd, J=8.4 Hz, J=4.4 Hz, 1H), 7.23 (d, J=8.4 Hz 1H), 7.05 (d, J=7.8 Hz, 1H), 6.8-6.83 (m, 2H ), 3.74 (s, 3H), 2.61 (t, J=7.4 Hz, 2H), 1.62-1.7 (m, 2H), 0.97 (t, J=7.4 Hz, 3H)

LC-MS m/z 289.1 (M+H)$^+$ b) 3-(2-Methoxy-4-propylphenoxy)-2-aminopyridine

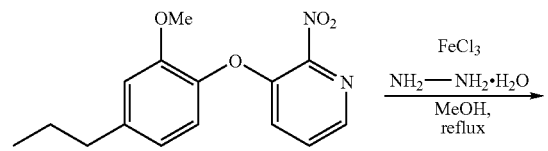

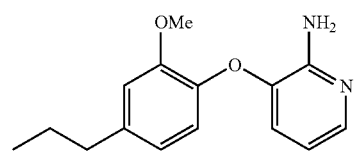

To a stirred solution of 3-(4-propyl-2-methoxyphenoxy)-2-nitropyridine (1.1 g, 3.8 mmol) in methanol (15 ml) was added anhydrous Ferric chloride (55 mg, 5% by wt) and activated charcoal (55 mg, 5% by wt). The resulting mixture was heated to reflux and hydrazine hydrate (570 mg, 11.45 mmol) was added dropwise. The reaction was allowed to stir under reflux condition overnight, then filtered through celite. The filtrate was concentrated under reduced pressure, taken in ethyl acetate (150 ml). The organic layer was washed with water followed by brine, dried over anhydrous sodium sulfate and concentrated under reduced pressure. The residue was passed through silica column (eluant ethylacetate/pet ether 1:3 to get 900 mg (91.3%) of title compound as a pale yellow solid.

$^1$H NMR (CDCl$_3$), δ (ppm): 7.74 (d, J=5.1 Hz, H), 6.9 (d, J=8 Hz, 1H), 6.8-6.83 (m, 2H), 6.76 (d, J=8.12 Hz, 1H), 6.56 (dd, J=7.8 Hz, J=5.2 Hz, 2H), 5.09 (bs, 2H), 3.82 (s, 3H), 2.59 (t, J=7.4 Hz, 2H), 1.60-1.66 (m, 2H), 0.97 (t, J=7.3 Hz, 3H)

LC-MS m/z 259.1 (M+H)$^+$ c) 2-(2-Aminopyridin-3-yloxy)-5-propylphenol

According to the procedure of example 1(b) except substituting 6-chloro-2-(2-methoxy-4-propylphenoxy)pyridin-3-amine for 3-(2-methoxy-4-propylphenoxy)pyridin-2-amine (0.9 g, 3.48 mmol), the title compound (0.52 g; 61%) was obtained.

$^1$H NMR (DMSO-d6), δ (ppm): 9.4 (s, D2O exchangeable, 1H), 7.59 (d, J=4.9 Hz, 1H), 6.83 (d, J=8.08 Hz, 1H), 6.77 (d, J=1.6 Hz, 1H), 6.66-6.61 (m, 2H), 6.43 (dd, J=7.6 Hz, J=4.88 Hz, 1H), 5.82 (bs, D2O exchangeable, 2H), 2.46 (t, J=7.6 Hz, 2H), 1.58-1.52 (m, 2H), 0.88 (t, J=7.3 Hz, 3H)

LC-MS m/z 244.8 (M+H)$^+$

EXAMPLE 56

N-[4-(4-Ethyl-2-hydroxy-phenoxy)-3-fluoro-phenyl]-4-morpholin-4-yl-4-oxo-butyramide a) 1-[4-(4-ethyl-2-methoxyphenoxy)-3-fluorophenyl]pyrrolidine-2,5-dione

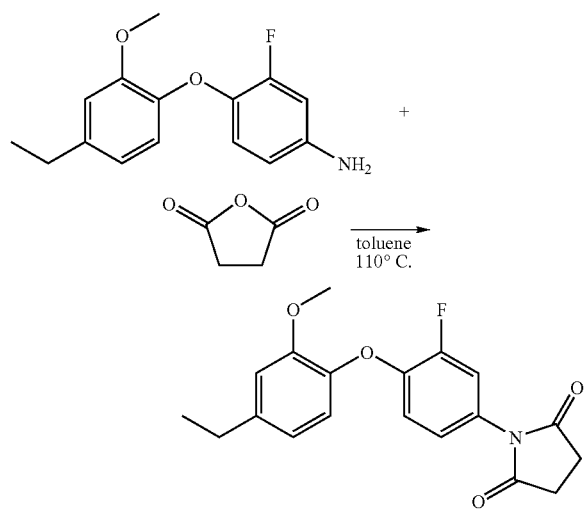

To 2-(4-aminophenoxy)-5-ethyl-4-fluorophenol (785 mg, 3 mmol) were added toluene (1.5 mL) and succinic anhydride (360.3 mg, 3.6 mmol). The reaction was left to stir for 3 days at 110° C. under argon, then concentrated, dissolved in dichloromethane, washed with a saturated solution of NaHCO₃ and a solution of KOH (1 M) and extracted with dichloromethane. Combined organic phases were dried over Na₂SO₄, concentrated in vacuo, to give the title product as a white solid (624.3 mg; 61%), after purification on silica gel (dichloromethane).

MS (ES) m/e 344 (M+H)⁺ b) N-[4-(4-Ethyl-2-methoxy-phenoxy)-3-fluoro-phenyl]-4-morpholin-4-yl-4-oxo-butyramide

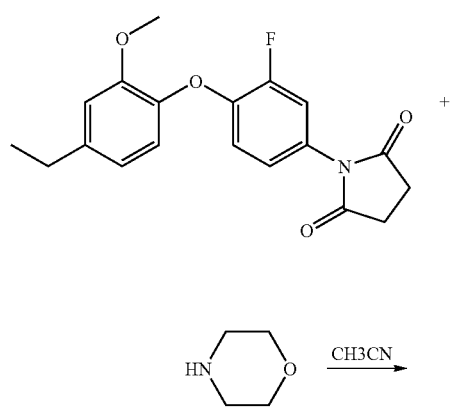

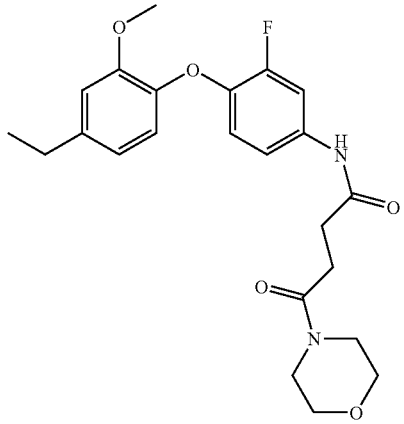

To 1-[4-(4-ethyl-2-methoxyphenoxy)-3-fluorophenyl]pyrrolidine-2,5-dione (40.4 mg, 0.12 mmol) were added acetonitrile (120 μL) and morpholine (20 μL, 0.24 mmol). The reaction mixture was stirred at 30° C. for 3 days under argon, then concentrated, dissolved in ethyl acetate, washed with saturated NH₄Cl and extracted with ethyl acetate. Combined organic phases were dried over Na₂SO₄, concentrated in vacuo, to give the title product (45.1 mg; 87%) after purification by preparative TLC (dichloromethane/methanol: 9/1).

MS (ES) m/e 431 (M+H)⁺ c) N-[4-(4-Ethyl-2-hydroxy-phenoxy)-3-fluoro-phenyl]-4-morpholin-4-yl-4-oxo-butyramide

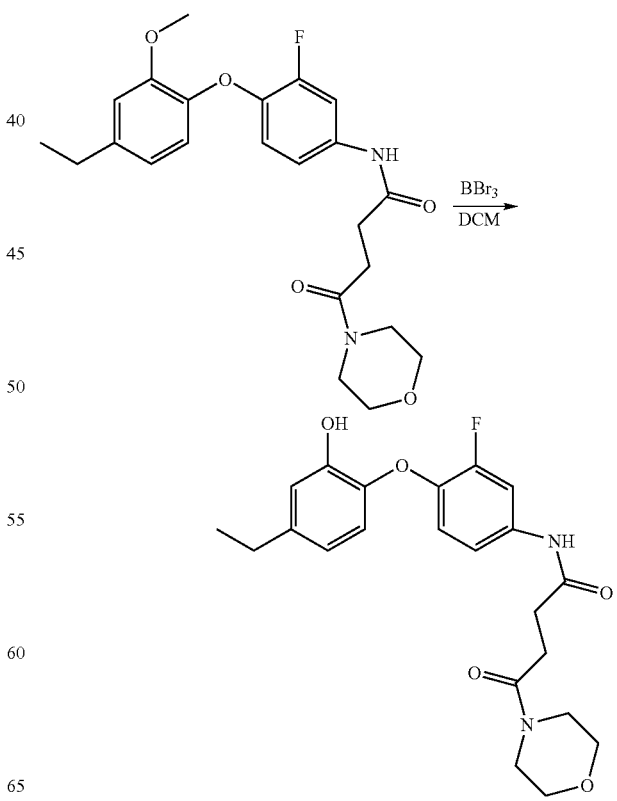

According to the procedure of example 1(b) except substituting 6-chloro-2-(2-methoxy-4-propylphenoxy)pyridin-3-amine for N-[4-(4-Ethyl-2-methoxy-phenoxy)-3-fluoro-phenyl]-4-morpholin-4-yl-4-oxo-butyramide (45 mg, 0.10 mmol), the title compound was prepared as a white solid (29 mg; 69%), after purification by preparative TLC (dichloromethane/methanol: 95/5).

MS (ES) m/e 417 (M+H)$^+$ $^1$H NMR (CDCl$_3$) δ (ppm): 7.64 (dd, 1H, J$_1$=2.4 Hz, J$_2$=12.4 Hz); 7.10-7.07 (m, 1H); 6.97 (t, 1H, J=8.8 Hz); 6.89 (d, 1H, J=1.6 Hz); 6.68 (d, 1H, J=8.0 Hz); 6.63 (dd, 1H, J$_1$=2 Hz, J$_2$=8.4 Hz), 3.73-3.66 (m, 8 H), 2.76-2.73 (m, 4 H), 2.60 (q, 2H, J=1.6 Hz), 1.23 (t, 3H, J=1.6 Hz).

EXAMPLE 57

2-fluoro-6-[(3-fluoro-4-ethyl-6-hydroxy)phenoxy)]pyridine a) 2-(4-bromo-5-fluoro-2-methoxyphenoxy)-6-fluoropyridine

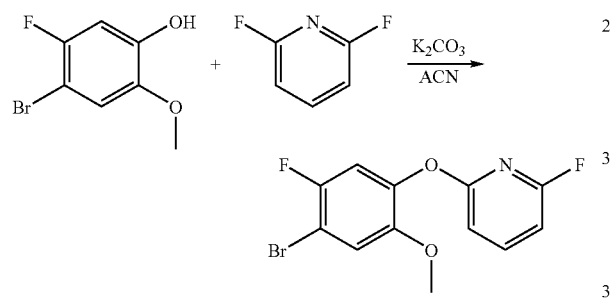

According to the procedure of example 20(a) except substituting 2-methoxy-4-propylphenol for 4-bromo-5-fluoro-2-methoxyphenol (441 mg; 2 mmol), and 1-fluoro-4-nitro-2-(trifluoromethyl)benzene for 2,6-Difluoropyridine (0.18 mL; 2 mmol), the title compound was prepared as a yellow oil (246 mg; 39%), after purification on silica gel (cyclohexane/ethyl acetate: 95/5).

MS (ES) m/e 317 (M+H)$^+$.

b) 2-fluoro-6-(5-fluoro-2-methoxy-4-vinylphenoxy)pyridine

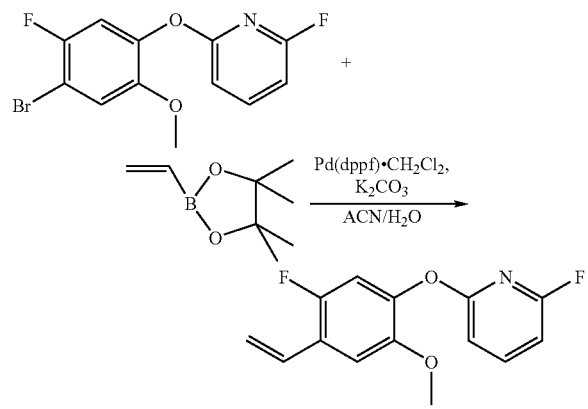

To 2-(4-bromo-5-fluoro-2-methoxyphenoxy)-6-fluoropyridine (227 mg, 0.71 mmol) were added [1,1'-Bis(diphenylphosphino)ferrocene]dichloropalladium(II) complex with dichloromethane (58.9 mg, 0.07 mmol) and potassium carbonate (597 mg, 4.26 mmol). To the mixture were added acetonitrile (4 mL), water (1.3 mL) and vinyl boronic acid pinacol ester (180 μL, 1.07 mmol). The reaction was flushed with argon, and left to stir for 3 days at 60° C. The reaction mixture was then filtered on celite, rinsed with dichloromethane and concentrated. After purification by preparative TLC (cyclohexane/ethyl acetate: 70/30), the title product was isolated as an orange oil (166 mg, 89%).

MS (ES) m/e 264 (M+H)$^+$.

c) 2-fluoro-6-[(3-fluoro-4-ethyl-6-methoxy)phenoxy)]pyridine

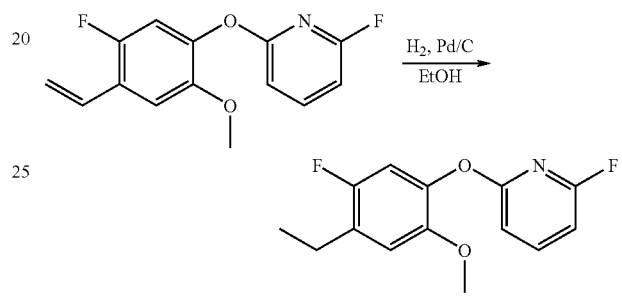

According to the procedure of example 20(b) except substituting 4-ethyl-2-methoxy-1-[4-nitro-2-(trifluoromethyl)phenoxy]benzene for 2-fluoro-6-[(3-fluoro-4-vinyl-6-methoxy)phenoxy)]pyridine (166 mg; 0.63 mmol) and tetrahydrofurane for ethanol (2 mL), the title product was isolated (145.4 mg, 87%) after purification by preparative TLC (cyclohexane/ethyl acetate: 80/20).

MS (ES) m/e 266 (M+H)$^+$.

d) 2-fluoro-6-[(3-fluoro-4-ethyl-6-hydroxy)phenoxy)]pyridine

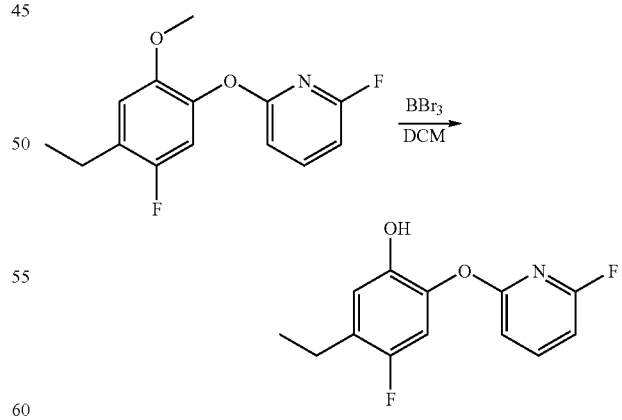

According to the procedure of example 1(b) except substituting 6-chloro-2-(2-methoxy-4-propylphenoxy)pyridin-3-amine for 2-fluoro-6-[(3-fluoro-4-ethyl-6-methoxy)phenoxy)]pyridine (145 mg, 0.55 mmol), the title compound (120.5 mg; 87%) was prepared as an oil, after purification by preparative TLC (cyclohexane/ethyl acetate: 7/3).

MS (ES) m/e 252 (M+H)+

$^1$H NMR (CDCl$_3$) δ (ppm): 7.83 (q, 1H, J=8 Hz); 6.92 (d, 1H, J=7.6 Hz); 6.84 (d, 2H, J=9.6 Hz); 6.70 (dd, 1H, J=8 Hz); 2.65 (q, 2H, J=7.6 Hz); 1.26 (t, 3H, J=3.6 Hz).

EXAMPLE 58

2-(4-{[2-(1,3-dioxolan-2-yl)ethyl]sulfonyl}phenoxy)-5-ethylphenol a) 2-{2-[4-(4-Ethyl-2-methoxy-phenoxy)-benzenesulfonyl]-ethyl}-[1,3]dioxolane

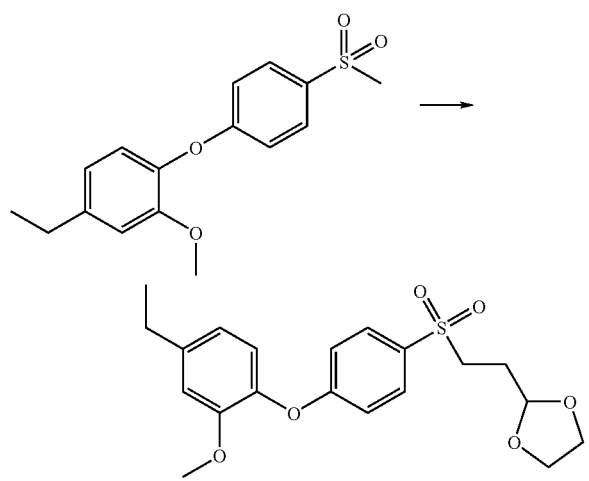

According to the procedure of example 49(a) except substituting 1-BOC-2-Pyrrolidinone for 2-Bromomethyl-1,3-dioxolane (0.05 mL; 0.47 mmol), the title compound (152 mg; 0.39 mmol; 100%) was prepared as a yellow oil, used without purification.

MS (ES) m/e 393 (M+H)+ b) 2-(4-{[2-(1,3-dioxolan-2-yl)ethyl]sulfonyl}phenoxy)-5-ethylphenol

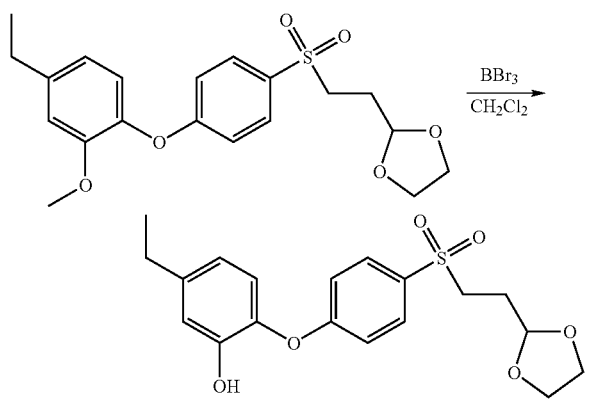

According to the procedure of example 1(b) except substituting 6-chloro-2-(2-methoxy-4-propylphenoxy)pyridin-3-amine for 2-{2-[4-(4-Ethyl-2-methoxy-phenoxy)-benzenesulfonyl]-ethyl}-[1,3]dioxolane (152 mg; 0.39 mmol), the title compound (3 mg; 0.02 mmol; 2%) was prepared as a clear oil, after purification by preparative TLC (dichloromethane/ethyl acetate).

MS (ES) m/e 379 (M+H)+

$^1$H RMN (CDCl$_3$) δ (ppm): 7.86 (d, 2H, J=8.8 Hz); 7.12 (d, 2H, J=8.8 Hz); 6.95 (d, 1H, J=1.7 Hz); 6.92 (d, 1H, J=8.2 Hz); 6.78 (d, 1H, J=8.2 Hz); 4.97 (t, 1H, J=3.9 Hz); 3.94 (m, 2H); 3.85 (m, 2H); 3.23 (m, 2H); 2.66 (q, 2H, J=7.6 Hz); 2.10 (m, 2H); 1.26 (t, 3H, J=7.6 Hz).

EXAMPLE 59

(5R)-3-[4-(4-ethyl-2-hydroxyphenoxy)-3-fluoro phenyl]-5-(hydroxymethyl)-1,3-oxazolidin-2-one a) [4-(2-Benzyloxy-4-ethyl-phenoxy)-3-fluoro-phenyl]-carbamic acid benzyl ester

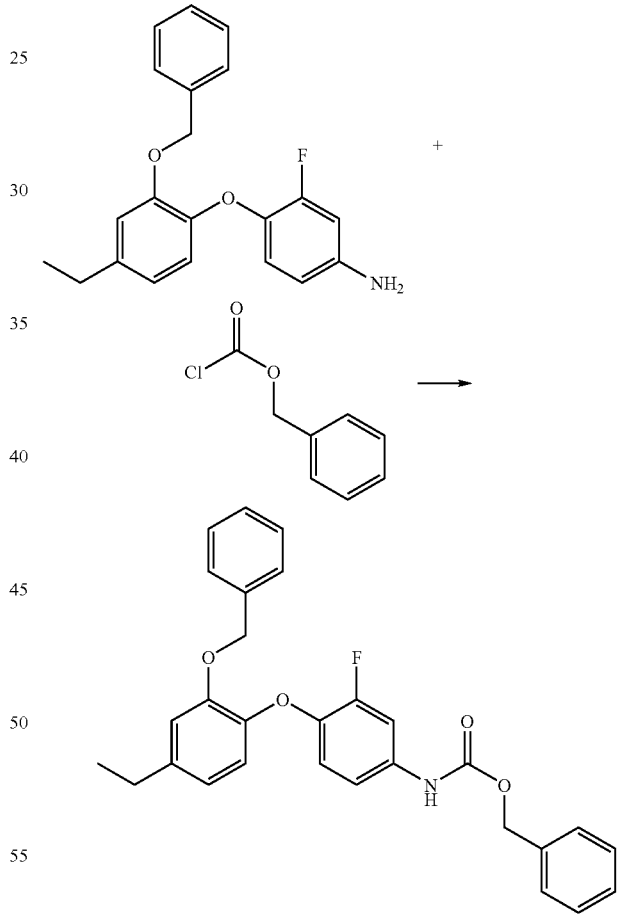

According to the procedure of example 44(a) except substituting 4-(4-ethyl-2-methoxyphenoxy)-3-fluoroaniline for 4-[2-(benzyloxy)-4-ethylphenoxy]-3-fluoroaniline (200 mg; 0.59 mmol) and ethylchloroformate by benzylchloroformate (150 µL; 0.73 mmol), the title compound (300 mg; quantitative) was prepared as a brown solid and used without further purification.

MS (ES) m/e 494 (M+Na)+ b) (5R)-3-[4-(2-Benzyloxy-4-ethyl-phenoxy)-3-fluoro-phenyl]-5-hydroxymethyl-oxazolidin-2-one c) (5R)-3-[4-(4-ethyl-2-hydroxyphenoxy)-3-fluorophenyl]-5-(hydroxylmethyl)-1,3-oxazolidin-2-one

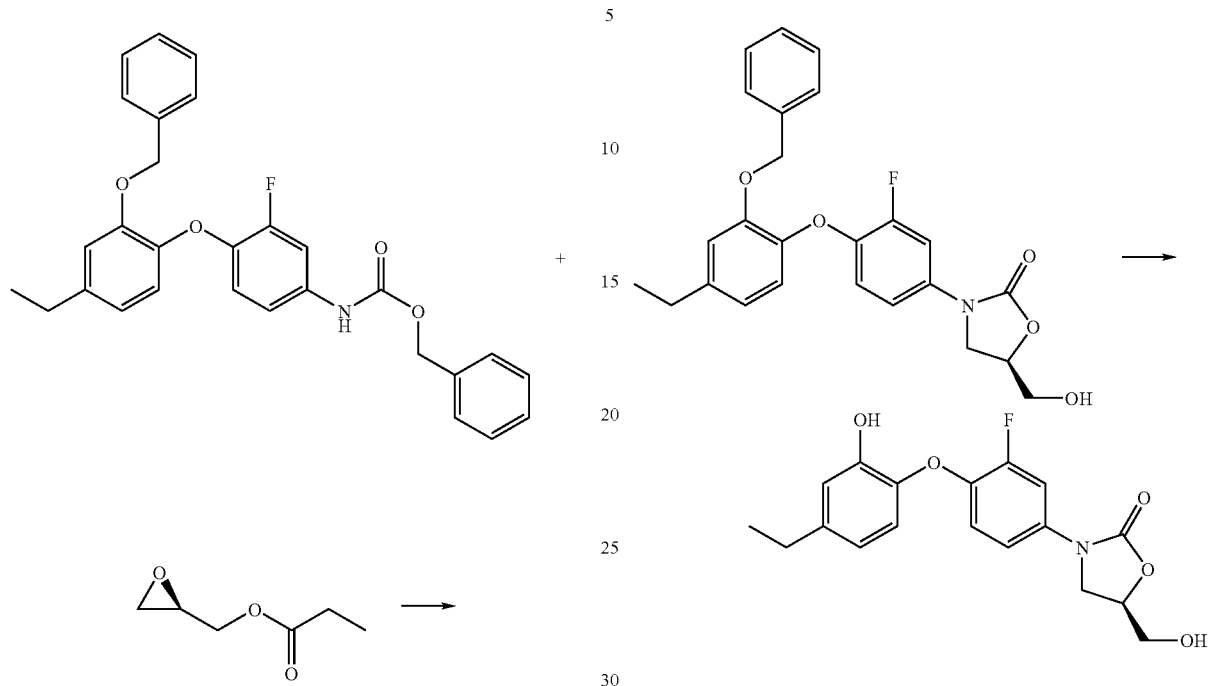

According to the procedure of example 20(b) except substituting 4-ethyl-2-methoxy-1-[4-nitro-2-(trifluoromethyl)phenoxy]benzene for (5R)-3-[4-(2-Benzyloxy-4-ethyl-phenoxy)-3-fluoro-phenyl]-5-hydroxymethyl-oxazolidin-2-one (0.16 mmol; 70 mg), the title compound (0.12 mmol; 41 mg; 73%) was obtained as a white solid after purification by preparative TLC (dichloromethane/methanol: 9/1).

MS (ES) m/e 438 (M+H)$^+$ $^1$H RMN (CDCl$_3$) δ (ppm): 7.55 (dd, 1H, J$_1$=12.6 Hz, J$_2$=2.6 Hz); 7.10-7.07 (m, 1H); 6.98 (t, 1H, J=8.9 Hz); 6.88 (d, 1H, J=1.6 Hz); 6.68 (d, 1H, J=6.7 Hz); 6.63 (dd, 1H, J$_1$=8.3 Hz, J$_2$=1.7 Hz); 4.74 (m, 1H); 4.02-3.96 (m, 3H); 3.75 (dd, 1H, J$_1$=12.7 Hz, J$_2$=3.7 Hz); 2.58 (q, 2H, J=7.6 Hz); 1.21 (t, 3H, J=7.6 Hz).

EXAMPLE 60

5-Aminomethyl-3-[4-(4-ethyl-2-hydroxyphenoxy)-3-fluorophenyl]oxazolidin-2-one a) 3-[4-(2-Benzyloxy-4-ethylphenoxy)-3-fluorophenyl]-5-hydroxymethyloxazolidin-2-one To a solution of [4-(2-Benzyloxy-4-ethyl-phenoxy)-3-fluoro-phenyl]-carbamic acid benzyl ester (0.31 mmol; 145 mg), under argon, in dry THF cooled to −78° C., was added n-Butyl lithium 2.3M in THF (0.46 mmol; 200 μL). the reaction mixture was stirred ten minutes and (R)-glycidyl butyrate (0.34 mmol; 48 μL) was added. The reaction was stirred overnight with slow warming to room temperature. The mixture was treated with saturated NH$_4$Cl and extracted with ethyl acetate. Combined organic phases were dried over Na$_2$SO$_4$ and concentrated in vacuo. The title compound (70 mg; 52%) was obtained as . . . after purification by preparative TLC (eluant: dichloromethane/methanol: 95/5).

MS (ES) m/e 438 (M+H)$^+$

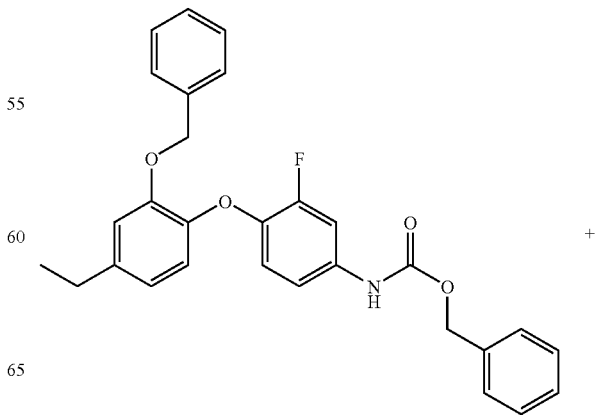

-continued

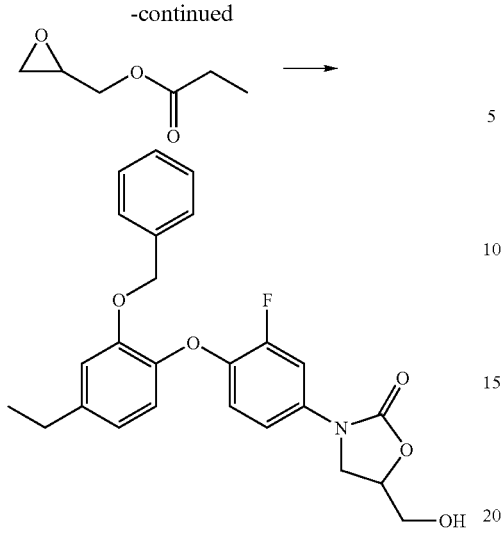

According to the procedure of example 59(b) except substituting (R)-glycidyl butyrate for (R,S)-glycidyl butyrate (0.43 mmol; 60 µL), the title compound (240 mg; quantitative) was prepared and used without further purification.
MS (ES) m/e 438 (M+Na)+ b) Methanesulfonic acid 3-[4-(2-Benzyloxy-4-ethylphenoxy)-3-fluorophenyl]-2-oxo-oxazolidin-5-ylmethyl ester

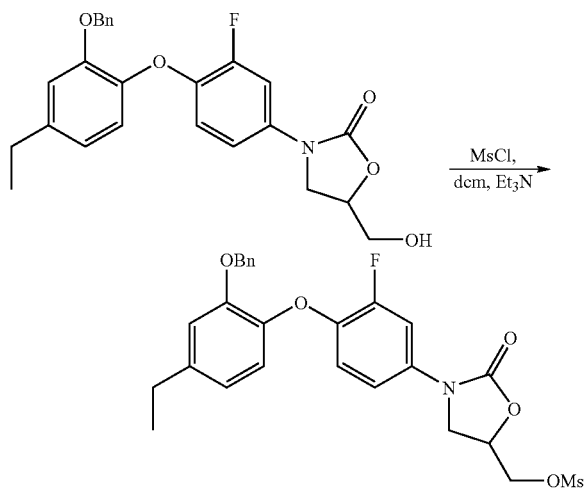

To a solution of 3-[4-(2-Benzyloxy-4-ethylphenoxy)-3-fluoro phenyl]-5-hydroxymethyloxazolidin-2-one (240 mg, 0.54 mmol) in 5 ml of dry dichloromethane and 0.16 ml (1.1 mmol) of triethylamine, cooled to 0° C., was added a solution of methanesulfonyl chloride (0.06 ml, 0.76 mmol) in 0.5 ml of dichloromethane dropwise. The reaction was allowed to warm to rt overnight. The reaction mixture was diluted with 20 ml water, 20 ml of dichloromethane were added and the layers separated. The aqueous layer was extracted with dichloromethane and the combined dichloromethane fraction was dried over anhydrous Na2SO4 and concentrated. The crude residue obtained was column purified over silica gel using 20% ethyl acetate in petroleum ether as eluant to get 120 mg, 42.8% of the title compound.
LC-MS m/z 516.1 (M+H)+ c) 5-Azidomethyl-3-[4-(2-Benzyloxy-4-ethylphenoxy)-3-fluorophenyl]-oxazolidin-2-one

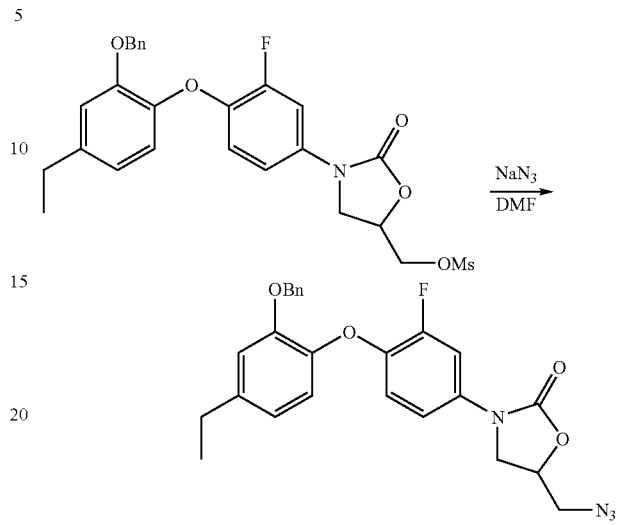

To a solution of methanesulfonic acid 3-[4-(2-Benzyloxy-4-ethylphenoxy)-3-fluorophenyl]-2-oxo-oxazolidin-5-ylmethyl ester (120 mg, 0.23 mmol) in 2 ml of dry DMF under nitrogen was added sodium azide (57 mg, 0.88 mmol). The reaction mixture was stirred at 75° C. overnight. The reaction mixture was diluted with 15 ml water and extracted with ethyl acetate. The combined organic phase was washed with water, saturated brine solution, dried over anhydrous Na2SO4 and concentrated in vacuo to get 100 mg of the title compound which was used as such for the next step.

d) 5-Aminomethyl-3-[4-(4-ethyl-2-hydroxyphenoxy)-3-fluoro phenyl]oxazolidin-2-one

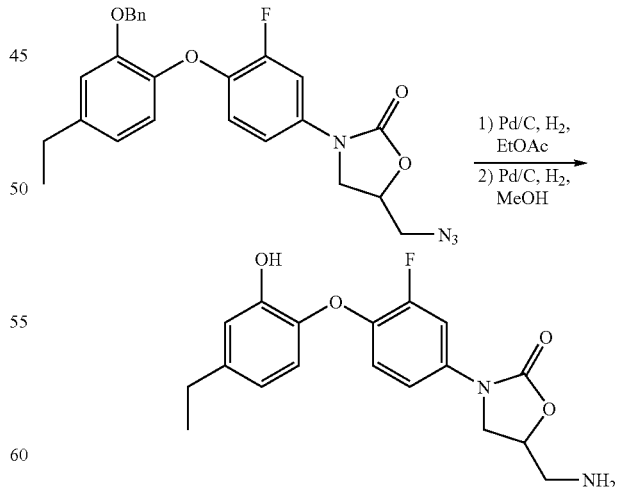

To a solution of 5-Azidomethyl-3-[4-(2-Benzyloxy-4-ethylphenoxy)-3-fluoro phenyl]-oxazolidin-2-one (100 mg, 0.16 mmol), in 15 ml of ethyl acetate, under nitrogen, was added palladium (10% Pd/C, 10 mg) and the mixture was stirred at rt under hydrogen overnight. The reaction mixture was filtered through celite and the residue was washed thoroughly with ethyl acetate. The combined filtrate was concentrated and the obtained crude compound was column purified over silica gel using a mixture of 5% methanol in chloroform as eluant to obtain 70 mg 74.4% of the reduced product 5-Aminomethyl-3-[4-(2-Benzyloxy-4-ethylphenoxy)-3-fluorophenyl]-oxazolidin-2-one. Debenzylation of this 70 mg was achieved by repeating the reaction using methanol as solvent, to obtain 30 mg, 54.1% of the title compound.

¹H NMR (CD₃OD), δ (ppm): 7.64 (dd, J=13.12, J=2.6 Hz, 1H), 7.17-7.14 (m, 1H), 6.87 (t, J=9 Hz, 1H), 6.8 (d, J=1.96 Hz, 1H), 6.74 (d, J=8.16 Hz, 1H), 6.64 (dd, J=8.16 Hz, J=1.88 Hz, 1H), 4.74-4.70 (m, 1H), 4.12 (t, J=8.96 Hz, 1H), 3.82 (dd, J=8.96 Hz, J=6.8 Hz, 1H), 2.99-2.92 (m, 2H), 2.57 (q, J=7.6 Hz, 2H), 1.22 (t, J=7.6 Hz, 3H)

LC-MS m/z 347.1 (M+H)⁺

EXAMPLE 61

N-{3-[4-(4-ethyl-2-hydroxyphenoxy)-3-fluoro phenyl]-2-oxo-oxazolidin-5-ylmethyl}-acetamide

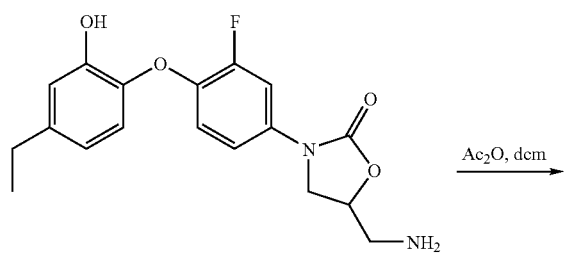

To a solution of 5-Aminomethyl-3-[4-(4-ethyl-2-hydroxyphenoxy)-3-fluorophenyl]-oxazolidin-2-one (10 mg, 0.028 mmol) in 2 ml of dry dichloromethane, cooled to 0° C., was added acetic anhydride (3 mg, 0.028 mmol) taken in 0.2 ml of dichloromethane. The reaction mixture was warmed to rt and stirred for 5 minutes until reaction was complete on TLC. The reaction mixture was diluted with 3 ml of water and the layers separated. The aqueous layer was extracted with dichloromethane and the combined organic fraction was dried over anhydrous Na₂SO₄ and concentrated. The crude residue obtained was purified by preparative HPLC (Column: C18 Symmetry (300×19 mm), 7μ, Mobile phase A: 20 mM ammonium acetate, Mobile phase B: Acetonitrile) to get 6 mg, 55.2% of the title compound.

¹H NMR (CDCl₃), δ (ppm): 7.58 (d, J=12.4, 1H), 7.09-7.02 (m, 2H), 6.9 (s, 1H), 6.71-6.64 (m, 2H), 6.15 (bs, 1H), 4.79 (bs, 1H), 4.04 (t, J=8.1 Hz, 1H), 3.80-3.62 (m, 3H), 2.57 (q, J=7.6 Hz, 2H), 2.25 (s, 3H), 1.22 (t, J=7.6 Hz, 3H)

LC-MS m/z 389.2 (M+H)⁺

EXAMPLE 62

2-(4-aminophenoxy)-5-ethyl-4-fluorophenol a) 4-[(3-fluoro-4-bromo-6-methoxy)phenoxy)]nitrobenzene

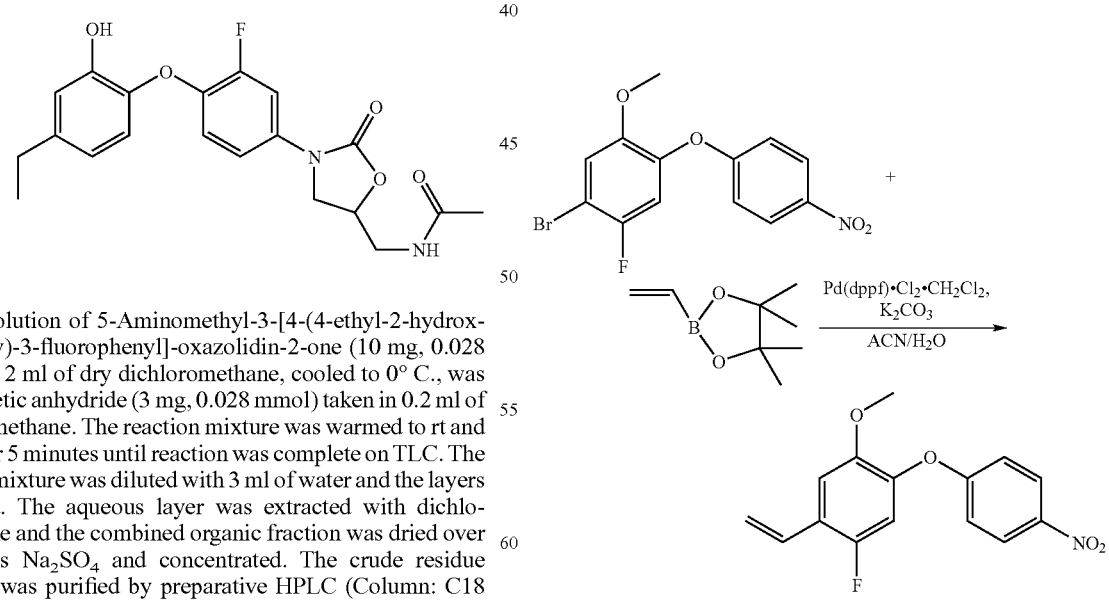

According to the procedure of example 20(a) except substituting 1-fluoro-4-nitro-2-(trifluoromethyl)benzene for 4-fluoronitrobenzene (210 μL; 2 mmol) and 2-methoxy-4-ethylphenol for 4-bromo-5-fluoro-2-methoxyphenol (444 mg; 2 mmol), the title compound (527 mg; 77%) was prepared as a light yellow solid after purification on silica gel (cyclohexane/ethyl acetate: 95/5).

b) 4-[(3-fluoro-4-vinyl-6-methoxy)phenoxy)]nitrobenzene

According to the procedure of example 57(b) except substituting 2-(4-bromo-5-fluoro-2-methoxyphenoxy)-6-fluoro pyridine for 4-[(3-fluoro-4-bromo-6-methoxy)phenoxy)]nitrobenzene (200.3 mg, 0.58 mmol), the title product was isolated as an orange oil (129.7 mg, 77%) after purification by preparative TLC (cyclohexane/ethyl acetate: 70/30).

MS (ES) m/e 290 (M+H)+.

c) 4-(4-ethyl-5-fluoro-2-methoxyphenoxy)aniline

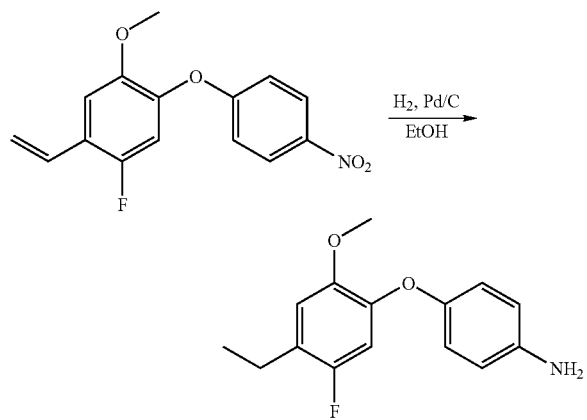

According to the procedure of example 20(b) except substituting 4-ethyl-2-methoxy-1-[4-nitro-2-(trifluoromethyl)phenoxy]benzene for 4-[(3-fluoro-4-vinyl-6-methoxy) phenoxy)]nitrobenzene (129 mg; 0.44 mmol) and tetrahydrofurane for ethanol (3 mL), the title compound was isolated as an oil (45 mg, 39%) after purification by preparative TLC (cyclohexane/ethyl acetate: 70/30).

MS (ES) m/e 262 (M+H)+.

d) 2-(4-aminophenoxy)-5-ethyl-4-fluorophenol

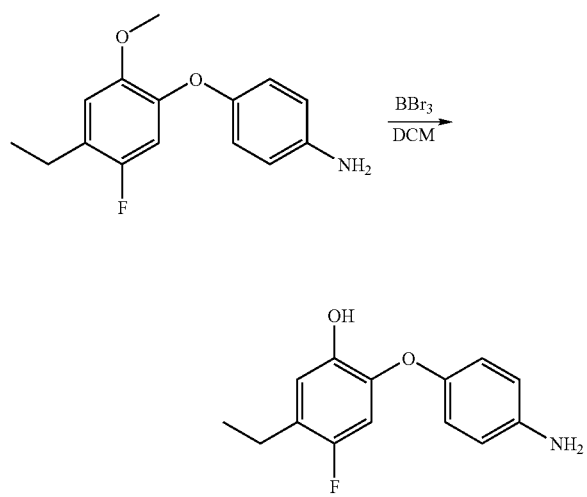

According to the procedure of example 1(b) except substituting 6-chloro-2-(2-methoxy-4-propylphenoxy)pyridin-3-amine for 4-(4-ethyl-5-fluoro-2-methoxyphenoxy)aniline (44 mg, 0.17 mmol), the title compound (7.9 mg; 19%) was prepared as a brown powder, after purification by preparative TLC (cyclohexane/ethyl acetate: 7/3).

MS (ES) m/e 248 (M+H)+

¹H NMR (CDCl₃) δ (ppm): 6.89 (d, 2H, J=8.8 Hz); 6.84 (d, 1H, J=7.2 Hz); 6.70 (d, 2H, J=9.2 Hz); 6.55 (d, 1H, J=10.4 Hz); 2.60 (q, 2H, J=7.6 Hz); 1.21 (t, 3H, J=7.6 Hz).

EXAMPLE 63

2-(4-amino-2-fluorophenoxy)-5-[2-(3-thienyl)ethyl]phenol a) 4-bromo-1-(2-fluoro-4-nitrophenoxy)-2-methoxybenzene

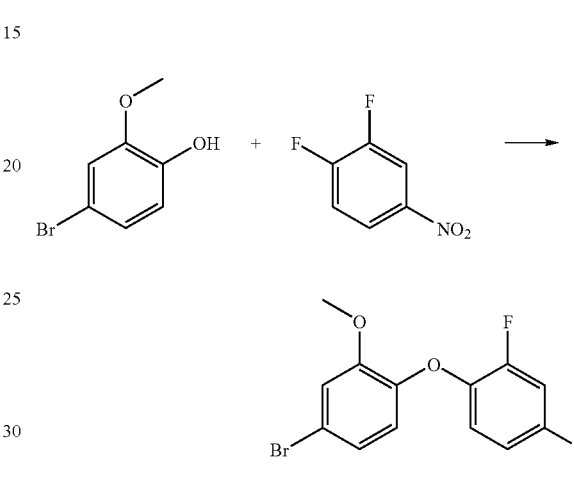

According to the procedure of example 21(a3) except substituting 4-Ethyl-2-methoxy phenol by 4-bromoguaïacol (2.51 mmol; 510 mg) and 3-Fluoro-2-nitropyridine by 3,4-difluoronitrobenzene (2.76 mmol; 305 µL), the title compound was prepared as a clear oil in quantitative yield (855 mg) and used without further purification.

b) 4-(4-bromo-2-methoxyphenoxy)-3-fluoroaniline

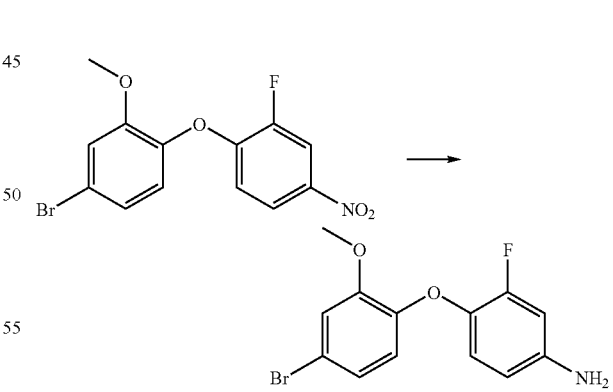

According to the procedure of example 50(b) except substituting 4-ethyl-1-(3-fluoro-4-nitrophenoxy)-2-methoxybenzene and 4-ethyl-1-(5-fluoro-2-nitrophenoxy)-2-methoxy benzene for 4-bromo-1-(2-fluoro-4-nitrophenoxy)-2-methoxy benzene (1.88 mmol; 644 mg), the title compound (87%, 512 mg) was obtained as a red oil, and used without further purification.

MS (ES) m/e 312, 314 (M+H)+ c) 2-(4-amino-2-fluorophenoxy)-5-bromophenol

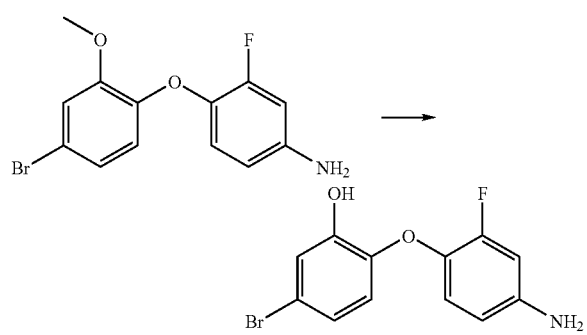

According to the procedure of example 1(b) except substituting 6-chloro-2-(2-methoxy-4-propylphenoxy)pyridin-3-amine for 4-(4-bromo-2-methoxyphenoxy)-3-fluoroaniline (1.64 mmol; 512 mg), the desired compound was prepared as a dark solid in 72% yield (350 mg) and used without further purification.

MS (ES) m/e 297, 299 (M+H$^+$)

d) O,N,N-triBoc-2-(4-amino-2-fluorophenoxy)-5-bromophenol

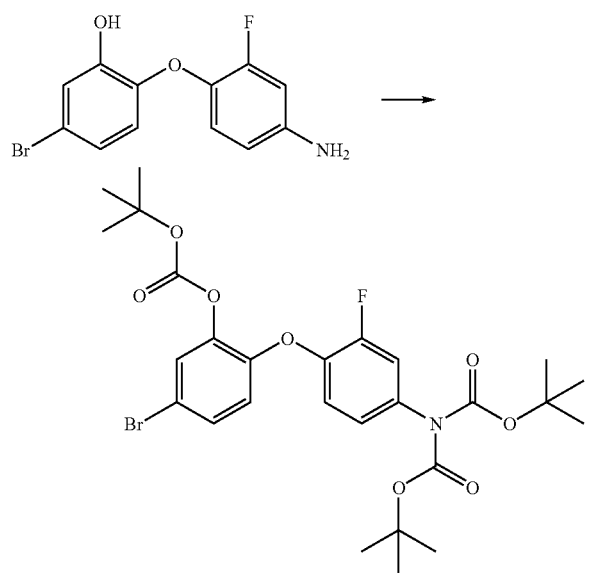

To a solution of 2-(4-amino-2-fluorophenoxy)-5-bromophenol (0.62 mmol; 185 mg) in dry dichloromethane (3 mL), under argon, were added to 0° C. diisopropylethylamine (2.01 mmol; 350 µL) and (Boc)$_2$O (2.01 mmol, 439 mg). The reaction was stirred with a gradual warming to room temperature. The mixture was treated with saturated NH$_4$Cl and extracted with dichloromethane. Combined organic layers were dried over Na$_2$SO$_4$ and concentrated in vacuo to give a brown oil (quantitative, 363 mg) used without further purification.

MS (ES) m/e 620, 622 (M+Na$^+$)

e) O,N-diBoc-2-(4-amino-2-fluorophenoxy)-5-(3-thienyl ethynyl)phenol

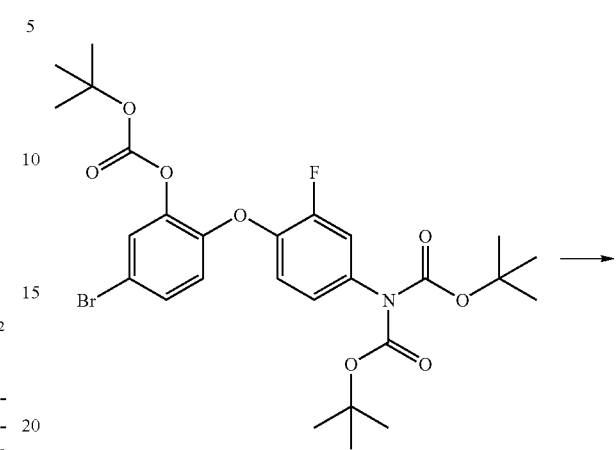

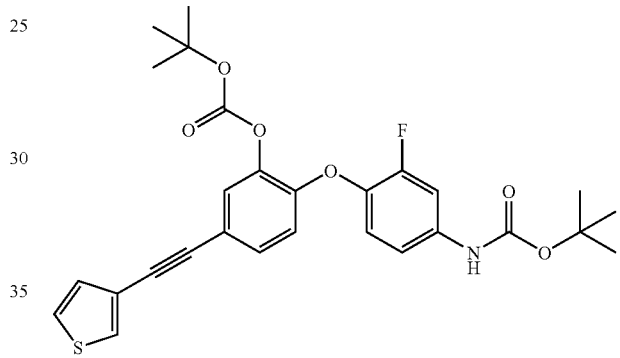

According to the procedure of example 11(a) except substituting 5-bromo-2-(2-methoxy-4-propylphenoxy)pyridine by O,N,N-triBoc-2-(4-amino-2-fluorophenoxy)-5-bromophenol (0.62 mmol; 363 mg) and 3-butyn-1-ol by 3-ethynylthiophene (1.55 mmol; 153 µL), the title compound was obtained as a yellow solid (60%, 195 mg) after purification on silica gel (cyclohexane/ethyl acetate gradient).

MS (ES) m/e 548 (M+Na)$^+$ f) O,N-diBoc-2-(4-amino-2-fluorophenoxy)-5-[2-(3-thienyl)ethyl]phenol and O,N-diBoc-2-(4-amino-2-fluorophenoxy)-5-[(E)-2-(3-thienyl)vinyl]phenol

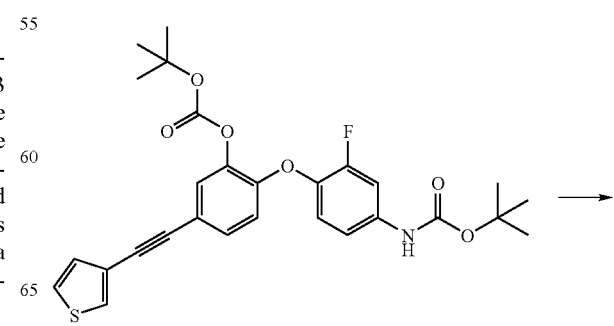

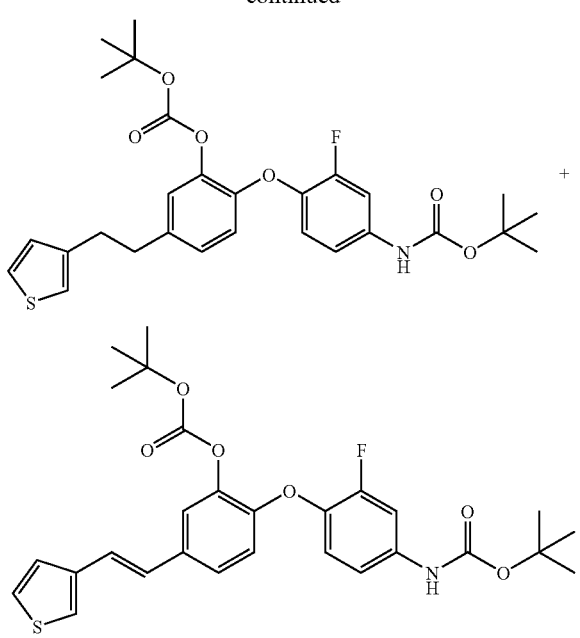

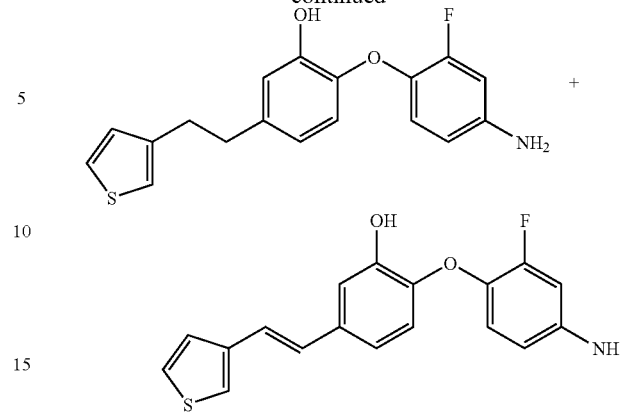

According to the procedure of example 20(b) except substituting 4-ethyl-2-methoxy-1-[4-nitro-2-(trifluoromethyl)phenoxy]benzene for O,N,N-triBoc-2-(4-amino-2-fluorophenoxy)-5-bromophenol (0.37 mmol; 195 mg) and THF by ethanol, a mixture of title compounds (167 mg; ≈80%) was obtained as a yellow oil, used without further purification.

MS (ES) m/e 550, 552 (M+H)⁺ g) 2-(4-amino-2-fluorophenoxy)-5-[2-(3-thienyl)ethyl]phenol and 2-(4-amino-2-fluorophenoxy)-5-[(E)-2-(3-thienyl)vinyl]phenol

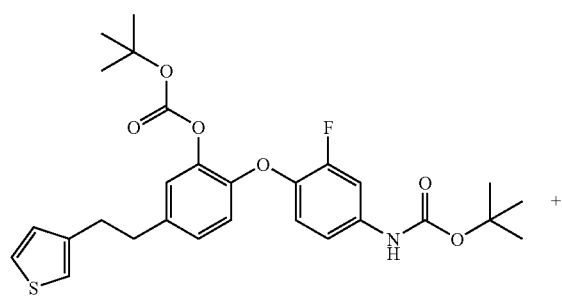

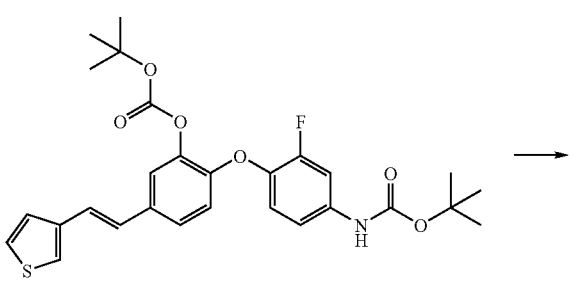

To a mixture of O,N-diBoc-2-(4-amino-2-fluorophenoxy)-5-[2-(3-thienyl)ethyl]phenol and O,N-diBoc-2-(4-amino-2-fluorophenoxy)-5-[(E)-2-(3-thienyl)vinyl]phenol (0.31 mmol; 162 mg) in dry THF (2 mL), cooled to 0° C. under argon, was added TFA (13 mmol, 1 mL). The reaction was stirred overnight with gradual warming to rt. The mixture was treated with saturated NaHCO₃ and extracted with ethyl acetate. Combined organic layers were dried and concentrated in vacuo, the title mixture was obtained (44 mg, ≈43%) as a white solid after purification on preparative TLC.

MS (ES) m/e 328, 330 (M+H)⁺ h) 2-(4-amino-2-fluorophenoxy)-5-[2-(3-thienyl)ethyl]phenol

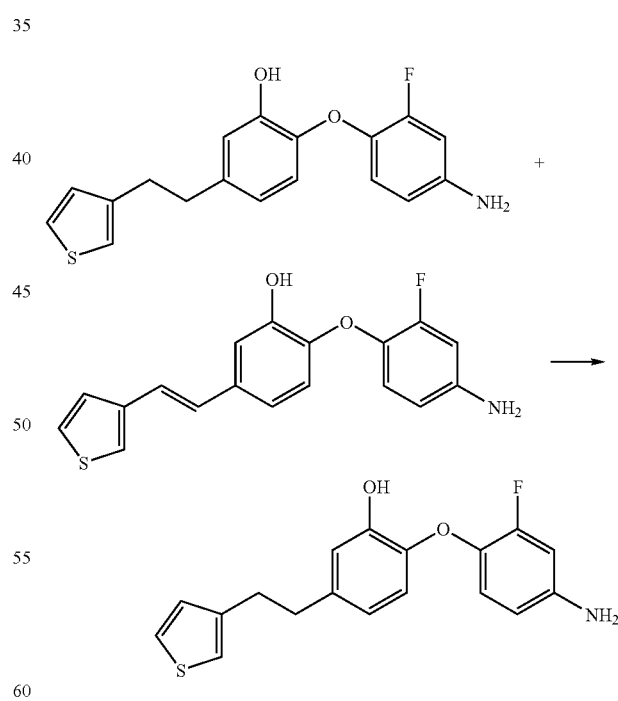

According to the procedure of example 20(b) except substituting 4-ethyl-2-methoxy-1-[4-nitro-2-(trifluoromethyl)phenoxy]benzene by a mixture of 2-(4-amino-2-fluorophenoxy)-5-[2-(3-thienyl)ethyl]phenol and 2-(4-amino-2-fluorophenoxy)-5-[(E)-2-(3-thienyl)vinyl]phenol (0.13 mmol; 44 mg), and THF by ethanol, the title compound was prepared in 14% yield (0.02 mmol; 6 mg) as a brown oil after purification by preparative TLC (cyclohexane/ethyl acetate—7/3).

MS (ES) m/e 330 (M+H)+

$^1$H RMN (MeOD) δ (ppm): 7.27 (dd, 1H, $J_1$=4.9 Hz, $J_2$=3.0 Hz); 6.98 (m, 1H); 6.93 (dd, 1H, $J_1$=4.9 Hz, $J_2$=1.2 Hz); 6.79 (t, 1H, J=8.9 Hz); 6.73 (d, 1H, J=1.3 Hz); 6.57-6.52 (m, 3H); 6.46 (ddd, 1H, $J_1$=8.6 Hz, $J_2$=2.6 Hz, $J_3$=1.2 Hz); 2.91-2.87 (m, 2H); 2.82-2.78 (m, 2H).

EXAMPLE 64

5-ethyl-2-[2-fluoro-4-(methylsulfonyl)phenoxy]phenol a) 4-(4-ethyl-2-methoxyphenoxy)-3-fluorophenyl methyl sulfone

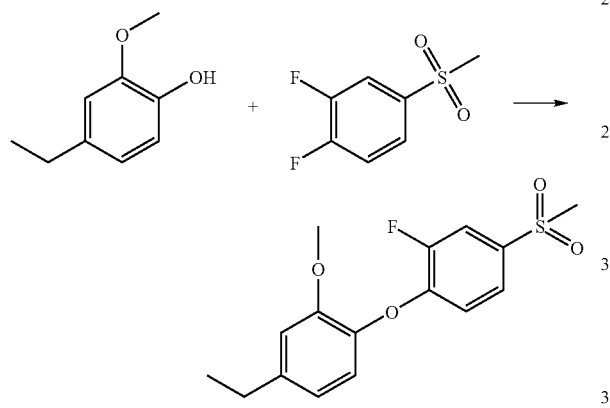

According to the procedure of example 20(a) except substituting 1-fluoro-4-nitro-2-(trifluoromethyl)benzene for 1,2-difluoro-4-(methylsulphonyl)benzene (310 mg; 1.6 mmol), the title compound (581 mg; 100%) was prepared as a light brown solid, used without further purification.

MS (ES) m/e 325 (M+H)+.

b) 5-ethyl-2-[2-fluoro-4-(methylsulfonyl)phenoxy]phenol

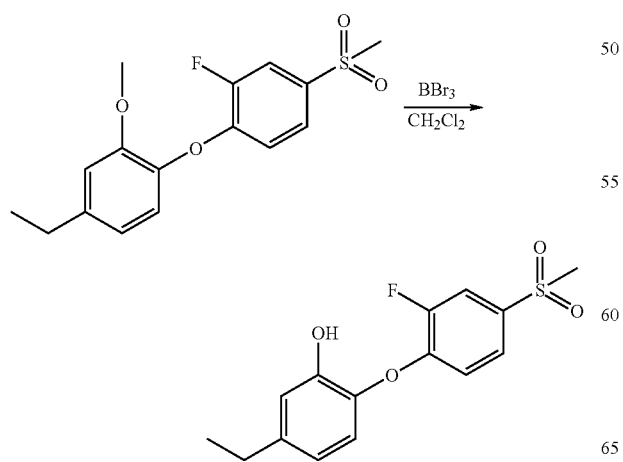

According to the procedure of example 1(b) except substituting 6-chloro-2-(2-methoxy-4-propylphenoxy)pyridin-3-amine for 4-(4-ethyl-2-methoxyphenoxy)-3-fluorophenyl methyl sulfone (63 mg; 0.19 mmol), the title compound (38 mg; 0.12%) was prepared as a clear oil, after purification by preparative TLC (dichloromethane/ethyl acetate).

MS (ES) m/e 311 (M+H)+

$^1$H RMN (CDCl$_3$) δ (ppm): 7.73 (dd, 1H, $J_1$=9.7 Hz, $J_2$=2.1 Hz); 7.61 (d, 1H, J=8.6 Hz); 7.03 (t, 1H, J=8.5 Hz); 6.94 (s, 1H); 6.89 (d, 1H, J=8.2 Hz); 6.77 (dd, 1H, $J_1$=8.2 Hz; $J_2$=2.0 Hz); 5.65 (sl, 1H); 3.07 (s, 3H); 2.64 (q, 2H, J=7.6 Hz); 1.25 (t, 3H, J=7.6 Hz).

EXAMPLE 65

4-(4-ethyl-2-hydroxyphenoxy)-3-fluorobenzene sulfonamide a) 4-(4-ethyl-2-methoxyphenoxy)-3-fluorobenzenesulfonyl chloride

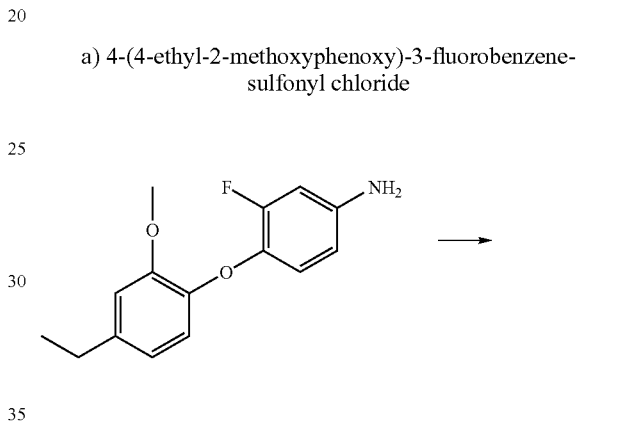

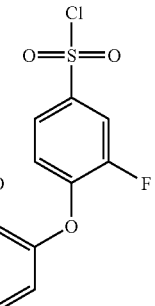

NaNO$_2$ (1.5 mmol; 103 mg) was slowly added to a solution of 4-(4-ethyl-2-methoxyphenoxy)-3-fluoroaniline (1.0 mmol; 261 mg) in acetonitrile (8 mL), AcOH (0.8 mL), and conc. HCl (0.5 mL), under argon at 0° C., in the dark. After 30 min. stirring, this solution was slowly added to a solution of H$_2$SO$_3$ (50 mmol; 4 mL), and NaCl (10 mmol; 580 mg) cooled to 0° C. CuCl$_2$ (2 mmol; 268 mg) was slowly added. The reaction was stirred with slow warming to room temperature for 3 hr, then heated to 50° C. for 30 min. Cooled to 0° C., the mixture was slowly hydrolysed with conc NH$_3$, extracted with dichloromethane (3*5 mL). Combined organic phases were dried over Na$_2$SO$_4$, concentrated, to yield a brown oil (344 mg; 1.0 mmol; quantitative), used as such in the following reactions.

MS (ES) m/e 341 (M−Cl+MeOH)

b) 4-(4-ethyl-2-methoxyphenoxy)-3-fluorobenzene-sulfonamide

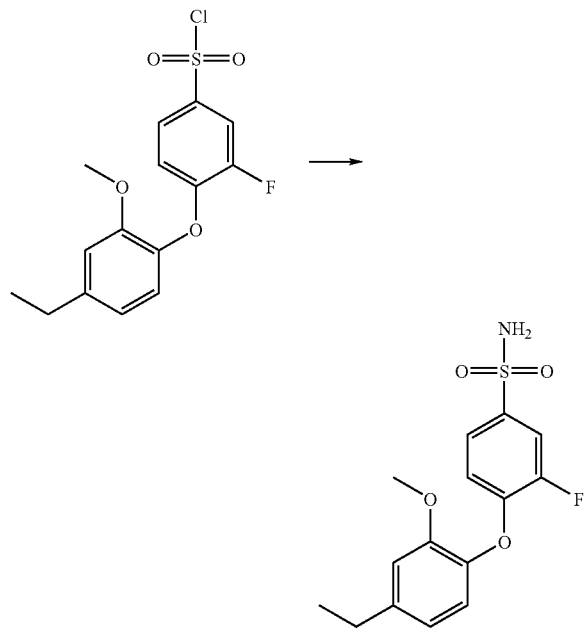

Conc. NH₃ (5.0 mmol; 0.28 mL) was slowly added to a solution of 4-(4-ethyl-2-methoxyphenoxy)-3-fluorobenzenesulfonyl chloride (1.0 mmol; 344 mg) in THF (5 mL), under argon at 0° C. The reaction was stirred overnight with slow warming to room temperature. Diluted with ethyl acetate (5 mL), the mixture was washed with HCl (1N), and sat. NH₄Cl. The organic phase was dried over MgSO₄, concentrated. The residue was purified by chromatography (dichloromethane/ethyl acetate gradient) to yield the title compound as an off-white solid (108 mg; 0.33 mmol; 33%).

MS (ES) m/e 326 (M+H)⁺ c) 4-(4-ethyl-2-hydroxyphenoxy)-3-fluorobenzene-sulfonamide

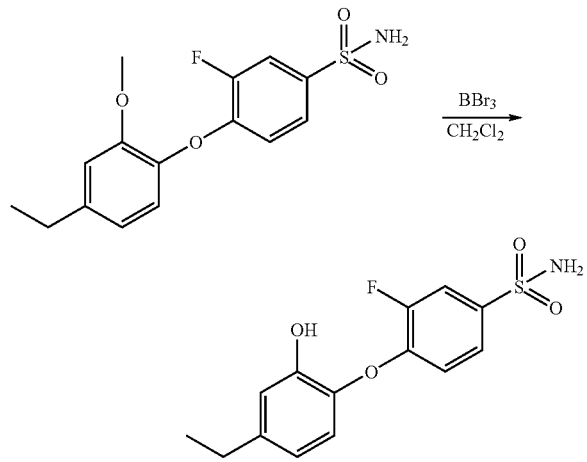

According to the procedure of example 1(b) except substituting 6-chloro-2-(2-methoxy-4-propylphenoxy)pyridin-3-amine for 4-(4-ethyl-2-hydroxyphenoxy)-3-fluorobenzenesulfonamide (108 mg; 0.33 mmol), the title compound (18 mg; 0.06 mmol; 18%) was obtained as a white solid, after purification by preparative TLC (dichloromethane/ethyl acetate).

MS (ES) m/e 311 (M+H)⁺

¹H RMN (MeOD) δ (ppm): 7.76 (dd, 1H, $J_1$=10.5 Hz, $J_2$=2.0 Hz); 7.61 (d, 1H, J=8.6 Hz); 6.96 (d, 1H, J=8.2 Hz); 6.90-6.86 (m, 2H); 6.77 (d, 1H, J=8.2 Hz); 2.66 (q, 2H, J=7.6 Hz); 1.29 (t, 3H, J=7.6 Hz).

EXAMPLE 66

5-ethyl-2-{2-fluoro-4-[(pyridin-3-ylmethyl)amino]phenoxy}phenol a) 4-(4-ethyl-2-methoxyphenoxy)-3-fluoro-N-(pyridin-3-yl methyl)aniline

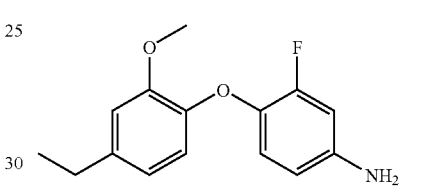

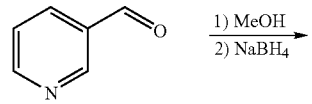

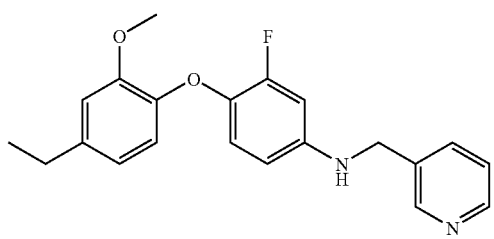

To 4-(4-ethyl-2-methoxyphenoxy)-3-fluoroaniline (261.2 mg, 1 mmol) were added methanol (4 mL) and nicotinaldehyde (120 μL, 1.2 mmol). The reaction was stirred at 30° C. for 17 h under argon. To the reaction mixture was added NaBH₄ (38 mg, 1 mmol). The reaction was stirred at 30° C. for 4 h under argon. The resulting mixture was concentrated in vacuo, dissolved in dichloromethane, washed with a saturated solution of NH₄Cl and extracted with dichloromethane. Combined organic phases were dried over Na₂SO₄, concentrated in vacuo, to give the title product as a yellow oil (160.5 mg; 46%), after purification by preparative TLC (cyclohexane/ethyl acetate: 7/3).

MS (ES) m/e 353 (M+H)⁺ b) 5-ethyl-2-{2-fluoro-4-[(pyridin-3-ylmethyl)amino]phenoxy}phenol

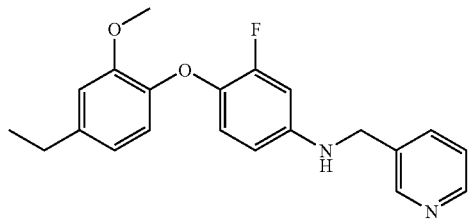

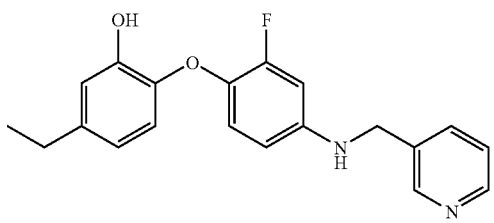

According to the procedure of example 5(b) except substituting 2-fluoro-6-(2-methoxy-4-propylphenoxy)pyridine for 4-(4-ethyl-2-methoxyphenoxy)-3-fluoro-N-(pyridin-3-ylmethyl)aniline (63.5 mg, 0.18 mmol), the title product as a brown solid (9.5 mg; 12%), after purification by preparative TLC (dichloromethane/methanol: 9/1).

MS (ES) m/e 339 (M+H)$^+$ $^1$H NMR (CDCl$_3$) δ (ppm): 8.65 (s, 1H); 8.57 (d, 1H, J=4 Hz); 7.53 (d, 1H, J=8 Hz); 7.32 (m, 1H); 6.95 (t, 1H, J=8 Hz); 6.87 (s, 1H); 6.62 (m, 2H); 6.45 (dd; 1H; J$_1$=12.4 Hz, J$_2$=2.8 Hz); 6.37 (dd, 1H, J$_1$=12 Hz, J$_2$=4 Hz); 4.36 (s, 2H); 2.58 (q, 2H, 7.6 Hz); 1.22 (t, 3H, J=7.6 Hz).

EXAMPLE 67

4-(4-ethyl-2-hydroxyphenoxy)-3-fluoro-N-(2-hydroxyethyl)benzenesulfonamide a) 4-(4-ethyl-2-methoxyphenoxy)-3-fluoro-N-(2-methoxyethyl)benzenesulfonamide

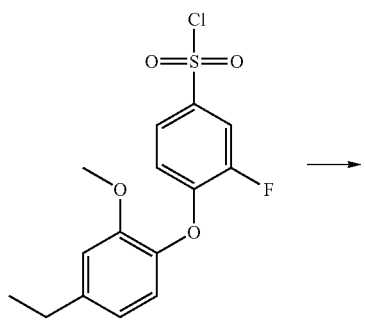

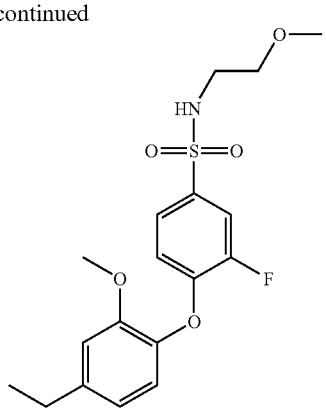

According to the procedure of example 65(b) except substituting NH$_3$ for 2-Methoxyethylamine (0.33 mL; 3.8 mmol), the title compound (118 mg; 0.30 mmol; 32%) was obtained as a yellow oil, after purification by chromatography (cyclohexane/dichloromethane gradient).

MS (ES) m/e 384 (M+H)$^+$ b) 4-(4-ethyl-2-hydroxyphenoxy)-3-fluoro-N-(2-hydroxyethyl)benzenesulfonamide

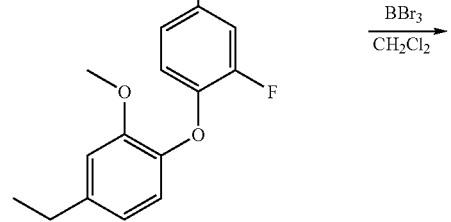

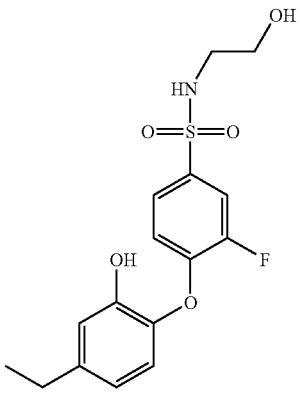

According to the procedure of example 1(b) except substituting 6-chloro-2-(2-methoxy-4-propylphenoxy)pyridin-3-amine for 4-(4-ethyl-2-methoxyphenoxy)-3-fluoro-N-(2-methoxy ethyl)benzenesulfonamide (116 mg; 0.30 mmol), the title compound (45 mg; 0.13 mmol; 42%) was obtained as a clear oil, after purification by preparative TLC (dichloromethane/ethyl acetate).

MS (ES) m/e 356 (M+H)+

$^1$H RMN (CDCl$_3$) δ (ppm): 7.63 (dd, 1H, J$_1$=10.0 Hz, J$_2$=2.0 Hz); 7.50 (d, 1H, J=8.7 Hz); 6.94-6.87 (m, 3H); 6.73 (d, 1H, J=8.3 Hz); 5.64 (t, 1H, J=5.8 Hz); 3.64 (t, 2H, J=4.7 Hz); 3.05 (q, 2H, J=4.8 Hz); 2.61 (q, 2H, J=7.6 Hz); 1.24 (t, 3H, J=7.6 Hz).

EXAMPLE 68

5-ethyl-2-{2-fluoro-4-[(1H-imidazol-2-ylmethyl)amino]phenoxy}phenol a) 4-(4-ethyl-2-methoxyphenoxy)-3-fluoro-N-(1H-imidazol-2-ylmethyl)aniline

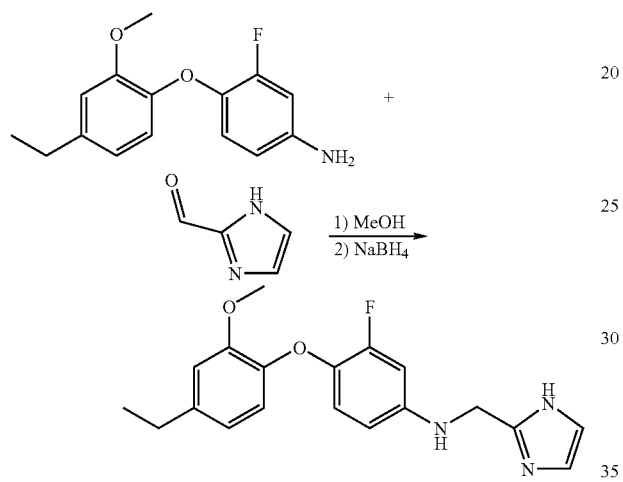

According to the procedure of example 66(a) except substituting nicotinaldehyde for 1H-imidazole-2-carboxaldehyde (119 mg, 1.2 mmol), the title compound was prepared as a light yellow solid (288.2 mg; 85%), after purification by preparative TLC (dichloromethane/methanol: 9/1).

MS (ES) m/e 342 (M+H)+ b) 5-ethyl-2-{2-fluoro-4-[(1H-imidazol-2-ylmethyl)amino]phenoxy}phenol

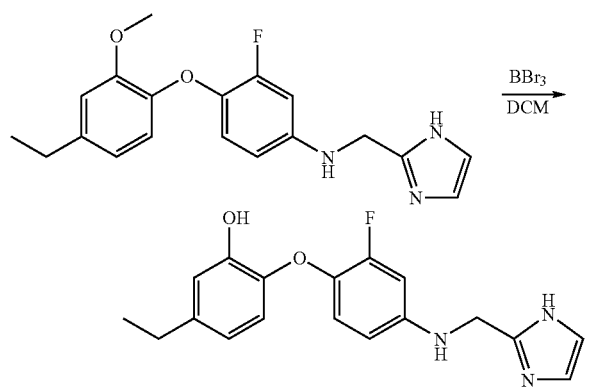

According to the procedure of example 1(b) except substituting 6-chloro-2-(2-methoxy-4-propylphenoxy)pyridin-3-amine for 4-(4-ethyl-2-methoxyphenoxy)-3-fluoro-N-(1H-imidazol-2-ylmethyl)aniline (288 mg, 0.84 mmol), the title compound was prepared as a brown oil (72.3 mg; 26%), after purification by preparative TLC (dichloromethane/methanol: 9/1).

MS (ES) m/e 328 (M+H)+

$^1$H NMR (MeOD) δ (ppm): 7.04 (s, 2H); 6.87 (t, 1H, J=8.8 Hz); 6.79 (d, 1H, J=1.2 Hz); 6.61-6.51 (m, 3H); 6.44 (dd, 1H, J$_1$=8.8 Hz, J$_2$=2.0 Hz); 4.41 (s, 2H); 2.58 (q, 2H, 7.6 Hz); 1.24 (t, 3H, 7.6 Hz).

EXAMPLE 69

N-{[4-(4-ethyl-2-hydroxyphenoxy)-3-fluorophenyl]sulfonyl}acetamide a) N-{[4-(4-ethyl-2-methoxyphenoxy)-3-fluorophenyl]sulfonyl}acetamide

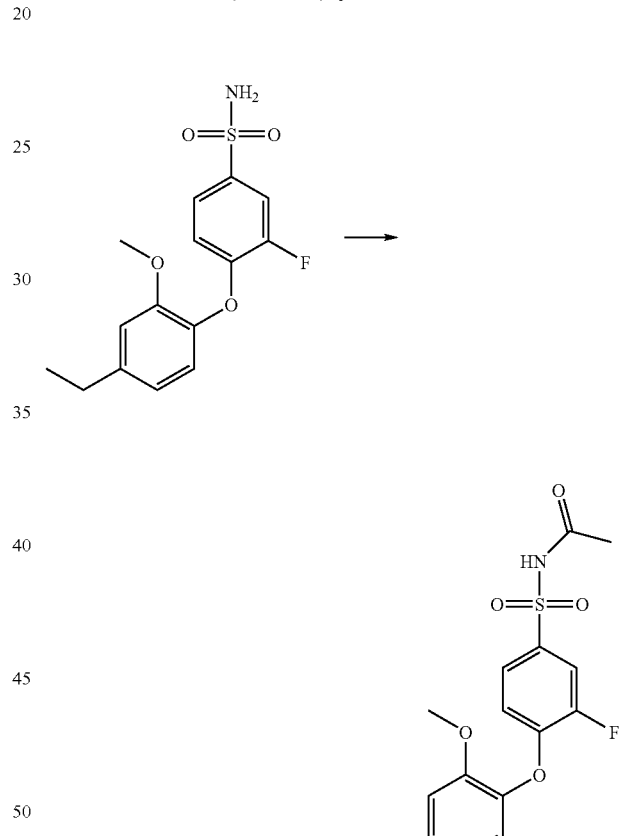

To a solution of 4-(4-ethyl-2-hydroxyphenoxy)-3-fluorobenzenesulfonamide (0.28 mmol; 90 mg) in anhydrous dichloromethane (1 mL), under argon were added EDAC (0.36 mmol; 69 mg), DMAP (0.31 mmol; 38 mg) and acetic acid (0.36 mmol; 0.02 mL). The reaction was stirred overnight at room temperature. Diluted with dichloromethane (3 mL), the mixture was washed with HCl (1N; 3 mL). The organic phase was dried over MgSO$_4$, concentrated to yield the desired compound as a yellow foam (90 mg; 0.25 mmol; 89%), used as such in the following reaction.

MS (ES) m/e 368 (M+H)+ b) N-{[4-(4-ethyl-2-hydroxyphenoxy)-3-fluorophenyl]sulfonyl}acetamide

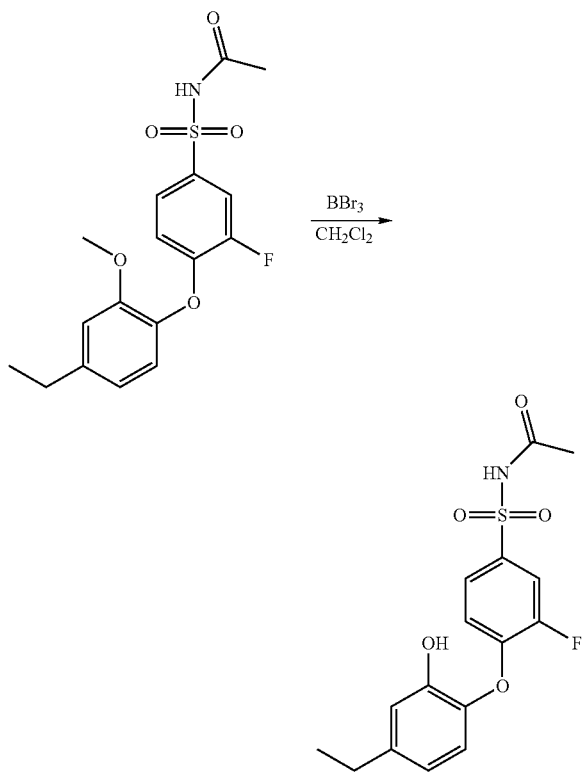

According to the procedure of example 1(b) except substituting 6-chloro-2-(2-methoxy-4-propylphenoxy)pyridin-3-amine for N-{[4-(4-ethyl-2-methoxyphenoxy)-3-fluorophenyl]sulfonyl}acetamide (90 mg; 0.25 mmol), the title compound (46 mg; 0.13 mmol; 52%) was obtained as a clear oil, after purification by preparative TLC (dichloromethane/ethyl acetate).

MS (ES) m/e 354 (M+H)$^+$ $^1$H RMN (CDCl$_3$) δ (ppm): 7.81 (dd, 1H, J$_1$=9.9 Hz, J$_2$=2.0 Hz); 7.70 (d, 1H, J=8.7 Hz); 6.96-6.86 (m, 3H); 6.75 (d, 1H, J=8.2 Hz); 2.62 (q, 2H, J=7.6 Hz); 2.06 (s, 3H); 1.25 (t, 3H, J=7.6 Hz).

EXAMPLE 70

N-{2-[4-(4-Ethyl-2-hydroxy-phenoxy)-3-fluorobenzenesulfonylamino]-ethyl}-acetamide a) N-{2-[4-(4-Ethyl-2-methoxy-phenoxy)-3-fluorobenzene sulfonylamino]-ethyl}-acetamide

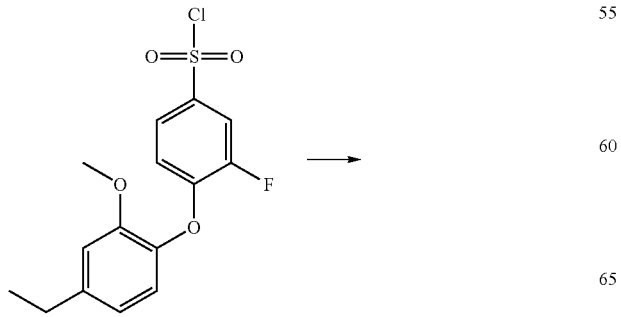

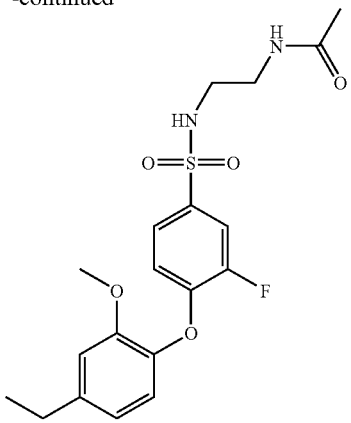

N-Acetylethylenediamine (1.1 mmol; 0.10 mL) was slowly added to a solution of 4-(4-ethyl-2-methoxyphenoxy)-3-fluorobenzenesulfonyl chloride (0.94 mmol; 325 mg) and TEA (2.8 mmol; 0.40 mL) in anhydrous THF (5 mL), under argon at 0° C. The reaction was stirred overnight with progressive warming to room temperature. Concentrated, the mixture was purified by chromatography (dichloromethane/methanol/ammonia gradient) to yield the title compound as a yellow oil (142 mg; 0.35 mmol; 37%) used as such in the following reaction.

MS (ES) m/e 411 (M+H)$^+$ b) N-{2-[4-(4-Ethyl-2-hydroxy-phenoxy)-3-fluorobenzene sulfonylamino]-ethyl}-acetamide

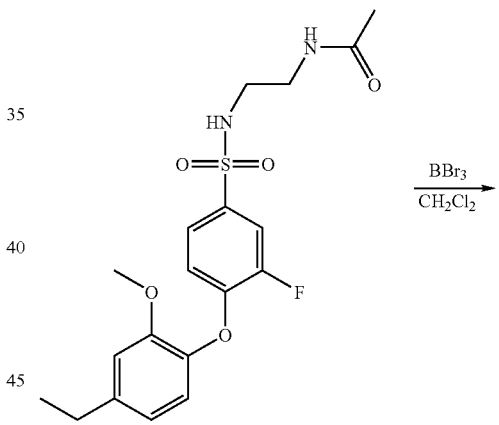

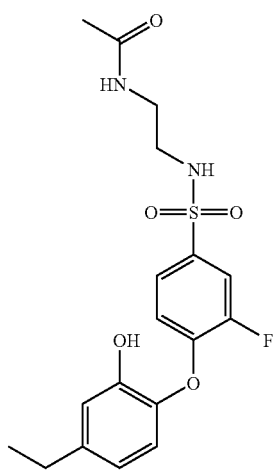

According to the procedure of example 1(b) except substituting 6-chloro-2-(2-methoxy-4-propylphenoxy)pyridin-3- amine for N-{2-[4-(4-Ethyl-2-methoxy-phenoxy)-3-fluoro-benzene sulfonylamino]-ethyl}-acetamide (142 mg; 0.35 mmol), the title compound (44 mg; 0.11 mmol; 32%) was obtained as a clear oil, after purification by preparative TLC (dichloromethane/methanol).

MS (ES) m/e 397 (M+H)+

¹H RMN (CDCl₃) δ (ppm): 7.58 (dd, 1H, J₁=10.0 Hz, J₂=2.0 Hz); 7.44 (d, 1H, J=8.7 Hz); 6.91-6.88 (m, 2H); 6.84 (t, 1H, J=8.2 Hz); 6.74-6.68 (m, 2H); 6.10 (br, 1H); 3.23 (br, 2H); 2.98 (br, 2H); 2.59 (q, 2H, J=7.6 Hz); 1.88 (s, 3H); 1.24 (t, 3H, J=7.6 Hz).

EXAMPLE 71

4-(4-ethyl-2-hydroxyphenoxy)-3-fluoro-N-propyl benzenesulfonamide a) 4-[2-(benzyloxy)-4-ethylphenoxy]-3-fluorobenzenesulfonyl chloride

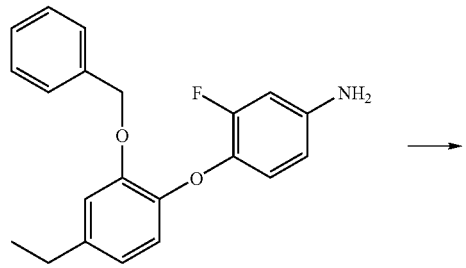

According to the procedure of example 65(a) except substituting 4-(4-ethyl-2-methoxyphenoxy)-3-fluoroaniline for 4-[2-(benzyloxy)-4-ethylphenoxy]-3-fluoroaniline (1.3 g; 3.8 mmol), the title compound (1.51 g; 3.6 mmol; 95%) was obtained as a brown oil used without purification in the following reaction.

MS (ES) m/e 417 (M−Cl+MeOH)+ b) 4-(2-Benzyloxy-4-ethyl-phenoxy)-3-fluoro-N-propyl-benzenesulfonamide

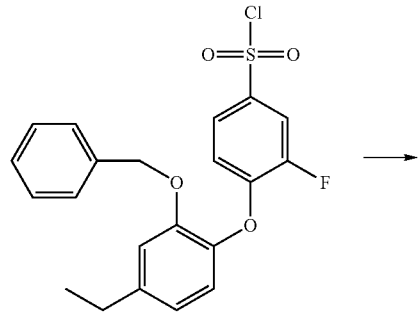

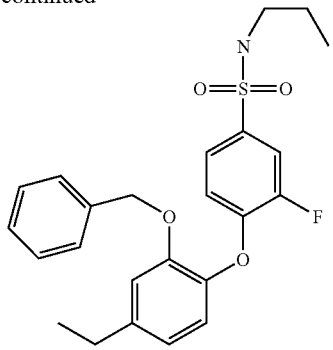

According to the procedure of example 65(b) except substituting 4-(4-ethyl-2-methoxyphenoxy)-3-fluorobenzene sulfonyl chloride for 4-[2-(benzyloxy)-4-ethylphenoxy]-3-fluorobenzene sulfonyl chloride and NH₃ for propylamine (1.7 mmol; 0.14 mL), the title compound (140 mg; 0.32 mmol; 41%) was obtained as a brown oil after purification on preparative TLC (dichloromethane).

MS (ES) m/e 444 (M+H)+ c) 4-(4-ethyl-2-hydroxyphenoxy)-3-fluoro-N-propyl benzenesulfonamide

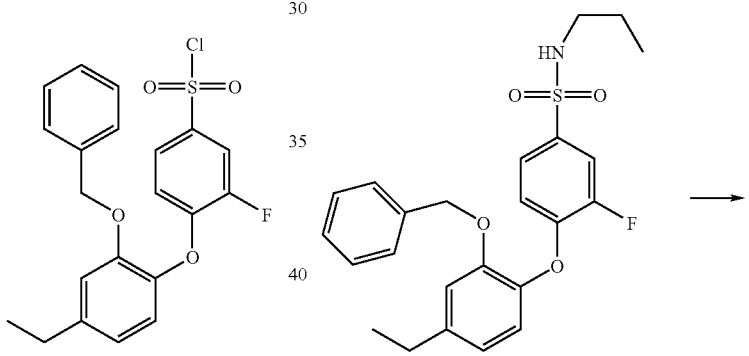

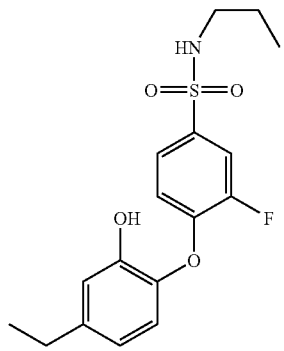

According to the procedure of example 20(b) except substituting 4-ethyl-2-methoxy-1-[4-nitro-2-(trifluoromethyl)phenoxy]benzene for 4-(2-Benzyloxy-4-ethyl-phenoxy)-3-fluoro-N-propyl-benzenesulfonamide (140 mg; 0.32 mmol) and tetrahydrofurane for ethanol (3 mL), the title compound (70 mg; 62%) was obtained as a clear oil, after purification on preparative TLC (dichloromethane)

MS (ES) m/e 354 (M+H)+

¹H RMN (CDCl₃) δ (ppm): 7.65 (dd, 1H, J₁=10.0 Hz, J₂=2.1 Hz); 7.54 (d, 1H, J=9.5 Hz); 6.95 (t, 1H, J=8.5 Hz);

6.93 (d, 1H, J=1.9 Hz); 6.87 (d, 1H, J=8.2 Hz); 6.75 (d, 1H, J=8.2 Hz); 5.84 (br, 1H); 4.92 (t, 2H, J=6.1 Hz); 2.92 (q, 2H, J=6.5 Hz); 2.63 (q, 2H, J=7.6 Hz); 1.51 (se, 2H, J=7.2 Hz); 1.24 (t, 3H, J=7.6 Hz); 0.88 (t, 3H, J=7.5 Hz).

EXAMPLE 72

N-[4-(4-ethyl-2-hydroxyphenoxy)-3-fluorophenyl]-4-hydroxybutanamide a) N-[4-(4-ethyl-2-methoxyphenoxy)-3-fluorophenyl]-4-hydroxybutanamide

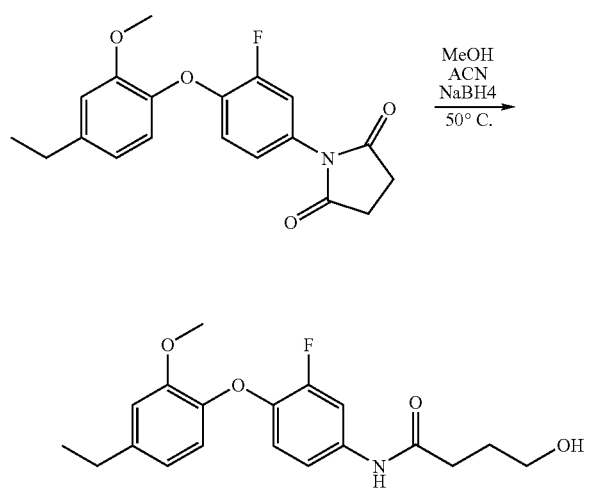 [SMILES: CCc1ccc(Oc2ccc(N3C(=O)CCC3=O)cc2F)c(OC)c1 ; CCc1ccc(Oc2ccc(NC(=O)CCCO)cc2F)c(OC)c1]

To 1-[4-(4-ethyl-2-methoxyphenoxy)-3-fluorophenyl] pyrrolidine-2,5-dione (169.8 mg, 0.49 mmol) was added methanol (2 mL). The reaction mixture was stirred for 1 h 30 at room temperature under argon. Acetonitrile (2 mL) and NaBH$_4$ (190.7 mg, 4.9 mmol) were added to the reaction. The reaction mixture was stirred at 50° C. for 17 h. Then it was concentrated, dissolved in dichloromethane, washed with a saturated solution of NH$_4$Cl and extracted with dichloromethane. Combined organic phases were dried over Na$_2$SO$_4$, concentrated in vacuo, to give the title product as a white solid used without further purification (169.5 mg; 100%).

MS (ES) m/e 348 (M+H)$^+$

According to the procedure of example 1(b) except substituting 6-chloro-2-(2-methoxy-4-propylphenoxy)pyridin-3-amine for N-[4-(4-ethyl-2-methoxyphenoxy)-3-fluorophenyl]-4-hydroxybutanamide (47.9 mg, 0.14 mmol), the title compound was prepared as a colorless oil (16.5 mg; 35%), after purification by preparative TLC (dichloromethane/methanol: 9/1).

MS (ES) m/e 334 (M+H)$^+$ $^1$H NMR (CD$_3$OD) δ (ppm): 7.68 (dd, 1H, J$_1$=12.8 Hz, J$_2$=2.4 Hz); 7.19 (m, 1H); 6.88 (m, 2H); 6.76 (d, 1H, J=8.0 Hz); 6.68 (dd, 1H, J$_1$=8.4 Hz, J$_2$=2.0 Hz); 3.68 (t, 2H, J=6.2 Hz); 2.62 (q, 2 H, J=7.6 Hz), 2.51 (t, 2H, J=7.6 Hz), 1.96 (qt, 2H, J=6.8 Hz); 1.27 (t, 3H, 7.6 Hz).

EXAMPLE 73

4-[4-(4-Ethyl-2-hydroxy-phenoxy)-3-fluoro-phenoxy]-butyric acid ethyl ester a) 1-{4-[2-(benzyloxy)-4-ethylphenoxy]-3-fluorophenyl}ethanone

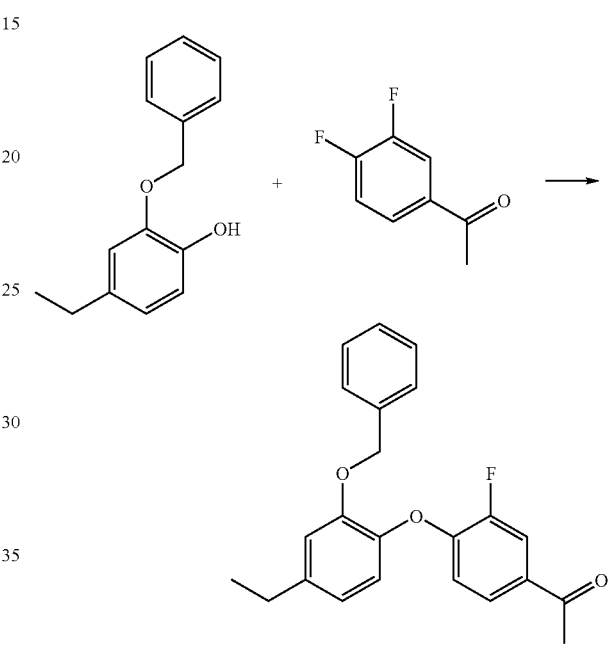

According to the procedure of example 21(a3) except substituting 4-Ethyl-2-methoxy phenol by 2-(benzyloxy)-4-ethylphenol (1.3 g, 5.7 mmol) and 3-Fluoro-2-nitropyridine by 1-(3,4-difluorophenyl)ethanone (0.98 g, 6.27 mmol), the title compound was prepared as a clear oil in 96% yield (2 g) and used without further purification.

LCMS m/z 365.0 (M+H)+ b) 4-[2-(benzyloxy)-4-ethylphenoxy]-3-fluorophenyl acetate

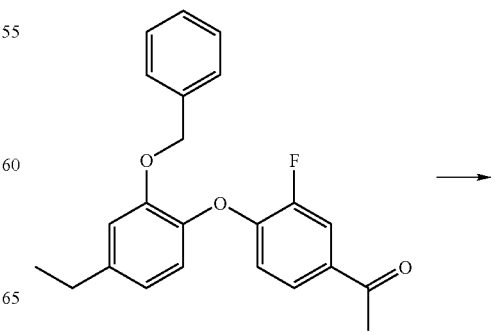

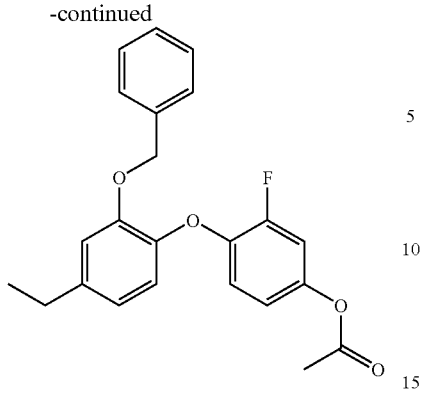

To a solution of 1-{4-[2-(benzyloxy)-4-ethylphenoxy]-3-fluorophenyl}ethanone (3 g, 8.24 mmol) in dry dichloromethane (30 ml), was added PTSA (0.047 g, 0.247 mmol). The reaction mixture was cooled in an ice bath and mCPBA (50% H2O) (2.84 g, 8.24 mmol) was added portionwise. The resulting mixture was stirred at RT for 3 days, then concentrated at 35-40 C. The residue was purified by column chromatography, (pet ether:EtOAC). The resulting solid was dissolved in pet ether, filtered then concentrated the yield the title compound (1.6 g; 51%)

LCMS m/z 379.2 (M–H)– c) 4-[2-(benzyloxy)-4-ethylphenoxy]-3-fluorophenol

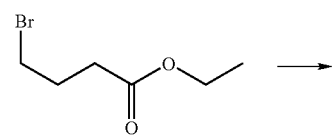

To a solution of 4-[2-(benzyloxy)-4-ethylphenoxy]-3-fluorophenyl acetate (1.6 g, 4.2 mmol) in MeOH:H₂O (35 ml:35 ml), was added KOH (0.83 g, 14.8 mmol). The mixture was heated at 65° C. for 4.5 hours, concentrated in vacuo, then extracted with EtOAC (25 ml*2). Combined organic phases were dried over Na₂SO₄ and concentrated. The residue was purified by column chromatography, (pet ether: EtOAC 95:5), to yield the title compound as a white solid (630 mg; 44%)

LCMS m/z 336.9 (M–H)– d) 4-[4-(2-Benzyloxy-4-ethyl-phenoxy)-3-fluoro-phenoxy]-butyric acid ethyl ester

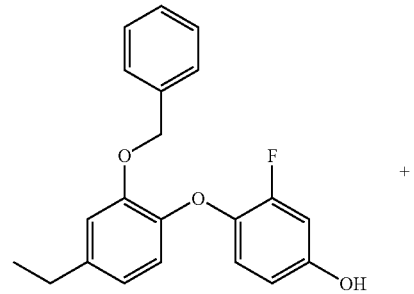

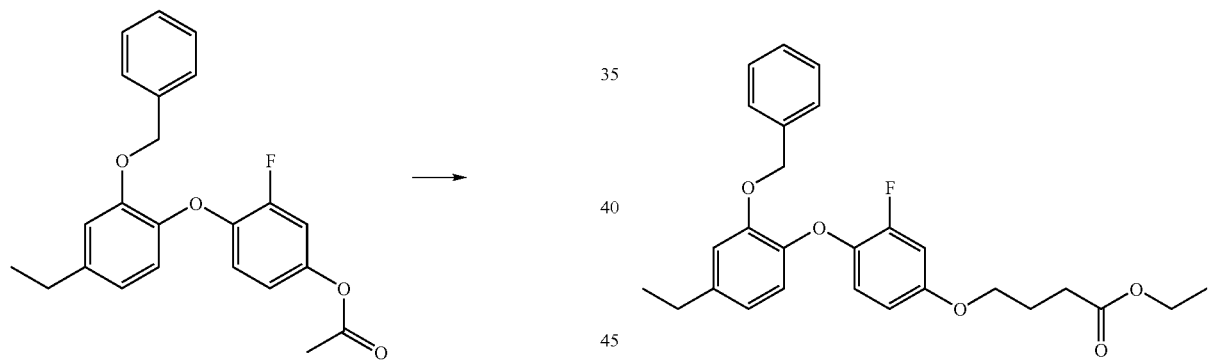

To a solution of 4-[2-(benzyloxy)-4-ethylphenoxy]-3-fluorophenol (0.30 mmol; 100 mg) in dry acetone (2 mL), under argon, were added potassium carbonate (0.35 mmol; 49 mg), NaI (0.06 mmol; 9 mg) and ethyl bromobutyrate (0.35 mmol; 51 µL). The reaction was stirred 14 hours at 60° C. Water (100 µL) and tetrabutylammonium hydroxyde (0.03 mmol; 8 mg) were added and the mixture was stirred 16 hours at 60° C. The reaction was hydrolysed with NH₄Cl sat. (5 mL) and extracted with ethyl acetate (3*3 mL). Combined organic phases were dried over Na₂SO₄, concentrated in vacuo. The title compound (100 mg; 0.22 mmol; 75%) was obtained as a yellow oil, after purification by preparative TLC (cyclohexane/ethyl acetate: 7/3).

MS (ES) m/e 475 (M+Na)⁺ e) 4-[4-(4-Ethyl-2-hydroxy-phenoxy)-3-fluoro-phenoxy]-butyric acid ethyl ester

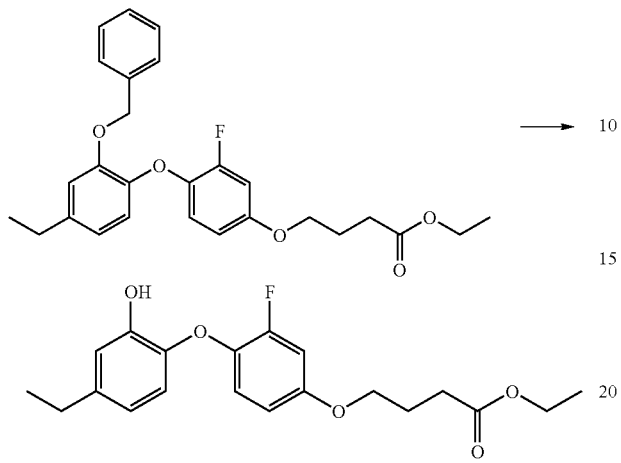

According to the procedure of example 48(d) except substituting 3-[4-(2-Benzyloxy-4-ethyl-phenoxy)-3-fluoro-phenylamino]-propan-1-ol for 4-[4-(2-Benzyloxy-4-ethyl-phenoxy)-3-fluoro-phenoxy]-butyric acid ethyl ester (0.22 mmol; 100 mg) the title compound was prepared as a clear oil (58 mg; 72%), after purification by preparative TLC (Cyclohexane/Ethyl acetate: 7/3)

MS (ES) m/e 363 (M+H)$^+$ $^1$H RMN (CDCl$_3$) δ (ppm): 7.00 (t, 1H, J=9.1 Hz); 6.87 (s, 1H); 6.74 (dd, 1H, J$_1$=12.1 Hz, J$_2$=2.8 Hz); 6.64-6.59 (m, 3H); 4.15 (q, 2H, J=7.1 Hz); 3.98 (t, 2H, J=6.1 Hz); 2.57 (q, 2H, J=7.6 Hz); 2.51 (t, 2H, J=7.3 Hz); 2.11 (qt, 2H, J=7.0 Hz); 1.27 (t, 3H, J=7.1 Hz); 1.21 (t, 3H, J=7.6 Hz).

EXAMPLE 74

4-[4-(4-Ethyl-2-hydroxy-phenoxy)-3-fluoro-phenoxy]-butyric acid

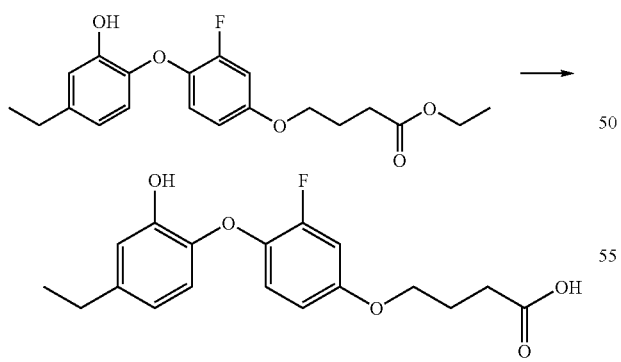

To a solution of ethyl ethyl 4-[4-(4-Ethyl-2-hydroxy-phenoxy)-3-fluoro-phenoxy]-butyric acid ethyl ester (0.16 mmol; 58 mg), in a THF/water mixture (1/1; 1 mL) was added lithium hydroxide (0.64 mmol; 15 mg). The reaction was heated 1 hour at 60° C. After cooling to 0° C., the reaction was treated with concentrated HCl, and extracted with ethyl acetate (3*2 mL). Combinated organic phases were dried over Na$_2$SO$_4$ and concentrated in vacuo. The title compound (0.16 mmol; 54 mg; quantitative) was obtained as a clear oil, used without purification.

MS (ES) m/e 335 (M+H)$^+$ $^1$H RMN (CDCl$_3$) δ (ppm): 7.00 (t, 1H, J=9.7 Hz); 6.87 (s, 1H); 6.74 (dd, 1H, J$_1$=12.1 Hz, J$_2$=2.8 Hz); 6.64-6.59 (m, 3H); 3.99 (t, 2H, J=6.0 Hz); 2.61-2.55 (m, 4H); 2.13 (qt, 2H, J=6.9 Hz); 1.23 (t, 3H, J=7.6 Hz).

EXAMPLE 75

4-(4-Ethyl-2-hydroxy-phenoxy)-3-fluoro-N-(2-pyridin-2-yl-ethyl)-benzenesulfonamide a) 4-(2-Benzyloxy-4-ethyl-phenoxy)-3-fluoro-N-(2-pyridin-2-yl-ethyl)-benzene sulfonamide

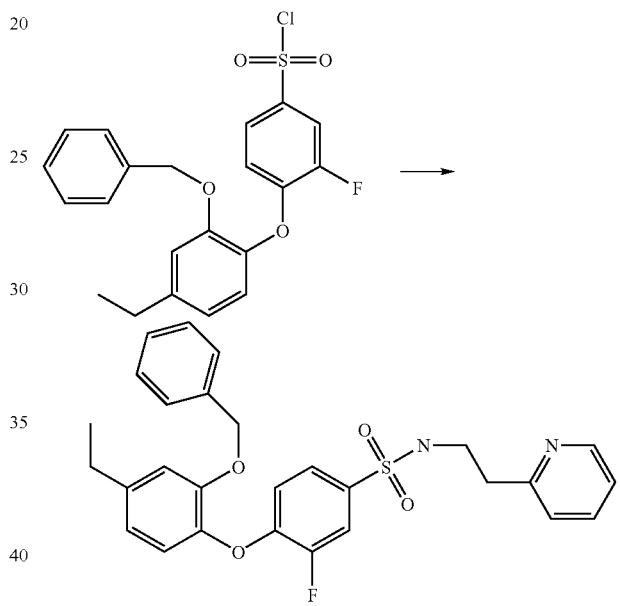

According to the procedure of example 70(a) except substituting N-Acetylethylenediamine for 2-(2-Aminoethyl) pyridine (1.5 mmol; 0.18 mL), the title compound (150 mg; 0.30 mmol; 24%) was obtained as a yellow oil after purification via chromatography. (gradient dichloromethane/ethyl acetate).

MS (ES) m/e 507 (M+H)$^+$ b) 4-(4-Ethyl-2-hydroxy-phenoxy)-3-fluoro-N-(2-pyridin-2-yl-ethyl)-benzenesulfonamide

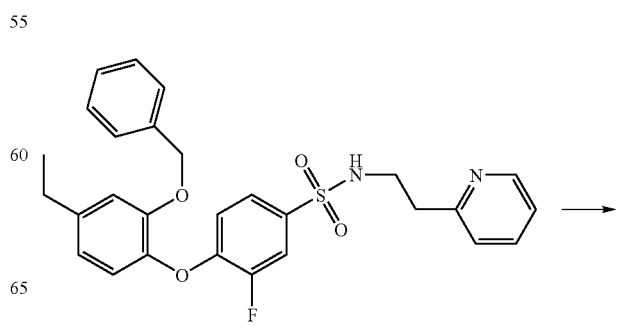

125

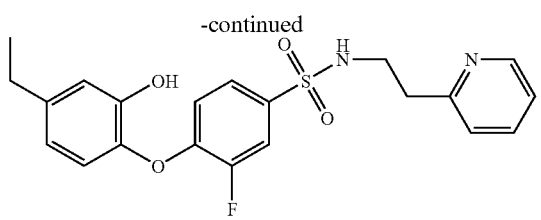

According to the procedure of example 20(b) except substituting 4-ethyl-2-methoxy-1-[4-nitro-2-(trifluoromethyl)phenoxy]benzene for 4-(2-Benzyloxy-4-ethyl-phenoxy)-3-fluoro-N-(2-pyridin-2-yl-ethyl)-benzene sulfonamide (150 mg; 0.30 mmol) and tetrahydrofurane for ethanol (3 mL), the title compound (70 mg; 62%) was obtained as a clear oil, after purification via preparative TLC (dichloromethane/ethyl acetate).

MS (ES) m/e 417 (M+H)+

¹H RMN (CDCl₃) δ (ppm): 8.41 (d, 1H, J=4.8 Hz); 7.62 (t, 1H, J=9.4 Hz); 7.53 (d, 1H, J=10.0 Hz); 7.45 (d, 1H, J=8.7 Hz); 7.17-7.13 (m, 2H); 6.91-6.85 (m, 3H); 6.73 (d, 1H, J=8.2 Hz); 6.14 (br, 1H); 3.32 (t, 2H, J=5.8 Hz); 2.94 (t, 2H, J=6.3 Hz); 2.62 (q, 2H, J=7.6 Hz); 1.23 (t, 3H, J=7.6 Hz)

EXAMPLE 76

4-(4-Ethyl-2-hydroxy-phenoxy)-3-fluoro-N-(3-imidazol-1-yl-propyl)-benzenesulfonamide a) 4-(2-Benzyloxy-4-ethyl-phenoxy)-3-fluoro-N-(3-imidazol-1-yl-propyl)-benzenesulfonamide

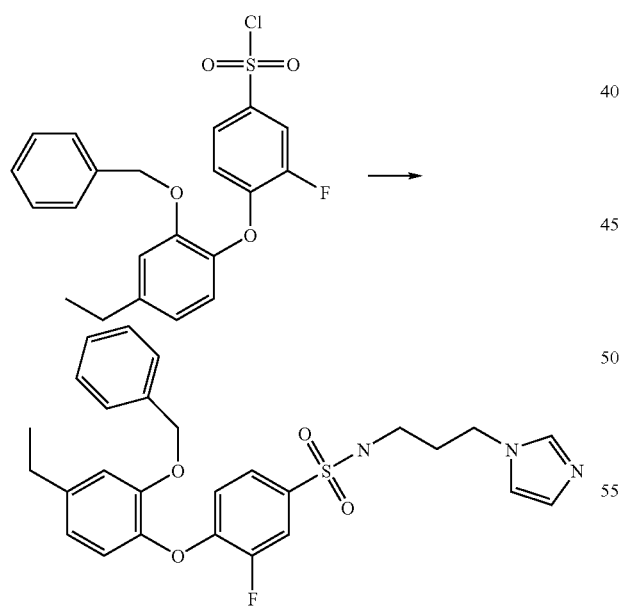

According to the procedure of example 70(a) except substituting N-Acetylethylenediamine for 1-(3-Aminopropyl)imidazole (1.5 mmol; 0.18 mL), the title compound (160 mg; 0.31 mmol; 25%) was obtained as a brown oil after purification by preparative TLC (dichloromethane/methanol).

MS (ES) m/e 510 (M+H)+

126 b) 4-(4-Ethyl-2-hydroxy-phenoxy)-3-fluoro-N-(3-imidazol-1-yl-propyl)-benzenesulfonamide

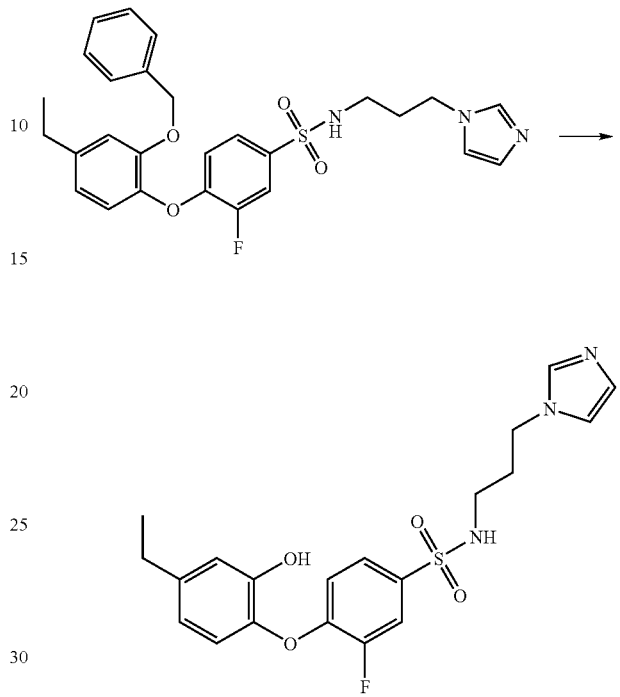

According to the procedure of example 20(b) except substituting 4-ethyl-2-methoxy-1-[4-nitro-2-(trifluoromethyl)phenoxy]benzene for 4-(2-Benzyloxy-4-ethyl-phenoxy)-3-fluoro-N-(3-imidazol-1-yl-propyl)-benzenesulfonamide (160 mg; 0.31 mmol) and tetrahydrofurane for ethanol (3 mL), the title compound (55 mg; 42%) was obtained as a clear oil, after purification via preparative TLC (dichloromethane/methanol/triethylamine)

MS (ES) m/e 420 (M+H)+

¹H RMN (CDCl₃) δ (ppm): 7.52 (d, 1H, J₁=10.0 Hz); 7.43 (d, 1H, J=8.7 Hz); 7.23 (s, 1H); 6.96-6.92 (m, 3H); 6.83-6.80 (m, 2H); 6.72 (d, 1H, J=8.2 Hz); 3.97 (t, 2H, J=6.4 Hz); 2.81 (t, 2H, J=6.3 Hz); 2.61 (q, 2H, J=7.6 Hz); 1.94 (q, 2H, J=6.3 Hz); 1.23 (t, 3H, J=7.6 Hz)

EXAMPLE 77

5-ethyl-2-(2-fluoro-4-[(1H-imidazol-4-ylmethyl)amino]phenoxy)phenol a) 4(4-ethyl-2-methoxyphenoxy)-3-fluoro-N-(1H-imidazol-4-yl methyl) aniline

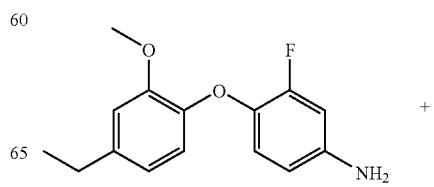

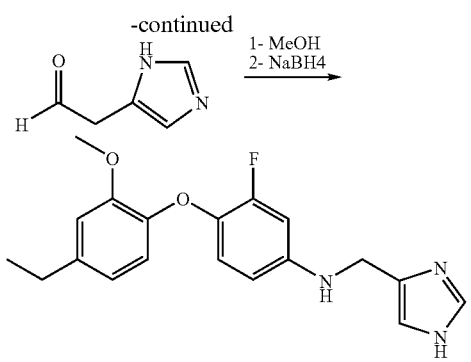

According to the procedure of example 66(a) except substituting nicotinaldehyde for 4(5)-imidazole carboxadehyde (115.27 mg, 1.2 mmol), the title compound was prepared as a colorless oil (300 mg; 88%), after purification by preparative TLC (dichloromethane/methanol: 95/5+1% NH4+).
MS (ES) m/e 342 (M+H)+ b) 5-ethyl-2-(2-fluoro-4-[(1H-imidazol-4-ylmethyl)amino]phenoxy)phenol

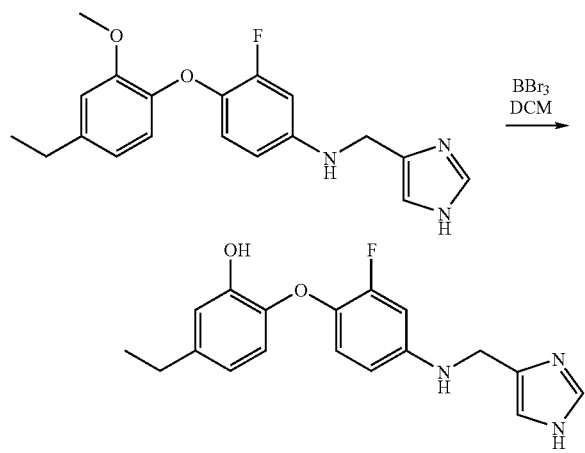

According to the procedure of example 1(b) except substituting 6-chloro-2-(2-methoxy-4-propylphenoxy)pyridin-3-amine for 4(4-ethyl-2-methoxyphenoxy)-3-fluoro-N-(1H-imidazol-4-ylmethyl)aniline (300 mg, 0.87 mmol), the title compound (101 mg, 35%) was prepared as a white solid, after purification by preparative TLC and washing with diethyl ether (dichloromethane/methanol: 95/5+1% NH4+).
MS (ES) m/e 328 (M+H)+
1H NMR (MeOD) δ (ppm): 7.62 (s, 1H), 6.97 (s, 1H), 6.79 (t, 1H, J=9.0 Hz), 6.71 (s, 1H), 6.51-6.50 (m, 3H), 6.42 (dd, 1H, J1=8.8 Hz, J2=3.8 Hz), 4.20 (s, 2H), 2.51 (q, 2H, J=7.6 Hz), 1.16 (t, 3H, J=7.6 Hz)

EXAMPLE 78

2-[(6-fluoropyridin-2-yl)oxy]-5-[3-(1H-1,2,4-triazol-1-yl)propyl]phenol a) 3-{4-[(6-fluoropyridin-2-yl)oxy]-3-methoxyphenyl}prop-2-yn-1-ol

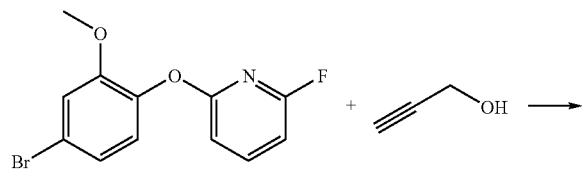

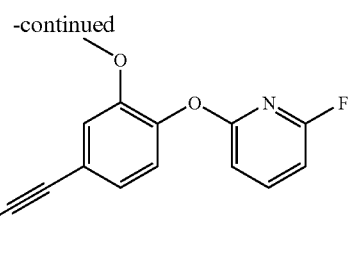

According to the procedure of example 11(a) except substituting 5-bromo-2-(2-methoxy-4-propylphenoxy)pyridine by 2-(4-bromo-2-methoxyphenoxy)-6-fluoropyridine (0.98 mmol; 300 mg) and 3-butyn-1-ol by propargylic alcohol (2.50 mmol; 150 μL), the title compound was obtained as a yellow solid (71%, 191 mg) after purification on silica gel (cyclohexane/ethyl acetate gradient).
MS (ES) m/e 274 (M+H)+ b) 3-{4-[(6-fluoropyridin-2-yl)oxy]-3-methoxyphenyl}prop-2-yn-ol

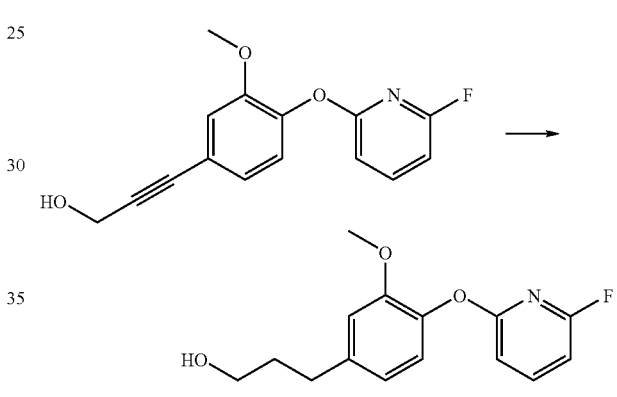

According to the procedure of example 20(b) except substituting 4-ethyl-2-methoxy-1-[4-nitro-2-(trifluoromethyl)phenoxy]benzene by 3-{4-[(6-fluoropyridin-2-yl)oxy]-3-methoxyphenyl}prop-2-yn-1-ol (0.33 mmol; 90 mg) and THF by absolute ethanol, the title compound (quantitative, 102 mg) was obtained as a yellow oil, and used without further purification.
MS (ES) m/e 339 (M+H)+ c) 2-[4-(3-chloropropyl)-2-methoxyphenoxy]-6-fluoropyridine

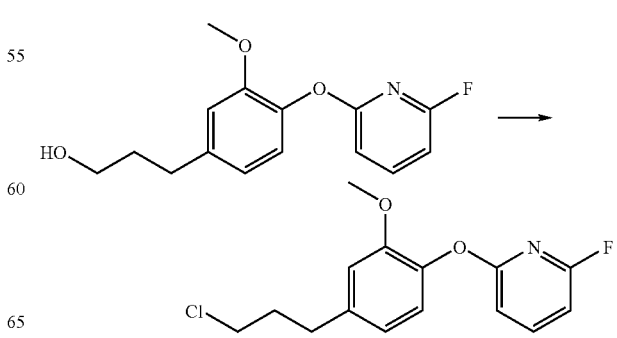

To a solution of 3-{4-[(6-fluoropyridin-2-yl)oxy]-3-methoxyphenyl}prop-2-yn-ol (0.37 mmol; 102 mg) in dry dichloromethane (2 mL), under argon, cooled to −40° C., was added triethylamine (0.41 mmol; 56 μL) then methanesulfonyl chloride (0.39 mmol; 30 μL). The reaction mixture was allowed to stir for 6 hr, with gradual warming to room temperature. The reaction was hydrolysed with saturated NH4Cl, extracted with ethyl acetate. Combined organic phases were dried over Na2SO4, concentrated in vacuo. The title compound (185 mg; 47%) was obtained as a light oil, after purification on preparative TLC (cyclohexane/ethyl acetate: 7/3).

MS (ES) m/e 296(M+H)+ d) 2-fluoro-6-{2-methoxy-4-[3-(1H-1,2,4-triazol-1-yl)propyl]phenoxy}pyridine

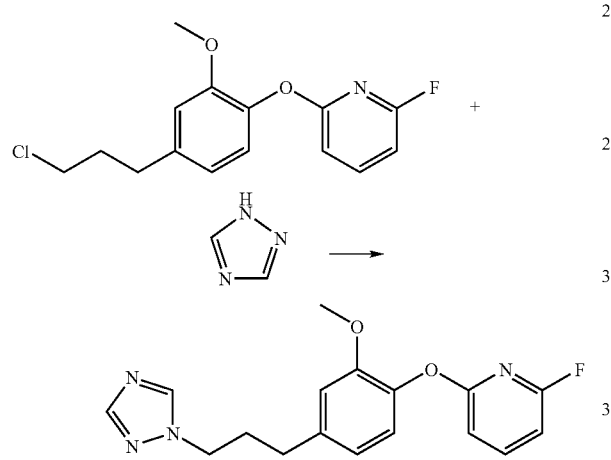

To a solution of 2-[4-(3-chloropropyl)-2-methoxyphenoxy]-6-fluoropyridine (0.14 mmol) in a THF/DMF mixture (340 μL/170 μL), under argon, was added NaI (0.14 mmol; 21 mg). The mixture was stirred 30 minutes at 50° C., before addition of diisopropylethylamine (0.28 mmol, 36 mg) and 1,2,4-triazol (0.28 mmol; 19 mg). The reaction mixture was allowed to stir overnight at 50° C. After concentration, the reaction was hydrolysed with saturated NH4Cl (1 mL), extracted with AcOEt (2*1 mL). Combined organic phases were dried over Na2SO4, concentrated in vacuo. The title compound (15 mg; 33%) was obtained as a yellow oil after purification on preparative TLC (dichloromethane/methanol: 9/1).

MS (ES) m/e 329 (M+H)+ e) 2-[(6-fluoropyridin-2-yl)oxy]-5-[3-(1H-1,2,4-triazol-1-yl)propyl]phenol

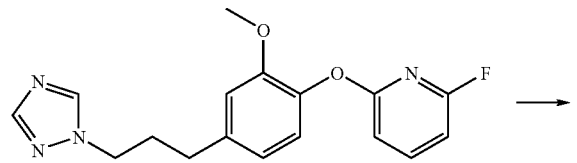

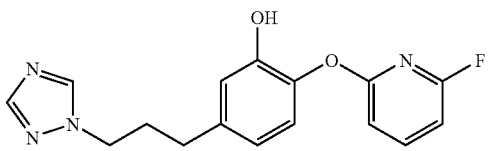

According to the procedure of example 1(b) except substituting 6-chloro-2-(2-methoxy-4-propylphenoxy)pyridin-3-amine for 2-fluoro-6-{2-methoxy-4-[3-(1H-1,2,4-triazol-1-yl)propyl]phenoxy}pyridine (0.05 mmol; 15 mg), the desired compound was prepared in 41% yield (6 mg) after purification by preparative TLC (dichloromethane/methanol: 9/1).

MS (ES) m/e 315(M+H+)

1H RMN (MeOD) δ (ppm): 8.48 (s, 1H); 8.02 (s, 1H); 7.85 (q, 1H, J=8.1 Hz); 6.96 (d, 1H, J=8.1 Hz); 6.79 (d, 1H, J=1.9 Hz); 6.73-6.69 (m, 2H); 6.66 (dd, 1H, J1=7.9 Hz, J2=2.2 Hz); 4.23 (t, 2H, J=7.0 Hz); 2.59 (t, 2H, J=7.6 Hz); 2.22 (qt, 2H, J=7.6 Hz).

EXAMPLE 79

N-methanesulfonyl-N1-[4-(4-ethyl-2-hydroxyphenoxy)-3-fluorophenyl]propan-1,3-diamine a) N1-[4-(2-Benzyloxy-4-ethylphenoxy)-3-fluorophenyl]propan-1,3-diamine

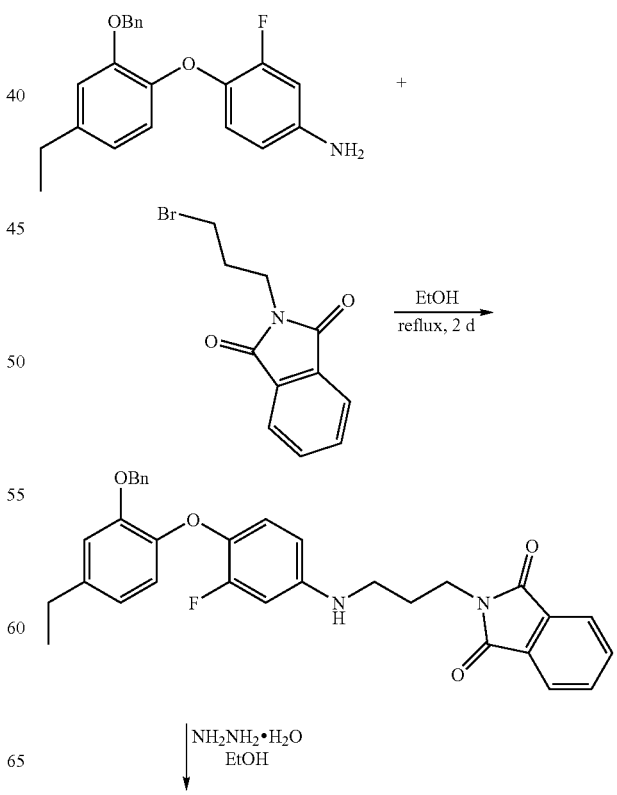

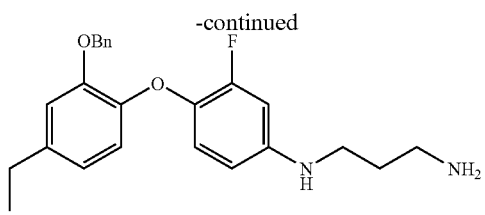

To 4-(2-benzyloxy-4-ethylphenoxy)-3-fluoroaniline (500 mg, 1.48 mmol) in 25 ml of ethanol was added 3-bromopropylphthalimide (440 mg, 1.64 mmol). The mixture was refluxed for 2 days. The reaction mixture was diluted with ethylacetate and washed with water, saturated brine solution, dried over anhydrous $Na_2SO_4$ and concentrated. The crude obtained was passed through a silica gel column using 15% ethylacetate in petroleum ether as eluant. The LCMS of the obtained mixture showed 53% mass of the coupled product. This was taken in 25 ml of ethanol and added 7 ml of hydrazine hydrate and refluxed overnight. Ethanol was removed in vacuo and added 20% KOH solution (20 ml) to the residue. The aqueous fraction was then extracted with dichlormethane and the combined dichloromethane fraction was dried over anhydrous $Na_2SO_4$ and concentrated. The crude product obtained was purified by column chromatography using 5% methanol in dichloromethane as eluant to obtain 110 mg (18.8% after 2 steps) of the $N^1$-[4-(2-Benzyloxy-4-ethylphenoxy)-3-fluorophenyl]propan-1,3-diamine.

LC-MS m/z 395.9 (M+H)$^+$ b) N-Methanesulfonyl-$N^1$-[4-(2-benzyloxy-4-ethylphenoxy)-3-fluorophenyl]propan-1,3-diamine

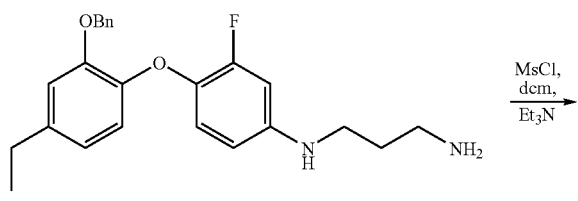

To a solution of $N^1$-[4-(2-Benzyloxy-4-ethylphenoxy)-3-fluorophenyl]propan-1,3-diamine (90 mg, 0.23 mmol) in 5 ml of dry dichloromethane and 0.08 ml (0.57 mmol) of triethylamine, cooled to 0° C., was added mesyl chloride (26 mg, 0.23 mmol) taken in 0.5 ml of dichloromethane dropwise. The reaction was quenched after 5 minutes as the reaction was complete on TLC. The reaction mixture was diluted with water and the layers separated. The aqueous layer was extracted with dichloromethane and the combined dichloromethane fraction was washed with water, dried over anhydrous $Na_2SO_4$ and concentrated. The crude residue obtained was combined with the crude obtained from an earlier 20 mg batch and column purified over silica gel using 2% methanol in dichloromethane as eluant to get 90 mg, 68.3% of title compound.

LC-MS m/z 473.2 (M+H)$^+$ c) N-methanesulfonyl-$N^1$-[4-(4-ethyl-2-hydroxyphenoxy)-3-fluorophenyl]propan-1,3-diamine

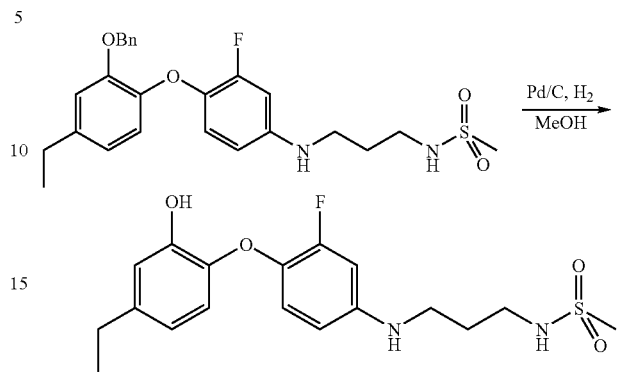

According to the procedure of example 20(b) except substituting 4-ethyl-2-methoxy-1-[4-nitro-2-(trifluoromethyl)phenoxy]benzene for N-Methanesulfonyl-$N^1$-[4-(2-benzyloxy-4-ethylphenoxy)-3-fluorophenyl]propan-1,3-diamine (90 mg, 0.19 mmol) and tetrahydrofurane for methanol (15 mL), the title compound (50 mg, 68%) was obtained as a brown liquid, after purification on silica gel (dichloromethane/ethyl acetate: 8/2)

$^1$H NMR (CDCl$_3$), δ (ppm): 6.93 (t, J=8.9 Hz, 1H), 6.87 (s, 1H), 6.66-6.57 (m, 3H), 6.49 (d, J=8.1 Hz, 1H), 4.78 (bs, 1H), 3.3-3.28 (m, 4H), 2.98 (s, 3H), 2.57 (q, J=7.5 Hz, 2H), 1.92 (m, 2H), 1.21 (t, J=7.5 Hz, 3H)

LC-MS m/z 383 (M+H)$^+$

EXAMPLE 80

N-acetyl-$N^1$-[4-(4-ethyl-2-hydroxyphenoxy)-3-fluoro phenyl]propan-1,3-diamine a) N-acetyl-$N^1$-[4-(2-Benzyloxy-4-ethylphenoxy)-3-fluorophenyl]propan-1,3-diamine

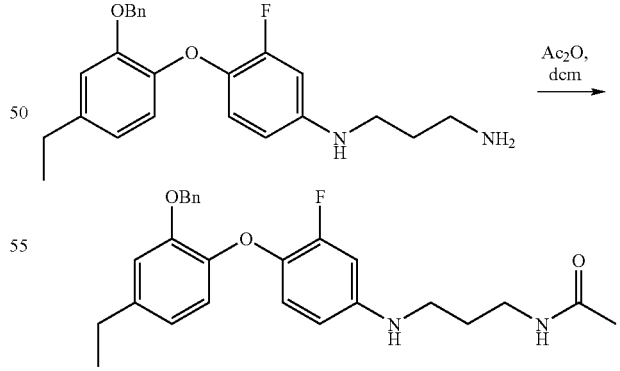

To a solution of $N^1$-[4-(2-Benzyloxy-4-ethylphenoxy)-3-fluorophenyl]propan-1,3-diamine (60 mg, 0.15 mmol) in 10 ml of dry dichloromethane, cooled to 0° C., was added acetic anhydride (20 mg, 0.19 mmol) taken in 0.5 ml of dichloromethane dropwise. The reaction mixture was warmed to rt and stirred for 1 h until reaction was complete on TLC. The reaction mixture was diluted with water and the layers separated. The aqueous layer was extracted with dichloromethane and the combined dichloromethane fraction was dried over anhydrous Na₂SO₄ and concentrated. The crude residue obtained was column purified over silica gel using 2% methanol in dichloromethane as eluant to get 50 mg, 75.4% of title compound.

LC-MS m/z 438.1 (M+H)⁺ b) N-acetyl-N¹-[4-(4-ethyl-2-hydroxyphenoxy)-3-fluorophenyl]propan-1,3-diamine

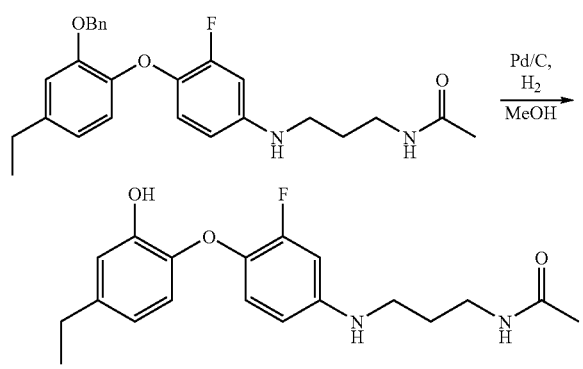

According to the procedure of example 20(b) except substituting 4-ethyl-2-methoxy-1-[4-nitro-2-(trifluoromethyl)phenoxy]benzene for N-acetyl-N¹-[4-(2-Benzyloxy-4-ethylphenoxy)-3-fluorophenyl]propan-1,3-diamine (70 mg, 0.16 mmol) and tetrahydrofurane for methanol (15 mL), the title compound (50 mg, 91%) was obtained as a brown liquid, after purification on silica gel (dichloromethane/ethyl acetate: 5/5)

¹H NMR (CDCl₃), δ (ppm): 6.93 (t, J=8.9 Hz, 1H), 6.86 (d, J=1.6 Hz, 1H), 6.64-6.58 (m, 2H), 6.46-6.42 (m, 1H), 6.36 (d, J=8.8 Hz, 1H), 5.64 (bs, 2H), 3.42-3.37 (m, 2H), 3.15 (t, J=6.4 HZ, 2H), 2.57 (q, J=7.59 Hz, 2H), 2.06 (s, 3H), 1.80 (qt, J=6.48 Hz, 2H), 1.21 (t, J=7.58 Hz, 3H)

LC-MS m/z 347.2 (M+H)⁺

EXAMPLE 81

5-Ethyl-2-[2-fluoro-4-(2-hydroxyethylamino)-phenoxy]phenol a) 3-[4-(2-Benzyloxy-4-ethylphenoxy)-3-fluorophenyl]oxazolidin-2-one

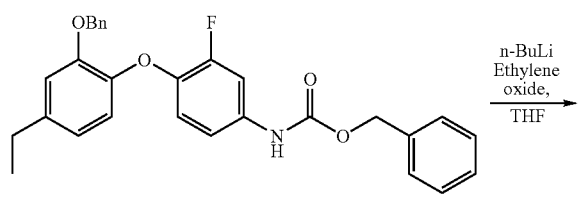

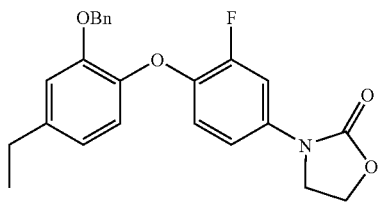

A solution of [4-(2-Benzyloxy-4-ethylphenoxy)-3-fluorophenyl]-carbamic acid-benzyl ester (500 mg, 1.06 mmol) in 5 ml tetrahydrofuran under nitrogen atmosphere was cooled to −78° C. To this added 2.8M n-butyl lithium (0.075 g, 1.16 mmol) dropwise and the stirring at −78° C. for 1 h. Condensed ethylene oxide (0.5 ml, 9.9 mmol) was then added dropwise to the reaction mixture and warmed slowly to rt. The reaction was stirred at rt overnight and then quenched with saturated ammonium chloride solution. The aqueous phase was extracted with dichloromethane and the combined organic phase was dried over anhydrous Na₂SO₄ and concentrated. The crude obtained was purified by column chromatography on silica gel using 25% ethyl acetate in petroleum ether as eluant to obtain 350 mg, 81% of the title compound as a brown oil.

LC-MS m/z 407 (M+H)⁺ b) N-[4-(2-Benzyloxy-4-ethylphenoxy)-3-fluorophenyl]-2-aminoethanol

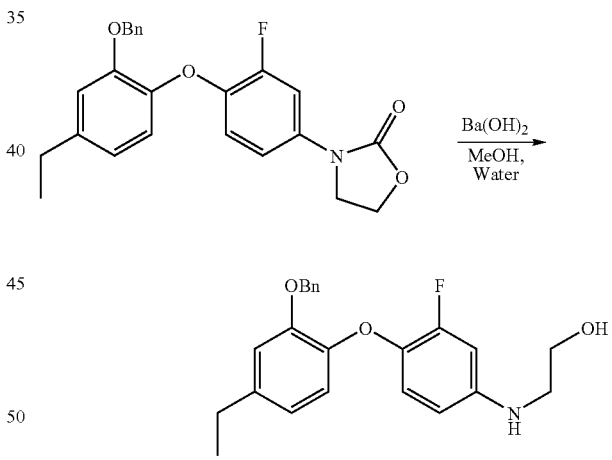

To a solution of 3-[4-(2-Benzyloxy-4-ethylphenoxy)-3-fluorophenyl]oxazolidin-2-one (350 mg, 0.85 mmol) in 5 ml of methanol was added barium hydroxide (245 mg, 1.28 mmol) taken in 5 ml of water. The reaction mixture was warmed to 65° C. and stirred overnight (reaction was complete on TLC). The reaction mixture concentrated in vacuo to remove methanol, diluted with water and the aqueous layer was extracted with ethyl acetate. The combined organic fraction was washed with brine, dried over anhydrous Na₂SO₄ and concentrated to get 300 mg, 91.57% of the title compound as a brown oil, used as such in the next step.

LC-MS m/z 382.3 (M+H)⁺ c) 5-Ethyl-2-[2-fluoro-4-(2-hydroxyethylamino)-phenoxy]phenol

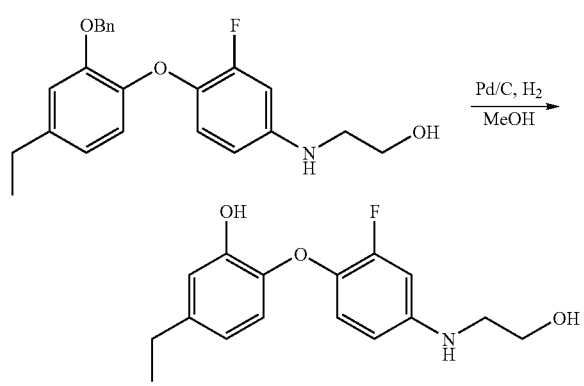

According to the procedure of example 20(b) except substituting 4-ethyl-2-methoxy-1-[4-nitro-2-(trifluoromethyl)phenoxy]benzene for N-[4-(2-Benzyloxy-4-ethylphenoxy)-3-fluorophenyl]-2-aminoethanol (350 mg, 0.92 mmol) and tetrahydrofurane for methanol (25 mL), the title compound (210 mg; 78%) was obtained as a yellow solid, after purification on silica gel (ethylacetate and petroleum ether: 5/5)

$^1$H NMR (CDCl$_3$), δ (ppm): 6.94 (t, J=8.9 Hz, 1H), 6.86 (d, J=1.2 Hz, 1H), 6.64-6.58 (m, 2H), 6.5 (dd, J=12.6 Hz, J=2.6 Hz, 1H), 6.41 (dd, J=8.7 Hz, J=2.6 Hz, 1H), 3.87 (t, J=5.1 Hz, 2H), 3.28 (t, J=5.1 Hz, 2H), 2.57 (q, J=7.58 Hz, 2H), 1.21 (t, J=7.58 Hz, 3H)

LC-MS m/z 292.3 (M+H)$^+$

EXAMPLE 82

5-ethyl-2-[2-fluoro-4-(propylamino)phenoxy]phenol a) 4-(4-ethyl-2-methoxyphenoxy)-3-fluoro-N-propylaniline

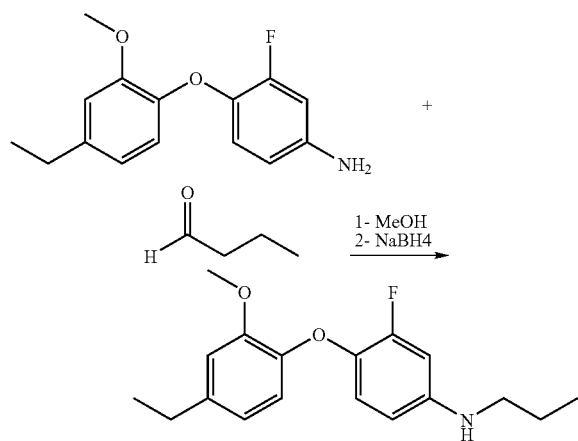

According to the procedure of example 66(a) except substituting nicotinaldehyde for propanaldehyde (28 μl, 0.45 mmol), the title compound was prepared as a colorless oil (20 mg; 18%), after purification by preparative TLC (cyclohexane/ethyl acetate: 80/20).

MS (ES) m/e 304 (M+H)$^+$ b) 5-ethyl-2-[2-fluoro-4-(propylamino)phenoxy]phenol

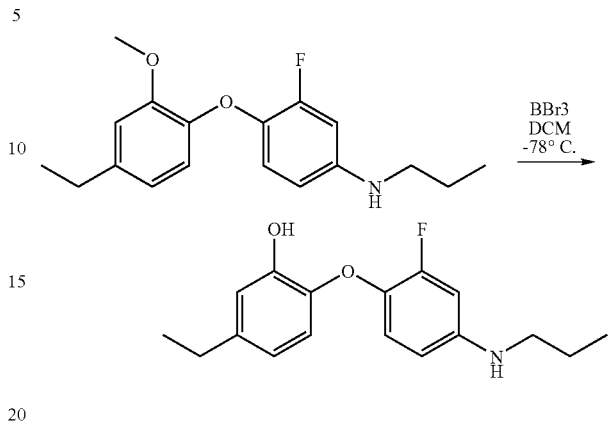

According to the procedure of example 1(b) except substituting 6-chloro-2-(2-methoxy-4-propylphenoxy)pyridin-3-amine for 4-(4-ethyl-2-methoxyphenoxy)-3-fluoro-N-propylaniline (20 mg, 0.066 mmol), the title compound (9.4 mg, 53%) was prepared as a white solid, after purification by preparative TLC (cyclohexane/ethyl acetate: 80/20).

MS (ES) m/e 290 (M+H)$^+$ $^1$H NMR (CDCl$_3$) δ (ppm): 7.28 (s, 1H), 6.93 (t, 1H, J=8.8 Hz), 6.89 (d, 1H, J=1.6 Hz), 6.70-6.56 (m, 3H), 3.10 (t, 2H, J=7.5 Hz), 2.60 (q, 2H, J=7.6 Hz); 1.72 (se, 2H, J=7.3 Hz,), 1.22 (t, 3H, J=7.6 Hz), 1.02 (t, 3H, J=7.4 Hz)

EXAMPLE 83

2-(4-amino-2-fluorophenoxy)-5-(2-pyridin-2-yl ethyl)phenol a) 4-bromo-1-(2-fluoro-4-nitrophenoxy)-2-methoxybenzene

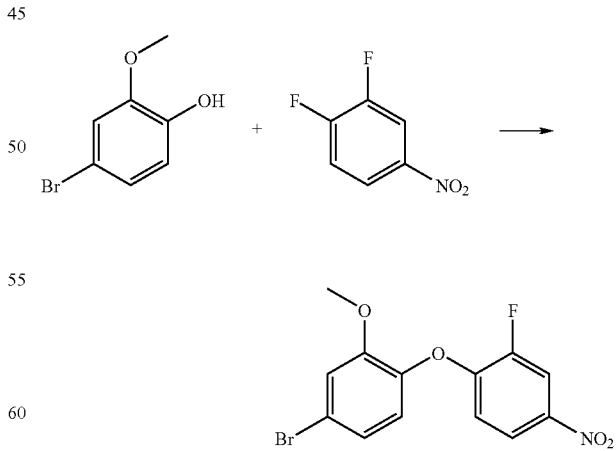

According to the procedure of example 21(a3) except substituting 4-Ethyl-2-methoxy phenol by 4-bromoguaïacol (2.51 mmol; 510 mg) and 3-Fluoro 2-nitro pyridine by 3,4-difluoronitrobenzene (2.76 mmol; 305 μL), the title compound was prepared as a clear oil in quantitative yield (855 mg) and used without further purification.

b) 2-{[4-(2-fluoro-4-nitrophenoxy)-3-methoxyphenyl]ethynyl}pyridine

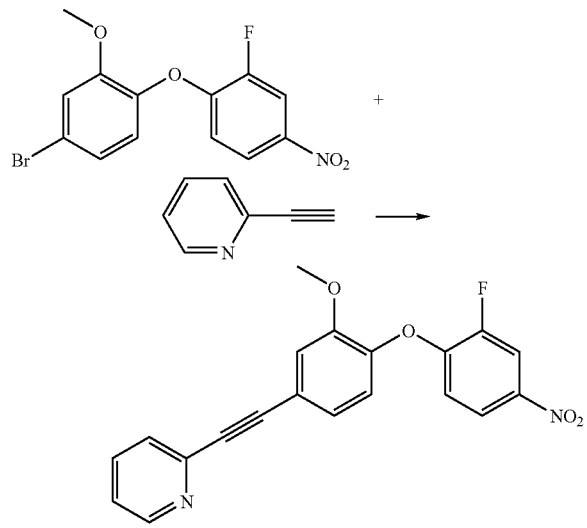

According to the procedure of example 11(a) except substituting 5-bromo-2-(2-methoxy-4-propylphenoxy)pyridine by 4-bromo-1-(2-fluoro-4-nitrophenoxy)-2-methoxybenzene (0.29 mmol; 100 mg) and 3-butyn-1-ol by 2-ethynylpyridine (0.73 mmol; 73 µL), the title compound was prepared as a yellow solid (81%; 87 mg) after purification on preparative TLC (cyclohexane/ethyl acetate: 7/3).

MS (ES) m/e 365 (M+H)+ c) 3-fluoro-4-[2-methoxy-4-(2-pyridin-2-ylethyl)phenoxy]aniline

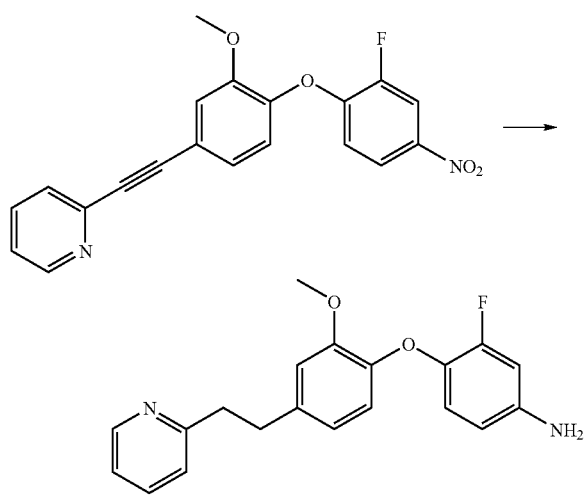

According to the procedure of example 20(b) except substituting 4-ethyl-2-methoxy-1-[4-nitro-2-(trifluoromethyl)phenoxy]benzene by 2-{[4-(2-fluoro-4-nitrophenoxy)-3-methoxy phenyl]ethynyl}pyridine (0.23 mmol; 84 mg) and THF by ethanol, the title compound was obtained as a clear oil (68%, 53 mg) 10 after purification on preparative TLC (cyclohexane/ethyl acetate: 6/4).

MS (ES) m/e 339 (M+H)+ d) 2-(4-amino-2-fluorophenoxy)-5-(2-pyridin-2-ylethyl)phenol

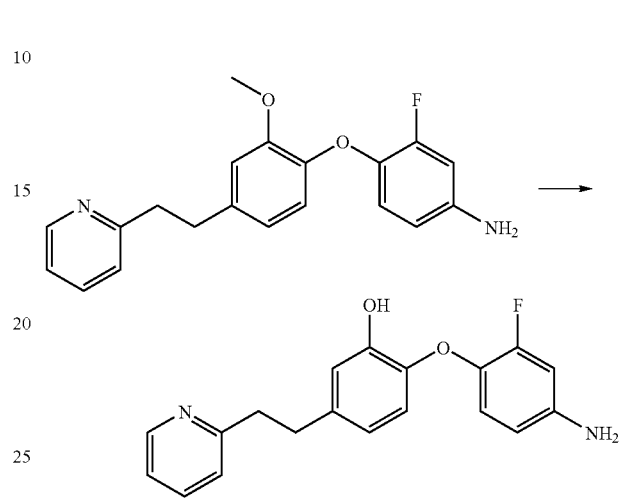

According to the procedure of example 1(b) except substituting 6-chloro-2-(2-methoxy-4-propylphenoxy)pyridin-3-amine for 3-fluoro-4-[2-methoxy-4-(2-pyridin-2-ylethyl)phenoxy]aniline (0.16 mmol; 53 mg), the title compound was prepared as a clear oil (45 mg; 15%) after purification by preparative TLC (dichloromethane/methanol/ammonia: 95/5/1).

MS (ES) m/e 325 (M+H)+

1H RMN (MeOD) δ (ppm): 8.46 (d, 1H, J=4.5 Hz); 7.78 (dt, 1H, J1=7.7 Hz, J2=1.8 Hz); 7.31-7.28 (m, 2H); 6.79 (t, 1H, J=8.9 Hz); 6.71 (s, 1H); 6.56 (dd, 1H, J1=12.7 Hz, J2=2.6 Hz); 6.51 (s, 2H); 6.47 (ddd, 1H, J1=8.7 Hz, J2=2.6 Hz, J3=1.2 Hz); 3.08-3.04 (m, 2H); 2.93-2.87 (m, 2H)

EXAMPLE 84

2-(2-aminopyridin-3yloxy)-5-ethyl-4-fluorophenol a) 3-(4-bromo-5-fluoro-2-methoxyphenoxy)-2-nitropyridine

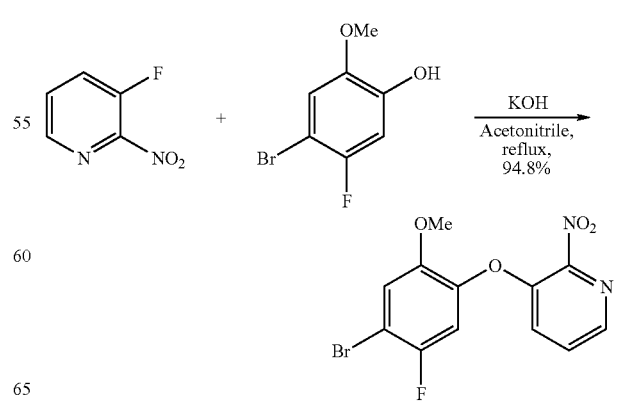

According to the procedure of example 21(a3) except substituting 4-ethyl-2-methoxyphenol by 4-bromo-5-fluoro-2-methoxyphenol (1.5 g, 5.7 mmol), the title compound was prepared in 95% yield (1.85 g) after purification on silica gel (eluant ethyl acetate/pet ether: 1/9) as a pale yellow solid.

$^1$H NMR (CDCl$_3$), δ (ppm): 8.25 (dd, J=4.48 Hz, J=1.28 Hz, 1H), 7.48 (dd, J=8.4 Hz, J=4.48 Hz, 1H), 7.28 (m, 1H), 7.18 (d, J=6.28 Hz, 1H), 7.01 (d, J=8.04 Hz, 1H), 3.76 (s, 3H), LC-MS m/z 343.5 (M+H)$^+$ b) 3-(5-fluoro-2-methoxy-4-vinylphenoxy)-2-nitropyridine

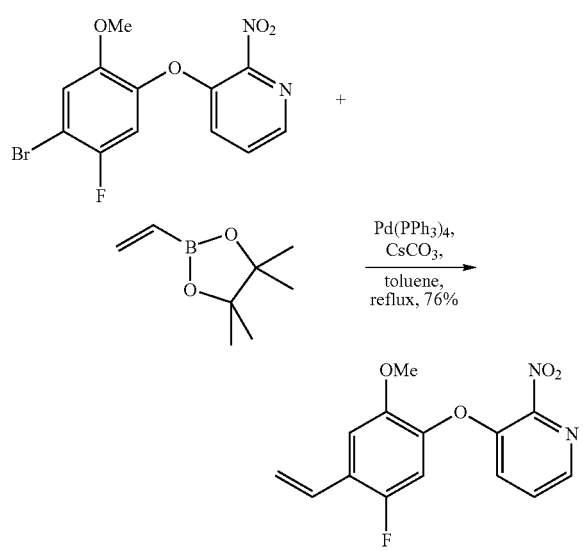

According to the procedure of example 57(b) except substituting 2-(4-bromo-5-fluoro-2-methoxyphenoxy)-6-fluoropyridine by 3-(4-bromo-5-fluoro-2-methoxyphenoxy)-2-nitropyridine (1.7 g, 4.9 mmol), the title compound was obtained (1.1 g; 76%) after purification on silica gel (eluant ethyl acetate/hexane: 15/85) as a pale yellow solid.

$^1$H NMR (CDCl$_3$), δ (ppm): 8.23 (dd, J=4.4 Hz, J=0.8 Hz, 1H), 7.47 (dd, J=8.4 Hz, J=4.8 Hz, 1H), 7.3 (dd, J=8.4 Hz, J=0.8 Hz, 1H), 7.08 (d, J=6.8 Hz, 1H), 6.91 (d, J=10 Hz, 1H), 6.85 (dd, J=17.6 Hz, J=11.2 Hz, 1H), 5.81 (d, J=17.6 Hz, 2H), 5.43 (d, J=11.2 Hz, 3H), 3.78 (s, 3H), LC-MS m/z 290.9 (M+H)$^+$ c) 3-(4-Ethyl-5-fluoro-2-methoxy-phenoxy)-2-aminopyridine

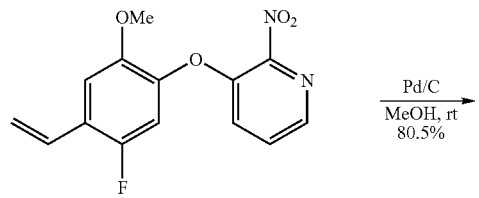

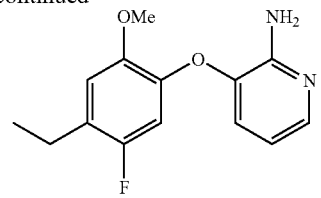

According to the procedure of example 20(b) except substituting 4-ethyl-2-methoxy-1-[4-nitro-2-(trifluoromethyl)phenoxy]benzene by 3-(5-fluoro-2-methoxy-4-vinylphenoxy)-2-nitropyridine (3.7 mmol, 1.1 g) and THF by methanol, the title compound was prepared as a white solid (800 mg; 80.5%) and used without further purification.

$^1$H NMR (CDCl$_3$), δ (ppm): 7.82 (dd, J=4.8 Hz, J=1.2 Hz, 1H), 6.89 (dd, J=8 Hz, J=1.2 Hz, 1H), 6.8 (d, J=6.8 Hz, 1H), 6.67 (d, J=10 Hz, 1H), 6.57-6.6.6 (m, 1H), 4.76 (bs, 2H, D2O exchangeable), 3.82 (s, 3H), 2.66 (q, J=7.6 Hz, 2H), 1.24 (t, J=7.6 Hz, 3H)

LC-MS m/z 263 (M+H)$^+$ d) 2-(2-Aminopyridin-3yloxy)-5-ethyl-4-fluorophenol

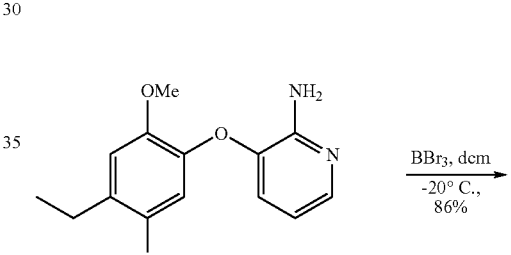

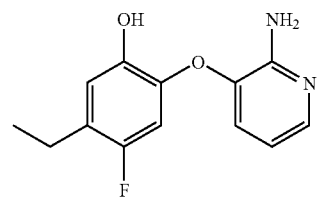

According to the procedure of example 1(b) except substituting 6-chloro-2-($^2$-methoxy-4-propylphenoxy)pyridin-3-amine for 3-(4-Ethyl-5-fluoro-2-methoxy-phenoxy)-2-aminopyridine (400 mg, 1.53 mmol), the title compound was prepared in 86% yield (325 mg) as a white solid after washing with hexane.

$^1$H NMR (CDCl$_3$), δ (ppm): 7.85 (dd, J=5.2 Hz, J=1.2 Hz, 1H), 6.98 (d, J=8 Hz, J=1.2Hz, 1H), 6.89 (d, J=7.6 Hz, 1H), 6.58-6.64 (m, 2H), 4.67 (bs, 2H, D2O exchangeable), 2.62 (q, J=7.6 Hz, 2H), 1.23 (t, J=7.6 Hz, 3H)

LC-MS m/z 249.1 (M+H)$^+$

EXAMPLE 85

2-(4-acetyl-2-fluorophenoxy)-5-ethylphenylamino acetate hydrochloride a) tert-Butoxycarbonylamino-acetic acid 2-(4-acetyl-2-fluoro-phenoxy)-5-ethyl-phenyl ester

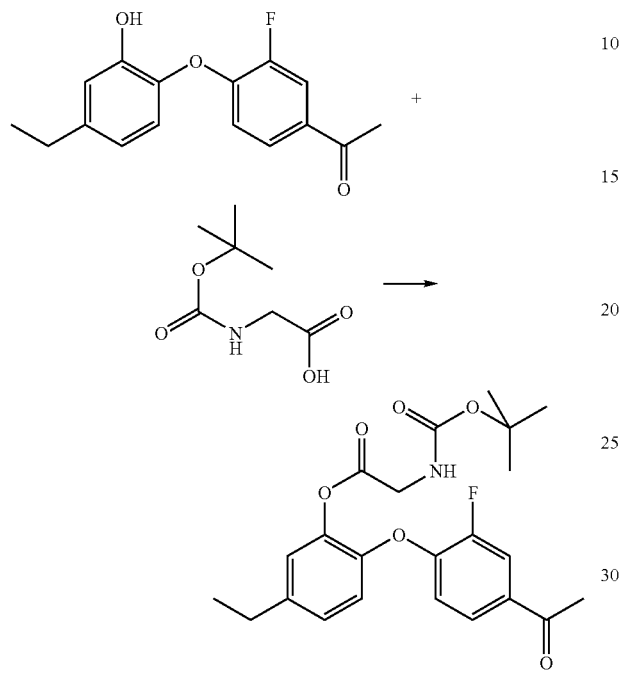

To a solution of 1-[4-(4-ethyl-2-hydroxyphenoxy)-3-fluorophenyl]ethanone (0.37 mmol; 100 mg) in dry THF (2 mL) cooled to 0° C. were added, N-Boc-glycine (0.37 mmol; 64 mg), benzotriazol-1-yloxytris(dimethylamino)phosphoniumhexafluoro phosphate (0.37 mmol; 190 mg) and triethylamine (1.09 mmol; 153 μL). The reaction was stirred at 0° C. for 3 hours and overnight at room temperature. The mixture was concentrated, treated with saturated NH$_4$Cl and extracted with dichloromethane. Combined organic phases were washed with water, dried over Na$_2$SO$_4$ and concentrated in vacuo. The title compound (91 mg; 58%) was obtained as clear oil after purification on preparative TLC (cyclohexane/ethyl acetate: 7/3).

MS (ES) m/e 454 (M+Na)$^+$ b) 2-(4-acetyl-2-fluorophenoxy)-5-ethylphenylaminoacetate hydrochloride

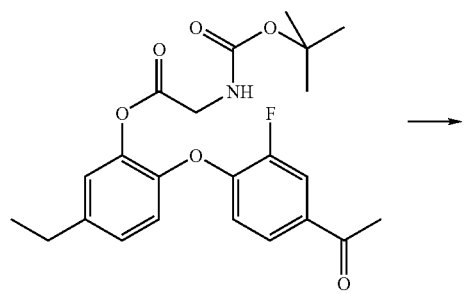

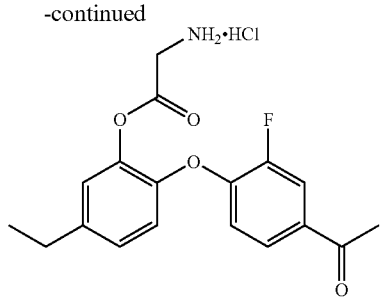

To a solution of tert-Butoxycarbonylamino-acetic acid 2-(4-acetyl-2-fluoro-phenoxy)-5-ethyl-phenyl ester (0.21 mmol; 91 mg) in dry dioxane (1 mL) cooled to 0° C., was added HCl/dioxane 4M (0.84 mmol; 211 μL). The reaction was stirred overnight at room temperature. A precipitate was formed. The mixture was cooled to 0° C., filtered and the solid was washed with diethylether. This white solid was dried in vacuo to give the title compound (8%; 7 mg).

$^1$H RMN (MeOD) δ (ppm): 7.85 (dd, 1H, J$_1$=11.5 Hz, J$_2$=2.0 Hz); 7.78 (d, 1H, J=8.7 Hz); 7.23-7.20 (m, 2H); 7.06-7.02 (m, 2H); 4.06 (s, 2H); 2.70 (q, 2H, J=7.6 Hz); 2.57 (s, 3H); 1.27 (t, 3H, J=7.6 Hz).

EXAMPLE 86

1-[4-(4-ethyl-2-hydroxyphenoxy)phenyl]-4-hydroxy butan-1-one a) 4-fluoro-N-methoxy-N-methylbenzamide

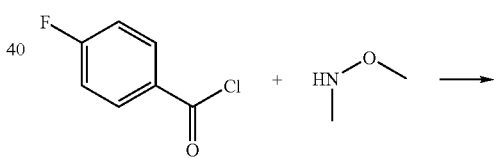

To a solution of N,O-dimethylhydroxylamine (1.51 mmol; 147 mg) in dry THF (3 mL), under argon, was added at −78° C. nbutyllithium 2.5M (3.02 mmol; 1.21 mL). The mixture was stirred 30 minutes at −78° C., before addition of 4-fluorobenzoyl chloride (1.26 mmol; 150 μL). The reaction was stirred overnight at room temperature, then treated with saturated NH$_4$Cl and extracted with ethyl acetate. Combined organic layers were washed with water, dried over Na$_2$SO$_4$ and concentrated in vacuo, to give the title compound (66%; 173 mg) as a yellow oil used without further purification.

$^1$H RMN (CDCl$_3$) δ (ppm): 7.78 (m, 2H); 7.10 (t, 2H, J=8.7 Hz); 3.56 (s, 3H); 3.38 (s, 3H).

b) 3-(1,3-dioxan-2-yl)-1-(4-fluorophenyl)propan-1-one

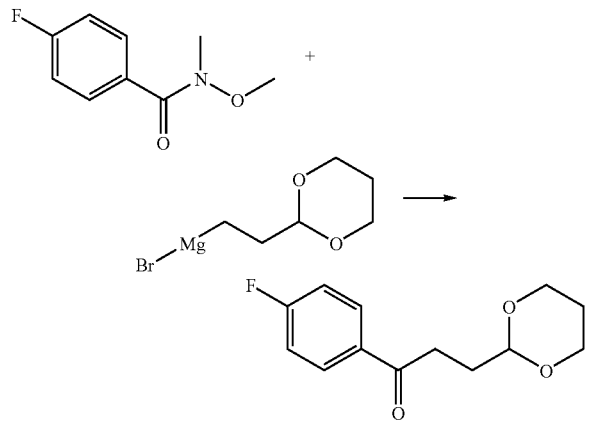

To a solution of 4-fluoro-N-methoxy-N-methylbenzamide (0.94 mmol; 173 mg) in anhydrous THF (2 mL), at −78° C. under argon, was added a solution of (1,3-dioxan-2-ylethyl) magnesium bromide, 0.5M in THF (1.04 mmol; 2.1 mL). The reaction was stirred 16 hours at room temperature. The mixture was cooled to −78° C. and (1,3-dioxan-2-ylethyl)magnesium bromide, 0.5M in THF (2.00 mmol; 4 mL) was added again. The reaction was stirred overnight at room temperature. The mixture was treated with saturated NH$_4$Cl and extracted with ethyl acetate. The organic layer was washed with water, dried over Na$_2$SO$_4$, and concentrated in vacuo. The title compound was prepared in quantitative yield, used without further purification.

MS (ES) m/e 239 (M+H)$^+$ c) 1-[4-(4-ethyl-2-methoxyphenoxy)phenyl]-3-(1,3-dioxan-2-yl)-1-phenylpropan-1-one

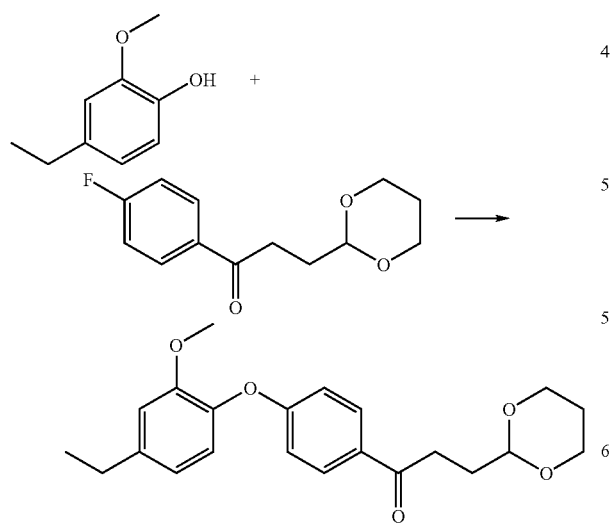

According to the procedure of example 21(a3) except substituting 3-Fluoro 2-nitro pyridine by 3-(1,3-dioxan-2-yl)-1-(4-fluorophenyl)propan-1-one (0.94 mmol; 401 mg), the title compound was obtained (42%, 149 mg) as a yellow oil after purification on preparative TLC (cyclohexane/ethyl acetate: 8/2).

MS (ES) m/e 371 (M+H)$^+$ d) 3-(1,3-dioxan-2-yl)-1-[4-(4-ethyl-2-hydroxyphenoxy)phenyl]propan-1-one and 4-[4-(4-ethyl-2-hydroxyphenoxy)phenyl]-4-oxobutanal

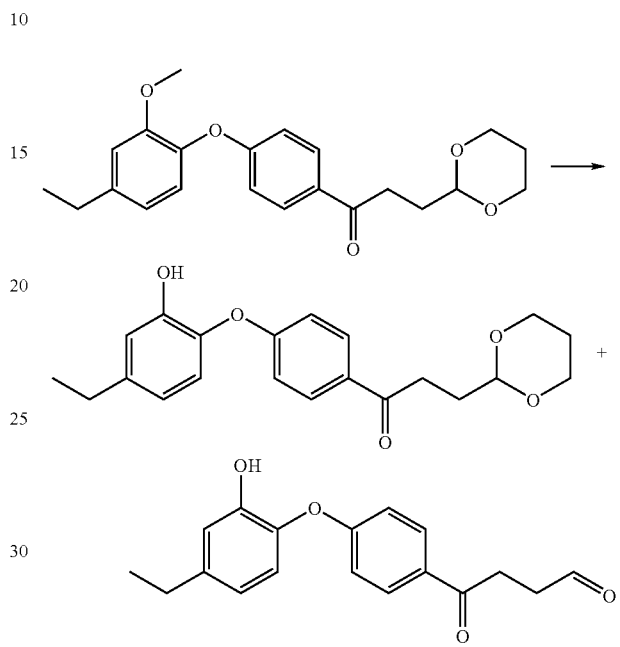

According to the procedure of example 1(b) except substituting 6-chloro-2-(2-methoxy-4-propylphenoxy)pyridin-3-amine for 1-[4-(4-ethyl-2-methoxyphenoxy)phenyl]-3-(1,3-dioxan-2-yl)-1-phenylpropan-1-one (0.25 mmol; 91 mg), the following compounds were obtained after purification by preparative TLC (cyclohexane/ethyl acetate: 7/3):

3-(1,3-dioxan-2-yl)-1-[4-(4-ethyl-2-hydroxyphenoxy) phenyl]propan-1-one (11 mg; 13%) as a white solid MS (ES) m/e 357 (M+H)$^+$ $^1$H RMN (CDCl$_3$) δ (ppm): 7.95 (d, 2H, J=8.9 Hz); 7.00 (d, 2H, J=8.9 Hz); 6.91 (d, 1H, J=1.9 Hz); 6.87 (d, 1H, J=8.2 Hz); 6.73 (dd, 1H, J$_1$=8.2 Hz, J$_2$=1.9 Hz); 5.46 (sl, 1H); 4.66 (t, 1H, J=4.9 Hz); 4.09 (dd, 2H, J$_1$=10.7 Hz, J$_2$=4.9 Hz); 3.76 (td, 2H, J$_1$=12.1 Hz, J$_2$=2.4 Hz);

3.05 (t, 2H, J=7.2 Hz); 2.63 (q, 2H, J=7.6 Hz); 2.06-2.01 (m, 3H); 1.33 (d, 1H, J=13.4 Hz); 1.22 (t, 3H, J=7.6 Hz).

4-[4-(4-ethyl-2-hydroxyphenoxy)phenyl]-4-oxobutanal (12.5 mg; 17%) as a clear oil.

MS (ES) m/e 299(M+H$^+$)

e) 1-[4-(4-ethyl-2-hydroxyphenoxy)phenyl]-4-hydroxybutan-1-one

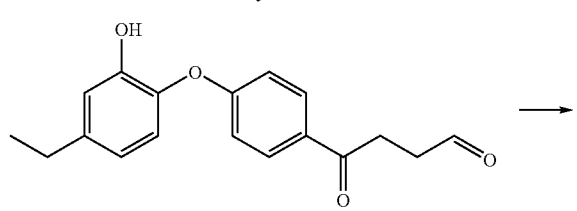

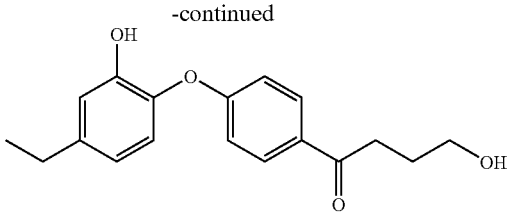

To a suspension of NaBH₄ (0.052 mmol; 2 mg) in dry methanol, under argon at −78° C., (0.5 mL) was added 4-[4-(4-ethyl-2-hydroxyphenoxy)phenyl]-4-oxobutanal (0.040 mmol; 12 mg). The reaction was stirred 5 hours with gradual warming to −5° C., and treated with acetic acid. The mixture was diluted with water and extracted with ethyl acetate. Combined organic layers were dried over Na₂SO₄ and concentrated in vacuo. The title compound was obtained as a clear oil (7.6 mg; 63%) after purification on preparative TLC (cyclohexane/ethyl acetate: 5/5).

MS (ES) m/e 301(M+H⁺)

¹H RMN (CDCl₃) δ (ppm): 7.30 (d, 2H, J=8.5 Hz); 6.97 (d, 2H, J=8.6 Hz); 6.89 (d, 1H, 1.9 Hz); 6.80 (d, 1H, J=8.2 Hz); 6.68 (dd, 1H, J₁=8.1 Hz, J₂=2.0 Hz); 4.70 (t, 1H, J=6.3 Hz); 3.69 (se, 2H, J=5.8 Hz); 2.61 (q, 2H, J=7.6 Hz); 1.85 (q, 2H, J=6.6 Hz); 1.68 (se, 2H, J=7.0 Hz); 1.23 (t, 3H, J=7.6 Hz).

EXAMPLE 87

5-Ethyl-4-fluoro-2-(2-fluoropyridin-3yloxy)phenol a)
5-Ethyl-4-fluoro-2-(2-fluoropyridin-3yloxy)phenol

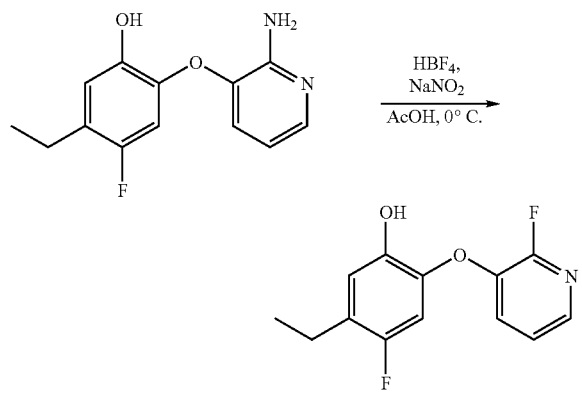

To a stirred solution of 2-(2-aminopyridin-3yloxy)-5-ethyl-4-fluorophenol (45 mg, 0.18 mmol) in glacial acetic acid (2.5 ml) was added 0.36 ml of tetrafluoroboric acid (48% in water). The reaction mixture was cooled to 0° C. and sodium nitrite (18 mg, 0.27 mmol) was added at 0° C. and stirred at 0° C. for 1.5 hours until reaction was complete on TLC. The reaction mixture was quenched by adding ice and sodium bicarbonate solution and stirred for 10 minutes before extracting the aqueous solution with ethylacetate. The combined ethyl acetate fraction was washed with saturated sodium bicarbonate solution, water, followed by brine, dried over anhydrous sodium sulfate and concentrated in vacuo to get the crude compound. The crude material was column purified over silica gel using Petroleum ether/ethyl acetate 9:1 as eluant and then further purified by preparative HPLC using 0.1% TFA in water and acetonitrile as solvent system to get 8 mg (17.6%) of 5-Ethyl-4-fluoro-2-(2-fluoropyridin-3yloxy) phenol as a white solid.

¹H NMR (CDCl₃), δ (ppm): 8.01-8.98 (m, 1H), 7.43-7.39 (m, 1H), 7.17-7.20 (m, 1H), 6.91 (d, J=7.2 Hz, 1H), 6.57 (d, J=9.6 Hz, 1H), 5.35 (s, 1H, D2O exchangeable), 2.63 (q, J=7.5 Hz, 2H), 1.25 (t, J=7.5 Hz, 3H)

LC-MS m/z 252 (M+H)

Alternatively the title compound can be synthesized from 3-(4-Ethyl-5-fluoro-2-methoxy-phenoxy)-2-aminopyridine of step c) of example 84 according to following steps:

b) 3-(4-Ethyl-5-fluoro-2-methoxy-phenoxy)-2-fluoropyridine

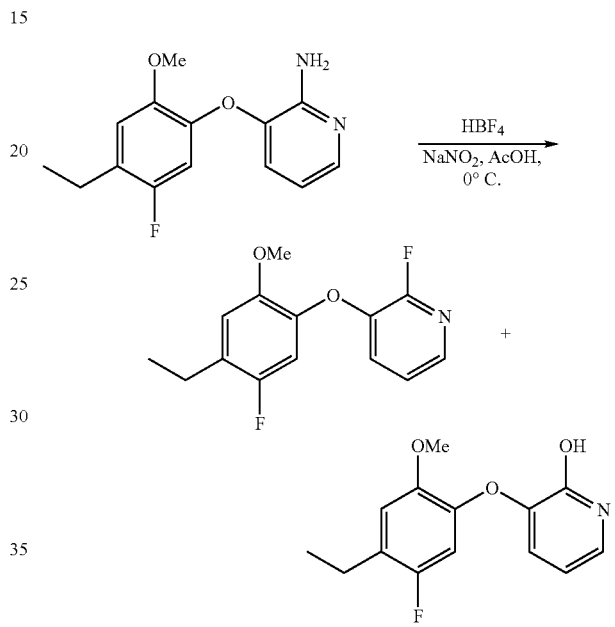

To a stirred solution of 3-(4-Ethyl-5-fluoro-2-methoxy-phenoxy)-2-aminopyridine (1.5 g, 5.7 mmol) in glacial acetic acid (10 ml) was added 12 ml of tetrafluoroboric acid (48% in water). The reaction mixture was cooled to 0° C. and sodium nitrite (590 mg, 8.5 mmol) was added at 0° C. and stirred at 0° C. for 45 minutes until reaction was complete on TLC. Formation of 2 compounds was observed on the TLC. The colourless reaction mixture turned pale yellow and then to deep yellow during this time. The reaction mixture was quenched by adding ice and sodium bicarbonate solution and the aqueous solution was extracted with ethyl acetate. The combined ethyl acetate fraction was washed with water, followed by brine, dried over anhydrous sodium sulfate and concentrated in vacuo to get the crude compound. The crude material was column purified over silica gel using pet ether/ethyl acetate 9:1 as eluant to obtain the first fraction yielding 610 mg, 40.39% of the title compound 3-(4-Ethyl-5-fluoro-2-methoxy-phenoxy)-2-fluoro pyridine as a colourless liquid. The column was then eluted with 100% ethyl acetate to collect the second fraction that gave 620 mg, 41.3% of the 3-(4-Ethyl-5-fluoro-2-methoxy-phenoxy)-pyridin-2-ol.

3-(4-Ethyl-5-fluoro-2-methoxy-phenoxy)-2-fluoropyridine

¹H NMR (CDCl₃), δ (ppm): 7.90-7.89 (m, 1H), 7.20 (t, J=8 Hz, 1H), 7.1-7.07 (m, 1H), 6.82 (d, J=6.96 Hz, 1H), 6.73 (d, J=9.68 Hz, 1H), 3.8 (s, 3H), 2.67 (q, J=7.53 Hz, 2H), 1.25 (t, J=7.58 Hz, 3H)

LC-MS m/z 266.2 (M+H)⁺

3-(4-Ethyl-5-fluoro-2-methoxy-phenoxy)-pyridin-2-ol $^1$H NMR (CDCl$_3$), δ (ppm): 7.15 (d, J=6.44 Hz, 1H), 6.82-6.78 (m, 2H), 6.72 (d, J=7.2 Hz, 1H), 6.17 (t, J=7.2 Hz, 1H), 3.81 (s, 3H), 2.67 (q, J=7.5 Hz, 2H), 1.27 (t, J=7.5 Hz, 3H)

LC-MS m/z 264.1 (M+H)$^+$ c)
5-Ethyl-4-fluoro-2-(2-fluoropyridin-3yloxy)phenol

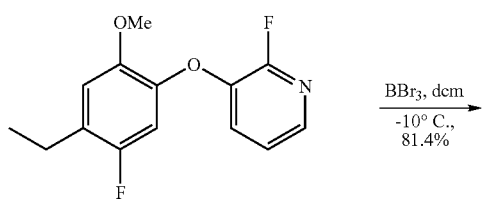

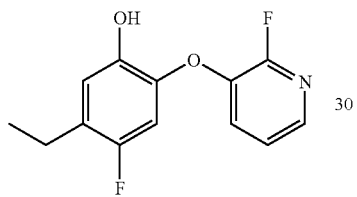

According to the procedure of example 1(b) except substituting 6-chloro-2-(2-methoxy-4-propylphenoxy)pyridin-3-amine by 3-(4-Ethyl-5-fluoro-2-methoxy-phenoxy)-2-fluoro pyridine (610 mg, 2.3 mmol), the title compound was prepared in 81% yield (470 mg) as a white solid after washing with hexane.

EXAMPLE 88

N-Ethyl-4-(4-ethyl-2-hydroxy-phenoxy)-3-fluoro benzene sulfonamide a) 4-(2-Benzyloxy-4-ethyl-phenoxy)-N-ethyl-3-fluoro-benzene sulfonamide

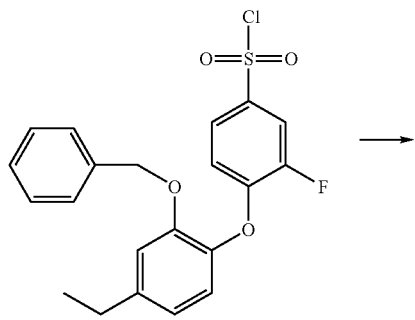

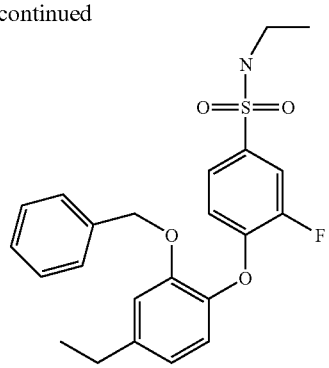

According to the procedure of example 70(a) except substituting N-Acetylethylenediamine for ethylamine.HCl ((8.4 mmol; 700 mg), the title compound (402 mg; 0.94 mmol; 25%) was obtained as a yellow oil, after purification on silica gel (gradient cyclohexane/dichloromethane/ethyl acetate).

MS (ES) m/e 430 (M+H)$^+$ b) N-Ethyl-4-(4-ethyl-2-hydroxy-phenoxy)-3-fluoro benzene sulfonamide According to the procedure of example 20(b) except substituting 4-ethyl-2-methoxy-1-[4-nitro-2-(trifluoromethyl)phenoxy]benzene for 4-(2-Benzyloxy-4-ethyl-phenoxy)-N-ethyl-3-fluoro-benzene sulfonamide (402 mg; 0.94 mmol) and tetrahydrofurane for ethanol (4 mL), the title compound (140 mg; 44%) was obtained as a clear oil, after purification on preparative TLC (dichloromethane).

MS (ES) m/e 340 (M+H)$^+$ $^1$H RMN (CDCl$_3$) δ (ppm): 7.63 (d, 1H, J=10.0 Hz); 7.53 (d, 1H, J=8.7 Hz); 6.95 (d, 1H, J=8.2 Hz); 6.92 (s, 1H); 6.87 (d, 1H, J=8.2 Hz); 6.74 (d, 1H, J=8.2 Hz); 6.03 (br, 1H); 5.01

(t, 1H, J=5.9 Hz); 3.00 (qt, 2H, J=7.0 Hz); 2.62 (q, 2H, J=7.6 Hz); 1.23 (t, 3H, J=7.6 Hz); 1.10 (t, 3H, J=7.3 Hz).

EXAMPLE 89

5-[(3-fluoropyridin-4-yl)methyl]-2-[(6-fluoro pyridin-2-yl)oxy]phenol a) [4-(tert-Butyl-dimethyl-silanyloxy)-3-methoxyphenyl]-(3-fluoro-pyridin-4-yl)-methanol

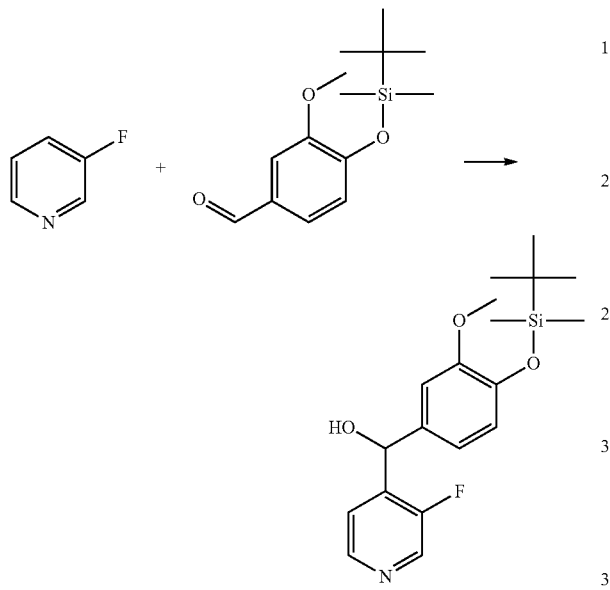

To a solution of 3-fluoropyridine (2.3 mmol; 220 mg), under argon, in anhydrous THF (1 mL) cooled to −78° C., was added nBuLi (2.3 mmol; 1 mL). The reaction was stirred 1 hr at −78° C. then a solution of vanilline-OTBS (2.3 mmol; 600 mg) in THF (1 mL) was added. The reaction was allowed to warm up to room temperature overnight. Hydrolysed by NH$_4$Cl sat. (3 mL), the mixture was extracted with dichloromethane (3 mL) and ethyl acetate (2*3 mL). Combined organic phases were dried over MgSO$_4$, concentrated to yield a light brown solid. Heating in diethyl ether, then filtering afforded the title compound as a white solid (125 mg; 0.34 mmol; 15%) used without further purification.

MS (ES) m/e 364 (M+H)$^+$ b)
4-[(3-fluoropyridin-4-yl)methyl]-2-methoxyphenol

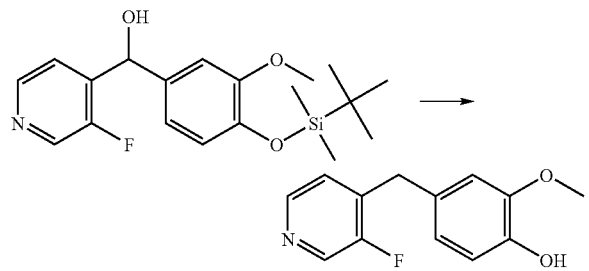

Pd/C (0.02 mmol; 40 mg) was added to a solution of [4-(tert-Butyl-dimethyl-silanyloxy)-3-methoxy-phenyl]-(3-fluoro-pyridin-4-yl)-methanol (0.19 mmol; 70 mg) in methanol (2 mL) and H$_2$SO$_4$ (0.5 mL). The mixture was flushed twice with hydrogen, and the reaction was stirred overnight at 35° C. The mixture was filtered on celite, washed with methanol. After concentration, water was added (3 mL) and K$_2$CO$_3$ until pH 8. The aqueous phase was extracted with ethyl acetate (2*3 mL). Combined organic phases were dried over MgSO$_4$, concentrated to yield the title compound as a white solid (32 mg; 0.14 mmol; 71%) used as such.

MS (ES) m/e 234 (M+H)$^+$ c) 2-fluoro-6-{4-[(3-fluoropyridin-4-yl)methyl]-2-methoxyphenoxy}pyridine

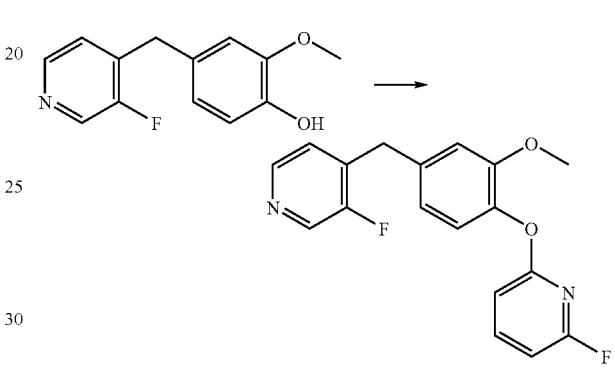

According to the procedure of example 21(a3) except substituting 4-Ethyl-2-methoxy phenol for 4-[(3-fluoropyridin-4-yl)methyl]-2-methoxyphenol (60 mg; 0.26 mmol), the title compound (85 mg; 100%) was prepared as a brown oil, used without any purification.

MS (ES) m/e 329 (M+H)$^+$ d) 5-[(3-fluoropyridin-4-yl)methyl]-2-[(6-fluoropyridin-2-yl)oxy]phenol

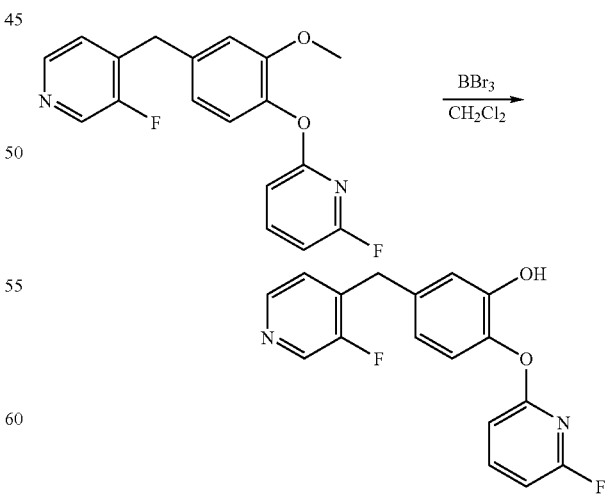

According to the procedure of example 1(b) except substituting 6-chloro-2-(2-methoxy-4-propylphenoxy)pyridin-3-amine for 2-fluoro-6-{4-[(3-fluoropyridin-4-yl)methyl]-2- methoxyphenoxy}pyridine (85 mg; 0.26 mmol), the title compound (23 mg; 28%) was prepared as a clear oil, after purification by preparative TLC (dichloromethane/ethyl acetate).

MS (ES) m/e 315 (M+H)$^+$ $^1$H RMN (CDCl$_3$) δ (ppm): 8.37 (s, 1H); 8.27 (d, 1H, J=4.7 Hz); 7.76 (q, 1H, J=8.0 Hz); 7.12 (t, 1H, J=5.7 Hz); 7.06 (d, 1H, J=8.2 Hz); 6.83 (d, 1H, J=1.8 Hz); 6.79-6.75 (m, 2H); 6.62 (dd, 1H, J$_1$=7.9 Hz, J$_2$=2.1 Hz); 3.98 (s, 2H).

EXAMPLE 90

3-(4-Ethyl-5-fluoro-2-hydroxyphenoxy)-pyridin-2-ol

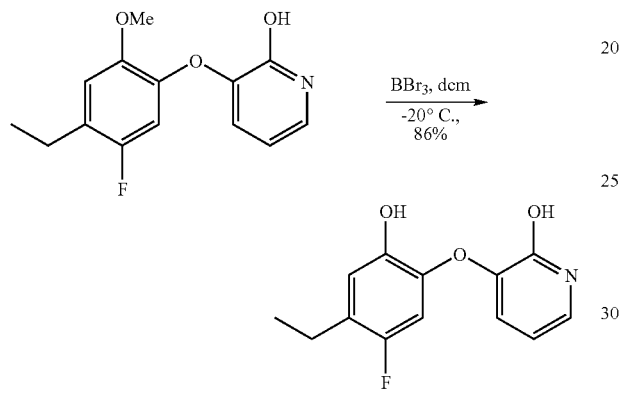

According to the procedure of example 1(b) except substituting 6-chloro-2-(2-methoxy-4-propylphenoxy)pyridin-3-amine for 3-(4-Ethyl-5-fluoro-2-methoxy-phenoxy)-pyridin-2-ol (50 mg, 0.19 mmol), the title compound (25 mg; 53%) was prepared as a white solid, after washing with hexane twice and with diethylether MS (ES) m/e 315 (M+H)$^+$ $^1$H NMR (CD$_3$OD), δ (ppm): 7.18 (d, J=6.5 Hz, 1H), 6.96 (d, J=7.4 Hz, 1H), 6.81 (d, J=7.4 Hz, 1H), 6.74 (d, J=10.1 Hz, 1H), 6.32 (t, J=6.98 Hz, 1H), 2.6 (q, J=7.5 Hz, 2H), 1.2 (t, J=7.5 Hz, 3H)

LC-MS m/z 250 (M+H)$^+$

EXAMPLE 91

2-amino-N-[4-(4-ethyl-2-methoxyphenoxy)-3-fluorophenyl]ethanesulfonamide a) 2-(1,3-Dioxo-1,3-dihydro-isoindol-2-yl)-ethane-sulfonic acid [4-(4-ethyl-2-methoxy-phenoxy)-3-fluoro-phenyl]-amide

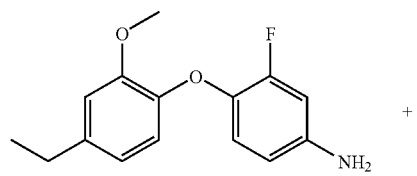 +

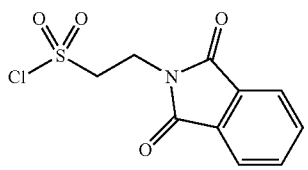

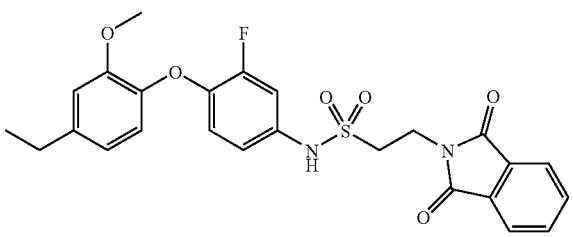

According to the procedure of example 42(a) except substituting 3-chloropropanesulfonyle chloride by 2-phtalimido ethanesulfonyl chloride (0.46 mmol; 125 mg), the title compound (77%; 147 mg) was obtained as a white gum after purification on preparative TLC (cyclohexane/ethyl acetate: 6/4).

MS (ES) m/e 499 (M+H)$^+$ b) 2-(1,3-Dioxo-1,3-dihydro-isoindol-2-yl)-ethane-sulfonic acid [4-(4-ethyl-2-hydroxy-phenoxy)-3-fluoro-phenyl]-amide

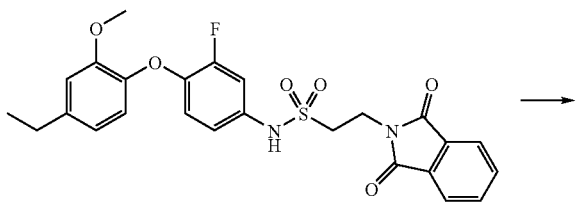

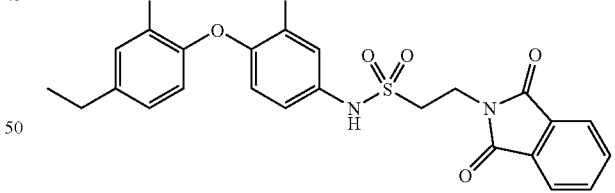

According to the procedure of example 1(b) except substituting 6-chloro-2-(2-methoxy-4-propylphenoxy)pyridin-3-amine for 2-(1,3-Dioxo-1,3-dihydro-isoindol-2-yl)-ethane sulfonic acid [4-(4-ethyl-2-methoxy-phenoxy)-3-fluoro-phenyl]-amide (0.30 mmol; 147 mg), the desired compound was prepared in 55% yield (79 mg) after purification by preparative TLC (cyclohexane/ethyl acetate: 7/3).

MS (ES) m/e 485(M+H$^+$)

$^1$H RMN (CDCl$_3$) δ (ppm): 7.86 (dd, 2H, J$_1$=5.5 Hz, J$_2$=3.1 Hz); 7.75 (dd, 2H, J$_1$=5.4 Hz, J$_2$=3.0 Hz); 7.43 (s, 1H); 7.23 (dd, 1H, J$_1$=11.5 Hz, J$_2$=2.4 Hz); 7.01 (d, 1H, J=8.8 Hz); 6.93 (t, 1H, J=8.6 Hz); 6.88 (d, 1H, J=1.77 Hz); 6.71 (d, 1H, J=8.2

Hz); 6.65 (dd, 1H, $J_1$=8.3 Hz, $J_2$=1.9 Hz); 5.82 (sl, 1H); 4.15 (t, 2H, J=6.3 Hz); 3.48 (t, 2H, J=6.2 Hz); 2.59 (q, 2H, J=7.6 Hz); 1.22 (t, 3H, J=7.6 Hz).

c) 2-amino-N-[4-(4-ethyl-2-methoxyphenoxy)-3-fluorophenyl]ethanesulfonamide

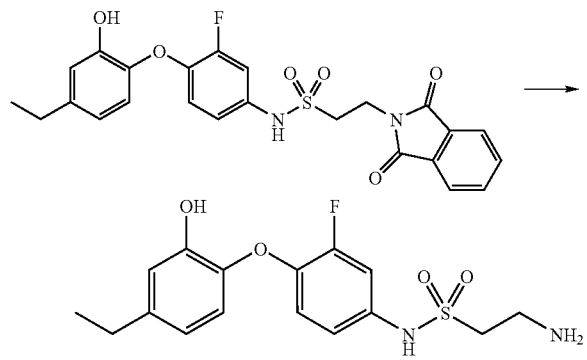

According to the procedure of example 39 except substituting 2-{3-[4-(4-Ethyl-2-hydroxy-phenoxy)-3-fluoro-phenoxy]-propyl}-isoindole-1,3-dione by 2-(1,3-Dioxo-1,3-dihydro-isoindol-2-yl)-ethanesulfonic acid [4-(4-ethyl-2-hydroxy-phenoxy)-3-fluoro-phenyl]-amide (0.13 mmol; 64 mg), the title compound was obtained as a yellow oil (20%, 10 mg) after purification on preparative TLC (dichloromethane/methanol/ammonia: 90/10/1).

MS (ES) m/e 355 (M+H)$^+$ $^1$H RMN (MeOD) δ (ppm): 7.22 (dd, 1H, $J_1$=12.3 Hz, $J_2$=2.5 Hz); 6.99 (d, 1H, J=8.8 Hz); 6.84-6.79 (m, 2H); 6.74 (d, 1H, J=8.2 Hz); 6.64 (dd, 1H, $J_1$=8.2 Hz, $J_2$=1.9 Hz); 3.25 (t, 2H, J=6.7 Hz); 3.10 (t, 2H, J=6.5 Hz); 2.57 (q, 2H, J=7.6 Hz); 1.21 (t, 3H, J=7.6 Hz).

FabI Inhibition:

The compounds of the present invention are useful inhibitors of bacterial FabI enzyme.

Compound inhibitory activity of FabI enzyme is measured in vitro by the IC50 determination using a fluorescent based assay.

The protein FabI from *E. coli* is prepared and purified using standard methods for recombinant protein expression after cloning of the gene in a prokaryotic expression vector.

The biochemical activity of the FabI enzyme is assessed using the following method.

The assay buffer "AB" contains 50 mM Hepes pH7.5, 100 µM Dithiothreitol, 0.006% Triton-X100. The following components are added in a black polystyrene Costar plate up to a final volume of 55 µL: 1.5 µL DMSO, or inhibitor dissolved in DMSO and 53.5 µL of a FabI/NADH/NAD+ mixture in AB. After 60 min of pre-incubation at room temperature, the reaction is started by addition of 5 µL of Crotonoyl-CoA to a final volume of 60 µL. This reaction mixture is then composed of 40 nM FabI (produced in house from *E. coli*, C-terminal 6-His tagged), 20 µM NADH (Biochemika), 10 µM NAD+ (Biochemika), 50 µM Crotonoyl-CoA (Biochemika) and compound at defined concentration. Fluorescence intensity of NADH ($l_{ex}$=360 nm, $l_{em}$=520 nm) is measured immediately after Crotonoyl-CoA addition, and 2 hours later by a Fluostar Optima (BMG). Enzyme activity is proportional to the signal decrease from which inhibition percentages are derived. For $IC_{50}$ determinations, the inhibitor is tested at 6 to 10 different concentrations, and the related inhibitions are fitted to a classical langmuir equilibrium model using XLFIT (IDBS).

In vitro Inhibition of Recombinant *E. coli* FabI Enzyme by Selected Compounds of Formula (I).

| Examples | $IC_{50}$ (µM) |
| --- | --- |
| 5 | 0.97 |
| 16 | 0.51 |
| 21 | 0.069 |
| 25B | 0.57 |
| 27 | 0.47 |
| 28 | 0.85 |
| 29 | 0.15 |
| 37 | 0.41 |
| 48 | 1 |
| 50 | 0.3 |
| 55 | 0.092 |
| 57 | 1.1 |
| 64 | 0.13 |
| 71 | 0.33 |
| 84 | 0.1 |
| 85 | 0.11 |
| 87 | 0.031 |

Antibacterial Activity

The compounds of the present invention are useful antibacterial agents having a selective spectrum of activity in vitro against standard bacterial strains which are used to screen for activity against pathogenic bacteria. Notably the compounds of the present invention show activity against *Staphyloccus aureus* including multiresistant strains and *Escherichia coli*. The activity is presented as Minimum Inhibitory Concentration (MIC) expressed in µg/ml.

Whole-cell antimicrobial activity was determined by broth microdilution method in microtiterplates. The compound was tested in serial 4-fold dilutions ranging from 0.06 to 64 mcg/mL. Test organisms were selected from the following laboratory strains: *Staphylococcus aureus* CIP 76.25, *Staphylococcus aureus* BAA39 MDR, *Staphylococcus aureus* NEM 14157 PeniR, *Staphylococcus aureus* CIP 54.146, *Escherichia coli* CIP 76.24. Bacteria were tested in Tryptic Soy (TS) or Mueller Hinton (MH) broth using an inoculum of 10$^4$ to 10$^6$ UFC/mL incubated at 37° C. for 20 h.

The minimum inhibitory concentration (MIC) was determined as the lowest concentration of compound at which no visible bacteria growth is observed (90% inhibition of absorbance of at 600 nM.)

Representative Examples of MIC (µg/ml)

| Compound Example N° | *E. coli* CIP 76.24 | *S. aureus* CIP 76.25 | *S. aureus* BAA39MDR | *S. aureus* NEM14157 |
| --- | --- | --- | --- | --- |
| Triclosan | 0.25 | 0.125 | | |
| 1 | 16 | 1 | 1 | 0.25 |
| 3 | 4 | 0.25 | 0.25 | 0.25 |
| 5 | 4 | 0.25 | 0.25 | 0.25 |
| 6 | 16 | 1 | 1 | 1 |
| 7 | >16 | 2 | | |
| 16 | 4 | 0.25 | 0.25 | 0.25 |
| 21 | 0.25 | 0.25 | 0.25 | 0.25 |
| 27 | 4 | 0.25 | 0.25 | 0.25 |
| 25A | 16 | 0.25 | | |
| 25B | 4 | 0.062 | 0.062 | 0.062 |
| 29 | 1 | 0.062 | 0.062 | 0.062 |
| 32 | 16 | 4 | | |

-continued

| Compound Example N° | E. coli CIP 76.24 | S. aureus CIP 76.25 | S. aureus BAA39MDR | S. aureus NEM14157 |
|---|---|---|---|---|
| 34 | 1 | 0.25 | 0.25 | 0.25 |
| 35 | 1 | 0.25 | | |
| 37 | 4 | 0.062 | 0.25 | 0.25 |
| 38 | 4 | 0.062 | 0.25 | 1 |
| 39 | 16 | 1 | 1 | 1 |
| 47 | 16 | 0.25 | | |
| 48 | 4 | 0.062 | | |
| 52 | 16 | 1 | | |
| 55 | 1 | 0.25 | | |
| 57 | 4 | 0.25 | | |
| 62 | 4 | 0.25 | | |
| 64 | 1 | 0.25 | 0.062 | 0.062 |
| 65 | 1 | 0.25 | | |
| 66 | 16 | 0.25 | | |
| 67 | 16 | 0.25 | | |
| 70 | 16 | 0.25 | | |
| 71 | 4 | <0.062 | 0.25 | 0.062 |
| 74 | 4 | 0.062 | 0.062 | 0.062 |
| 79 | 16 | 0.25 | 0.25 | 0.25 |
| 81 | 4 | 0.25 | | |
| 82 | 16 | 0.25 | | |
| 84 | 0.25 | 0.25 | 0.25 | 0.25 |
| 85 | 1 | 0.062 | | |
| 86 | 4 | 0.062 | 0.062 | 0.062 |
| 87 | 0.25 | 0.062 | 0.062 | 0.016 |

In vitro Activities Against Resistant Stains of *S. aureus*

| MIC (µg/ml) | S. aureus MRSA* | S. aureus USA300 MRSA* | S. aureus 1651 LRSA* | S. aureus 1652 LRSA | S. aureus 2012 VISA | S. aureus 2018 VISA* |
|---|---|---|---|---|---|---|
| Vancomycin | 1 | 0.5 | 1 | 1 | 8 | 4 |
| Example 21 | 0.12 | 0.5 | 0.12 | 0.5 | 0.12 | 0.25 |
| Example 48 | 0.06 | 0.5 | 0.12 | 0.5 | 0.12 | 0.25 |

MRSA = Methicillin Resistant *S. aureus*;
LRSA = Linezolid resistant *S. aureus*;
VISA = Vancomycin Resistant *S. aureus*;

In vivo Antibacterial Activity of Compounds

An experimental model of infection by *S. aureus* was used to assess the antibacterial activity of FabI inhibitors.

Briefly in vivo studies were performed using 5-6-week-old female BALB/c@Rj mice as follows Groups of six mice are used for each condition.

The virulent strain of *Staphylococcus aureus* CIP 54.146 is grown to exponential phase in Tryptic soy (TS) broth culture. The bacterial culture is diluted to obtain a bacterial suspension of $1.10^8$ UFC/ml. Then 200 µl of the suspension is administered by intraperitoneal injection to each mouse, this infecting dose has been determined to be the LD90 (Lethal dose 90%). The inoculums count was determined by plating 10-fold dilutions of the suspension on TH agar plates immediately after inoculation.

Compounds to be assessed are dissolved and diluted in an aqueous solution containing 15% cyclodextrin and 200 µl of the solution is injected sub cuteanously to each mice, just after the infection.

For 48 hours post-infection, mice are monitored and survival recorded at 18 h and 24 h postinfection. The negative control group receives the 15% cyclodextrin solution alone and vancomycin at 10 mg/kg is used as the positive control.

All animal experiments were carried out in accordance with institutional guidelines. Compound activity is measure by its effect at a given dose on the percentage of surviving animal.

As shown in FIGS. 1 and 2 results obtained with compound derivative of the formula are able to protect mice against the lethal effect of bacterial multiplication.

Example of Pharmaceutical Composition:

An injectable preparation was prepared comprising 500 mg of a compound of example 87 and sufficient quantity of aqueous sterile excipient for preparing 10 to 50 ml of injectable solution.

Tablets have been prepared containing:
300 mg of compound of example 21
Sufficient quantity of excipient for a 1 g tablet
Detail of the excipient, starch, talc, magnesium stearate

The invention claimed is:
1. A hydroxyphenyl derivative of formula (I)

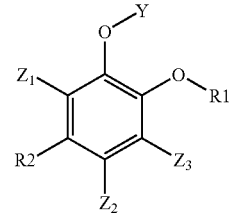

(I)

R1 is phenyl optionally substituted by 1 to 3 R identical or different, R being selected from the group comprising H, fluoro, $C_1$-$C_8$ alkyl, $C_1$-$C_4$ fluoroalkyl, $C_2$-$C_8$ alkenyl, $C_2$-$C_8$ alkynyl, $COOR_a$, $COR_a$, $CONR_aR_b$, $OCOR_a$, CN, $OR_a$, $NR_aR_b$, $CR_a$=$NOR_b$, $NR_aCOOR_b$, $OCONR_aR_b$, $NR_aCONR_bR_c$, $SR_a$, $SO_2R_a$, $SO_2NR_aR_b$ and $NR_aC(S)NR_bR_c$, all being possibly substituted by R', R2 is $C_1$-$C_8$ alkyl, $C_2$-$C_8$ alkenyl, $C_2$-$C_8$ alkynyl, $C_1$-$C_4$fluoro-alkyl, $C_2$-$C_4$fluoro-alkenyl, $OR_a$, $SR_a$, all being possibly substituted by 1 to 3 identical or different R', $R_a$, $R_b$ and $R_c$, identical or different, are selected from the group consisting of H, $C_1$-$C_8$ alkyl, $C_2$-$C_8$ alkenyl, and $C_2$-$C_8$ alkynyl, as defined above for R2, R' is selected from the group comprising $C_1$-$C_8$ alkyl, $CH_2CO_2R''$, $CO_2R''$, $COR''$, $CONR''R'''$, $OCOR''$, $OR''$, $NR''R'''$, $NR''COR'''$, $NR''COOR'''$, $OCONR''R'''$, $NR''CONR''R'''$, $NR''SO_2R'''$, $SO_2R''$, $NR''SO_2R'''$, halogen and CN, R'' and R''', identical or different, are H or $C_1$-$C_8$ alkyl Y represents H Z1 and Z3, identical or different, are halogen or H, and Z2 is fluoro;

or a pharmaceutically acceptable organic or mineral salt thereof, in case the derivative of formula (I) has one or more chiral centres, both a chiral and non-chiral derivative, in cases the derivative of formula (I) has unsaturated carbon=carbon double bonds, both the cis (Z) and trans (E) isomers, and any N-oxide form of the derivatives, wherein the hydroxyphenyl derivative of formula (I) is not

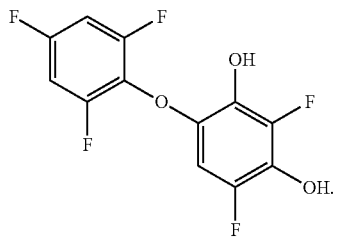 [SMILES: Oc1c(F)cc(Oc2c(F)cc(F)cc2F)c(O)c1F]

2. The hydroxyphenyl derivative according to claim 1, wherein R1 is substituted by 1 to 3 substituents selected from the group comprising F, $COR_a$, $OR_a$, $NR_aR_b$, alkynyl, $SO_2R_a$, $SO_2NR_aR_b$, $NR_aCOOR_b$ and $CR_a=NOR_b$.

3. The hydroxyphenyl derivative according to claim 1, wherein Y represents a labile chemical group selected from the group consisting of $C(O)R_a$, $CO(O)R_a$, $C(O)NR_aR_b$, $P(O)(OH)_2$ and $COCHR_aNR_bR_c$.

4. A process for making a hydroxyphenyl derivative according to claim 1, comprising the steps of
a) reacting with AR1, a phenol derivative of formula (II)

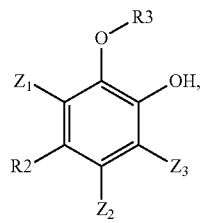

R3 represents an alkyl group, and A is a reactive group capable of reacting with the OH group of (II), under basic conditions, to give a derivative of formula (III)

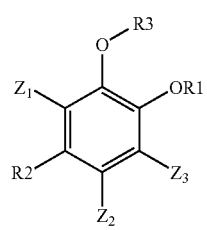

b) reacting the derivative of formula (III) with a Lewis acid to give the desired derivative of formula (I).

5. The process according to claim 4, wherein to obtain hydroxyphenyl derivative with R2 representing a functional group, the desired function is introduced prior removal of R3.

6. A process for making a hydroxyphenyl derivative according to claim 1, comprising the steps of
a) reacting the protected phenol derivative of formula (II) with TosCl to give a derivative of formula (IV)

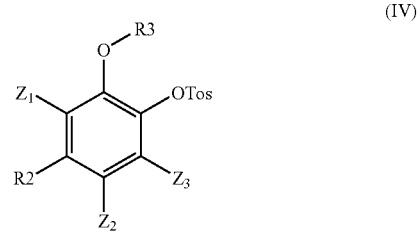

b) reacting the derivative of formula (IV) with a Lewis acid to give a derivative of formula (V)

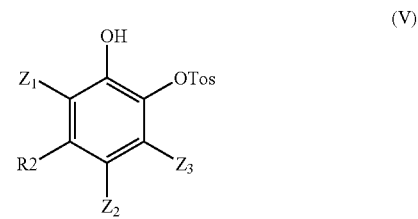

c) treating the derivative of formula (V) under basic or acidic conditions, to introduce R4, R4 being a protecting group selected from the group consisting of benzyl, BOM, SEM, MOM, MEM, TBDMS, THP and analogs, to obtain a derivative of formula (VI),

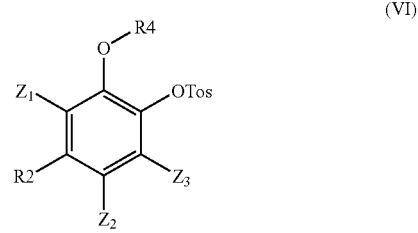

d) reacting said derivative of formula (VI) under basic conditions or with Mg in an alcohol, to remove the Tos group, to obtain a derivative of formula (VII)

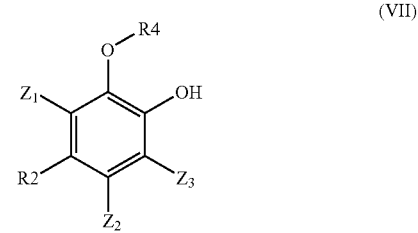

e) reacting the derivative of formula (VII) with ARI to obtain a product of formula (III')

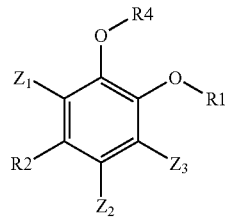

f) deprotecting the phenol group to obtain the desired derivative of formula (I) with Y representing H.

7. A process for making the hydroxyphenyl derivative according to claim 1 wherein Z2 is fluor, comprising the steps of a) reacting the bromophenol of formula (VIII):

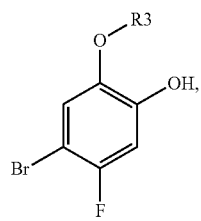

in the presence of a base to obtain the compound of formula (IX):

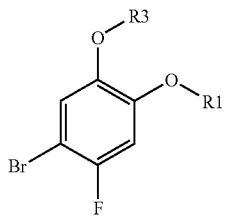

then reacting the compound of formula (IX) with a palladium catalyst in the presence of a base and a boronic reactant of formula R2B, R2 is as above defined and B is a boronic ester residue, to obtain a derivative of formula (X),

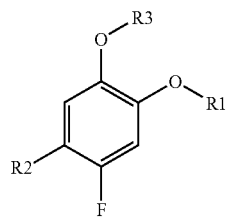

b) alternatively protecting the compound of formula (VIII), with a benzyl group prior to reacting it with a palladium catalyst in the presence of a base and a boronic reactant of formula R2B, to obtain the benzylated derivative (XI),

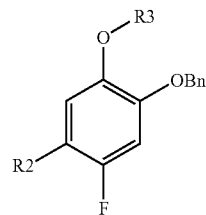

debenzylating it with palladium on charcoal and hydrogen to obtain the free phenol of formula (XII)

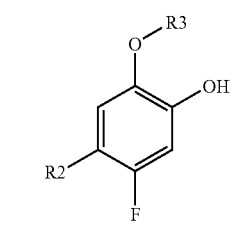

and reacting (XII) with ARI to generate the derivative of formula (X)

c) Dealkylalating the compound of formula (X) to generate the derivative of formula (I).

8. A process according to claim 4, wherein a compound of formula (III), (VI), (VII), (X) or (I) is obtained from a compound of formula (XIII)

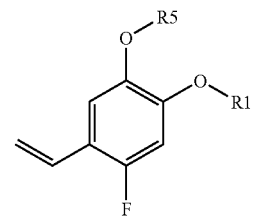

in which R2 is vinyl, and R5 being H, R3 or R4 as above defined by hydrogenation with palladium on charcoal to give the corresponding ethyl compound derivative (XIV)

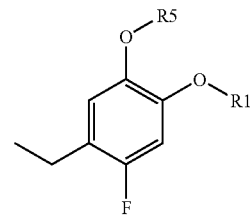

which can be further deprotected.

9. A process according to claim 4, wherein a hydroxyphenyl derivative of formula (I) in which Y =H is converted into a compound in which Y is $C(O)R_a$, $CO(O)R_a$, $C(O)NR_aR_b$, $P(O)(OH)_2$, and $COCHR_aNR_bR_c$.

10. A pharmaceutical composition comprising, as active ingredient, a therapeutically effective amount of a hydroxyphenyl derivative of formula (I) as defined in claim 1, in combination with a pharmaceutically acceptable carrier.

11. The pharmaceutical composition of claim 10, which is formulated to be administered under oral, injectable, or parental routes, to a patient.

12. A hydroxyphenyl derivative of formula (I)

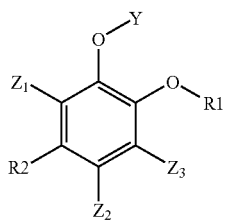

(I)

R1 is phenyl substituted by 1 to 3 R identical or different, R being selected from the group comprising H, fluoro, $C_1$-$C_8$ alkyl, $C_1$-$C_4$fluoro-alkyl, $C_2$-$C_8$ alkenyl, $C_2$-$C_8$ alkynyl, $COOR_a$, $COR_a$, $CONR_aR_b$, $OCOR_a$, CN, $OR_a$, $NR_aR_b$, $CR_a$=$NOR_b$, $NR_aCOOR_b$, $OCONR_aR_b$, $NR_a$-$CONR_bR_c$, $SR_a$, $SO_2R_a$, $SO_2NR_aR_b$ and $NR_aC(S)NR_bR_c$, R2 is $C_1$-$C_8$ alkyl, $C_2$-$C_8$ alkenyl, $C_2$-$C_8$ alkynyl, $C_1$-$C_4$fluoro-alkyl, $C_2$-$C_4$fluoro-alkenyl, $OR_a$ or $SR_a$, $R_a$, $R_b$ and $R_c$, identical or different, are selected from the group consisting of H, $C_1$-$C_8$ alkyl, $C_2$-$C_8$ alkenyl and $C_2$-$C_8$ alkynyl, Y represents H, Z1 and Z3 are both H, Z2 is fluor, or a pharmaceutically acceptable organic or mineral salt thereof, in case the derivative of formula (I) has one or more chiral centres, both a chiral and non-chiral derivative, in cases the derivative of formula (I) has unsaturated carbon=carbon double bonds, both the cis (Z) and trans (E) isomers, and any N-oxide form of the derivatives.

13. The derivative according to claim 12, wherein R1 is phenyl and R is fluoro.

14. A pharmaceutical composition comprising, as active ingredient, a therapeutically effective amount of a hydroxyphenyl derivative of formula (I) as defined in claim 12, in combination with a pharmaceutically acceptable carrier.

15. The pharmaceutical composition of claim 14, in an orally administrable, injectible, or parenterally administrable form.

16. The hydroxyphenyl derivative according to claim 1, wherein R2 is $C_1$-$C_8$ alkyl.

17. The hydroxyphenyl derivative according to claim 12, wherein R2 is $C_1$-$C_8$ alkyl.

* * * * *